United States Patent
Sidhu et al.

(10) Patent No.: US 8,685,893 B2
(45) Date of Patent: Apr. 1, 2014

(54) PHAGE DISPLAY

(75) Inventors: Sachdev S. Sidhu, Toronto (CA);
 Gregory A. Weiss, Irvine, CA (US);
 James A. Wells, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 1047 days.

(21) Appl. No.: 12/181,222

(22) Filed: Jul. 28, 2008

(65) Prior Publication Data

US 2012/0165226 A1  Jun. 28, 2012

Related U.S. Application Data

(63) Continuation of application No. 09/380,447, filed as application No. PCT/US99/16596 on Jul. 22, 1999, now abandoned.

(60) Provisional application No. 60/094,291, filed on Jul. 27, 1998, provisional application No. 60/103,514, filed on Oct. 8, 1998, provisional application No. 60/133,296, filed on May 10, 1999, provisional application No. 60/134,870, filed on May 19, 1999.

(51) Int. Cl.
 *C40B 40/02* (2006.01)

(52) U.S. Cl.
 USPC .......................................................... 506/14

(58) Field of Classification Search
 None
 See application file for complete search history.

(56) References Cited

U.S. PATENT DOCUMENTS

| | | |
|---|---|---|
| 4,822,740 A | 4/1989 | Vandenbergh |
| 4,848,355 A | 7/1989 | Nakamura et al. |
| 4,910,140 A | 3/1990 | Dower |
| 4,956,288 A | 9/1990 | Barsoum |
| 4,987,071 A | 1/1991 | Cech et al. |
| 5,098,843 A | 3/1992 | Calvin |
| 5,116,742 A | 5/1992 | Cech et al. |
| 5,124,259 A | 6/1992 | Tada |
| 5,128,257 A | 7/1992 | Baer |
| 5,139,935 A | 8/1992 | Fukuhara et al. |
| 5,173,158 A | 12/1992 | Schmukler |
| 5,186,800 A | 2/1993 | Dower |
| 5,223,409 A | 6/1993 | Ladner et al. |
| 5,232,856 A | 8/1993 | Firth et al. |
| 5,270,170 A | 12/1993 | Schatz et al. |
| 5,283,194 A | 2/1994 | Schmukler |

(Continued)

FOREIGN PATENT DOCUMENTS

| | | |
|---|---|---|
| EP | 0 844 306 A1 | 5/1998 |
| EP | 0 844 306 B1 | 5/1998 |

(Continued)

OTHER PUBLICATIONS

Ahn, A. et al. (Feb. 2, 1996). "The Three Human Syntrophin Genes are Expressed in Diverse Tissues, have Distinct Chromosomal Locations, and Each Bind to Dystrophin and Its Relatives," *J. Biol. Chem.* 271:2724-2730.

(Continued)

*Primary Examiner* — Christian Boesen
(74) *Attorney, Agent, or Firm* — Morrison & Foerster LLP

(57) ABSTRACT

The transformation yield of electroporation is increased by using higher DNA concentrations and DNA affinity purification. Fusion proteins of a viral coat protein variant and a heterologous polypeptide are useful in phage display systems.

10 Claims, 17 Drawing Sheets

(56) References Cited

U.S. PATENT DOCUMENTS

| | | | |
|---|---|---|---|
| 5,403,484 A | 4/1995 | Ladner et al. |
| 5,422,272 A | 6/1995 | Papp et al. |
| 5,427,908 A | 6/1995 | Dower et al. |
| 5,432,018 A | 7/1995 | Dower et al. |
| 5,498,530 A | 3/1996 | Schatz et al. |
| 5,498,538 A | 3/1996 | Kay et al. |
| 5,514,548 A | 5/1996 | Krebber et al. |
| 5,516,637 A | 5/1996 | Huang et al. |
| 5,534,257 A | 7/1996 | Mastico et al. |
| 5,552,314 A | 9/1996 | Greener |
| 5,565,332 A | 10/1996 | Hoogenboom et al. |
| 5,571,689 A | 11/1996 | Heuckeroth et al. |
| 5,580,717 A | 12/1996 | Dower et al. |
| 5,580,723 A | 12/1996 | Wells et al. |
| 5,622,699 A | 4/1997 | Ruoslahti et al. |
| 5,627,024 A | 5/1997 | Maruyama et al. |
| 5,658,727 A | 8/1997 | Barbas et al. |
| 5,663,143 A | 9/1997 | Ley et al. |
| 5,667,988 A | 9/1997 | Barbas et al. |
| 5,698,426 A | 12/1997 | Huse |
| 5,702,892 A | 12/1997 | Mulligan-Kehoe |
| 5,707,841 A | 1/1998 | Greener |
| 5,712,089 A | 1/1998 | Borrebaeck et al. |
| 5,723,286 A | 3/1998 | Dower et al. |
| 5,723,287 A | 3/1998 | Russell et al. |
| 5,723,323 A | 3/1998 | Kauffman et al. |
| 5,733,743 A | 3/1998 | Johnson et al. |
| 5,734,018 A | 3/1998 | Rutter et al. |
| 5,750,373 A | 5/1998 | Garrard et al. |
| 5,756,345 A | 5/1998 | Camakaris et al. |
| 5,759,817 A | 6/1998 | Barbas |
| 5,763,192 A | 6/1998 | Kauffman et al. |
| 5,766,905 A | 6/1998 | Studier et al. |
| 5,770,356 A | 6/1998 | Light, II et al. |
| 5,770,434 A | 6/1998 | Huse |
| 5,780,279 A | 7/1998 | Matthews et al. |
| 5,834,250 A | 11/1998 | Wells et al. |
| 5,858,657 A | 1/1999 | Winter et al. |
| 6,054,312 A | 4/2000 | Larocca et al. |
| 6,190,908 B1 | 2/2001 | Kang |
| 6,794,128 B2 | 9/2004 | Marks et al. |
| 2002/0058607 A1 | 5/2002 | Sato et al. |
| 2002/0081570 A1 | 6/2002 | Lilien et al. |
| 2003/0148264 A1 | 8/2003 | Held et al. |
| 2005/0019841 A1 | 1/2005 | Garman et al. |

FOREIGN PATENT DOCUMENTS

| | | | |
|---|---|---|---|
| JP | 07-236476 A | 9/1995 | |
| WO | WO-92/06176 A1 | 4/1992 | |
| WO | WO-92/09690 A2 | 6/1992 | |
| WO | WO-92/09690 A3 | 6/1992 | |
| WO | WO-92/14829 A1 | 9/1992 | |
| WO | WO-94/05781 A1 | 3/1994 | |
| WO | WO 94/05781 A1 * | 3/1994 | ............ C12N 15/00 |
| WO | WO-94/11496 A1 | 5/1994 | |
| WO | WO-95/27045 A1 | 10/1995 | |
| WO | WO-95/34648 A1 | 12/1995 | |
| WO | WO-95/34683 A1 | 12/1995 | |
| WO | WO-96/22393 A1 | 7/1996 | |
| WO | WO-97/02342 A1 | 1/1997 | |
| WO | WO-97/09436 A1 | 3/1997 | |
| WO | WO-97/09446 A1 | 3/1997 | |
| WO | WO-97/12048 A1 | 4/1997 | |
| WO | WO-97/29185 A1 | 8/1997 | |
| WO | WO-97/35196 A1 | 9/1997 | |
| WO | WO-97/40141 A2 | 10/1997 | |
| WO | WO-97/40141 A3 | 10/1997 | |
| WO | WO-97/44491 A1 | 11/1997 | |
| WO | WO-97/46251 A1 | 12/1997 | |
| WO | WO-97/47314 A1 | 12/1997 | |
| WO | WO-98/14277 A1 | 4/1998 | |
| WO | WO-98/15833 A1 | 4/1998 | |
| WO | WO-98/20036 A1 | 5/1998 | |
| WO | WO-98/20159 A1 | 5/1998 | |
| WO | WO-98/20169 A1 | 5/1998 | |
| WO | WO-98/53100 A1 | 11/1998 | |
| WO | WO-98/05344 A1 | 12/1998 | |
| WO | WO-99/58655 A2 | 11/1999 | |
| WO | WO-99/58655 A3 | 11/1999 | |
| WO | WO-00/06717 A2 | 2/2000 | |
| WO | WO-00/06717 A3 | 2/2000 | |
| WO | WO-00/09715 A1 | 2/2000 | |
| WO | WO-00/69896 A2 | 11/2000 | |
| WO | WO-00/69896 A3 | 11/2000 | |
| WO | WO-01/04753 A1 | 1/2001 | |
| WO | WO-01/38541 A1 | 5/2001 | |
| WO | WO-03/004604 A2 | 1/2003 | |
| WO | WO-03/004604 A3 | 1/2003 | |

OTHER PUBLICATIONS

Allen et al. (1995). "Finding Prospective Partners in the Library: The Two-Hybrid System and Phage Display Find a Match," *TIBS* 20:511-516.

Andersson, B. et al. (1996). "A 'Double-Adaptor' Method for Improved Shotgun Library Construction," *Anal. Biochem.* 236:107-113.

Arimura, Y. et al. (1992). "cDNA Cloning of New Protein Tyrosine Phosphatases in the Human Colon," *Tumor Biol.* 13:180-186.

Azim, A.A. et al. (1995). "DLG1: Chromosome Location of the Closest Human Homologue of the *Drosophila* Discs Large Tumor Suppressor Gene," *Genomics* 30:613-616.

Baier, M. et al. (May 1997). "Molecular Cloning, Sequence, Expression, and Processing of the Interleukin 16 Precursor," *Proc. Natl. Acad. Sci. USA* 94:5273-5277.

Bannert, N. et al. (May 2, 1996). "Interleukin-16 or not?," *Nature* 381:30.

Barbas (1993). "Recent Advances in Phage Display," *Current Opinion in Biotechnology* 4:526-530.

Barbas et al. (1991). "Assembly of Combinatorial Libraries on Phage Surfaces: The Gene III Site," *Proc. Natl. Acad. Sci. USA* 88:7978-7982.

Barbas et al. (1992). "Semisynthetic Combinatorial Antibody Libraries: A Chemical Solution to the Diversity Problem," *Proc. Natl. Acad. Sci. USA* 89:4457-4461.

Barrett, R.W. et al. (1992). "Selective Enrichment and Characterization of High Affinity Ligands from Collections of Random Peptides on Filamentous Phage," *Anal. Biochem.* 204:357-364.

Bashirova, A.A. et al. (1998). "The Human *RIL* Gene: Mapping to Human Chromosome 5q31.1, Genomic Organization and Alternative Transcripts," *Gene* 210:239-245.

Bass et al. (1990). "Hormone Phage: An Enrichment Method for Variant Proteins with Altered Binding Properties," *Proteins: Structure, Function, and Genetics* 8(4):309-314.

Beatch, M. et al. (Oct. 18, 1996). "The Tight Junction Protein ZO-2 Contains Three PDZ (PSD-95/Discs-Large/ZO-1) Domains and an Alternatively Spliced Region," *J. Biol. Chem.* 271(42):25723-25726.

Bonnycastle et al. (1996). "Probing the Basis of Antibody Reactivity with a Panel of Constrained Peptide Libraries Displayed by Filamentous Phage," *J. Mol. Biol.* 258:747-762.

Borg, J-P. et al. (Nov. 27, 1998). "Identification of an Evolutionarily Conserved Heterotrimeric Protein Complex Involved in Protein Targeting," *J. Biol. Chem.* 273(48):31633-31636.

Bouju, S. et al. (1999). "Exclusion of Muscle Specific Actinin-Associated LIM Protein (ALP) Gene from 4q35 Facioscapulohumeral Muscular Dystrophy (FSHD) Candidate Genes," *Neuromuscul. Disorders* 9:3-10.

Bradbury et al. (1995). "The Use of Phage Display in Neurobiology," *Trends in Neuroscience* 18:243-249.

Brückner, K. et al. (Mar. 1999). "EphrinB Ligands Recruit GRIP Family PDZ Adaptor Proteins into Raft Membrane Microdomains," *Neuron* 22:511-524.

Bryant, P.J. et al. (Feb. 21, 1992). "A Major Palmitoylated Membrane Protein of Human Erythrocytes Shows Homology to Yeast Guanylate Kinase and to the Product of a *Drosophila* Tumor Suppressor Gene," *Cell* 68:621-622.

(56) References Cited

OTHER PUBLICATIONS

Butz, S. et al. (Sep. 18, 1998). "A Tripartite Protein Complex with the Potential to Couple Synaptic Vesicle Exocytosis to Cell Adhesion in Brain," *Cell* 94:773-782.

Cason, J. et al. (Nov. 1989). "Identification of Immunogenic Regions of the Major Coat Protein of Human Papollomavirus Type 16 that Contain Type-Restricted Epitopes," *Journal of General Virology* 70(11):2973-2987.

Castelló, A. et al. (1996). "Characterization of the Dystrophin-Syntrophin Interaction Using the Two-Hybrid System in Yeast," *FEBS Letters* 383:124-128.

Chappel et al. (1998). "Modulation of Antibody Display on M13 Filamentous Phage," *J. Immunol. Meth.* 221:25-34.

Chen, H. et al. (1995). "Localization of a Human Homolog of the Mouse *Tiam-1* Gene to Chromosome 21q22.1," *Genomics* 30:123-127.

Chiu, C-Y. et al. (1999). "Cloning and Characterization of T-Cell Lymphoma Invasion and Metastasis 2 (TIAM2), a Novel Guanine Nucleotide Exchange Factor Related to TIAM1," *Genomics* 61:66-73.

Choo et al. (1995). "Designing DNA-Binding Proteins on the Surface of Filamentous Phage," *Current Opinion in Biotechnology* 6:431-436.

Clackson et al. (1991). "Making Antibody Fragments Using Phage Display Libraries," *Nature* 352:624-628.

Clackson et al. (1994). "In vitro Selection from Protein and Peptide Libraries," *Trends Biotechnol.* 12:173-184.

Cohen, A.R. et al. (Jul. 13, 1998). "Human CASK/LIN-2 Binds Syndecan-2 and Protein 4.1 and Localizes to the Basolateral Membrane of Epithelial Cells," *J. Cell. Biol.* 142(1):129-138.

Cortese et al. (1995). "Identification of Biologically Active Peptides Using Random Libraries Displayed on Phage," *Current Opinion in Biotechnology* 6:73-80.

Cortese et al. (1996). "Selection of Biologically Active Peptides by Phage Display of Random Peptide Libraries," *Current Opinion in Biotechnology* 7:616-621.

Cowburn, D. et al. (Oct. 1997). "A Never Ending Frontier," *Nat. Struct. Biol.* 4(10):761-762.

Craven, S.E. et al. (May 15, 1998). "PDZ Proteins Organize Synaptic Signaling Pathways," *Cell* 93:495-498.

Cull, M.G. et al. (Mar. 1992). "Screening for Receptor Ligands Using Large Libraries of Peptides Linked to the C Terminus of the *lac* Repressor," *Proc. Natl. Acad. Sci. USA* 89:1865-1869.

Cwirla et al. (1990). "Peptides on Phage: A Vast Library of Peptides for Identifying Ligands," *Proc. Natl. Acad. Sci. USA* 87(16):6378-6382.

Daniels, D.L. et al. (Apr. 1998). "Crystal Structure of the hCASK PDZ Domain Reveals the Structural Basis of Class II PDZ Domain Target Recognition," *Nat. Struct. Biol.* 5(4):317-325.

De Kruif et al. (1995). "Selection and Application of Human Single Chain Fv Antibody Display Library with Designed CDR3 Regions," *J. Mol. Biol.* 248:97-105.

De Vries, L. et al. (Oct. 1998). "GIPC, a PDZ Domain Containing Protein, Interacts Specifically with the C Terminus of RGS-GAIP," *Proc. Natl. Acad. Sci. USA* 95:12340-12345.

Deber et al. (1993). "Val→Ala Mutation Selectively Alter Helix-Helix Packing in the Transmembrane Segment of Phage M13 Coat Protein," *Proc. Natl. Acad. Sci. USA* 90:11648-11652.

Deguchi, M. et al. (Sep. 22, 2000, e-pub. Jul. 13, 2000). "PAPIN: A Novel Multiple PSD-95/Dlg-A/ZO-1 Protein Interacting with Neural Plakophilin-Related *Armadillo* Repeat Protein/δCatenin and p0071," *J. Biol. Chem.* 275(38):29875-29880.

Demartis et al. (1999). "A Strategy for the Isolation of Catalytic Activites from Repertoires of Enzymes Displayed on Phage," *J. Mol. Biol.* 286:617-633.

Dimitratos, S.D. et al. (1998). "The Location of Human *CASK* at Xp11.4 Identifies This Gene as a Candidate for X-Linked Optic Atrophy," *Genomics* 51:308-309.

Dixon, B. et al. (1993). "Cloning a cDNA from Human NK/T Cells Which Codes for an Unusual Leucine Zipper Containing Protein," *Biochim. Biophys. Acta* 1216:321-324.

Dower et al. (1998). "High Efficacy Transformation of *E. coli* by High Voltage Electroporation," *Nucleic Acids Research* 16(13):6127-6145.

Doyle, D.A. et al. (Jun. 28, 1996). "Crystal Structures of a Complexed and Peptide-Free Membrane Protein-Binding Domain: Molecular Basis of Peptide Recognition by PDZ," *Cell* 85:1067-1076.

Duclos, F. et al. (Jan. 1993). "Gene in the Region of the Friedreich Ataxia Locus Encodes a Putative Transmembrane Protein Expressed in the Nervous System," *Proc. Natl. Acad. Sci. USA* 90:109-113.

Duclos, F. et al. (1994). "The Friedreich Ataxia Region: Characterization of Two Novel Genes and Reduction of the Critical Region to 300 kb," *Hum. Mol. Genet.* 3(6):909-914.

Duclos, F. et al. (1995). "Comparison of Primary Structure of a Neuron-Specific Protein, X11, Between Human and Mouse," *Mamm. Genome* 6:57-58.

Dunn, I.S. (1996). "Phage Display of Proteins," *Current Opinion in Biotechnology* 7:547-553.

Edwards, D.C. et al. (Apr. 16, 1999). "Structural Features of LIM Kinase That Control Effects on the Actin Cytoskeleton," *J. Biol. Chem.* 274(16):11352-11361.

Efimov, V. et al. (1995). "Bacteriophage T4 as a Surface Display Vector," *Virus Genes* 10:173.

Fanning, A.S. et al. (Mar. 1999). "PDZ Domains: Fundamental Building Blocks in the Organization of Protein Complexes at the Plasma Membrane," *J. Clin. Invest.* 103(6):767-772.

Frangiskakis, J.M. et al. (Jul. 12, 1996). "*LIM-Kinase1* Hemizygosity Implicated in Impaired Visuospatial Constructive Cognition," *Cell* 86:59-69.

Fuh, G. et al. (Jul. 14, 2000). "Analysis of PDZ Domain-Ligand Interactions Using Carboxyl-Terminal Phage Display," *J. Biol. Chem.* 275(28):21486-21491.

Fujisawa, H. et al. (1994). "Expression of Two Types of Nitric Oxide Synthase of mRNA in Human Neuroblastoma Cell Lines," *J. Neurochem.* 63(1):140-145.

Fukuhara, S. et al. (Feb. 26, 1999). "A Novel PDZ Domain Containing Guanine Nucleotide Exchange Factor Links Heterotrimeric G Proteins to Rho," *J. Biol. Chem.* 274(9):2868-2879.

Gee, S.H. et al. (Aug. 21, 1998). "Cyclic Peptides as Non-Carboxyl-Terminal Ligands of Syntrophin PDZ Domains," *J. Biol. Chem.* 273(34):21980-21987.

Greco, T.L. et al. (1996). "Dishevelled-2 Maps to Human Chromosome 17 and Distal to *Wnt3a* and Vestigial Tail (*vt*) on Mouse Chromosome 11," *Mamm. Genome* 7:475-476.

Greenwood et al. (1991). "Regulation of Filamentous Bacteriophage Length by Modification of Electrostatic Interactions Between Coat Protein and DNA," *J. Mol. Biol.* 217:223-227.

Griffiths et al. (1994). "Isolation of High Affinity Human Antibodies Directly From Large Synthetic Repertoires," *EMBO Journal* 13:3245-3260.

Gu, M. et al. (Jul. 1991). "Identification, Cloning, and Expression of a Cytosolic Megakaryocyte Protein-Tyrosine-Phosphatase with Sequence Homology to Cytoskelatal Protein 4.1," *Proc. Natl. Acad. Sci. USA* 88:5867-5871.

Habets, G.G.M. et al. (1995). "The Invasion-Inducing TIAM1 Gene Maps to Human Chromosome Band 21q22 and Mouse Chromosome 16," *Cytogenet. Cell Genet.* 70:48-51.

Habets, G.G.M. et al. (1995). "Sequence of the Human Invasion-Inducing *TIAM1* Gene, its Conservation in Evolution and its Expression in Tumor Cell Lines of Different Tissue Origin," *Oncogene* 10:1371-1376.

Haigh et al. (1998). "The Major Coat Protein of Filamentous Bacteriophage f1 Specifically Pairs in the Bacterial Cytoplasmic Membrane," *J. Mol. Biol.* 279:19-29.

Hall, R.A. et al. (Jul. 1998). "A C-Terminal Motif Found in the β2-Adrenergic Receptor, P2Y1 Receptor and Cystic Fibrosis Transmembrane Conductance Regulator Determines Binding to the Na+/H+ Exchanger Regulatory Factor Family of PDZ Proteins," *Proc. Natl. Acad. Sci. USA* 95:8496-8501.

(56) References Cited

OTHER PUBLICATIONS

Harrison, S.C. (Aug. 9, 1996). "Peptide-Surface Association: The Case of PDZ and PTB Domains," *Cell* 86:341-343.

Hasan, N. et al. (1986). "Boundaries of the nutL Antiterminator of Coliphage Lambda and Effects of Mutations in the Spacer Region between boxA and boxB," *Gene* 50(1-3):87-96.

Hatzfeld, M. et al. (1996). "Cloning and Characterization of a New *armadillo* Family Member, p0071, Associated with the Junctional Plaque: Evidence for a Subfamily of Closely Related Proteins," *Journal of Cell Science* 109:2767-2778.

Hillier, B.J. et al. (Apr. 30, 1999). "Unexpected Modes of PDZ Domain Scaffolding Revealed by Structure of nNOS-Syntrophin Complex," *Science* 284:812-815.

Holmes et al. (1996). "Bacteriophage Display of Chymotrypsin Inhibitor 2," *Protein Pept. Lett.* 3:415-422.

Hoogenboom (Feb. 1997). "Designing and Optimizing Library Selection Strategies for Generating High-Affinity Antibodies," *Trends in Biotechnology* 15(2):62-70.

Hoogenboom et al. (1992). "By-Passing Immunisation: Human Antibodies from Synthetic Repertoires of Germline $V_H$ Gene Segments Rearranged in vitro," *J. Mol. Biol.* 227:318-388.

Hou, J. et al. (Sep. 16, 1994). "An Interleukin-4-Induced Transcription Factor: IL-4 Stat," *Science* 265:1701-1706.

Hu, S-I. et al. (Dec. 18, 1998). "Human HtrA, an Evolutionarily Conserved Serine Protease Identified as a Differentially Expressed Gene Product in Osteoarthritic Cartilage," *J. Biol. Chem.* 273(51):34406-34412.

Hunter et al. (1987). "Interaction Between DNA and Coat Protein in the Structure and Assembly of Filamentous Bacteriophage fd," *Nature* 327:252-254.

Imai, K. et al. (1998). "Genomic Structure and Sequence of a Human Homologue (NTHL1/NTH1) of *Escherichia coli* Endonuclease III with Those of the Adjacent Parts of *TSC2* and *SLC9A3R2* Genes," *Gene* 222:287-295.

Inazawa, J. et al. (1996). "PTPN13, a Fas-Associated Protein Tyrosine Phosphatase, Is Located on the Long Arm of Chromosome 4 at Band q21.3," *Genomics* 31:240-242.

International Search Report mailed Apr. 27, 2000, for PCT Application No. PCT/US99/16596, filed Jul. 22, 1999, four pages.

International Search Report mailed Feb. 10, 2004, for PCT Application No. PCT/US02/20993, filed Jul. 3, 2002, four pages.

Itoh, F. et al. (1993). "Expression and Chromosomal Assignment of PTPH1 Gene Encoding a Cytosolic Protein Tyrosine Phosphatase Homologous to Cytoskeletal-Associated Proteins," *Int. J. Cancer* 55:947-951.

Janda et al. (1994). "Direct Selection for a Catalytic Mechanism from Combinatorial Antibody Libraries," *Proc. Natl. Acad. Sci. USA* 91:2532-2536.

Janda et al. (1997). "Chemical Selection for Catalysis in Combinatorial Antibody Libraries," *Science* 275:945-948.

Jefferies, D. (1998). "Selection of Novel Ligands from Phage Display Libraries: An Alternative Approach to Drug and Vaccine Discovery," *Parasitology Today* 14(5):202-206.

Jespers et al. (1995). "Surface Expression and Ligand-Based Selection of cDNAs Fused to Filamentous Phage Gene VI," *Biotechnology* 13:378-382.

Jiang, J. (Nov. 1997). "Display of a PorA Peptide from *Neisseria meningitidis* on the Bacteriophage T4 Capsid Surface," *Infection and Immunity* 65(11):4770-4777.

Jo, K. et al. (Jun. 1, 1999). "Characterization of MALS/Velis-1, -2, and -3: A Family of Mammalian LIN-7 Homologs Enriched at Brain Synapses in Association with the Postsynaptic Density-95/NMDA Receptor Postsynaptic Complex," *J. Neurosci.* 19(11):4189-4199.

Kaech, S.M. et al. (Sep. 18, 1998). "The LIN-2/LIN-7/LIN-10 Complex Mediates Basolateral Membrane Localization of the *C. elegans* EGF Receptor LET-23 in Vulval Epithelial Cells," *Cell* 94:761-771.

Kameya, S. et al. (Jan. 22, 1999). "α1-Syntrophin Gene Disruption Results in the Absence of Neuronal-Type Nitric-Oxide Synthases at the Sarcolemma but Does Not Induce Muscle Degeneration," *J. Biol. Chem.* 274(4):2193-2200.

Kang, A. et al. (1991). "Linkage of Recognition and Replication Functions by Assembling Combinatorial Antibody Fab Libraries Along Phage Surfaces," *Proc. Natl. Acad. Sci. USA* 88:42363-4366.

Kim, E. et al. (Nov. 2, 1995). "Clustering of Shaker-Type K+ Channels by Interaction with a Family of Membrane-Associated Guanylate Kinases," *Nature* 378:85-88.

Kim, E. et al. (Jul. 1996). "Heteromultimerization and NMDA Receptor-Clustering Activity of Chapsyn-110, a Member of the PSD-95 Family of Proteins," *Neuron* 17:103-113.

Kobayshi, I. et al. (1999). "Identification of an Autoimmune Enteropathy-Related 75-Kilodalton Antigen," *Gastroenterology* 117(4):823-830.

Kocher, O. et al. (1998). "Identification and Partial Characterization of PDZK1: A Novel Protein Containing PDZ Interaction Domains," *Lab. Invest.* 78(1):117-125.

Kornau, H.C. et al. (Sep. 22, 1995). "Domain Interaction Between NMDA Receptor Subunits and the Postsynaptic Density Protein PSD-95," *Science* 269:1737-1740.

Laura, R.P. et al. (Apr. 12, 2002). "The Erbin PDZ Domain Binds with High Affinity and Specificity to the Carboxyl Termini of δ-Catenin and ARCVF," *J. Biol. Chem.* 277(15):12906-12914.

Leek, J.P. et al. (1997). "Assignment of the STAT6 Gene (STAT6) to Human Chromosome Band 12q13 by in Situ Hybridization," *Cytogenet. Cell Genet.* 79:208-209.

Lennon, G. et al. (1996). "The I.M.A.G.E. Consortium: An Integrated Molecular Analysis of Genomes and Their Expression," *Genomics* 33:151-152.

Lerchl, J. et al. (Jun. 22, 2001). "Sequence 101 from Patent WO 01/38541," Database Accession No. AX150760, *Genome Quest, Inc*, four pages.

Li et al. (1998). "Filamentous Bacteriophage Display of a Bifunctional Protein A::scFv Fusion," *Mol. Biotech.* 9:187-193.

Li et al. (Mar. 5, 1993). "Conformational States of Mutant M13 Coat Proteins are Regulated by Transmembrane Residues," *J. Biol. Chem.* 268(7):4584-4587.

Lin, J. et al. (1998). "Melanoma Differentiation Associated Gene-9, *mda-9*, is a Human Gamma Interferon Responsive Gene," *Gene* 207:105-110.

Lincke, C.R. et al. (Mar. 15, 1991). "Structure of the Human *MDR3* Gene and Physical Mapping of the Human *MDR* Locus," *J. Biol. Chem.* 266(8):5303-5310.

Lindqvist et al. (1995). "Peptide Presentation by Bacteriophage P4," *FEMS Microbiology Reviews* 17:33-39.

Lowman et al. (1991). "Monovalent Phage Display: A Method for Selecting Variant Proteins from Random Libraries," *Methods: Comp. to Methods Enzymol.* 3:205-216.

Lowman et al. (1991). "Selecting High-Affinity Binding Proteins by Monovalent Phage Display," *Biochemistry* 30(45):10832-10838.

Lowman et al. (1998). "Molecular Mimics of Insulin-Like Growth Factor 1 (IGF-1) for Inhibiting IGF-1: IGF-Binding Protein Interactions," *Biochemistry* 37(25):8870-8878.

Lue, R. et al. (Oct. 1994). "Cloning and Characterization of hdlg: The Human Homologue of the *Drosophila* Discs Large Tumor Suppressor Binds to Protein 4.1," *Proc. Natl. Acad. Sci. USA* 91:9818-9822.

Luzzago et al. (Jun. 15, 1993). "Mimicking of Discontinous Epitopes by Phage-Displayed Peptides, I. Epitope Mapping of Human H Ferritin Using a Phage Library of Constrained Peptides," *Gene* 128(1):51-57.

Maekawa, K. et al. (1994). "Molecular Cloning of a Novel Protein-Tyrosine Phosphatase Containing a Membrane-Binding Domain and GLGF Repeats," *FEBS Lett.* 337:200-206.

Makino, K. et al. (1997). "Cloning and Characterization of NE-dlg: A Novel Human Homolog of the *Drosophila* Discs Large (dlg) Tumor Suppressor Protein Interacts with the APC Protein," *Oncogene* 14:2425-2433.

Makowski, L. (1995). "Structural Constraints on the Display of Foreign Peptides on Filamentous Bacteriophages," *Gene* 128:5-11.

Malik et al. (1996). "Role of Capsid Structure and Membrane Protein Processing in Determining the Size and Number of Peptides Displayed on the Major Coat Protein of Filamentous Bacteriophage," *J. Mol. Biol.* 260:9-21.

(56) References Cited

OTHER PUBLICATIONS

Marfatia, S.M. et al. (Jan. 13, 1995). "Identification of the Protein 4.1 Binding Interface on Glycophorin C and p55, a Homologue of the *Drosophila Discs-Large* Tumor Suppressor Protein," *J. Biol. Chem.* 270(2):715-719.

Marks et al. (1991). "By-passing Immunization: Human Antibodies from V-Gene Libraries Displayed on Phage," *J. Mol. Biol.* 222:581-597.

Marvin, D.A. (1998). "Filamentous Phage Structure, Infection and Assembly," *Current Opinions in Structural Biology* 8:150-158.

Matthews et al. (1993). "Substrate Phage: Selection of Protease Substrates by Monovalent Phage Display," *Science* 260:1113-1117.

Mazoyer, S. et al. (1995). "A Gene (*DLG2*) Located at 17q12-q21 Encodes a New Homologue of the *Drosophila* Tumor Suppressor dlg-A," *Genomics* 28:25-31.

McGregor (1996). "Selection of Proteins and Peptides from Libraries Displayed on Filamentous Bacteriophage," *Molecular Biotechnology* 6:155-162.

McLafferty et al. (1993). "M13 Bacteriophage Displaying Disulfide-Contrained Microproteins," *Gene* 128:29-36.

McLoughlin, D.M. et al. (1996). "The Intracellular Cytoplasmic Domain of the Alzheimer's Disease Amyloid Precursor Protein Interacts with Phosphotyrosine-Binding Domain Proteins in the Yeast Two-Hybrid System," *FEBS Lett.* 397:197-200.

Metzenberg, A.B. et al. (1992). "The Gene Encoding the Palmitoylated Erythrocyte Membrane Protein, p55, Originates at the CpG Island 3' to the Factor VIII Gene," *Hum. Mol. Genet.* 1(2):97-101.

Michael et al. (1996). "In vitro and in vivo Characterisation of a Recombinant Carboxypeptidase $G_2$::Anti-CEA scFv Fusion Protein," *Immunotechnology* 2:47-57.

Michiels, F. et al. (May 25, 1995). "A Role for Rac in Tiam1-Induced Membrane Ruffling and Invasion," *Nature* 375:338-340.

Mizuno, K. et al. (1994). "Identification of a Human cDNA Encoding a Novel Protein Kinase with Two Repeats of the LIM/Double Zinc Finger Motif," *Oncogene* 9:1605-1612.

Mohandas, T.K. et al. (1995). "Localization of the Tight Junction Protein Gene TJP1 to Human Chromosome 15q13, Distal to the Prader-Willi/Angelman Region, and to Mouse Chromosome 7," *Genomics* 30:594-597.

Morais Cabral, J.H. et al. (Aug. 15, 1996). "Crystal Structure of a PDZ Domain," *Nature* 382:649-652.

Muller, N. et al. (1989). "Application of a Recombinant *Echinococcus multilocularis* Antigen in an Enzyme-Linked Immunosorbent Assay for Immunodiagnosis of Human Alveolar *Echinococcosis*," *Molecular and Biochemical Parasitology* 36(1):151-159.

Murthy, A. et al. (Jan. 16, 1998). "NHE-RF, a Regulatory Cofactor for $Na^+-H^+$ Exchange, is a Common Interactor for Merlin and ERM (MERM) Proteins," *J. Biol. Chem.* 273(3):1273-1276.

Nakamura, H. et al. (1998). "Identification of a Novel Human Homolog of the *Drosophila* Dlg, P-dlg, Specifically Expressed in the Gland Tissues and Interacting with p55," *FEBS Lett.* 433:63-67.

Neri et al. (Aug. 1995). "Engineering Recombinant Antibodies for Immunotherapy," *Cell Biophysics* 27(1):47-61.

Nomoto, S. et al. (1999). "Cloning and Characterization of the Alternative Promoter Regions of the Human *LIMK2* Gene Responsible for Alternative Transcripts with Tissue-Specific Expression," *Gene* 236:259-271.

O'Boyle et al. (1997). "Identification of a Novel Peptide Substrate of HSV-1 Protease Using Substrate Phage Display," *Virology* 236:338-347.

O'Neil et al. (1995). "Phage Display: Protein Engineering by Directed Evolution," *Current Opinion in Structural Biology* 5:443-449.

Okamoto, M. et al. (Dec. 12, 1997). "Mints, Munc18-Interacting Proteins in Synaptic Vesicle Exocytosis," *J. Biol. Chem.* 272(50):31459-31464.

Okano, I. et al. (Dec. 29, 1995). "Identification and Characterization of a Novel Family of Serine/Threonine Kinases Containing Two N-Terminal LIM Motifs," *J. Biol. Chem.* 270(52):31321-31330.

Osada, H. et al. (1996). "Subcellular Localization and Protein Interaction of the Human LIMK2 Gene Expressing Alternative Transcripts with Tissue-Specific Regulation," *Biochem. Biophys. Res. Commun.* 229:582-589.

Osborne, L.R. et al. (1996). "Identification of Genes From a 500-kb Region at 7q11.23 That is Commonly Deleted in Williams Syndrome Patients," *Genomics* 36:328-336.

Oschkinat, H. (May 1999). "A New Type of PDZ Domain Recognition," *Nat. Struct. Biol.* 6(5):408-410.

Palzkill, T. et al. (1998). "Mapping Protein-Ligand Interactions Using Whole Genome Phage Display Libraries," *Gene* 221:79-83.

Patel, B.K.R. et al. (1998). "Localization of the Human Stat6 Gene to Chromosome 12q13.3-q14.1, a Region Implicated in Multiple Solid Tumors," *Genomics* 52:192-200.

Pedersen et al. (1998). "A Method for Directed Evolution and Functional Cloning of Enzymes," *Proc. Natl. Acad. Sci. USA* 95:10523-10528.

Pizzuti, A. et al. (1996). "cDNA Characterization and Chromosomal Mapping of Two Human Homologues of the *Drosophila Dishevelled* Polarity Gene," *Hum. Mol. Genet.* 5(7):953-958.

Pizzuti, A. et al. (1996). "Human Homologue Sequences to the *Drosophila Dishevelled* Segment-Polarity Gene are Deleted in the DiGeorge Syndrome," *Am. J. Hum. Genet.* 58:722-729.

Poulat, F. et al. (Mar. 14, 1997). "The Human Testis Determining Factor *SRY* Binds a Nuclear Factor Containing PDZ Protein Interaction Domains," *J. Biol. Chem.* 272(11):7167-7172.

Prasad, R. et al. (Dec. 1, 1993). "Cloning of the *ALL-1* Fusion Partner, the *AF-6* Gene, Involved in Acute Myeloid Leukemias with the t(6;11) Chromosome Translocation," *Cancer Res.* 53:5624-5628.

Reczek, D. et al. (Oct. 6, 1997). "Identification of EBP50: A PDZ-Containing Phosphoprotein that Associates with Members of the Ezrin-Radixin-Moesin Family," *J. Cell. Biol.* 139(1):169-179.

Ren, Z. et al. (1996). "Phage Display of Intact Domains at High Copy Number: A System Based on SOC, the Small Outer Capsid Protein of Bacteriophage T4," *Protein Science* 5:1833-1843.

Ren, Z. et al. (1998). "Phage T4 SOC and HOC Display of Biologically Active, Full-length Proteins on the Viral Capsid," *Gene* 215:439-444.

Rosenberg, A. et al. (1987). "Vectors for Selective Expression of Cloned DNAs by T7 RNA Polymerase," *Gene* 56:125-135.

Rousset, R. et al. (1998). "The C-Terminus of the HTLV-1 Tax Oncoprotein Mediates Interaction with the PDZ Domain of Cellular Proteins," *Oncogene* 16:643-654.

Rudolph, S. et al. (Sep. 1990). "Prokaryotic Expression of the Major Capsid Protein of Human Cytomegalovirus and Antigenic Cross-Reactions with Herpes simplex Virus Type 1," *Journal of General Virology* 71(9):2023-2031.

Ruff, P. et al. (1999). "Exon Skipping Truncates the PDZ Domain of Human Erythroid p55 in a Patient with Chronic Myeloid Leukemia in Acute Megakaryoblastic Blast Crisis," *Leuk. Res.* 23:247-250.

Saha, V. et al. (1995). "*AF6* Gene on Chromosome Band 6q27 Maps Distal to the Minimal Region of Deletion in Epithelial Ovarian Cancer," *Genes Chromosomes & Cancer* 14:220-222.

Saito, S. et al. (1998). "Complete Genomic Structure DNA Polymorphisms, and Alternative Splicing of the Human *AF-6* Gene," *DNA Res.* 5:115-120.

Sanchez et al. (Dec. 22-29, 1994). "Role of SAPK/ERK Kinase-1 in the Stress-Activated Pathway Regulating Transcription Factor c-Jun," *Nature* 372(6508):794-798.

Scanlan, M.J. et al. (1998). "Characterization of Human Colon Cancer Antigens Recognized by Autologous Antibodies," *Int. J. Cancer* 76:652-658.

Schaefer, G. et al. (Jan. 8, 1999). "A Discrete Three-amino Acid Segment (LVI) at the C-terminal End of Kinase-impaired ErbB3 is Required for Transactivation of ErbB2," *J. Biol. Chem.* 274(2):859-866.

Schiaffino, M.V. et al. (1995). "Cloning of a Human Homologue of the *Xenopus laevis* APX Gene from the Ocular Albinism Type 1 Critical Region," *Hum. Mol. Genet.* 4(3):373-382.

Scott, J.K. et al. (1990). "Searching for Peptide Ligands with an Epitope Library," *Science* 249(4967):386-390.

Semenov, M.V. et al. (1997). "Human Dishevelled Genes Constitute a DHR-Containing Multigene Family," *Genomics* 42:302-310.

(56) References Cited

OTHER PUBLICATIONS

Shiratsuchi, T. et al. (1998). "Cloning and Characterization of BAI-Associated Protein 1: A PDZ Domain-Containing Protein that Interacts with BAI1," *Biochem. Biophys. Res. Commun.* 247(3):597-604.

Sirotkin, H. et al. (1997). "Identification of a New Human Catenin Gene Family Member (*ARVCF*) from the Region Deleted in Velo-Cardio-Facial Syndrome," *Genomics* 41:75-83.

Smit, J.J.M. et al. (1995). "Characterization of the Promoter Region of the Human *MDR3* P-Glycoprotein Gene," *Biochim. Biophys. Acta* 1261:44-56.

Smith (1985). "Filamentous Fusion Phage: Novel Expression Vectors that Display Cloned Antigens on the Virion Surface," *Science* 228(4705):1315-1317.

Smith et al. (1995). "Expression, Purification, and Use as an Antigen of Recombinant Sugarcase Mosaic Virus Coat Protein," *Archives of Virology* (Medline Abstract only) 140(10):1817-1831.

Smith, F.D. et al. (Jul. 9, 1999). "Association of the D2 Dopamine Receptor Third Cytoplasmic Loop with Spinophilin, a Protein Phosphatase-1-Interacting Protein," *J. Biol. Chem.* 274(28):19894-19900.

Smith, G. et al. (1993). "Libraries of Peptides and Proteins Displayed on Filamentous Phage," *Methods in Enzymology* 217:228-257.

Smith, G.P. (1991). "Surface Presentation of Protein Epitopes using Bacteriophage Expression Systems," *Current Opinion in Biotechnology* 2(5):668-673.

Smith, S.A. et al. (1996). "Isolation of a Gene (DLG3) Encoding a Second Member of the Discs-Large Family on Chromosome 17q12-q21," *Genomics* 31:145-150.

Snow, B.E. et al. (Jul. 10, 1998). "GTPase Activating Specificity of RGS12 and Binding Specificity of an Alternatively Spliced PDZ (PSD-95/Dlg/ZO-1) Domain," *J. Biol. Chem.* 273(28):17749-17755.

Soderlind et al. (Dec. 1992). "Phage Display Technology in Antibody Engineering: Design of Phagemid Vectors and in vitro Maturation Systems," *Immunological Reviews* 130:109-124.

Songyang, Z. et al. (Jan. 3, 1997). "Recognition of Unique Carboxyl-Terminal Motifs by Distinct PDZ Domains," *Science* 275:73-77.

Soumillion et al. (1994). "Phage Display of Enzymes and in vitro Selection for Catalytic Activity," *Applied Biochemistry and Biotechnology* 47:175-190.

Spencer, J. et al. (Feb. 17, 1997). "Structure of the Herpes Simplex Virus Capsid: Peptide A862-H880 of the Major Capsid Protein is Displayed on the Rim of the Capsomer Protrusions," *Virology* 228(2):229-235.

Spruijt et al. (1996). "Accessibility and Environment Probing Cysteine Residues Introduced along the Putative Transmembrane Domain of the Major Coat Protein Bacteriophage M13," *Biochemistry* 35:10383-10391.

Stathakis, D.G. et al. (1997). "Human Postsynaptic Density-95 (PSD95): Location of the Gene (*DLG4*) and Possible Function in Nonneural as Well as in Neural Tissues," *Genomics* 44:71-82.

Stathakis, D.G. et al. (1998). "Fine-Scale Physical Map of the 11q21 Region Surrounding the Human *DLG2* Locus, the Gene Encoding Chapsyn-110," *Genomics* 54:186-188.

Stricker, N.L. et al. (Apr. 1997). "PDZ Domain of Neuronal Nitric Oxide Synthase Recognizes Novel C-Terminal Peptide Sequences," *Nat. Biotechnol.* 15:336-342.

Supplementary Partial European Search Report mailed Nov. 7, 2005, for EP Application No. 02756366.7, filed Jul. 3, 2002, six pages. (48.43).

Supplementary Partial European Search Report mailed May 12, 2006, for EP Application No. 02756366.7, filed Jul. 3, 2002, seven pages. (48.00, 48.43).

Symmons et al. (1995). "Matching Electrostatic Charge Between DNA and Coat Protein in Filamentous Bacteriophage. Fibre Diffraction of Charge-Deletion Mutants," *J. Mol. Biol.* 245:86-91.

Tanahashi, H. et al. (Aug. 20, 1999). "Genomic Organizations of the Human X11L2 Gene (APBA3), a Third Member of the X11 Protein Family Interacting with Alzheimer's β-Amyloid Precursor Protein," *NeuroReport* 10(12):2575-2578.

Tanahashi, H. et al. (1999). "X11L2, a New Member of the X11 Protein Family, Interacts with Alzheimer's β-Amyloid Precursor Protein," *Biochem Biophys Res. Commun.* 255(3):663-667.

Tassabehji, M. et al. (Jul. 1996). "LIM-Kinase Deleted in Williams Syndrome," *Nat. Genet.* 13:272-273.

Tejedor, F.J. et al. (Jan. 1, 1997). "Essential Role for *dlg* in Synaptic Clustering of Shaker K$^+$ Channels in Vivo," *J. Neurosci.* 17(1):152-159.

Therrien, M. et al. (Oct. 30, 1998). "CNK, a RAF-Binding Multidomain Protein Required for RAS Signaling," *Cell* 95:343-353.

Therrien, M. et al. (Nov. 9, 1999). "Functional Analysis of CNK in RAS Signaling," *Proc. Natl. Acad. Sci. USA* 96(23):13259-13263.

Thomas, M. et al. (2001). "HPV E6 and MAGUK Protein Interactions: Determination of the Molecular Basis for Specific Protein Recognition and Degradation," *Oncogene* 20:5431-5439.

Tochio, H. et al. (May 1999). "Solution Structure of the Extended Neuronal Nitric Oxide Synthase PDZ Domain Complexed with an Associated Peptide," *Nat. Struct. Biol.* 6(5):417-421.

Tomita, S. et al. (Jan. 22, 1999). "Interaction of a Neuron-Specific Protein Containing PDZ Domains with Alzheimer's Amyloid Precursor Protein," *J. Biol. Chem.* 274(4):2243-2254.

Tsunoda, S. et al. (Jul. 17, 1997). "A Multivalent PDZ-Domain Protein Assembles Signalling Complexes in a G-Protein-Coupled Cascade," *Nature* 388:243-249.

Tsunoda, S. et al. (1998). "Specificity in Signaling Pathways: Assembly into Multimolecular Signaling Complexes," *Curr. Opin. Genet. Dev.* 8:419-422.

Ueki, N. et al. (1999). "Isolation, Tissue Expression, and Chromosomal Assignment of a Human LIM Protein Gene, Showing Homology to Rat Engima Homologue (ENH)," *J. Hum. Genet.* 44:256-260.

Ullmer, C. et al. (1998). "Cloning and Characterization of MUPP1, a Novel PDZ Domain Protein," *FEBS Lett.* 424:63-68.

Van Der Bliek, A.M. et al. (1987). "The Human *mdr3* Gene Encodes a Novel P-Glycoprotein Homologue and Gives Rise to Alternatively Spliced mRNAs in Liver," *EMBO J.* 6(1):3325-3331.

Van Der Bliek, A.M. et al. (1988). "Sequence of *mdr3* cDNA Encoding a Human P-Glycoprotein," *Gene* 71:401-411.

Vaughan et al. (1996). "Human Antibodies with Sub-Nanomolar Affinities Isolated From a Large Non-Immunized Phage Display Library," *Nature Biotecnology* 14:309-314.

Vogel, M. et al. (1988). "Production of a Recombinant Antigen of *Echinococcus multilocularis* with High Immundiagnostic Sensitivity and Specificity," *Molecular and Biochemical Parasitology* 31:117-125.

Walker, S. et al. (1994). "ToxR (RegA)-mediated in vitro Transcription of *Pseudomonas aeruginosa toxA*," *Gene* 150:87-92.

Watanabe, T.K. et al. (1998). "cDNA Cloning and Characterization of a Human Proteasomal Modulator Subunit, p27 (*PSMD9*)," *Genomics* 50:241-250.

Wells et al. (1992). Rapid Evolution of Peptide and Protein Binding Properties in vitro, *Current Opinion in Biotechnology* 3:355-362.

Williams et al. (1995). "Packing of Coat Protein Amphipathic and Transmembrane Helices in Filamentous Bacteriophage M13: Role of Small Residues in Protein Oligomerization," *J. Mol. Biol.* 252:6-14.

Williams et al. (Aug. 13, 1996). "Biophysical Characterization of Wild-Type and Mutant Bacteriophage Ike Major Coat Protein in the Virion and in Detergent Micelles," *Biochemistry* 35(32):10472-10483.

Winter et al. (1994). "Making Antibodies by Phage Display Technology," *Annual Review of Immunology* 12:433-455.

White, K.E. et al. (1998). "A PDZ Domain-Containing Protein with Homology to Diphor-1 Maps to Human Chromosome Iq21," *Ann. Hum. Genet.* 62:287-290.

Willott, E. et al. (1992). "Localization and Differential Expression of Two Isoforms of the Tight Junction Protein ZO-1," *Am. J. Physiol.* 262:C1119-C1124.

Willott, E. et al. (Aug. 1993). "The Tight Junction Protein ZO-1 is Homologous to the *Drosophila* Discs-Large Tumor Suppressor Protein of Septate Junctions," *Proc. Natl. Acad. Sci. USA* 90:7834-7838.

Wung et al. (1997). "Selection of Phage-Displayed Superantigen by Binding to Cell-Surface MHC Class II," *J. Immunol. Methods* 204:33-41.

(56) References Cited

OTHER PUBLICATIONS

Yang, Q. et al. (Jul. 1991). "Isolation of a cDNA Clone Encoding a Human Protein-Tyrosine Phosphatase with Homology to the Cytoskeletal-Associated Proteins Band 4.1, Ezrin, and Talin," *Proc. Natl. Acad. Sci. USA* 88:5949-5953.

Yun, C.H.C. et al. (Apr. 1997). "cAMP-Mediated Inhibition of the Epithelial Brush Border Na+/H+ Exchanger, NHE3, Requires an Associated Regulatory Protein," *Proc. Natl. Acad. Sci. USA* 94:3010-3015.

Zumbrunn, J. et al. (1996). "Primary Structure of a Putative Serine Protease Specific for IGF-Binding Protein," *FBES Lett.* 398:187-192.

Zumbrunn, J. et al. (1997). "Localization of the Gene for a Serine Protease with IGF-Binding Domain (PRSS11) to Human Chromosome 10q25.3-q26.2," *Genomics* 45:461-462.

U.S. Appl. No. 09/380,447, filed Jul. 22, 1999, by Sidhu et al.

* cited by examiner

Zone 1: codons 1 to 10

| | 1 | 2 | 3 | 4 | 5 | 6 | 7 | 8 | 9 | 10 | |
|---|---|---|---|---|---|---|---|---|---|---|---|
| L | RNT | NAS | RNT | NAS | NAS | NYC | RNT | RNA | RNT | RNT | (SEQ ID NO. 139) |
| i | A | D | A | D | D | A | A | A | A | A | |
| b | D | E | D | E | E | F | D | E | D | D | |
| r | G | H | G | H | H | I | G | G | G | G | |
| a | I | K | I | K | K | L | I | I | I | I | |
| r | N | N | N | N | N | P | N | K | N | N | |
| y | S | Q | S | Q | Q | S | S | R | S | S | |
|   | T | Y | T | Y | Y | T | T | T | T | T | |
|   | V |   | V |   |   | V | V | V | V | V | |

| | 1 | 2 | 3 | 4 | 5 | 6 | 7 | 8 | 9 | 10 | |
|---|---|---|---|---|---|---|---|---|---|---|---|
| wt | GCC | GAG | GGT | GAC | GAT | CCC | GCA | AAA | GCG | GCC | (SEQ ID NO. 140) |
|    | A   | E   | G   | D   | D   | P   | A   | K   | A   | A   | (SEQ ID NO. 141) |
| 1a | GAT | AAG | AGT | GAG | AAG | TTC | GCT | AGA | GAT | GCT | (SEQ ID NO. 142) |
|    | D   | K   | S   | E   | K   | F   | A   | R   | D   | A   | (SEQ ID NO. 143) |
| 1b | AAT | AAG | GAT | GAG | CAG | TTC | GCT | AGA | GCT | GCT | (SEQ ID NO. 144) |
|    | I   | K   | D   | E   | Q   | F   | A   | R   | A   | A   | (SEQ ID NO. 145) |
| 1c | ATT | TAC | ATT | AAG | GAG | ACC | AGT | AAA | AAT | GCT | (SEQ ID NO. 146) |
|    | I   | Y   | I   | K   | E   | T   | S   | K   | N   | A   | (SEQ ID NO. 147) |
| 1d | AAT | TAC | GTT | GAC | CAG | GTC | AGT | AAA | AAT | GCT | (SEQ ID NO. 148) |
|    | N   | Y   | V   | D   | Q   | V   | S   | K   | N   | A   | (SEQ ID NO. 149) |
| 1e | GCT | AAG | GCT | GAG | GAG | TTC | GCT | GAA | GCT | GCT | (SEQ ID NO. 150) |
|    | A   | K   | A   | E   | E   | F   | A   | E   | A   | A   | (SEQ ID NO.151) |
| 1f | GCT | GAC | ATT | GAC | GAC | TTC | GCT | AGA | AGT | GCT | (SEQ ID NO. 152) |
|    | A   | D   | I   | D   | D   | F   | A   | R   | S   | A   | (SEQ ID NO. 153) |

FIG. 1A

Zone 2: codons 11 to 20

|   | 11 | 12 | 13 | 14 | 15 | 16 | 17 | 18 | 19 | 20 |   |
|---|----|----|----|----|----|----|----|----|----|----|---|
| L | NWT | NAS | RNT | NYT | NAS | RNT | RNT | RNT | RNT | NAS | (SEQ ID NO. 154) |
| i | D | D | A | A | D | A | A | A | A | D | |
| b | F | E | D | F | E | D | D | D | D | E | |
| r | H | H | G | I | H | G | G | G | G | H | |
| a | I | K | I | L | K | I | I | I | I | K | |
| r | L | N | N | P | N | N | N | N | N | N | |
| y | N | Q | S | S | Q | S | S | S | S | Q | |
|   | V | Y | T | T | Y | T | T | T | T | Y | |
|   | Y |   | V | V |   | V | V | V | V |   | |

| | 11 | 12 | 13 | 14 | 15 | 16 | 17 | 18 | 19 | 20 | |
|---|---|---|---|---|---|---|---|---|---|---|---|
| wt | TTT | AAC | TCC | CTG | CAA | GCC | TCA | GCG | ACC | GAA | (SEQ ID NO. 155) |
|    | F | N | S | L | Q | A | S | A | T | E | (SEQ ID NO. 156) |
| 2a | TAT | GAG | GCT | CTT | GAG | GAT | ATT | GCT | ACT | AAC | (SEQ ID NO. 157) |
|    | Y | E | A | L | E | D | I | A | T | N | (SEQ ID NO. 158) |
| 2b | TAT | GAG | GCT | CTT | GAG | GAT | ATT | GCT | ACT | AAC | (SEQ ID NO. 159) |
|    | Y | E | A | L | E | D | I | A | T | N | (SEQ ID NO. 160) |
| 2c | TAT | GAG | GCT | CTT | GAG | GAT | ATT | GCT | ACT | AAC | (SEQ ID NO. 161) |
|    | Y | E | A | L | E | D | I | A | T | N | (SEQ ID NO. 162) |
| 2d | TAT | GAC | GTT | CTT | CAG | ATT | GCT | GCT | ATT | AAC | (SEQ ID NO. 163) |
|    | Y | D | V | L | Q | I | A | A | I | N | (SEQ ID NO. 164) |
| 2e* | CTT | AAG | GAT | CTT | AAG | GCT | ACT | GTT | ATT | CAG | (SEQ ID NO. 165) |
|     | L | K | D | L | K | A | T | V | I | Q | (SEQ ID NO. 166) |
| 2f* | TAT | GAG | ACT | ATT | AAG | GAT | GAT | ATT | GTT | AAG | (SEQ ID NO. 167) |
|     | Y | E | T | I | K | D | D | I | V | K | (SEQ ID NO. 168) |
| 2g* | CTT | CAG | AAT | ATT | CAC | AGT | AGT | ATT | AGT | AAG | (SEQ ID NO. 169) |
|     | L | Q | N | I | H | S | S | I | S | K | (SEQ ID NO. 170) |
| 2h* | TAT | AAG | ACT | GTT | CAG | GGT | GCT | ATT | GCT | AAG | (SEQ ID NO. 171) |
|     | Y | K | T | V | Q | G | A | I | A | K | (SEQ ID NO. 172) |
| 2i* | TAT | AAG | ACT | ATT | AAG | AGT | ATT | GCT | AAT | AAG | (SEQ ID NO. 173) |
|     | Y | K | T | I | K | S | I | A | N | K | (SEQ ID NO. 174) |
| 2j* | TAT | TAG | AGT | CTT | CAG | ATT | ATT | GCT | GCT | CAG | (SEQ ID NO. 175) |
|     | Y | Q | S | L | Q | I | I | A | A | Q | (SEQ ID NO. 176) |
| 2k* | TTT | CAG | AGT | CTT | AAG | GAT | ACT | GCT | GAT | GAG | (SEQ ID NO. 177) |
|     | F | Q | S | L | K | D | T | A | D | E | (SEQ ID NO. 178) |
| 2m* | TTT | GAG | AAT | CTT | TAG | GCT | ACT | ATT | ACT | AAG | (SEQ ID NO. 179) |
|     | F | E | N | L | Q | A | T | I | T | K | (SEQ ID NO. 180) |

FIG. 1B

Zone 3: codons 21 to 30

|   | 21 | 22 | 23 | 24 | 25 | 26 | 27 | 28 | 29 | 30 |   |
|---|----|----|----|----|----|----|----|----|----|----|---|
| L | *NWC* | *NWC* | *NKT* | *NWC* | *NYT* | *NKG* | *NYT* | *NKG* | *NWT* | *NWT* | (SEQ ID NO. 181) |
| i | D | D | C | D | A | G | A | G | D | D | |
| b | F | F | F | F | F | L | F | L | F | F | |
| r | H | H | G | H | I | M | I | M | H | H | |
| a | I | I | I | I | L | R | L | R | I | I | |
| r | L | L | L | L | P | V | P | V | L | L | |
| y | N | N | R | N | S | W | S | W | N | N | |
|   | V | V | S | V | T |   | T |   | V | V | |
|   | Y | Y | V | Y | V |   | V |   | Y | Y | |

|    |    |    |    |    |    |    |    |    |    |    |   |
|----|----|----|----|----|----|----|----|----|----|----|---|
| wt | *TAT* | *ATC* | *GGT* | *TAT* | *GCG* | *TGG* | *GCG* | *ATG* | *GTT* | *GTT* | (SEQ ID NO. 182) |
|    | Y | I | G | Y | A | W | A | M | V | V | (SEQ ID NO. 183) |
| 3a | *CTT* | *TTC* | *TTT* | *CTC* | *CTT* | *GGG* | *ACT* | *GTG* | *CAT* | *CTT* | (SEQ ID NO. 184) |
|    | L | F | F | L | L | G | T | V | H | L | (SEQ ID NO. 185) |
| 3b | *TAC* | *TAC* | *CTT* | *AAC* | *ATT* | *TTG* | *GCT* | *GTG* | *TAT* | *GTT* | (SEQ ID NO. 186) |
|    | Y | Y | L | N | I | L | A | V | Y | V | (SEQ ID NO. 187) |
| 3c | *TTC* | *ATC* | *CGT* | *GTC* | *ACT* | *TGG* | *ACT* | *ATG* | *TAT* | *GTT* | (SEQ ID NO. 188) |
|    | F | I | R | V | T | W | T | M | Y | V | (SEQ ID NO. 189) |
| 3d | *GTC* | *ATC* | *CGT* | *TAC* | *GTT* | *ATG* | *TCT* | *ATG* | *TAT* | *GTT* | (SEQ ID NO. 190) |
|    | V | I | R | Y | V | M | S | M | Y | V | (SEQ ID NO. 191) |

FIG. 1C

| | 1 | 2 | 3 | 4 | 5 | 6 | 7 | 8 | 9 | 10 | 11 | 12 | 13 | 14 | |
|---|---|---|---|---|---|---|---|---|---|---|---|---|---|---|---|
| Link1 | GAC D | CCC A | AGC S | AAC N | AGC S | ACC T | CAC H | CCC P | CAC H | CCC R | CAC H | AAC N | CCC R | CCC R | (SEQ ID NO. 192) |
| Link2 | ACC T | CCC A | CCC R | CAC H | CCC A | AAC N | GAC D | CCC P | CAC H | CCC R | CAC H | AAC H | CCC R | CCC R | (SEQ ID NO. 193) |
| Link3 | ACC T | CAC H | CCC R | AAC N | CCC A | AAC N | AAC N | AAC N | GAC D | CCC G | CCC A | CAC H | CCC R | CCC P | (SEQ ID NO. 194) |
| Link4 | CAC H | CCC R | CCC P | CCC G | CCC P | CCC R | CCC P | CCC G | CCC A | CCC G | CCC P | CCC A | CCC P | CCC G | (SEQ ID NO. 195) |
| Link5 | CCC A | CCC R | AAC N | GAC D | ACC T | GAC D | CCC A | CCC G | CCC G | CCC P | CCC R | CCC A | CCC R | CAC H | (SEQ ID NO. 196) |
| Link6 | ACC T | CCC R | CCC R | GAC D | ACC T | ACC T | CCC A | CAC H | CCC R | CAC H | GAC D | CCC A | CCC R | CAC H | (SEQ ID NO. 197) |
| Link7 | CCC P | CCC R | AGC S | AGC S | CCC T | AGC S | AGC S | AAC N | ACC T | AAC N | ACC T | CAC H | CAC H | CAC H | (SEQ ID NO. 198) |
| Link8 | ACC T | CCC A | CCC P | AGC S | CCC R | AGC S | AGC S | AAC N | GAC D | CCC A | GAC D | CCC A | CCC P | GAC D | (SEQ ID NO. 199) |
| Link9 | GCC G | AGC S | CCC P | AGC S | AAC N | CCC P | CCC G | CCC A | CCC R | ACC T | CCC R | CCC A | CCC G | ACC T | (SEQ ID NO. 200) |

PHAGE DISPLAY

CROSS-REFERENCE TO RELATED APPLICATIONS

This application is continuation of U.S. Patent Application No. 09/380,447, filed Sep. 1, 1999, which is a National Phase filing under 35 U.S.C.§371 of International Application No. PCT/US99/16596, filed Jul. 22, 1999, which claims priority benefit under 35 U.S.C.§119 (e) to U.S. Provisional Patent Application No. 60/094,291, filed Jul. 27, 1998; U.S. Provisional Patent Application No. 60/103,514, filed Oct. 8, 1998; U.S. Provisional Patent Application No. 60/133,296, filed May 10, 1999; and U.S. Provisional Patent Application No. 60/134,870, filed May 19, 1999, the entire content of each of which is incorporated herein by reference.

FIELD OF THE INVENTION

The invention relates to fusion proteins of a polypeptide and a coat protein of a virus, where a coat protein is not a wild type coat protein. The invention also relates to replicable expression vectors which contain a gene encoding the fusion protein, host cells containing the expression vectors, a virus which displays the fusion protein on the surface of the virus, libraries of the virus displaying a plurality of different fusion proteins on viral surfaces and methods of using these compositions.

The invention also relates to a method of transforming cells by electroporating cells to improve transformation efficiency. In various preferred embodiments, the transformation is performed in the presence of a high concentration of DNA; in the presence of a high concentration of cells; with highly purified DNA; with specific host cells; or with combinations of these. When used to prepare libraries, for example phage display libraries, these improvements allow for the construction of larger libraries in a single electroporation step than has been previously possible. The invention is also directed to a method of producing a product polypeptide by transforming host cells using the method of the invention.

DISCUSSION OF THE BACKGROUND

Bacteriophage (phage) display is a technique by which variant polypeptides are displayed as fusion proteins to the coat protein on the surface of bacteriophage particles (Scott, J. K. and Smith, G. P. (1990) *Science* 249: 386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al. (1990) *Proc. Natl. Acad. Sci. USA*, 87:6378) or protein (Lowman, H. B. et al. (1991) *Biochemistry*, 30:10832; Clackson, T. et al. (1991) *Nature*, 352: 624; Marks, J. D. et al. (1991), *J. Mol. Biol.*, 222:581; Kang, A. S. et al. (1991) *Proc. Natl. Acad. Sci. USA*, 88:8363) libraries on phage have been used for screening millions of polypeptides for ones with specific binding properties (Smith, G. P. (1991) *Current Opin. Biotechnol.*, 2:668). Sorting phage libraries of random mutants requires a strategy for constructing and propagating a large number of variants, a procedure for affinity purification using the target receptor, and a means of evaluating the results of binding enrichments. U.S. Pat. Nos. 5,223,409; 5,403,484; 5,571,689; 5,663,143.

Typically, variant polypeptides are fused to a gene III protein, which is displayed at one end of the viron. Alternatively, the variant polypeptides may be fused to the gene VIII protein, which is the major coat protein of the viron. Such polyvalent display libraries are constructed by replacing the phage gene III with a cDNA encoding the foreign sequence fused to the amino terminus of the gene III protein. This can complicate efforts to sort high affinity variants from libraries because of the avidity effect; phage can bind to the target through multiple point attachment. Moreover, because the gene III protein is required for attachment and propagation of phage in the host cell, e.g., *E. coli*, the fusion protein can dramatically reduce infectivity of the progeny phage particles.

To overcome these difficulties, monovalent phage display was developed in which a protein or peptide sequence is fused to a portion of a gene III protein and expressed at low levels in the presence of wild-type gene III protein so that particles display mostly wild-type gene III protein and one copy or none of the fusion protein (Bass, S. et al. (1990) *Proteins*, 8:309; Lowman, H. B. and Wells, J. A. (1991) *Methods: a Companion to Methods in Enzymology*, 3:205). Monovalent display has advantages over polyvalent phage display in that progeny phagemid particles retain full infectivity. Avidity effects are reduced so that sorting is on the basis of intrinsic ligand affinity, and phagemid vectors, which simplify DNA manipulations, are used. See also U.S. Pat. No. 5,750,373 and U.S. Pat. No. 5,780,279. Others have also used phagemids to display proteins, particularly antibodies. U.S. Pat. Nos. 5,667,988; 5,759,817; 5,770,356; and 5,658,727.

A two-step approach has been used to select high affinity ligands from peptide libraries displayed on M13 phage. Low affinity leads were first selected from naive, polyvalent libraries displayed on the major coat protein (protein VIII). The low affinity selectants were subsequently transferred to the gene III minor coat protein and matured to high affinity in a monovalent format. Unfortunately, extension of this methodology from peptides to proteins has been difficult. Display levels on protein VIII vary with fusion length and sequence. Increasing fusion size generally decreases display. Thus, while monovalent phage display has been used to affinity mature many different proteins, polyvalent display on protein VIII has not been applicable to most protein scaffolds.

Although most phage display methods have used filamentous phage, lambdoid phage display systems (WO 95/34683; U.S. Pat. No. 5,627,024), T4 phage display systems (Ren, Z-J. et al. (1998) *Gene* 215:439; Zhu, Z. (1997) *CAN* 33:534; Jiang, J. et al. (1997) can 128:44380; Ren, Z-J. et al. (1997) *CAN* 127:215644; Ren, Z-J. (1996) *Protein Sci.* 5:1833; Efunov, V. P. et al. (1995) *Virus Genes* 10:173) and T7 phage display systems (Smith, G. P. and Scott, J. K. (1993) *Methods in Enzymology*, 217, 228-257; U.S. Pat. No. 5,766,905) are also known.

Many other improvements and variations of the basic phage display concept have now been developed. These improvements enhance the ability of display systems to screen peptide libraries for binding to selected target molecules and to display functional proteins with the potential of screening these proteins for desired properties. Combinatorial reaction devices for phage display reactions have been developed (WO 98/14277) and phage display libraries have been used to analyze and control bimolecular interactions (WO 98/20169; WO 98/20159) and properties of constrained helical peptides (WO 98/20036). WO 97/35196 describes a method of isolating an affinity ligand in which a phage display library is contacted with one solution in which the ligand will bind to a target molecule and a second solution in which the affinity ligand will not bind to the target molecule, to selectively isolate binding ligands. WO 97/46251 describes a method of biopanning a random phage display library with an affinity purified antibody and then isolating binding phage, followed by a micropanning process using microplate wells to isolate high affinity binding phage. The use of *Staphylococcus aureus* protein A as an affinity tag has also been reported (Li et al. (1998) *Mol. Biotech.,* 9:187). WO 97/47314 describes the use of substrate subtraction libraries to distinguish enzyme specificities using a combinatorial library which may be a phage display library. A method for selecting enzymes suitable for use in detergents using phage display is described in WO 97/09446. Additional methods of selecting specific binding proteins are described in U.S. Pat. Nos. 5,498,538; 5,432,018; and WO 98/15833.

Methods of generating peptide libraries and screening these libraries are also disclosed in U.S. Pat. Nos. 5,723,286; 5,432,018; 5,580,717; 5,427,908; and 5,498,530. See also U.S. Pat. Nos. 5,770,434; 5,734,018; 5,698,426; 5,763,192; and 5,723,323.

Methods which alter the infectivity of phage are also known. WO 95/34648 and U.S. Pat. No. 5,516,637 describe a method of displaying a target protein as a fusion protein with a pilin protein of a host cell, where the pilin protein is preferably a receptor for a display phage. U.S. Pat. No. 5,712,089 describes infecting a bacteria with a phagemid expressing a ligand and then superinfecting the bacteria with helper phage containing wild type protein III but not a gene encoding protein III followed by addition of a protein III-second ligand where the second ligand binds to the first ligand displayed on the phage produced. See also WO 96/22393. A selectively infective phage system using non-infectious phage and an infectivity mediating complex is also known (U.S. Pat. No. 5,514,548).

Phage systems displaying a ligand have also been used to detect the presence of a polypeptide binding to the ligand in a sample (WO/9744491), and in an animal (U.S. Pat. No. 5,622,699). Methods of gene therapy (WO 98/05344) and drug delivery (WO 97/12048) have also been proposed using phage which selectively bind to the surface of a mammalian cell.

Further improvements have enabled the phage display system to express antibodies and antibody fragments on a bacteriophage surface, allowing for selection of specific properties, i.e., binding with specific ligands (EP 844306; U.S. Pat. Nos. 5,702,892; 5,658,727) and recombination of antibody polypeptide chains (WO 97/09436). A method to generate antibodies recognizing specific peptide-MHC complexes has also been developed (WO 97/02342). See also U.S. Pat. Nos. 5,723,287; 5,565,332; and 5,733,743.

U.S. Pat. No. 5,534,257 describes an expression system in which foreign epitopes up to about 30 residues are incorporated into a capsid protein of a MS-2 phage. This phage is able to express the chimeric protein in a suitable bacterial host to yield empty phage particles free of phage RNA and other nucleic acid contaminants. The empty phage are useful as vaccines.

The degree of expression of polypeptides as fusion proteins on the surface of bacteriophage particles is variable and depends, to some extent, on the size of the polypeptide. Conventional phage display systems use wild type phage coat proteins and fuse the heterologous polypeptide to the amino terminus of the wild type amino acid sequence or an amino terminus resulting from truncation of the wild type coat protein sequence. Segments of linker amino acids have also been added to the amino terminus of the wild type coat protein sequence to improve selection and target binding.

Notwithstanding numerous modifications and improvements in phage technology, a need continues to exist for improved methods of displaying polypeptides as fusion proteins in phage display methods.

Methods of transforming cells to introduce new DNA are of great practical interest in molecular biology and modern genetic engineering. Early methods involved chemical treatment of bacteria with solutions of metal ions, generally calcium chloride, followed by heating to produce competent bacteria capable of functioning as recipient bacteria and able to take up heterologous DNA derived from a variety of sources. These early protocols provided transformation yields of about $10^5$-$10^6$ transformed colonies per µgram of plasmid DNA. Subsequent improvements using different cations, longer treatment times and other chemical agents have allowed improvements in transformation efficiency of up to about $10^8$ colonies/µgram of DNA. Sambrook et al., *Molecular Cloning: A Laboratory Manual,* 2nd edition, (1989) Cold Spring Harbor Laboratory Press, Cold Spring Harbor, N.Y., page 1.74.

Cells can also be transformed using high-voltage electroporation. Electroporation is suitable to introduce DNA into eukaryotic cells (e.g. animal cells, plant cells, etc.) as well as bacteria, e.g., *E. coli*. Sambrook et al., ibid, pages 1.75, 16.54-16.55. Different cell types require different conditions for optimal electroporation and preliminary experiments are generally conducted to find acceptable levels of expression or transformation. For mammalian cells, voltages of 250-750 V/cm result in 20-50% cell survival. An electric pulse length of 20-100 ms at a temperature ranging from room temperature to 0° C. and below using a DNA concentration of 1-40 µgram/mL are typical parameters. Transfection efficiency is reported to be higher using linear DNA and when the cells are suspended in buffered salt solutions than when suspended in nonionic solutions. Sambrook et al., above, pages 16.54-16.55.

Dower et al., 1988, *Nucleic Acids Research,* 16:6127-6145 extensively studied high-efficiency transformation of *E. coli* by high-voltage electroporation. This study evaluated numerous parameters, including electrical variables such as the effect of field strength and pulse length, the effect of DNA concentration and cell concentration on the recovery of transformants, accuracy, reproducibility, etc. and provided a protocol for high-efficiency electrotransformation of *E. coli* cells. The optimized protocol of Dower et al. uses cells concentrated in a range of at least 2 and up to $4 \times 10^{10}$/mL, a DNA concentration of from about 1 to 10 µgrams/mL, 12.5-16.7 kV/cm, 3-25 µF and the electroporation is conducted at 0° C. (ice temperature). These studies were conducted with highly purified closed circular plasmid DNA, which is known to give high transformation efficiencies. Dower et al. report transformation efficiencies of $10^9$-$10^{10}$ transformants/µgram of DNA achieved by highly optimizing these parameters. For library formation, Dower et al. suggests using a DNA concentration of less than 10 nanogram/mL and a cell concentration of greater than $3 \times 10^{10}$ to minimize co-transformants. See also U.S. Pat. Nos. 4,910,140 and 5,186,800 to Dower et al. and U.S. Pat. No. 4,849,355 to Wong.

Several attempts have been made to improve the design of electroporation apparatus (see, for example, U.S. Pat. Nos. 5,173,158; 5,098,843; 5,422,272; 5,232,856; and 5,283,194) and to improve electroporation of specific cells (see U.S. Pat. No. 5,128,257). U.S. Pat. No. 5,124,259 describes an improved buffer for electroporation. U.S. Pat. No. 4,956,288 describes a method for producing cells containing foreign DNA in high copy numbers.

The attainment of higher transformation efficiencies by optimizing the electroporation parameters has been difficult. The use of higher voltages and longer pulses results in an increase in cell death, decreasing the total number of transformed cells. Highly optimized electroporation still results in about 50-75% cell death. Dower et al. represents an important investigation of the parameters of electroporation and the protocol described in this paper has formed the basis of more recent electroporation procedures An important emerging use of cell transformations, including electroporation, is the preparation of peptide and protein variant libraries. In these applications, a replicable transcription vector, for example a plasmid, is reacted with a restriction enzyme to open the plasmid DNA, desired coding DNA is ligated into the plasmid to form a library of vectors each encoding a different variant, and cells are transformed with the library of transformation vectors in order to prepare a library of polypeptide variants differing in amino acid sequence at one or more residues. The library of peptides can then be selectively panned for peptides which have or do not have particular properties. A common property is the ability of the variant peptides to bind to a cell surface receptor, an antibody, a ligand or other binding partner, which may be bound to a solid support. Variants may also be selected for their ability to catalyze specific reactions, to inhibit reactions, to inhibit enzymes, etc.

In one application, bacteriophage (phage), such as filamentous phage, are used to create phage display libraries by transforming host cells with phage vector DNA encoding a library of peptide variants. J. K. Scott and G. P. Smith, *Science*, (1990), 249:386-390. Phagemid vectors may also be used for phage display. Lowman and Wells, 1991, *Methods: A Companion to Methods in Enzymology*, 3:205-216. The preparation of phage and phagemid display libraries of peptides and proteins, e.g. antibodies, is now well known in the art. These methods generally require transforming cells with phage or phagemid vector DNA to propagate the libraries as phage particles having one or more copies of the variant peptides or proteins displayed on the surface of the phage particles. See, for example, Barbas et al., *Proc. Natl. Acad. Sci., USA*, (1991), 88:7978-7982; Marks et al., *J. Mol. Biol.*, (1991), 222:581-597; Hoogenboom and Winter, *J. Mol. Biol.*, (1992), 227:381-388; Barbas et al., *Proc. Natl. Acad. Sci., USA*, (1992), 89:4457-4461; Griffiths et al., *EMBO Journal*, (1994), 13:3245-3260; de Kruif et al., *J. Mol. Biol.*, (1995), 248:97-105; Bonnycastle et al., *J. Mol. Biol.*, (1996), 258: 747-762; and Vaughan et al., *Nature Biotechnology* (1996), 14:309-314. The library DNA is prepared using restriction and ligation enzymes in one of several well known mutagenesis procedures, for example, cassette mutagenesis or oligonucleotide-mediated mutagenesis.

A recurring problem with transformation by electroporation, in particular with phage or phagemid vector DNA libraries, is the low transformation efficiency which has generally been in the range of $10^7$-$10^8$ transformations/µgram of DNA. The low transformation efficiency has limited the size of libraries which can be prepared with a single electroporation step. Vaughan et al., above, describe a modified procedure in which several hundred electroporations were conducted to achieve a library with about $10^{10}$ recombinants.

Reaction mixtures obtained by enzymatic manipulation of DNA and RNA contain proteins, salts, etc., which are contaminants of the desired DNA or RNA. To obtain the purified nucleic acid, these mixtures are usually extracted with phenol/chloroform or similar solvent and then the DNA is precipitated with ethanol and resuspended in an appropriate amount of water or buffer to provide the DNA concentrations recommended by Dower et al. Bonnycastle et al., above, describe extracting a ligation reaction with chloroform/phenol/isoamyl alcohol followed by resuspension of the DNA in water and desalting by filtration over an exclusion membrane. This procedure allowed electroporation of electrocompetent MC1061 *E. coli* cells using a DNA concentration of about 20 µgrams/mL.

Despite two decades of research into electroporation and parameters affecting transformation efficiency, a need continues to exist for improved electroporation processes, in particular, for the transformation of cells with libraries of phage and phagemid DNA vectors.

SUMMARY OF THE INVENTION

Conventional phage display methods use wild type coat protein sequences, presumably to enhance stability of the phage particles and to increase the frequency of incorporation of fusion proteins into the coat of stable phage particles. It has now been discovered that stable viral particles can be prepared which incorporate fusion proteins containing a heterologous polypeptide of interest fused to a coat protein of the virus, preferably a major coat protein, where the coat protein is not a wild type coat protein of the virus, that is, where the coat protein has one or more amino acid substitutions, deletions or additions. This result is unexpected since prior phage display techniques have utilized wild type coat protein sequences and the incorporation of heterologous polypeptides as fusion proteins into phage particles is expected to have a generally deleterious effect on normal phage packaging and phage particle production.

One object of the present invention is to provide a fusion protein containing a heterologous polypeptide fused to a coat protein of a virus where the coat protein does not have the wild type coat protein sequence. A further object is to provide a replicable expression vector containing a gene fusion which encodes this fusion protein. A further object is to provide host cells containing the replicable expression vector.

Another object of the invention is to provide a library of the replicable expression vectors where the vectors contain a plurality of different gene fusions encoding a plurality of variant fusion proteins. A further object is to provide a library of virus particles which display a plurality of variant fusion proteins where the fusion proteins contain a coat protein variant which does not have the wild type coat protein sequence, and the host cells containing the vector libraries.

An additional object of the invention is to provide a method of constructing the libraries of expression vectors and virus particles.

A further object is to provide a method of modulating the number of fusion proteins which are displayed on the surface of a phage or phagemid particle through the use of the fusion protein of the invention.

Another object of the present invention is to provide an improved method of transforming cells by electroporating competent cells in the presence of heterologous DNA.

A further object of the invention is to provide an improved strain of *E. coli* cells which have improved characteristics and allow higher transformation yields with electroporation.

A further object is to provide a method of producing a product polypeptide by culturing a host cell transformed with a replicable expression vector where the host cells have been transformed using the method of the present invention, and product polypeptides produced by this process.

One embodiment of the invention is a method, which includes constructing a library containing a plurality of replicable expression vectors, each expression vector containing a transcription regulatory element operably linked to a gene fusion encoding a fusion protein, where the gene fusion contains a first gene encoding a first polypeptide and a second gene encoding a phage major coat protein, where the library contains a plurality of second genes encoding variant phage major coat proteins. The method may further include transforming suitable host cells with the library of vectors and culturing the transformed cells under conditions suitable to form the fusion proteins. Preferably, the vector is phage or phagemid DNA and the culturing is sufficient to form phage or phagemid particles which display fusion proteins on the surfaces thereof. The method may also include contacting the phage or phagemid particles with a target molecule so that at least a portion of the particles bind to the target molecule, and separating the particles that bind from those that do not bind. The method may further include selecting a bound particle, constructing a second library containing a plurality of replicable expression vectors, each expression vector containing a transcription regulatory element operably linked to a second gene fusion encoding a second fusion protein, where the second gene fusion contains a third gene encoding a second polypeptide and a fourth gene encoding the major coat protein variant of the fusion protein displayed on the surface of the selected bound particle, where the library contains a plurality of third genes encoding variant second polypeptides. The first polypeptide and the third polypeptide may be the same or different.

In another embodiment, the invention is a method including the steps:
(a) constructing a first library containing a plurality of first replicable expression vectors, each expression vector comprising a transcription regulatory element operably linked to a first gene fusion encoding a first fusion protein, wherein the first gene fusion comprises
  a first gene encoding a first polypeptide and
  a second gene encoding a phage major coat protein, and
wherein the first library contains a plurality of first vectors encoding second genes encoding variant phage major coat proteins;
(b) transforming suitable host cells with the first library of vectors and culturing the transformed cells under conditions suitable to form phage or phagemid particles;
(c) contacting the phage or phagemid particles with a target molecule so that at least a portion of the particles bind to the target molecule;
(d) separating particles that bind from those that do not bind;
(e) selecting a particle;
(f) constructing a second replicable expression vector comprising a transcription regulatory element operably linked to a second gene fusion encoding a second fusion protein, wherein the second gene fusion comprises
  a third gene encoding a second polypeptide and
  a fourth gene encoding the major coat protein variant of the fusion protein displayed on the surface of the selected bound particle;
(g) transforming suitable host cells with the second vector, culturing the transformed cells under conditions suitable to form phage or phagemid particles displaying the second fusion protein on the surface thereof; and
(h) separating particles that bind from those that do not bind.

The method may also include constructing a second library of second vectors containing a plurality of third genes encoding variant second polypeptides. The method may further include steps:
(i) selecting a particle;
(j) constructing a third expression vector comprising a transcription regulatory element operably linked to the third gene of the particle selected in step (i); and
(k) transforming suitable host cells with the third vector obtained in step (j) and culturing the transformed cells under conditions suitable for forming the second polypeptide.

These and other objects which will become apparent in the course of the following descriptions of exemplary embodiments have been achieved by the present method of transforming cells by electroporating competent cells in the presence of heterologous DNA, where the DNA is purified by affinity purification, and is preferably present at a concentration of about 1 picogram/mL to about 500 μgram/mL. The DNA is generally present at a concentration of a few to several hundred nanograms/mL or greater, preferably about 1 to about 50 μgrams/mL or greater, even more preferably about 70 μgrams/mL or greater, and may be present at a concentration of greater than 100 μgrams/mL to about 500 μgrams/mL.

In part, the present invention is also based on the discovery that prior art methods of preparing DNA for electroporation, for example the preparation of clonable recombinant DNA, using phenol extractions and ethanol precipitation, have generally resulted in DNA solutions having unacceptably high conductance. Electroporation instruments are generally configured to have a sample cell in parallel with a capacitor and a resistor (R2) to control the electric pulse duration through the sample. Ideally, the resistance of the sample (R1) should be much greater than that of R2 so that the electric pulse decays mainly through R2. In a preferred electroporation, where essentially the entire discharge occurs through R2, the time constant would approach the theoretical maximum where R1 is infinite. DNA is an ionic molecule, and thus DNA electroporation samples have an inherent conductance. Furthermore, DNA preparations containing electrically charged impurities such as proteins, salts, buffers, etc., introduce additional conductance. The volume of a DNA preparation (and thus the mass of DNA) which can be introduced into an electroporation reaction is limited by the conductance of the preparation. As the conductance of the sample increases, R1 decreases and becomes significant in comparison to R2, i.e. a significant proportion of the electric pulse is discharged through R1. This results in a decrease in the time constant and a decrease in the transformation efficiency. Further increases in sample conductance result in electric arcing across the electrodes and a failure of the electroporation. The high conductance of DNA solutions prepared using prior art methods practically limits electroporation reactions to low DNA concentrations, since higher concentrations results in electrical arcing. The invention solves this problem, in part, by providing a method of electroporating cells with affinity purified DNA and/or at DNA concentrations much greater than was thought possible. It has been discovered that the DNA in prior art DNA preparations contributes only a small proportion of the total conductance; the majority of the conductance in these preparations is due to ionic impurities. The present invention uses affinity DNA purification to reduce ionic impurities and thus reduce the conductance associated with a unit mass of DNA. Although the prior art generally suggests using purified DNA for electroporation and several standard purifications have been used, for example, DNA precipitation and membrane filtration, the use of affinity purification has not been utilized and the very high DNA concentrations which can be used in the method of the invention and the resulting high transformation yields are surprising.

The invention provides an improved method of transforming cells by highly purifying DNA, for example recombinant clonable DNA, preferably closed circular DNA, more preferably phage or phagemid vector DNA. The invention enables one to prepare DNA solutions of high concentration, preferably an aqueous solution having very low conductance, for example a non-buffer aqueous or water/glycerol solution at concentrations up to hundreds of micrograms of DNA per mL through the use of affinity purification of DNA to remove impurities which increase the conductance and shorten the time constant during electroporation. Electroporation using the higher DNA concentrations of this invention improves the transformation yield, but does not result in unacceptably higher cell death or loss of host cell viability. The method of the invention increases the amount of heterologous DNA, for example recombinant clonable DNA, which can be transformed into a cell. This increase in DNA entering the host cell provides a greater number of transformants per electroporation and allows one to prepare larger combinatorial libraries which overcomes the prior art problem of small library size using recombinant DNA.

The method of the invention also provides improved transformation yield using host cell concentrations higher than those used in the prior art to further improve transformation yield and combinatorial library size.

The invention also provides a novel *E. coli* strain containing a phage F' factor which is particularly useful for the preparation of phage and phagemid libraries of variant peptides, proteins and antibodies for use in phage display systems.

BRIEF DESCRIPTION OF THE DRAWINGS

FIGS. 1A, 1B, and 1C: Protein VIII variants selected for increased display of fusion proteins. FIG. 1A show a Zone-1 library encompassing protein VIII residues 1 through 10. FIG. 1B shows a Zone-2 library encompassing protein VIII residues 11 through 20. FIG. 1C shows a Zone-3 library encompassing protein VIII residues 21 through 30. The possible variations at each position within the library are shown followed by wild-type and selected sequences. The DNA sequence is shown above in italics with the deduced amino acid sequence below in normal text (the amber stop codon (TAG) is suppressed as glutamine in *E. coli* XL1-Blue). DNA degeneracies are represented in the IUB code (K=G/T, N=A/C/G/T, R=A/G, S=G/C, W=A/T, Y=C/T). *Selected for streptavidin (SAV) display. All others were selected for hGH display.

FIG. 4A shows results using anti-SAV polyclonal antibody as target. FIG. 4B shows results using Biotin-BSA conjugate as target. Display was measured for SAV-protein VIII (circles), SAV-protein VIII (2e) (triangles), SAV-protein VIII (2f) (diamonds), and SAV-protein VIII (2a) (squares). Phage were produced from uninduced cultures.

FIGS. 7A and 7B: Linkers selected for hGH display or SAV display. 7A) Linkers selected for display of hGH. Linkers were of the form $(Gly)_3(Xaa)_{14}(Gly)_2$, where (Xaa)14 is the selected sequence shown. 7B) Linkers selected for display of SAV.

Figure 15:
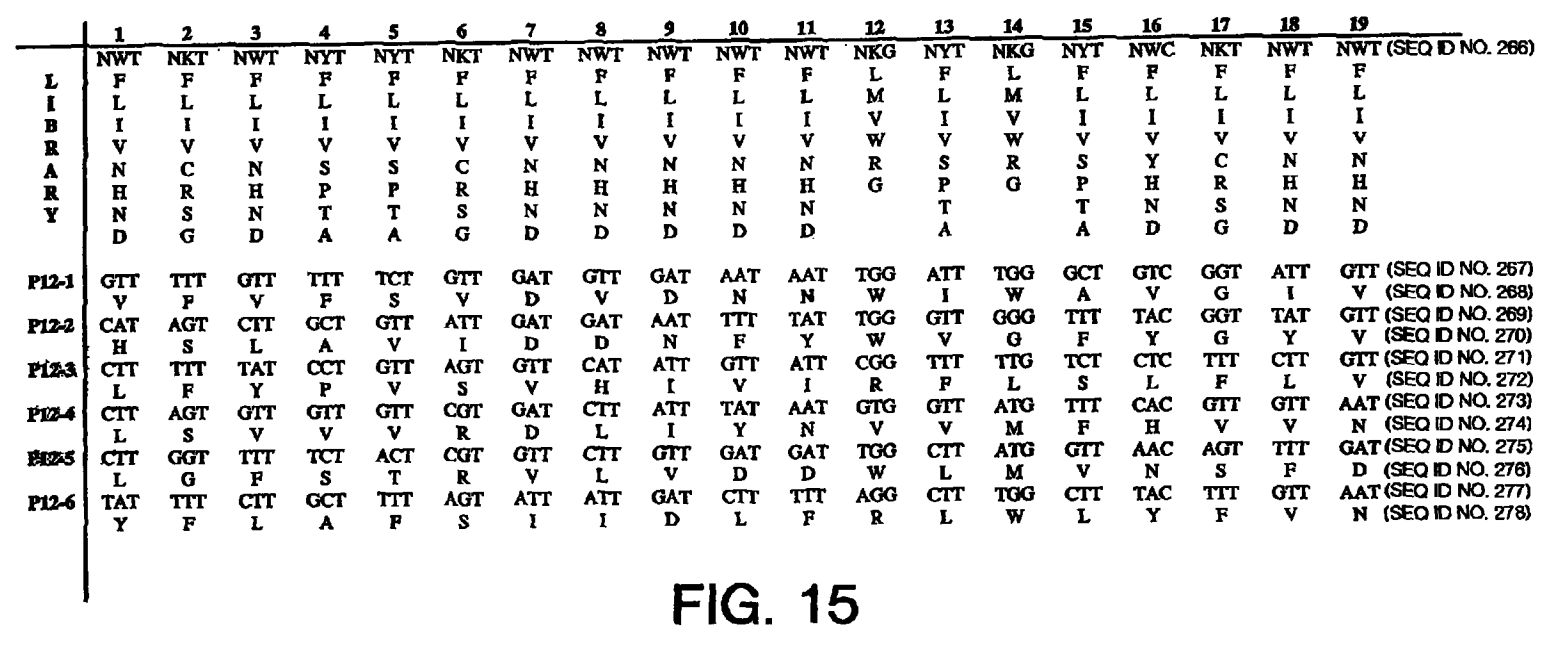

FIG. 15: P12 variants selected for the display of a polyHis flag as a C-terminal fusion.

The variable region of each P12 is shown. The complete sequence for each P12 is as follows:

(SEQ ID NO. 1)
MSKSTFKKFLK-(x)19-ETASAQLSNFAAKAPDDGEA.

Where "(x)19" is the nineteen residue sequence inserted in the library construction as shown in the figure. The possible variations at each position within the library are shown followed by the selected sequences. The DNA sequence is shown with the deduced amino acid sequence below. The numerical designation for each sequence is shown to the left. The numbering above refers to the position of each codon within the nineteen residue library insertion. See Example 24.

Figure 16:
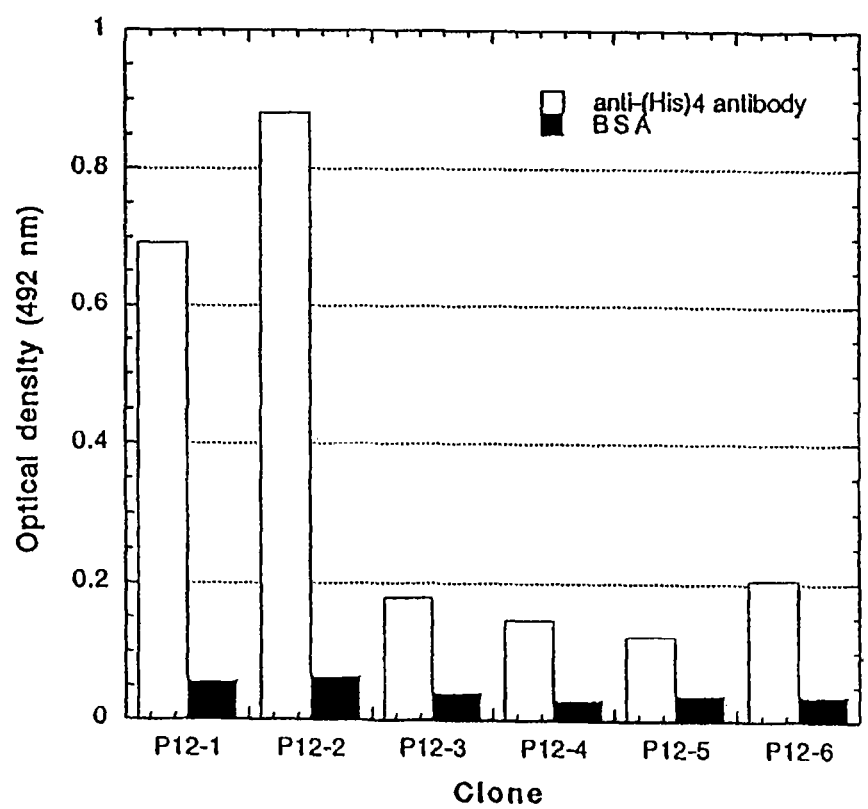

FIG. 16: Phage ELISAs for the display of a polyHis flag as a C-terminal fusion with P12 variants. An anti-(His)4 antibody was used as the capture target (unfilled bars). As a negative control, phage binding to a BSA-blocked plate was also measured (filled bars). The phage were used at a concentration of $10^{13}$ phage/mL. See Example 24.

Figure 17:
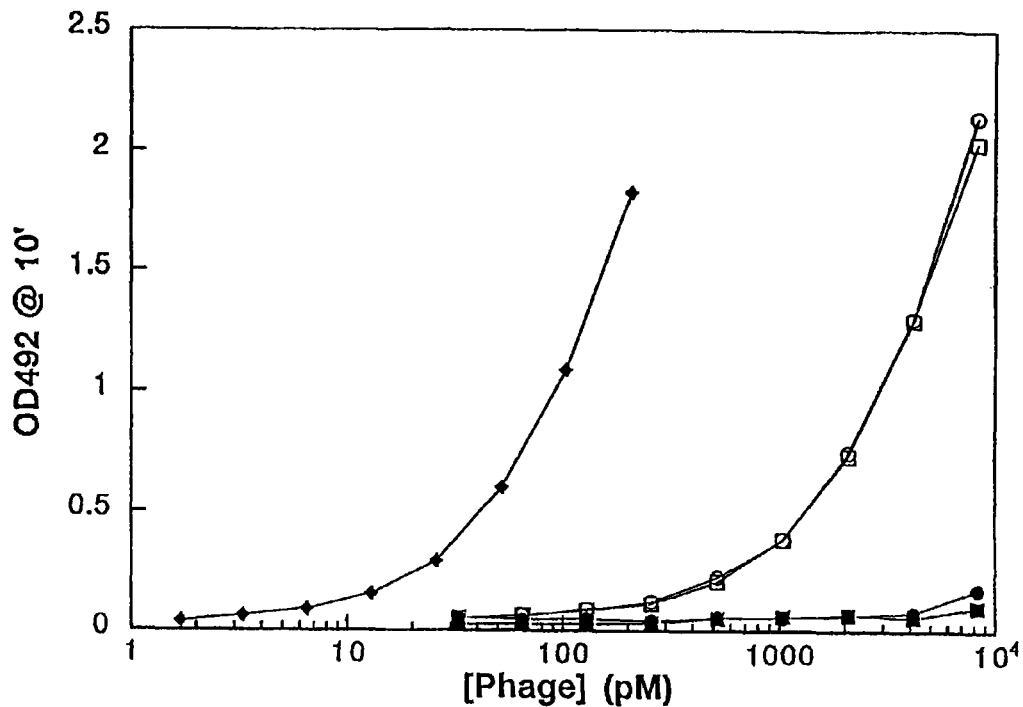

FIG. 17: Phage ELISAs for hGH or hGHsm display with P12-7. Display was measured for hGHsm fused to the C-terminus of P12-7 (phagemid pS1258, open circles), hGH fused to the C-terminus of P12-7 (phagemid pW930a, open squares), hGHsm fused to the C-terminus of P12-1 (phagemid pS1239b, filled circles), hGH fused to the C-terminus of P12-1 (phagemid pS1239a, filled squares), or hGH fused to the N-terminus of protein VIII (phagemid pS1607, filled diamonds). An anti-hGH monoclonal antibody was used as target. See Example 25.

Figure 18:
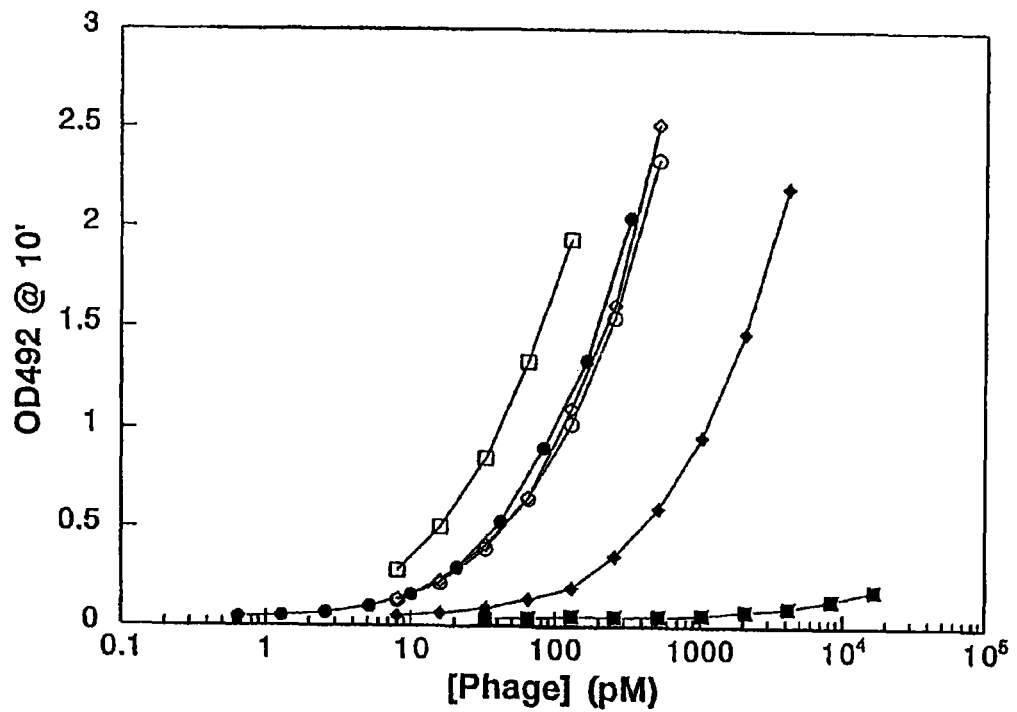

FIG. 18: Phage ELISAs for the display of a peptide fused to the C-terminus of the protein III C-terminal domain using selected linkers. A hexaHis flag was displayed with intervening linker sequences as follows: linker-g3-1 (open circles), linker-g3-2 (open squares), linker-g3-3, (open diamonds).

Display was also measured for polyHis flags displayed as either N-terminal fusions with protein VIII (filled circles) or as C-terminal fusions with protein VIII using optimized linker-1 (filled diamonds). Phage derived from a phagemid not encoding a polyHis flag were also included as a negative control (filled squares). See Example 26.

DETAILED DESCRIPTION OF THE PREFERRED EMBODIMENTS

Definitions

The term "affinity purification" means the purification of a molecule based on a specific attraction or binding of the molecule to a chemical or binding partner to form a combination or complex which allows the molecule to be separated from impurities while remaining bound or attracted to the partner moiety.

The term "antibody" is used in the broadest sense and specifically covers single monoclonal antibodies (including agonist and antagonist antibodies), antibody compositions with polyepitopic specificity, affinity matured antibodies, humanized antibodies, chimeric antibodies, as well as antibody fragments (e.g., Fab, F(ab')$_2$, scFv and Fv), so long as they exhibit the desired biological activity. An affinity matured antibody will typically have its binding affinity increased above that of the isolated or natural antibody or fragment thereof by from 2 to 500 fold. Preferred affinity matured antibodies will have nanomolar or even picomolar affinities to the receptor antigen. Affinity matured antibodies are produced by procedures known in the art. Marks, J. D. et al. *Bio/Technology* 10:779-783 (1992) describes affinity maturation by VH and VL domain shuffling. Random mutagenesis of CDR and/or framework residues is described by: Barbas, C. F. et al. *Proc Nat. Acad. Sci*, USA 91:3809-3813 (1994), Schier, R. et al. *Gene* 169:147-155 (1995), Yelton, D. E. et al. *J. Immunol.* 155:1994-2004 (1995), Jackson, J. R. et al., *J. Immunol.* 154(7):3310-9 (1995), and Hawkins, R. E. et al, *J. Mol. Biol.* 226:889-896 (1992). Humanized antibodies are known. Jones et al., *Nature,* 321:522-525 (1986); Reichmann et al., *Nature,* 332:323-329 (1988); and Presta, *Curr. Op. Struct. Biol.,* 2:593-596 (1992)).

An "Fv" fragment is the minimum antibody fragment which contains a complete antigen recognition and binding site. This region consists of a dimer of one heavy and one light chain variable domain in tight, non-covalent association. It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other, chemical couplings of antibody fragments are also known.

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in *The Pharmacology of Monoclonal Antibodies*, vol. 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA* 90:6444-6448 (1993).

The expression "linear antibodies" refers to the antibodies described in Zapata et al. *Protein Eng.* 8(10):1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

"Cell," "cell line," and "cell culture" are used interchangeably herein and such designations include all progeny of a cell or cell line. Thus, for example, terms like "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The terms "competent cells" and "electoporation competent cells" mean cells which are in a state of competence and able to take up DNAs from a variety of sources. The state may be transient or permanent. Electroporation competent cells are able to take up DNA during electroporation.

"Control sequences" when referring to expression means DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

The term "coat protein" means a protein, at least a portion of which is present on the surface of the virus particle. From a functional perspective, a coat protein is any protein which associates with a virus particle during the viral assembly process in a host cell, and remains associated with the assembled virus until it infects another host cell. The coat protein may be the major coat protein or may be a minor coat protein. A "major" coat protein is a coat protein which is present in the viral coat at 10 copies of the protein or more. A major coat protein may be present in tens, hundreds or even thousands of copies per virion.

The "detection limit" for a chemical entity in a particular assay is the minimum concentration of that entity which can be detected above the background level for that assay. For example, in the phage ELISA of Example 5, the "detection limit" for a particular phage displaying a particular protein (e.g. hGH) is the phage concentration at which the particular phage produces an ELISA signal above that produced by a control phage not displaying the protein.

The terms "electoporation" and "electoporating" mean a process in which foreign matter (protein, nucleic acid, etc.) is introduced into a cell by applying a voltage to the cell under conditions sufficient to allow uptake of the foreign matter into the cell. The foreign matter is typically DNA.

An "F factor" or "F' episome" is a DNA which, when present in a cell, allows bacteriophage to infect the cell. The episome may contain other genes, for example selection genes, marker genes, etc. Common F' episomes are found in well known *E. coli* strains including CJ236, CSH18, DH5alphaF', JM 101 (same as in JM103, JM105, JM107, JM109, JM110), KS1000, XL1-BLUE and 71-18. These strains and the episomes contained therein are commercially available (New England Biolabs) and many have been deposited in recognized depositories such as ATCC in Manassas, Va.

A "fusion protein" is a polypeptide having two portions covalently linked together, where each of the portions is a polypeptide having a different property. The property may be a biological property, such as activity in vitro or in vivo. The property may also be a simple chemical or physical property, such as binding to a target molecule, catalysis of a reaction, etc. The two portions may be linked directly by a single peptide bond or through a peptide linker containing one or more amino acid residues. Generally, the two portions and the linker will be in reading frame with each other.

"Heterologous DNA" is any DNA that is introduced into a host cell. The DNA may be derived from a variety of sources including genomic DNA, cDNA, synthetic DNA and fusions or combinations of these. The DNA may include DNA from the same cell or cell type as the host or recipient cell or DNA from a different cell type, for example, from a mammal or plant. The DNA may, optionally, include selection genes, for example, antibiotic resistance genes, temperature resistance genes, etc.

"Ligation" is the process of forming phosphodiester bonds between two nucleic acid fragments. For ligation of the two fragments, the ends of the fragments must be compatible with each other. In some cases, the ends will be directly compatible after endonuclease digestion. However, it may be necessary first to convert the staggered ends commonly produced after endonuclease digestion to blunt ends to make them compatible for ligation. For blunting the ends, the DNA is treated in a suitable buffer for at least 15 minutes at 15° C. with about 10 units of the Klenow fragment of DNA polymerase I or T4 DNA polymerase in the presence of the four deoxyribonucleotide triphosphates. The DNA is then purified by phenol-chloroform extraction and ethanol precipitation. The DNA fragments that are to be ligated together are put in solution in about equimolar amounts. The solution will also contain ATP, ligase buffer, and a ligase such as T4 DNA ligase at about 10 units per 0.5 µg of DNA. If the DNA is to be ligated into a vector, the vector is first linearized by digestion with the appropriate restriction endonuclease(s). The linearized fragment is then treated with bacterial alkaline phosphatase or calf intestinal phosphatase to prevent self-ligation during the ligation step.

A "mutation" is a deletion, insertion, or substitution of a nucleotide(s) relative to a reference nucleotide sequence, such as a wild type sequence.

A "silent mutation" is a mutation which does not change the amino acid sequence of the translated polypeptide product of a given DNA sequence.

A "non-silent mutation" is a mutation which changes the amino acide sequence of the translated polypeptide product of a given DNA sequence.

"Operably linked" when referring to nucleic acids means that the nucleic acids are placed in a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adapters or linkers are used in accord with conventional practice.

"Phage display" is a technique by which variant polypeptides are displayed as fusion proteins to a coat protein on the surface of phage, e.g. filamentous phage, particles. A utility of phage display lies in the fact that large libraries of randomized protein variants can be rapidly and efficiently sorted for those sequences that bind to a target molecule with high affinity. Display of peptides and proteins libraries on phage has been used for screening millions of polypeptides for ones with specific binding properties. Polyvalent phage display methods have been used for displaying small random peptides and small proteins through fusions to either gene III or gene VIII of filamentous phage. Wells and Lowman, *Curr. Opin. Struct. Biol.,* 1992, 3:355-362 and references cited therein. In monovalent phage display, a protein or peptide library is fused to a gene 111 or a portion thereof and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. Lowman and Wells, *Methods: A companion to Methods in Enzymology,* 1991, 3:205-216.

A "phagemid" is a plasmid vector having a bacterial origin of replication, e.g., ColE1, and a copy of an intergenic region of a bacteriophage. The phagemid may be based on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle. Sambrook et al., above, 4.17.

The term "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as an M13, f1, fd, Pf3 phage or a derivative thereof, or a lambdoid phage, such as lambda, 21, phi80, phi81, 82, 424, 434, etc., or a derivative thereof.

"Preparation" of DNA from cells means isolating the plasmid DNA from a culture of the host cells. Commonly used methods for DNA preparation are the large- and small-scale plasmid preparations described in sections 1.25-1.33 of Sambrook et al., supra. After preparation of the DNA, it can be purified by methods well known in the art such as that described in section 1.40 of Sambrook et al., supra.

"Oligonucleotides" are short-length, single- or double-stranded polydeoxynucleotides that are chemically synthesized by known methods (such as phosphotriester, phosphite, or phosphoraraidite chemistry, using solid-phase techniques such as described in EP 266,032 published 4 May 1988, or via deoxynucleoside H-phosphonate intermediates as described by Froehler et al., *Nucl. Acids Res.,* 14:5399-5407 (1986)). Further methods include the polymerase chain reaction defined below and other autoprimer methods and oligonucleotide syntheses on solid supports. All of these methods are described in Engels et al., *Agnew. Chem. Int. Ed. Engl.,* 28:716-734 (1989). These methods are used if the entire nucleic acid sequence of the gene is known, or the sequence of the nucleic acid complementary to the coding strand is available. Alternatively, if the target amino acid sequence is known, one may infer potential nucleic acid sequences using known and preferred coding residues for each amino acid residue. The oligonucleotides are then purified on polyacrylamide gels.

"Polymerase chain reaction" or "PCR" refers to a procedure or technique in which minute amounts of a specific piece of nucleic acid, RNA and/or DNA, are amplified as described in U.S. Pat. No. 4,683,195 issued 28 Jul. 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.,* 51:263 (1987); Erlich, ed., *PCR Technology,* (Stockton Press, NY, 1989). As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

DNA is "purified" when the DNA is separated from non-nucleic acid impurities. The impurities may be polar, non-polar, ionic, etc.

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al., *Nucleic Acids Res.,* 9:6103-6114 (1981), and Goeddel et al., *Nucleic Acids Res.,* 8:4057 (1980).

A chemical group or species having a "specific binding affinity for DNA" means a molecule or portion thereof which forms a non-covalent bond with DNA which is stronger than the bonds formed with other celular components including proteins, salts, and lipids.

A "survivor" is a cell which remains viable after a transformation process.

A "transcription regulatory element" will contain one or more of the following components: an enhancer element, a promoter, an operator sequence, a repressor gene, and a transcription termination sequence. These components are well known in the art. U.S. Pat. No. 5,667,780.

A "transformant" is a cell which has taken up and maintained DNA as evidenced by the expression of a phenotype associated with the DNA (e.g., antibiotic resistance conferred by a protein encoded by the DNA).

"Transformation" means a process whereby a cell takes up DNA and becomes a "transformant". The DNA uptake may be permanent or transient.

"Transformation efficiency" means the number of transformants produced per unit mass of DNA following a transformation procedure (e.g. transformants per microgram of DNA).

"Transformation frequency" means the ratio of the number of transformants to the number of survivors.

"Transformation yield" means the number of transformants produced in a single electroporation reaction.

A "variant" or "mutant" of a starting polypeptide, such as a fusion protein or a heterologous polypeptide (heterologous to a phage), is a polypeptide that 1) has an amino acid sequence different from that of the starting polypeptide and 2) was derived from the starting polypeptide through either natural or artificial (manmade) mutagenesis. Such variants include, for example, deletions from, and/or insertions into and/or substitutions of, residues within the amino acid sequence of the polypeptide of interest. Any combination of deletion, insertion, and substitution may be made to arrive at the final variant or mutant construct, provided that the final construct possesses the desired functional characteristics. The amino acid changes also may alter post-translational processes of the polypeptide, such as changing the number or position of glycosylation sites. Methods for generating amino acid sequence variants of polypeptides are described in U.S. Pat. No. 5,534,615, expressly incorporated herein by reference.

Generally, a variant coat protein will possess at least 20% or 40% sequence identity and up to 70% or 85% sequence identity, more preferably up to 95% or 99.9% sequence identity, with the wild type coat protein. Percentage sequence identity is determined, for example, by the Fitch et al., *Proc. Natl. Acad. Sci. USA* 80:1382-1386 (1983), version of the algorithm described by Needleman et al., *J. Mol. Biol.* 48:443-453 (1970), after aligning the sequences to provide for maximum homology. Amino acid sequence variants of a polypeptide are prepared by introducing appropriate nucleotide changes into DNA encoding the polypeptide, or by peptide synthesis. An "altered residue" is a deletion, insertion or substitution of an amino acid residue relative to a reference amino acid sequence, such as a wild type sequence.

A "functional" mutant or variant is one which exhibits a detectable activity or function which is also detectably exhibited by the wild type protein. For example, a "functional" mutant or variant of the major coat protein is one which is stably incorporated into the phage coat at levels which can be experimentally detected. Preferably, the phage coat incorporation can be detected in a range of about 1 fusion per 1000 virus particles up to about 1000 fusions per virus particle.

A "hyper-functional" mutant or variant is a functional mutant or variant whose activity exceeds that of the wild type. For example, a hyper-functional mutant or variant of the major coat protein is one which is stably incorporated into the phage coat at levels greater than those of the wild type protein in an identical context.

A "hypo-functional" mutant or variant is a functional mutant or variant whose activity is less than that of the wild type. For example, a hypo-functional mutant or variant of the major coat protein is one which is stably incorporated into the phage coat at levels less than those of the wild type protein in an identical context.

A "wild type" sequence or the sequence of a "wild type" protein, such as a coat protein, is the reference sequence from which variant polypeptides are derived through the introduction of mutations. In general, the "wild type" sequence for a given protein is the sequence that is most common in nature. Similarly, a "wild type" gene sequence is the sequence for that gene which is most commonly found in nature. Mutations may be introduced into a "wild type" gene (and thus the protein it encodes) either through natural processes or through man induced means. The products of such processes are "variant" or "mutant" forms of the original "wild type" protein or gene.

DETAILED DESCRIPTION OF THE PREFERRED EMBODIMENTS

A. Novel Methods and Cells

The present invention provides a method of transforming cells by electroporating competent cells in the presence of heterologous DNA, where the DNA has been purified by DNA affinity purification. Preferably, for library construction in bacteria, the DNA is present at a concentration of 25 micrograms/mL or greater. Preferably, the DNA is present at a concentration of about 30 micrograms/mL or greater, more preferably at a concentration of about 70 micrograms/mL or greater and even more preferably at a concentration of about 100 micrograms/mL or greater even up to several hundreds of micrograms/mL. Generally, the method of the invention will utilize DNA concentrations in the range of about 50 to about 500 micrograms/mL. It has been discovered that by highly purifying the heterologous DNA, a time constant during electroporation greater than 3.0 milliseconds (ms) is possible even when the DNA concentration is very high, which results in a high transformation efficiency. Over the DNA concentration range of about 50 microgram/mL to about 400 microgram/mL, the method of the invention allows the use of time constants in the range of about 3.6 to about 4.4 ms using standard electroporation instruments. The invention therefore provides a method with greater dynamic range in DNA concentration than previously known.

The high DNA concentrations used in the method of the invention are obtained by highly purifying DNA used to transform the competent cells. In the method of the invention, the DNA is purified to remove contaminants which increase the conductance of the DNA solution used in the electroporating process. The DNA may be purified by any known method, however, a preferred purification method is the use of DNA affinity purification. The purification of DNA, e.g., recombinant linear or plasmid DNA, using DNA binding, resins and affinity reagents is well known and any of the known methods can be used in this invention (Vogelstein, B. and Gillespie, D., 1979, *Proc. Natl. Acad. Sci. USA*, 76:615; Callen, W., 1993, *Strategies*, 6:52-53). Commercially available DNA isolation and purification kits are also available from several sources including Stratagene (CLEARCUT Miniprep Kit), and Life Technologies (GLASSMAX DNA Isolation Systems). Suitable nonlimiting methods of DNA purification include column chromatography (U.S. Pat. No. 5,707,812), the use of hydroxylated silical polymers (U.S. Pat. No. 5,693,785), rehydrated silica gel (U.S. Pat. No. 4,923,978), boronated silicates (U.S. Pat. No. 5,674,997), modified glass fiber membranes (U.S. Pat. Nos. 5,650,506; 5,438,127), fluorinated adsorbents (U.S. Pat. Nos. 5,625,054; 5,438,129), diatomaceous earth (U.S. Pat. No. 5,075,430), dialysis (U.S. Pat. No. 4,921,952), gel polymers (U.S. Pat. No. 5,106,966) and the use of chaotropic compounds with DNA binding reagents (U.S. Pat. No. 5,234,809). After purification, the DNA is eluted or otherwise resuspended in water, preferably distilled or deionized water, for use in electroporation at the concentrations of the invention. The use of low salt buffer solutions is also contemplated where the solution has low electrical conductivity, i.e., is compatible with the use of the high DNA concentrations of the invention with time constants greater than about 3.0 ms.

Any cells which can be transformed by electroporation may be used as host cells in the method of the present invention. Suitable host cells which can be transformed with heterologous DNA in the method of the invention include animal cells (Neumann et al., *EMKO J.*, (1982), 1:841; Wong and Neumann, *Biochem. Biophys. Res. Commun.*, (1982), 107: 584; Potter et al., *Proc. Natl. Acad. Sci., USA*, (1984) 81:7161; Sugden et al., *Mol. Cell. Biol.*, (1985), 5:410; Toneguzzo et al., Mol. Cell. Biol., (1986), 6:703; Pur-Kaspa et al., *Mol. Cell. Biol.*, (1986), 6:716), plant cells (Fromm et al., *Proc. Natl. Acad. Sci.*, USA, (1985), 82:5824; Fromm et al., *Nature*, (1986), 319:791; Ecker and Davis, *Proc. Natl. Acad. Sci., USA*, (1986) 83:5372) and bacterial cells (Chu et al., *Nucleic Acids Res.*, (1987), 15:1311; Knutson and Yee, *Anal. Biochem.*, (1987), 164:44). Prokaryotes are the preferred host cells for this invention. See also Andreason and Evans, *Biotechniques*, (1988), 6:650 which describes parameters which effect transfection efficiencies for varying cell lines. Suitable bacterial cells include *E. coli* (Dower et al., above; Taketo, *Biochim. Biophys. Acta*, (1988), 149:318), *L. casei* (Chassy and Flickinger, *FEMS Microbiol. Lett.*, (1987), 44:173), *Strept. lactis* (Powell et al., *Appl. Environ. Microbiol.*, (1988), 54:655; Harlander, *Streptococcal Genetics*, ed. J. Ferretti and R. Curtiss, III), page 229, American Society for Microbiology, Washington, D.C., (1987)), *Strept. thermophilus* (Somkuti and Steinberg, *Proc. 4th Eur. Cong. Biotechnology,* 1987, 1:412); *Campylobacter jejuni* (Miller et al., *Proc. Natl. Acad. Sci., USA*, (1988) 85:856), and other bacterial strains (Fielder and Wirth, *Anal. Biochem.*, (1988), 170:38) including bacilli such as *Bacillus subtilis*, other enterobacteriaceae such as *Salmonella typhimurium* or *Serratia marcesans*, and various *Pseudomonas* species which may all be used as hosts. Suitable *E. coli* strains include JM101, *E. coli* $K_{12}$ strain 294 (ATCC number 31,446), *E. coli* strain W3110 (ATCC number 27,325), *E. coli* X1776 (ATCC number 31,537), *E. coli* XL-1Blue (Stratagene), and *E. coli* B; however many other strains of *E. coli*, such as XL1-Blue MRF', SURE, ABLE C, ABLE K, WM1100, MC1061, HB101, CJ136, MV1190, JS4, JS5, NM522, NM538, NM539, TG1 and many other species and genera of prokaryotes may be used as well.

Cells are made competent using known procedures. Sambrook et al., above, 1.76-1.81, 16.30.

The heterologous DNA is preferably in the form of a replicable transcription or expression vector, such as a plasmid, phage or phagemid which can be constructed with relative ease and readily amplified. These vectors generally contain a promoter, a signal sequence, phenotypic selection genes, origins of replication, and other necessary components which are known to those of ordinary skill in this art. Construction of suitable vectors containing these components as well as the gene encoding one or more desired cloned polypeptides are prepared using standard recombinant DNA procedures as described in Sambrook et al., above. Isolated DNA fragments to be combined to form the vector are cleaved, tailored, and ligated together in a specific order and orientation to generate the desired vector.

The gene encoding the desired polypeptide (i.e., a peptide or a polypeptide with a rigid secondary structure) can be obtained by methods known in the art (see generally, Sambrook et al.). If the sequence of the gene is known, the DNA encoding the gene may be chemically synthesized (Merrfield, *J. Am. Chem. Soc.*, 85:2149 (1963)). If the sequence of the gene is not known, or if the gene has not previously been isolated, it may be cloned from a cDNA library (made from RNA obtained from a suitable tissue in which the desired gene is expressed) or from a suitable genomic DNA library. The gene is then isolated using an appropriate probe. For cDNA libraries, suitable probes include monoclonal or polyclonal antibodies (provided that the cDNA library is an expression library), oligonucleotides, and complementary or homologous cDNAs or fragments thereof. The probes that may be used to isolate the gene of interest from genomic DNA libraries include cDNAs or fragments thereof that encode the same or a similar gene, homologous genomic DNAs or DNA fragments, and oligonucleotides. Screening the cDNA or genomic library with the selected probe is conducted using standard procedures as described in chapters 10-12 of Sambrook et al., above.

An alternative means to isolating the gene encoding the protein of interest is to use polymerase chain reaction methodology (PCR) as described in section 14 of Sambrook et al., above. This method requires the use of oligonucleotides that will hybridize to the gene of interest; thus, at least some of the DNA sequence for this gene must be known in order to generate the oligonucleotides.

After the gene has been isolated, it may be inserted into a suitable vector (preferably a plasmid) for amplification, as described generally in Sambrook et al.

The DNA is cleaved using the appropriate restriction enzyme or enzymes in a suitable buffer. In general, about 0.2-1 µg of plasmid or DNA fragments is used with about 1-2 units of the appropriate restriction enzyme in about 20 µl of buffer solution. Appropriate buffers, DNA concentrations, and incubation times and temperatures are specified by the manufacturers of the restriction enzymes. Generally, incubation times of about one or two hours at 37° C. are adequate, although several enzymes require higher temperatures. After incubation, the enzymes and other contaminants are removed by extraction of the digestion solution with a mixture of phenol and chloroform, and the DNA is recovered from the aqueous fraction by precipitation with ethanol or other DNA purification technique.

To ligate the DNA fragments together to form a functional vector, the ends of the DNA fragments must be compatible with each other. In some cases, the ends will be directly compatible after endonuclease digestion. However, it may be necessary to first convert the sticky ends commonly produced by endonuclease digestion to blunt ends to make them compatible for ligation. To blunt the ends, the DNA is treated in a suitable buffer for at least 15 minutes at 15 C with 10 units of the Klenow fragment of DNA polymerase I (Klenow) in the presence of the four deoxynucleotide triphosphates. The DNA is then purified by phenol-chloroform extraction and ethanol precipitation or other DNA purification technique.

The cleaved DNA fragments may be size-separated and selected using DNA gel electrophoresis. The DNA may be electrophoresed through either an agarose or a polyacrylamide matrix. The selection of the matrix will depend on the size of the DNA fragments to be separated. After electrophoresis, the DNA is extracted from the matrix by electroelution, or, if low-melting agarose has been used as the matrix, by melting the agarose and extracting the DNA from it, as described in sections 6.30-6.33 of Sambrook et al., supra.

The DNA fragments that are to be ligated together (previously digested with the appropriate restriction enzymes such that the ends of each fragment to be ligated are compatible)

are put in solution in about equimolar amounts. The solution will also contain ATP, ligase buffer and a ligase such as T4 DNA ligase at about 10 units per 0.5 µg of DNA. If the DNA fragment is to be ligated into a vector, the vector is at first linearized by cutting with the appropriate restriction endonuclease(s). The linearized vector is then treated with alkaline phosphatase or calf intestinal phosphatase. The phosphatasing prevents self-ligation of the vector during the ligation step.

After ligation, the vector with the foreign gene now inserted is purified as described above and transformed into a suitable host cell such as those described above by electroporation using known and commercially available electroporation instruments and the procedures outlined by the manufacturers and described generally in Dower et al., above. The invention provides high transformation yields, a single electroporation reaction typically yields greater than $1 \times 10^{10}$ transformants. However, more than one (a plurality) electroporation may be conducted to increase the amount of DNA which is transformed into the host cells. Repeated electroporations are conducted as described in the art. See Vaughan et al., above. The number of additional electroporations may vary as desired from several (2, 3, 4, . . . 10) up to tens (10, 20, 30, . . . 100) and even hundreds (100, 200, 300, . . . 1000). Repeated electroporations may be desired to increase the size of a combinatorial library, e.g. an antibody library, transformed into the host cells. With a plurality of electroporations, it is possible to produce a library having at least $1.0 \times 10^{12}$, even $2.0 \times 10^{12}$, different members (clones, DNA vectors such as phage, phagemids, plasmids, etc., cells, etc.).

Electroporation may be carried out using methods known in the art and described, for example, in U.S. Pat. Nos. 4,910,140; 5,186,800; 4,849,355; 5,173,158; 5,098,843; 5,422,272; 5,232,856; 5,283,194; 5,128,257; 5,750,373; 4,956,288 or any other known batch or continuous electroporation process together with the improvements of the invention.

Typically, electrocompetent cells are mixed with a solution of DNA at the desired concentration at ice temperatures. An aliquot of the mixture is placed into a cuvette and placed in an electroporation instrument, e.g., GENE PULSER (Biorad) having a typical gap of 0.2 cm. Each cuvette is electroporated as described by the manufacturer. Typical settings are: voltage=2.5 kV, resistance=200 ohms, capacitance=25 mF. The cuvette is then immediately removed, SOC media (Maniatis) is added, and the sample is transferred to a 250 mL baffled flask. The contents of several cuvettes may be combined after electroporation. The culture is then shaken at 37° C. to culture the transformed cells.

The transformed cells are generally selected by growth on an antibiotic, commonly tetracycline (tet) or ampicillin (amp), to which they are rendered resistant due to the presence of tet and/or amp resistance genes in the vector.

After selection of the transformed cells, these cells are grown in culture and the vector DNA (plasmid or other vector with the foreign gene inserted) may then be isolated. Vector DNA can be isolated using methods known in the art. Two suitable methods are the small scale preparation of DNA and the large-scale preparation of DNA as described in sections 1.25-1.33 of Sambrook et al., supra. The isolated DNA can be purified by methods known in the art such as that described in section 1.40 of Sambrook et al., above and as described above. This purified DNA is then analyzed by restriction mapping and/or DNA sequencing. DNA sequencing is generally performed by either the method of Messing et al., *Nucleic Acids Res.*, 9:309 (1981) or by the method of Maxam et al., *Meth. Enzymol.*, 65:499 (1980).

This invention also contemplates fusing the gene encoding the desired polypeptide (gene 1) to a second gene (gene 2) such that a fusion protein is generated during transcription. Gene 2 is typically a coat protein gene of a filamentous phage, preferably phage M13 or a related phage, and the gene is preferably the coat protein III gene or the coat protein VIII gene, or a fragment thereof. See U.S. Pat. No. 5,750,373; WO 95/34683. Fusion of genes 1 and 2 may be accomplished by inserting gene 2 into a particular site on a plasmid that contains gene 1, or by inserting gene 1 into a particular site on a plasmid that contains gene 2 using the standard techniques described above.

Alternatively, gene 2 may be a molecular tag for identifying and/or capturing and purifying the transcribed fusion protein. For example, gene 2 may encode for Herpes simplex virus glycoprotein D (Paborsky et al., 1990, *Protein Engineering*, 3:547-553) which can be used to affinity purify the fusion protein through binding to an anti-gD antibody. Gene 2 may also code for a polyhistidine, e.g., $(his)_6$ (Sporeno et al., 1994, *J. Biol. Chem.*, 269:10991-10995; Stuber et al., 1990, *Immunol. Methods*, 4:121-152, Waeber et al., 1993, *FEBS Letters*, 324:109-112), which can be used to identify and/or purify the fusion protein through binding to a metal ion (Ni) column (QIAEXPRESS Ni-NTA protein Purification System, Quiagen, Inc.). Other affinity tags known in the art may be used and encoded by gene 2.

Insertion of a gene into a plasmid requires that the plasmid be cut at the precise location that the gene is to be inserted. Thus, there must be a restriction endonuclease site at this location (preferably a unique site such that the plasmid will only be cut at a single location during restriction endonuclease digestion). The plasmid is digested, phosphatased, and purified as described above. The gene is then inserted into this linearized plasmid by ligating the two DNAs together. Ligation can be accomplished if the ends of the plasmid are compatible with the ends of the gene to be inserted. If the restriction enzymes are used to cut the plasmid and isolate the gene to be inserted create blunt ends or compatible sticky ends, the DNAs can be ligated together directly using a ligase such as bacteriophage T4 DNA ligase and incubating the mixture at 16° C. for 1-4 hours in the presence of ATP and ligase buffer as described in section 1.68 of Sambrook et al., above. If the ends are not compatible, they must first be made blunt by using the Klenow fragment of DNA polymerase I or bacteriophage T4 DNA polymerase, both of which require the four deoxyribonucleotide triphosphates to fill-in overhanging single-stranded ends of the digested DNA. Alternatively, the ends may be blunted using a nuclease such as nuclease S1 or mung-bean nuclease, both of which function by cutting back the overhanging single strands of DNA. The DNA is then religated using a ligase as described above. In some cases, it may not be possible to blunt the ends of the gene to be inserted, as the reading frame of the coding region will be altered. To overcome this problem, oligonucleotide linkers may be used. The linkers serve as a bridge to connect the plasmid to the gene to be inserted. These linkers can be made synthetically as double stranded or single stranded DNA using standard methods. The linkers have one end that is compatible with the ends of the gene to be inserted; the linkers are first ligated to this gene using ligation methods described above. The other end of the linkers is designed to be compatible with the plasmid for ligation. In designing the linkers, care must be taken to not destroy the reading frame of the gene to be inserted or the reading frame of the gene contained on the plasmid. In some cases, it may be necessary to design the linkers such that they code for part of an amino acid, or such that they code for one or more amino acids.

Between gene 1 and gene 2, DNA encoding a termination codon may be inserted, such termination codons are UAG (amber), UAA (ocher) and UGA (opel). (*Microbiology*, Davis et al. Harper & Row, New York, 1980, pages 237, 245-47 and 274). The termination codon expressed in a wild type host cell results in the synthesis of the gene 1 protein product without the gene 2 protein attached. However, growth in a suppressor host cell results in the synthesis of detectable quantities of fused protein. Such suppressor host cells contain a tRNA modified to insert an amino acid in the termination codon position of the mRNA thereby resulting in production of detectable amounts of the fusion protein. Such suppressor host cells are well known and described, such as *E. coli* suppressor strain (Bullock et al., *BioTechniques* 5:376-379 [1987]). Any acceptable method may be used to place such a termination codon into the mRNA encoding the fusion polypeptide.

The suppressible codon may be inserted between the first gene encoding a polypeptide, and a second gene encoding at least a portion of a phage coat protein. Alternatively, the suppressible termination codon may be inserted adjacent to the fusion site by replacing the last amino acid triplet in the polypeptide or the first amino acid in the phage coat protein. When the plasmid containing the suppressible codon is grown in a suppressor host cell, it results in the detectable production of a fusion polypeptide containing the polypeptide and the coat protein. When the plasmid is grown in a non-suppressor host cell, the polypeptide is synthesized substantially without fusion to the phage coat protein due to termination at the inserted suppressible triplet encoding UAG, UAA, or UGA. In the non-suppressor cell the polypeptide is synthesized and secreted from the host cell due to the absence of the fused phage coat protein which otherwise anchored it to the host cell.

Gene 1 may encode a mammalian protein, and preferably the protein will be selected from human growth hormone (hGH), N-methionyl human growth hormone, bovine growth hormone, parathyroid hormone, thyroxine, insulin A-chain, insulin B-chain, proinsulin, relaxin A-chain, relaxin B-chain, prorelaxin, glycoprotein hormones such as follicle stimulating hormone(FSH), thyroid stimulating hormone(TSH), leutinizing hormone(LH), glycoprotein hormone receptors, calcitonin, glucagon, factor VIII, an antibody, lung surfactant, urokinase, streptokinase, human tissue-type plasminogen activator (t-PA), bombesin, coagulation cascade factors including factor VII, factor IX, and factor X, thrombin, hemopoietic growth factor, tumor necrosis factor-alpha and -beta, enkephalinase, human serum albumin, mullerian-inhibiting substance, mouse gonadotropin-associated peptide, a microbial protein, such as betalactamase, tissue factor protein, inhibin, activin, vascular endothelial growth factor (VEGF), receptors for hormones or growth factors; integrin, thrombopoietin (TPO), protein A or D, rheumatoid factors, nerve growth factors such as NGF-alpha, platelet-growth factor, transforming growth factors (TGF) such as TGF-alpha and TGF-beta, insulin-like growth factor-I and -II, insulin-like growth factor binding proteins, CD-4, DNase, latency associated peptide, erythropoietin (EPO), osteoinductive factors, interferons such as interferon-alpha, -beta, and -gamma, colony stimulating factors (CSFs) such as M-CSF, GM-CSF, and G-CSF, interleukins (ILs) such as IL-1, IL-2, IL-3, IL-4, IL-6, IL-8, IL-10, IL-12, superoxide dismutase; decay accelerating factor, viral antigen, HIV envelope proteins such as GP 120, GP 140, atrial natriuretic peptides A, B, or C, immunoglobulins, as well as variants and fragments of any of the above-listed proteins.

The first gene may encode a peptide containing as few as 4-10 amino acid residues and up to about 50-80 residues. These smaller peptides are useful in determining the antigenic properties of the peptides, in mapping the antigenic sites of proteins, etc. The first gene may also encode a polypeptide of one or more subunits containing more than about 100 amino acid residues which may be folded to form a plurality of rigid secondary structures displaying a plurality of amino acids capable of interacting with the target. Preferably the first gene will be mutated at codons corresponding to only the amino acids capable of interacting with the target so that the integrity of the rigid secondary structures will be preserved.

Phage display of proteins, peptides and mutated variants thereof, including constructing a family of variant replicable vectors containing a transcription regulatory element operably linked to a gene fusion encoding a fusion polypeptide, transforming suitable host cells, culturing the transformed cells to form phage particles which display the fusion polypeptide on the surface of the phage particle, contacting the recombinant phage particles with a target molecule so that at least a portion of the particle bind to the target, separating the particles which bind from those that do not are known and may be used with the transformation method of the invention. See U.S. Pat. No. 5,750,373; WO 97/09446; U.S. Pat. Nos. 5,514,548; 5,498,538; 5,516,637; 5,432,018; WO 96/22393; U.S. Pat. Nos. 5,658,727; 5,627,024; WO 97/29185; O'Boyle et al, 1997, *Virology*, 236:338-347; Soumillion et al, 1994, *Appl. Biochem. Biotech.*, 47:175-190; O'Neil and Hoess, 1995, *Curr. Opin. Struct. Biol.*, 5:443-449; Makowski, 1993, *Gene*, 128:5-11; Dunn, 1996, *Curr. Opin. Struct. Biol.*, 7:547-553; Choo and Klug, 1995, *Curr. Opin. Struct. Biol.*, 6:431-436; Bradbury and Cattaneo, 1995, *TINS*, 18:242-249; Cortese et al., 1995, *Curr. Opin. Struct. Biol.*, 6:73-80; Allen et al., 1995, *TIBS*, 20:509-516; Lindquist and Naderi, 1995, *FEMS Micro. Rev.*, 17:33-39; Clarkson and Wells, 1994, *Tibtech*, 12:173-184; Barbas, 1993, *Curr. Opin. Biol.*, 4:526-530; McGregor, 1996, *Mol. Biotech.*, 6:155-162; Cortese et al., 1996, *Curr. Opin. Biol.*, 7:616-621; McLafferty et al., 1993, *Gene*, 128:29-36.

In a particularly preferred embodiment, gene 1 encodes the light chain or the heavy chain of an antibody or fragments thereof, such Fab, F(ab')$_2$, Fv, diabodies, linear antibodies, etc. Gene 1 may also encode a single chain antibody (scFv). The preparation of libraries of antibodies or fragments thereof is well known in the art and any of the known methods may be used to construct a family of transformation vectors which may be transformed into host cells using the method of the invention. Libraries of antibody light and heavy chains in phage (Huse et al, 1989, *Science*, 246:1275) and as fusion proteins in phage or phagemid are well known and can be prepared according to known procedures. See Vaughan et al., Barbas et al., Marks et al., Hoogenboom et al., Griffiths et al., de ICruif et al., noted above, and WO 98/05344; WO 98/15833; WO 97/47314; WO 97/44491; WO 97/35196; WO 95/34648; U.S. Pat. Nos. 5,712,089; 5,702,892 ; 5,427,908; 5,403,484; 5,432,018; 5,270,170; WO 92/06176; U.S. Pat. No. 5,702,892. Reviews have also published. Hoogenboom, 1997, *Tibtech*, 15:62-70; Neri et al., 1995, *Cell Biophysics*, 27:47; Winter et al., 1994, *Annu. Rev. Immunol.*, 12:433-455; Soderlind et al., 1992, *Immunol. Rev.*, 130:109-124; Jefferies, 1998, *Parasitology*, 14:202-206.

Specific antibodies contemplated as being encoded by gene 1 include antibodies which bind to human leukocyte surface markers, cytokines and cytokine receptors, enzymes, etc. Specific leukocyte surface markers include CD1a-c, CD2, CD2R, CD3-CD 10, CD11a-c, CDw12, CD 13, CD14, CD15, CD15s, CD16, CD16b, CDw17, CD18-C41, CD42a-d, CD43, CD44, CD44R, CD45, CD45A, CD45B, CD450, CD46-CD48, CD49a-f, CD50-CD51, CD52, CD53-CD59, CDw60, CD61, CD62E, CD62L, CD62P, CD63, CD64, CDw65, CD66a-e, CD68-CD74, CDw75, CDw76, CD77, CDw78, CD79a-b, CD8O-CD83, CDw84, CD85-CD89, CDw90, CD91, CDw92, CD93-CD98, CD99, CD99R, CD100, CDw101, CD102-CD106, CD107a-b, CDw108, CDw109, CD115, CDw116, CD117, CD119, CD120a-b, CD121a-b, CD122, CDw124, CD126-CD129, and CD130. Other antibody binding targets include cytokines and cytokine superfamily receptors, hematopoietic growth factor superfamily receptors and preferably the extracellular domains thereof, which are a group of closely related glycoprotein cell surface receptors that share considerable homology including frequently a WSXWS domain and are generally classified as members of the cytokine receptor superfamily (see e.g. Nicola et al., *Cell*, 67:1-4 (1991) and Skoda, R. C. et al. *EMBO J.* 12:2645-2653 (1993)). Generally, these targets are receptors for interleukins (IL) or colony-stimulating factors (CSF). Members of the superfamily include, but are not limited to, receptors for: IL-2 (b and g chains) (Hatakeyama et al., *Science*, 244:551-556 (1989); Takeshita et al., *Science*, 257:379-382 (1991)), IL-3 (Itoh et al., *Science*, 247:324-328 (1990); Gorman et al., *Proc. Natl. Acad. Sci. USA*, 87:5459-5463 (1990); Kitamura et al., *Cell*, 66:1165-1174 (1991a); Kitamura et al., *Proc. Natl. Acad. Sci. USA*, 88:5082-5086 (1991b)), IL-4 (Mosley et al., *Cell*, 59:335-348 (1989), IL-5 (Takaki et al., *EMBO J.*, 9:4367-4374 (1990); Tavernier et al., *Cell*, 66:1175-1184 (1991)), IL-6 (Yamasaki et al., *Science*, 241:825-828 (1988); Hibi et al., *Cell*, 63:1149-1157 (1990)), 11-7 (Goodwin et al., *Cell*, 60:941-951 (1990)), IL-9 (Renault et al., *Proc. Natl. Acad. Sci. USA*, 89:5690-5694 (1992)), granulocyte-macrophage colony-stimulating factor (GM-CSF) (Gearing et al., *EMBO J.*, 8:3667-3676 (1991); Hayashida et al., *Proc. Natl. Acad. Sci. USA*, 244:9655-9659 (1990)), granulocyte colony-stimulating factor (G-CSF) (Fukunaga et al., *Cell*, 61:341-350 (1990a); Fukunaga et al., *Proc. Natl. Acad. Sci. USA*, 87:8702-8706 (1990b); Larsen et al., *J. Exp. Med.*, 172:1559-1570 (1990)), EPO (D'Andrea et al., *Cell*, 57:277-285 (1989); Jones et al., *Blood*, 76:31-35 (1990)), Leukemia inhibitory factor (LIF) (Gearing et al., *EMBO J.*, 10:2839-2848 (1991)), oncostatin M (OSM) (Rose et al., *Proc. Natl. Acad. Sci. USA*, 88:8641-8645 (1991)) and also receptors for prolactin (Boutin et al., *Proc. Natl. Acad. Sci. USA*, 88:7744-7748 (1988); Edery et al., *Proc. Natl. Acad. Sci. USA*, 86:2112-2116 (1989)), growth hormone (G11) (Leung et al., *Nature*, 330:537-543 (1987)), ciliary neurotrophic factor (CNTF) (Davis et al., *Science*, 253:59-63 (1991) and c-Mpl (M. Souyri et al., *Cell* 63:1137 (1990); I. Vigon et al., *Proc. Natl. Acad. Sci.* 89:5640 (1992)). Still other targets for antibodies made by the invention are erb2, erb3, erb4, IL-10, IL-12, IL-13, IL-15, etc.

Gene 1, encoding the desired polypeptide, may be altered at one or more selected codons. An alteration is defined as a substitution, deletion, or insertion of one or more codons in the gene encoding the polypeptide that results in a change in the amino acid sequence of the polypeptide as compared with the unaltered or native sequence of the same polypeptide. Preferably, the alterations will be by substitution of at least one amino acid with any other amino acid in one or more regions of the molecule. The alterations may be produced by a variety of methods known in the art. These methods include but are not limited to oligonucleotide-mediated mutagenesis and cassette mutagenesis.

Oligonucleotide-mediated mutagenesis is preferred method for preparing substitution, deletion, and insertion variants of gene 1. This technique is well known in the art as described by Zoller et al., *Nucleic Acids Res.*, 10: 6487-6504 (1987). Briefly, gene 1 is altered by hybridizing an oligonucleotide encoding the desired mutation to a DNA template, where the template is the single-stranded form of the plasmid containing the unaltered or native DNA sequence of gene 1. After hybridization, a DNA polymerase is used to synthesize an entire second complementary strand of the template will thus incorporate the oligonucleotide primer, and will code for the selected alteration in gene 1.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Nat'l. Acad. Sci. USA*, 75: 5765 (1978).

The DNA template is generated by those vectors that are either derived from bacteriophage M13 vectors (the commercially available M 13 mpl8 and M13 mp 19 vectors are suitable), or those vectors that contain a single-stranded phage origin of replication as described by Viera et al., *Meth. Enzymol.*, 153: 3 (1987). Thus, the DNA that is to be mutated can be inserted into one of these vectors in order to generate single-stranded template. Production of the single-stranded template is described in sections 4.21-4.41 of Sambrook et al., above.

To alter the native DNA sequence, the oligonucleotide is hybridized to the single stranded template under suitable hybridization conditions. A DNA polymerizing enzyme, usually T7 DNA polymerase or the Klenow fragment of DNA polymerase I, is then added to synthesize the complementary strand of the template using the oligonucleotide as a primer for synthesis. A heteroduplex molecule is thus formed such that one strand of DNA encodes the mutated form of gene 1, and the other strand (the original template) encodes the native, unaltered sequence of gene 1. This heteroduplex molecule is then transformed into a suitable host cell, usually a prokaryote such as *E. coli* JM101. After growing the cells, they are plated onto agarose plates and screened using the oligonucleotide primer radiolabelled with 32-Phosphate to identify the bacterial colonies that contain the mutated DNA.

The method described immediately above may be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-(aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

Mutants with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

Cassette mutagenesis is also a preferred method for preparing substitution, deletion, and insertion variants of gene 1. The method is based on that described by Wells et al., *Gene*, 34:315 (1985). The starting material is the plasmid (or other vector) comprising gene 1, the gene to be mutated. The codon(s) in gene 1 to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in gene 1. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated DNA sequence of gene 1.

In a preferred embodiment, gene 1 is linked to gene 2 encoding at least a portion of a phage coat protein. Preferred coat protein genes are the genes encoding coat protein 3 and coat protein 8 of filamentous phage specific for *E. coli*, such as M13, f1 and fd phage. Transfection of host cells containing a replicable expression vector which encodes the gene fusion of gene 1 and gene 2 and production of phage particles according to standard procedures provides phage particles in which the polypeptide encoded by gene 1 is displayed on the surface of the phage particle.

Although published protocols suggest using a final cell concentration of about $10^{10}$ colony forming units (cfu)/mL, the present invention allows one to obtain cell concentrations of $5 \times 10^{10}$ cfu/mL of viable living cells and greater for use in electroporation. Preferably, the viable cells are concentrated to about $1 \times 10^{11}$ to about $4 \times 10^{11}$ cfu/mL in the method of the invention. Preferred cells which may be concentrated to this range are the SS320 cells described below. Although Dower et al. indicate that the yield of transformants should increase with the number of cells present during electroporation, it is believed that cell concentrations above about $5 \times 10^{10}$ cells/mL have not been used in practice. It has now been discovered that some cells, in particular, *E. coli* strains, can be concentrated to concentrations far greater than has been previously suggested. A crucial factor in determining the maximum final concentration of a given strain is the resistance of the strain to the standard washing steps used in the preparation of electrocompetent cells. It has been discovered that the proportion of cells surviving the washing procedure varies. As a part of this invention, it has been discovered that prior methods of preparing cells for electroporation often result in higher numbers of non-viable cells and lower transformation yields. In this embodiment, cells are grown in culture in standard culture broth, optionally for about 6-48 hrs (or to $OD_{600}$=0.6-0.8) at about 37° C., and then the broth is centrifuged and the supernatant removed (e.g. decanted). Initial purification is preferably by resuspending the cell pellet in a buffer solution (e.g. HEPES pH 7.4) followed by recentrifugation and removal of supernatant. The resulting cell pellet is resuspended in dilute glycerol (e.g. 5-20% v/v) and again recentrifuged to form a cell pellet and the supernatant removed. The final cell concentration is obtained by resuspending the cell pellet in water or dilute glycerol to the desired concentration. As noted above, it has been discovered that these washing steps have an effect on cell survival, that is on the number of viable cells in the concentrated cell solution used for electroporation. It is preferred to use cells which survive the washing and centrifugation steps in a high survival ratio relative to the number of starting cells prior to washing. Most preferably, the ratio of the number of viable cells after washing to the number of viable cells prior to washing is 1.0, i.e., there is no cell death. However, the survival ratio may be about 0.8 or greater, preferably about 0.9-1.0.

A particularly preferred recipient cell is the electroporation competent *E. coli* strain of the present invention, which is *E. coli* strain MC1061 containing a phage F' episome. Any F' episome which enables phage replication in the strain may be used in the invention. Suitable episomes are available from strains deposited with ATCC or are commercially available (CJ236, CSH18, DH5alphaF', JM101, JM103, TM105, JM107, JM109, JM110), KS1000, XL1-BLUE, 71-18 and others). Strain SS320 was prepared by mating MC1061 cells with XL1-BLUE cells under conditions sufficient to transfer the fertility episome (F' plasmid) of XL1-BLUE into the MC1061 cells. In general, mixing cultures of the two cell types and growing the mixture in culture medium for about one hour at 37° C. is sufficient to allow mating and episome transfer to occur. The new resulting *E. coli* strain has the genotype of MC1061 which carries a streptomycin resistance chromosomal marker and the genotype of the F' plasmid which confers tetracycline resistance. The progeny of this mating is resistant to both antibiotics and can be selectively grown in the presence of streptomycin and tetracycline. Strain SS320 has been deposited with the American Type Culture Collection (ATCC), 10801 University Boulevard, Manassas, Va., USA on Jun. 18, 1998 and assigned Deposit Accession No. 98795.

This deposit of strain SS320 was made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The organisms will be made available by ATCC under the terms of the Budapest Treaty, and subject to an agreement between Genentech, Inc. and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 8860G 638).

The assignee of the present application has agreed that if the cultures on deposit should die or be lost or destroyed when cultivated under suitable conditions, they will be promptly replaced on notification with a viable specimen of the same culture. Availability of the deposited cultures is not to be construed as a license to practice the invention in contravention of the rights granted under the authority of any government in accordance with its patent laws.

SS320 cells have properties which are particularly favorable for electroporation. It has been discovered that SS320 cells are particularly robust and are able to survive multiple washing steps with higher cell viability than most other electroporation competent cells. The ability of SS320 cells to survive washing steps allows one to prepare cell concentrations which are greater than the cell concentrations suggested by the Dower et al. protocol. Other strains suitable for use with the higher cell concentrations include TB1, MC1061, etc. These higher cell concentrations provide greater transformation efficiency for the process of the invention.

The use of higher DNA concentrations during electroporation (about 10×) increases the transformation efficiency and increases the amount of DNA transformed into the host cells. The use of higher cell concentrations also increases the efficiency (about 10×). The larger amount of transferred DNA produces larger libraries having greater diversity and representing a greater number of unique members of a combinatorial library. The method of the invention is useful to increase the size of an expressible combinatorial library by a factor of about 100× with a single electroporation event which allows one to select, amplify and identify rare library members present in amounts 100× lower than with comparable conventional methods.

Dower et al. have demonstrated that saturation (transformation of most survivors of an electroporation) can be achieved with closed circular DNA concentrations of about 10 microgram/mL. However, the construction of libraries, for example a library of fusion genes encoding fusion polypeptides, necessarily involves the introduction of DNA fragments representing the library into a suitable vector to provide a family or library of vectors. In the case of cassette mutagenesis, the synthetic DNA is a double stranded cassette while in fill-in mutagenesis the synthetic DNA is single stranded DNA. In either case, the synthetic DNA is incorporated into a vector to yield a reaction product containing closed circular double stranded DNA which can be transformed into a cell to produce the library. However, processes used to incorporate synthetic DNA into closed circular DNA are generally less than 100% efficient, and often the desired closed circular product represents only a small fraction of the total DNA. To achieve saturation with a ligation or fill-in reaction product may require significantly higher DNA concentrations than those necessary when using pure closed circular DNA. Prior methods do not allow or suggest using DNA concentrations which are sufficient to achieve saturation in the electroporation reactions using DNA incorporating synthetic DNA fragments into transformation vectors, e.g. plasmids, phage vectors, phagemid vectors, etc.

For example, the reaction of Example 6 below, demonstrates that using the method of the invention, a DNA concentration of 19 microgram/mL results in transformation of 53% of surviving cells. In this example, the fill-in reaction was very efficient yielding about 95% of the desired closed circular DNA product as evidenced by agarose gel electrophoresis. The DNA concentration can be increased to hundreds (e.g., 300-500 microgram/mL) of micrograms/mL without adversely affecting either the cell survival or the transformation. The maximum number of transformants is obtained at a DNA concentration 20-fold lower than the maximum DNA concentration tested and even the largest DNA concentration tested had no detrimental effect on the electroporation reaction. The invention provides a useable dynamic range of DNA concentration in electroporation which far exceeds that possible with prior methods. Using the method of the invention, inefficient transformation vector formation reactions which yield only small amounts of the desired clonable DNA, for example only 10-50%, or even 1-10%, can be made to saturate the electroporation survivors by using DNA concentrations up to about 400-500 micrograms/mL.

The method of the invention also allows the facile introduction of two or more vectors into a single cell, even with a DNA reaction preparation in which the desired vector (e.g. closed circular DNA) represents only a fraction of the total DNA in the preparation. This makes possible the simultaneous introduction of multiple foreign genes in separate vectors, for example, two or more libraries into a single transformant. The introduction multiple members of a library into a single cell expands the library diversity beyond the number of transformants. For example, if on average a transformant in an electroporation reaction maintains two plasmids, the library diversity will be twice the number of transformants.

The saturation concentration for a given DNA preparation can be defined as the concentration beyond which further increases in DNA concentration do not result in increased transformation yields.

At the saturation concentration, all cells capable of taking up and maintaining DNA have been transformed. Dower et al., above, have shown that transformation efficiency is directly proportional to DNA concentration. An increase in DNA concentration should result in corresponding increases in the average number of unique plasmids per survivor. For example, if at a given DNA concentration, electroporation results in survivors carrying one unique plasmid each on average, then doubling the DNA concentration will result in the survivors carrying two unique plasmids each on average.

The current invention allows for the use of DNA concentrations in electroporation at least an order of magnitude above that possible with prior art methods. This in turn allows for the simultaneous introduction of two or more unique plasmids (containing different library members) into a single cell during a single electroporation reaction, even with DNA preparations which have been enzymatically manipulated.

Several members of a single library can be introduced into a single cell and thus the library diversity can be expanded beyond the number of transformants. For example, if on average a transformant produced in a given electroporation reaction maintains two plasmids, the library diversity will be twice the number of transformants. In the case of phage display libraries, packaging of phage DNA or phagemids maintained within the same transformant will result in a random display of the different fusion proteins produced from the different phage DNA or phagemids. Thus, some of the fusion proteins will be displayed in association with their cognate DNA sequences while others will be associated with completely unrelated sequences which happened to co-transform by random chance.

In the case of highly polyvalent display (e.g., peptide display on protein-8) where the number of incorporated fusion proteins per phage particle greatly exceeds the number of co-transformed phage DNA or phagemids, each phage particle will display its cognate fusion protein along with other unrelated fusion proteins. This will result in an increase in background during the first round of sorting due to the capture of fusion proteins associated with phage containing unrelated DNA. If the phage captured in the first round are amplified by infection into *E. coli* at a low multiplicity of infection so that each *E. coli* cell is infected by only one phage, the correlation between displayed fusion protein and its DNA sequence will be restored. The second round of sorting will then eliminate DNA sequences which do not encode proteins with affinity for the target.

In the case of monovalent display (e.g., protein display on protein-3) where the ratio of fusion protein to phage is less than one, each displayed fusion protein may associate either with its cognate DNA sequence or with an unrelated co-transformed DNA sequence. Provided that the number of phage used in the first sort is large enough to ensure that at least some DNA sequences are linked with the fusion proteins they encode, phage displaying fusion proteins with affinity for a given target (and containing the cognate DNA sequence) will be selectable. As in the case of polyvalent display, incorrect linkage between fusion protein and phage DNA will result in the first round capture of incorrect DNA sequences, but these sequences can be eliminated in the second round as described above.

The use of DNA concentrations far above the saturation concentration also allows for the co-transformation of a cell with plasmids from different libraries in a single electroporation. Thus the current invention can be used to facilitate and simplify any methodology which requires that a single cell maintain two or more plasmids from distinct libraries, since two or more libraries can be introduced simultaneously rather than serially.

For example, Griffiths et al. (*EMBO Journal* 13(14):3245-3260, 1994) used the process of combinatorial infection and in vivo recombination to increase the size of a phage antibody repertoire. The process involved the separate electroporation of light chain and heavy chain repertoires to produce two distinct libraries; a third step combined the two libraries to yield the desired antibody library. The DNA concentrations achievable with the current invention enables the co-transformation of the two libraries in a single electroporation.

The transformed cells are generally selected by growth on an antibiotic, commonly tetracycline (tet) or ampicillin (amp), to which they are rendered resistant due to the presence of tet and/or amp resistance genes in the vector.

Suitable phage and phagemid vectors for use in this invention include all known vectors for phage display. Additional examples include pComb8 (Gram, H., Marconi, L. A., Barbas, C. F., Collet, T. A., Lerner, R. A., and Kang, A. S. (1992) *Proc. Natl. Acad. Sci. USA* 89:3576-3580); pC89 (Felici, F., Catagnoli, L., Musacchio, A., Jappelli, R., and Cesareni, G. (1991) *J. Mol. Biol.* 222:310-310); pIF4 (Bianchi, E., Folgori, A., Wallace, A., Nicotra, M., Acali, S., Phalipon, A., Barbato, G., Bazzo, R., Cortese, R., Felici, F., and Pessi, A. (1995) *J. Mol. Biol.* 247:154-160); PM48, PM52, and PM54 (Iannolo, G., Minenkova, 0., Petruzzelli, R., and Cesareni, G. (1995) *J. Mol. Biol.*, 248:835-844); fdH (Greenwood, J., Willis, A. E., and Perham, R. N. (1991) *J. Mol. Biol.*, 220:821-827); pfd8SHU, pfd8SU, pfdSSY, and fdISPLAY8 (Malik, P. and Perham, R. N. (1996) *Gene*, 171:49-51); "88" (Smith, G. P. (1993) *Gene*, 128:1-2); f88.4 (Zhong, G., Smith, G. P., Berry, J. and Brunham, R. C. (1994) *J. Biol. Chem.*, 269:24183-24188); p8V5 (Affymax); MB1, MB20, MB26, MB27, MB28, MB42, MB48, MB49, MB56: Markland, W., Roberts, B. L., Saxena, M. J., Guterman, S. K., and Ladner, R. C. (1991) *Gene*, 109:13-19). Similarly, any known helper phage may be used when a phagemid vector is employed in the phage display system. Examples of suitable helper phage include M13-KO7 (Pharmacia), M13-VCS (Stratagene), and R408 (Stratagene).

After selection of the transformed cells, these cells are grown in culture and the vector DNA may then be isolated. Phage or phagemid vector DNA can be isolated using methods known in the art, for example, as described in Sambrook et al., *Molecular Cloning: A Laboratory Manual*, 2nd edition, (1989) Cold Spring Harbor Laboratory Press, Cold Spring Harbor, N.Y. The isolated DNA can be purified by methods known in the art such as that described in section 1.40 of Sambrook et al., above and as described above. This purified DNA can then be analyzed by DNA sequencing. DNA sequencing may be performed by the method of Messing et al., *Nucleic Acids Res.*, 9:309 (1981), the method of Maxam et al., *Meth. Enzymol.*, 65:499 (1980), or by any other known method.

The invention also contemplates producing product polypeptides which have been obtained by culturing a host cell transformed with a replicable expression vector, where the replicable expression vector contains DNA encoding a product polypeptide operably linked to a control sequence capable of effecting expression of the product polypeptide in the host cell; where the DNA encoding the product polypeptide has been obtained by:

(a) constructing a family of variant replicable plasmids containing a transcription regulatory element operably linked to a gene fusion encoding a fusion protein, wherein the gene fusion contains a first gene encoding a polypeptide and a second gene encoding at least a portion of a phage coat protein, where the variant replicable plasmids contain variant first genes encoding variant polypeptides;

(b) transforming suitable host cells with the plasmids using the method of the invention;

(c) optionally, when the plasmid is a phagemid which requires a helper phage to produce phage particles, infecting the transformed host cells with an amount of helper phage encoding the phage coat protein sufficient to produce recombinant phagemid particles which display the fusion protein on the surface of the particles, preferably where no more than a minor amount of the phagemid particles display one or more copies of the fusion protein on the surface of the phagemid particles;

(d) culturing the transformed infected host cells under conditions suitable for forming recombinant phage particles containing at least a portion of the plasmid and capable of transforming the host cells;

(e) contacting the recombinant phage particles with a target molecule so that at least a portion of the phage particles bind to the target molecule;

(f) separating phage particles that bind to the target molecule from those that do not bind;

(g) selecting one of the variant polypeptides encoded in a phage particle which binds or does not bind to the target molecule as the product polypeptide and cloning DNA encoding the product polypeptide into the replicable expression vector; and recovering the expressed product polypeptide; and product polypeptides produced by the process.

U.S. Pat. No. 5,750,373 describes generally how to produce and recover a product polypeptide by culturing a host cell transformed with a replicable expression vector (e.g., a phagemid) where the DNA encoding the polypeptide has been obtained by steps (a)-(f) above using conventional helper phage where a minor amount (<20%, preferably <10%, more preferably <1%) of the phage particles display the fusion protein on the surface of the particle. Any suitable helper phage may be used to produce recombinant phagemid particles, e.g., VCS, etc. The present invention provides an improved method by transforming the host cells by electroporation using the high DNA concentrations and other embodiments of the invention. One of the variant polypeptides obtained by the phage display process may be selected for larger scale production by recombinant expression in a host cell. Culturing of a host cell transformed with a replicable expression vector which contains DNA encoding a product polypeptide which is the selected variant operably linked to a control sequence capable of effecting expression of the product polypeptide in the host cell and then recovering the product polypeptide using known methods is part of this invention.

B. Novel Coat Proteins, Coat Fusion Proteins, Vectors, Cells and Methods

The expression of polypeptides on the surface of bacteriophage has been developed and refined over several years. In particular, systems have been developed for displaying recombinant peptides, proteins, antigens and antibodies on the surface of filamentous bacteriophage. A number of filamentous phage have been identified which are able to infect gram negative bacteria, such as *E. coli*. These phage have a single stranded covalently closed DNA genome containing only about 10 genes encased in a cylinder of coat proteins. Due to the relative simplicity of these viruses and the ease with which they can be genetically manipulated, filamentous phage have been well studied. All strains of filamentous phage have a similar virion structure and life cycle. Upon infection, viral DNA enters the cell and is converted to a double stranded replicative form by host enzymes. Progeny DNA is replicated by a rolling circle mechanism and is assembled with a viral replication assembly protein into an elongated DNA/protein complex. The virion is extruded through the membrane of the host cell where the replication assembly protein is replaced by coat proteins. The virion sheath contains several thousand identical a-helical proteins as the major coat protein.

Foreign DNA can be inserted as a separate gene in a viral intergenic region. When the heterologous DNA is inserted as a separate gene, the virus or a virus-derived plasmid (phagemid) becomes a cloning vector. When the heterologous DNA is inserted as a gene fusion with a coat protein of the virus, the virus or phagemid is capable of displaying the polypeptide encoded by the heterologous DNA as a fusion protein on the surface of the virion. Fusion proteins containing variants of the major coat protein of any bacteriophage which is suitable for use in a known phage display system are within the scope of the present invention. Class I and class II filamentous phage are included within the scope of the invention. Class I includes strains Ff, IKe and If1; class II includes strains Pf1, Pf3 and Xf. The Ff phage include the virtually identical strains fd, f1 and M13.

The structure and function of the major coat protein of filamentous bacteriophage have been studied in order to understand the interactions between phage DNA and the coat proteins, as well as to understand the forces which effect packing of the coat proteins into bacteriophage particles. Point mutations in the major coat proteins of filamentous bacteriophage have been prepared to assist in these studies. Hunter, E. J. et al., (1987) *Nature*, 327:252; Greenwood, J. et al., (1991) *J. Mol. Biol.* 217: 223; Deber, C. M. et al., (1993) *Proc. Natl. Acad. ScL USA,* 90:11648; Symmons, M. S. et al., (1995) *J. Mol. Biol.* 245:86; Williams, K. A. et al., (1995) *J. Mol. Biol.* 252:6; Spruijt, R. B. et al., (1996) *Biochemistry* 35:10383; Marvin, D. A. (1998) *Current Opinion in Structural Biology* 8:150; Haigh, N. G. and Webster, R. E., (1998) *J. Mol. Biol.,* 279:19. These studies suggest that some point mutations are tolerated by phage and result in packaging of phage particles containing the mutant major coat proteins. None of these studies involve fusion proteins of heterologeous polypeptides to variant phage coat proteins, however. Furthermore, it is known that the inclusion of fusion proteins in a phage coat may hinder phage packaging giving rise to poor phage yields and/or may prevent display of the fusion protein on the surface of the phage even when a wild type coat protein sequence is used (Smith, G. P. (1985), *Science,* 228: 1315). Whereas small peptides (10-15 amino acid residues) can generally be displayed in up to about 800-1000 copies per virion, full length proteins are displayed in many fewer numbers (1-10 copies per virion). Malik, P. et al. (1996) *J. Mol. Biol.* 260:9.

The sequences of several known mature major coat proteins of filamentous bacteriophage aligned with the mature M 13 coat protein VIII (SEQ ID NO: 2) are shown in the Table below. Segments of the coat proteins were aligned with M13 protein VIII so as to provide maximum identity with the M 13 protein without the introduction of any deletions or insertions. Numbering above the sequences refers to the residues of mature M 13 protein VIII. Protein sequences are taken from the Dayhoff protein database (accession numbers:M13, COAB_BPFD (SEQ ID NO: 2); F1, COAB_BPFD (SEQ ID NO: 3); Fd, COAB_BPFD (SEQ ID NO: 4); Zj-2, COAB BPZJ2 (SEQ ID
NO: 5); If-1,COAT BPIF1 (SEQ ID NO: 6);12-2, COAB BPI22 (SEQ ID NO: 7); Ike, COAB BPIKE (SEQ ID NO: 8)). Homologous residues are indicated with dashes. A sequence having a single deletion is also known (WO 92/18619 ). It can be seen that there is considerable homology among the sequences of these coat proteins, particularly among the M 13, f1, fd and Zj-2 coat proteins and among the If1 , 122 and Ike coat proteins.

TABLE

|  | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|---|
| M13 | A | E | G | D | D | P | A | K | A | A | F | N | S | L | Q | A | S | A | T | E | Y | I | G | Y | A |
| F1 | — | — | — | — | — | — | — | — | — | — | — | D | — | — | — | — | — | — | — | — | — | — | — | — | — |
| Fd | — | — | — | — | — | — | — | — | — | — | — | D | — | — | — | — | — | — | — | — | — | — | — | — | — |
| Zj-2 | — | — | — | — | — | — | — | — | — | — | — | D | — | — | — | — | — | — | — | — | — | — | — | — | — |
| If1 | D | D | A | T | S | Q | — | — | — | — | — | D | — | — | T | — | Q | — | — | — | M | S | — | — | — |

TABLE-continued

| | | | | | | | | | | | | | | | | | | | | | | | | | |
|---|---|---|---|---|---|---|---|---|---|---|---|---|---|---|---|---|---|---|---|---|---|---|---|---|---|
| I2-2 | S | T | A | T | S | Y | – | T | E | – | M | – | – | – | K | T | Q | – | – | D | L | – | D | Q | T |
| Ike | N | A | A | T | N | Y | – | T | E | – | M | D | – | – | K | T | Q | – | I | D | L | – | S | Q | T |

| | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 |
|---|---|---|---|---|---|---|---|---|---|---|---|---|---|---|---|---|---|---|---|---|---|---|---|---|---|
| M13 | W | A | M | V | V | V | I | V | G | A | T | I | G | I | K | L | F | K | K | F | T | S | K | A | S |
| F1 | – | – | – | – | – | – | – | – | – | – | – | – | – | – | – | – | – | – | – | – | – | – | – | – | – |
| Fd | – | – | – | – | – | – | – | – | – | – | – | – | – | – | – | – | – | – | – | – | – | – | – | – | – |
| Zj-2 | – | – | – | – | – | – | – | – | – | – | – | – | – | – | – | – | – | – | – | – | A | – | – | – | – |
| If1 | – | – | L | – | – | L | V | – | – | – | – | V | – | – | – | – | – | – | – | – | V | – | R | – | – |
| I2-2 | – | P | V | – | T | S | V | A | V | – | G | L | A | – | R | – | – | – | – | – | S | – | – | – | V |
| Ike | – | P | V | – | T | T | V | – | V | – | G | L | V | – | R | – | – | – | – | – | S | – | – | – | V |

(SEQ ID NOS. 2-8)

Filamentous phage particle are formed when the phage genes are transcribed, translated and replicated in a host cell. Phage coat proteins are directed to the periplasm and temporarily lodge in the cell membrane with a portion of the coat protein in the periplasm (the periplasmic domain), a portion of the coat protein in the cytoplasm (the cytoplasmic domain), and a portion of the coat protein spanning the cell membrane (the transmembrane domain). Phage particles are formed when the coat proteins assemble around the phage DNA as the phage particle passes through the cell membrane. The M13 major coat protein contains 50 residues which can be divided into three regions: The periplasmic domain contains residues 1 to 20, the transmembrane domain contains residues 21 to 39, and the cytoplasmic domain contains residues 40 to 50 (Marvin, D. A. (1998) *Current Opinion in Structural Biology* 8:150). The other major coat proteins in the table above have a similar domain structure.

Surprisingly, applicants have also discovered that fusion proteins of heterologous polypeptides to variants of the major coat proteins of bacteriophage are well tolerated in phage display systems. This result was unexpected since previous phage display systems have used the wild type coat protein sequences, generally of M13 or fragments thereof, T4, T7 or lambda phage coat proteins. In one aspect of the present invention, phage display and selection have been used to obtain bacteriophage displaying fusion proteins on the surface thereof where the fusion protein is a heterologous polypeptide fused to a phage major coat protein variant having one or more amino acid substitutions, deletions or additions. Fusion proteins having a heterologous polypeptide linked to a variant of the coat proteins in the Table above are within the scope of this invention.

Preferred variants of M13, f1 and fd coat protein VIII (SEQ ID NO: 2-4 ) contain at least one amino acid residue selected from the lists below in the position indicated:

| Residue Number | Sample Substitutions | Preferred Amino Acids |
|---|---|---|
| 1 | E, L, V, Q (neg. charged, hydrophobic, polar) | D, I, N |
| 2 | R, H, F, W, E (charged, large aromatic) | K, Y, D |
| 3 | T, E, L (small polar, neg. charged, hydrophobic) | S, D, I, V, A |
| 4 | D, R, H (charged) | E, K |
| 5 | R, H, N, D (charged, polar) | K, Q, E |
| 6 | Y, W, S, I, L (aromatic, small polar, hydrophobic) | F, T, V |
| 7 | T, N (small polar) | S |
| 8 | D, H (charged) | R, E, K |
| 9 | E, Q, T (neg. charged, polar) | D, N, S |
| 11 | W, I, V (aromatic, hydrophobic) | Y, L, F |
| 12 | R, H, N (charged, polar) | E, D, K, Q |

-continued

| Residue Number | Sample Substitutions | Preferred Amino Acids |
|---|---|---|
| 13 | I, L, E, Q (neg. charged, polar) | A, V, D, T, N, S |
| 14 | L (hydrophobic) | I, V |
| 15 | D, R, N (charged, polar) | E, K, H, Q |
| 16 | E, V, L, T (neg. charged, hydrophobic, polar) | D, I, A, S, G |
| 17 | E, V, L (neg. charged, hydrophobic, polar) | I, A, T, D |
| 18 | L (hydrophobic) | V, I |
| 19 | L, T, Q, E (hydrophobic, polar, neg. charged) | I, V, S, A, N, D |
| 20 | R, D, H (charged) | N, Q, K, E |
| 21 | W, Y, I (aromatic, hydrophobic) | L, F, V |
| 22 | W (aromatic) | F, Y |
| 23 | W, Y, I, V, H, K (aromatic, hydrophobic, pos. charged) | F, L, R |
| 24 | I, Q (hydrophobic, polar) | L, N, V |
| 25 | S (hydrophobic, polar) | L, I, T, V |
| 26 | A, I, V (hydrophobic) | G, L, M |
| 27 | N (small polar) | T, S |
| 28 | I, L (hydrophobic) | V |
| 29 | K, R, F, W (aromatic, pos. charged) | H, Y |
| 30 | I, V (hydrophobic) | L |

In these tables, the letter code refers to amino acid residues as follows: A (Ala) alanine; B (Asx) asparagine or aspartic acid; C (Cys) cysteine; D (Asp) aspartic acid; E (glu) glutamic acid; F (Phe) phenylalanine; G (Gly) glycine; H(His) histidine; I (Ile) isoleucine; K (Lys) lysine; L (Leu) leucine; M (Met) methionine; N (Asn) asparagine; O (Xaa) stop codon; P (Pro) proline; Q (Gin) glutamine; R (Arg) arginine; S (Ser) serine; T (Thr) threonine; V (Val) valine; W (Trp) tryptophan; X (Xaa) unknown or non-standard; Y (Tyr) tyrosine; Z (Glx) gluamine or glutamic acid.

As a part of this invention, it has been discovered that the amino acid sequence of phage major coat proteins can be modified to produce variants of the major coat protein which are useful as components of fusion proteins in phage display systems and methods. Fusion proteins containing variants of the major coat protein of a bacteriophage influence the ability of phage to package the fusion proteins into complete virus particles (virions). That is, variants of the major coat proteins can be used to alter the number of fusion proteins incorporated into a virus particle. Hyper-functional variants of the major coat protein can be used to increase the number of fusion proteins incorporated into a virus particle. Conversely, hypo-functional variants can be used to decrease fusion protein incorporation. In this way, the present invention provides a method for tailoring the incorporation of fusion proteins into virus particles to achieve a desired level of valency. This is particularly important for fusion proteins in which the heterologous polypeptide is relatively large, for example, where the heterologous polypeptide contains 50 or more amino acids, preferably 100 or more amino acids, and even more preferably 200 or more amino acid residues and also where the heterologous polypeptide is a protein having secondary and tertiary structure. The method of the invention, therefore, provides a means of overcoming the deficiencies of prior art phage display methods which utilize the major coat protein of a bacteriophage and which generally obtain only limited incorporation of the fusion protein into the virus coat. The fusion polypeptides of the invention are able to function in known phage display systems by substituting for the conventionally used wild type coat protein fusions with heterologous polypeptides. The fusion polypeptides of the invention will function in a similar manner to conventional fusion proteins in each of the known phage display systems, in which the fusion is with the major coat protein of the virus, further allowing one to select the degree of valency or number of fusion proteins displayed on the surface of the phage with more reliability. For example, the phage and phagemid vectors and the phage display systems described in U.S. Pat. Nos. 5,223,409; 5,403,484; 5,571,689; 5,750,373, and 5,780,279 (and others noted above) can be modified to use the fusion proteins of the invention to improve display of peptides, proteins, antibodies and fragments thereof on the surface of phage. The phage is preferably a DNA phage.

In addition to filamentous phage, the invention is suitable for use in phage display systems using lambda phage, Baculovirus, T4 phage and T7 phage. In each of these display systems, the coat protein used to display a heterologous polypeptide is mutated to form variants of the coat protein using the method of the invention and variants having the desired degree of display (hyper-functional or hypo-functional variants) are selected. The selected variant coat protein is then used to form a fusion protein with a heterologous polypeptide which is to be displayed on the surface of the virus particles. The scope of this invention includes the method(s) of the invention using these phage as well as fusion proteins, replicable expression vectors containing a gene encoding the fusion protein, virus particles containing the fusion proteins or vectors, host cells containing the virus particles, fusion proteins or vectors, libraries containing a plurality of different individuals of these fusion proteins, vectors, virions, cells, etc.

Polypeptides may be displayed on lambdoid phage using coat proteins in either the head or the tail portions of the phage particle (U.S. Pat. No. 5,627,024). Suitable head proteins include proteins pE, pD, pB, pW, pFII, pB* (a cleavage product of pB), pXI, and pX.2; suitable tail proteins include pJ, pV, pG, pM, and pT. The structure and location of these coat proteins is well known. See Georgeopoulos, et al. and Katsura in "Lambda II", R. W. Hendrix et al. eds. Cold Spring Harbor Laboratory, Cold Spring Harbor, N.Y., 1983. Preferred lambda proteins for use in the invention are the tail coat proteins, particularly pV. U.S. Pat. No. 5,627,024 describes how to display polypeptides on lambda phage, preferably using pV. The fusion proteins of the invention, therefore, include at least a portion of variants of pE, pD, pB, pW, pFII, pB*, pXI, pX.2, pJ, pV, pG, pM, and pT fused to a heterologous polypeptide.

Polypeptides can also be displayed on T4 phage. The structure of the T4 virion is well studied. See Eiserling in "Bacteriophage T4", C. K. Mathews et al. eds. American Society for Microbiology, Washington, D.C., 1983, pp 11-24. Peptides and full length proteins may be displayed as fusions with the SOC (small outer capsid protein) and the HOC (highly antigenic outer capsid protein) coat proteins of T4 phage. Further, the minor T4 fibrous protein fibritin encoded by the wax (whisker's antigen control) gene can be lengthened at the C terminus with a heterologous polypeptide to form a fusion protein which is displayed on the T4 whisker protein. See Ren, Z-J. et al. (1998) *Gene* 215:439; Zhu, Z. (1997) *CAN* 33:534; Jiang, J et al. (1997) can 128:44380; Ren, Z-J. et al. (1997) *CAN* 127:215644; Ren, Z-J. (1996) *Protein Sci.* 5:1833; and Efimov, V. P. et al. (1995) *Virus Genes* 10:173.

T7 phage may also be used to display polypeptides and proteins. Smith, G. P. and Scott, J. K. (1993) *Methods in Enzymology*, 217, 228-257; U.S. Pat. No. 5,766,905. Commercial kits (T7Select 1-1 and T7Select415-1 from Novagen) are available for display of polypeptides as fusion proteins with the 10B capsid protein (397 amino acids) and with the 10A capsid protein (344 amino acids). These systems are easy to use and have the capacity to display peptides up to about 50 amino acids in size in high copy number (415 per phage), and proteins up to about 1200 amino acids in low copy number (0.1-1 per phage). T7 is a double stranded DNA phage that has been extensively studied (Dunn, J. J. and Studier, F. W. (1983) *J. Mol. Biol.* 166:477-535; Steven, A. C. and Trus, B. L. (1986) *Electron Microscopy of Proteins* 5:1-35). Phage assembly takes place inside the host (*E. coli*) cell and mature phage are released by cell lysis. Fusion proteins of heterologous polypeptides to variants of T7 coat proteins, such as 10B and 10A, vectors containing a gene encoding the fusion protein, etc. are within the of the invention. Preferably, fusion proteins are prepared by altering, preferably by mutating to a non-wild type amino acid, one or more of residues 1-348 of capsid protein 10B.

The invention also includes fusion proteins of heterologous polypeptides with Baculovirus coat protein variants. Baculovirus expression vectors, particularly those based on *Autographa californica* nuclear polyhedrosis virus, are easily generated and are now widely used for the expression of heterologous polypeptides in cultured insect cells and insect larvae (Weyer, U. and Possee, R. D. (1991) *J. Gen. Virol.* 72:2967). These viruses contain a double stranded, circular genome, where foreign genes can be inserted easily. Tarui, H. et al. (1995) *J. Fac. Agr. Kyushu Univ.*, 40; 45. It is possible to display a glycosylated eukaryotic protein on the surface of baculovirus particles, using a fusion with the baculovirus major coat protein gp64 or at least by fusing the heterologous polypeptides to the membrane anchorage domain of gp64 only. The efficiency of various promoters (polyhedrin, basic, gp64-promoter) have been examined, including the "very late" polyhedrin promoter and the "early and late" gp64 promoter. In order to express a foreign gene on the surface of baculoviruses efficiently, it is necessary to choose a regulating promoter, that on one hand will transcribe sufficient amounts of the target protein, and on the other hand start transcription early enough in the viral replication cycle, to guarantee efficient packaging, complete glycosylation and correct folding.

As a further aspect of the invention, it has been discovered that phage display technology can be applied to the major coat protein itself to generate useful major coat protein variants and fusion proteins thereof. In this aspect of the invention, a library of replicable expression vectors is constructed where the expression vector includes a transcription regulatory element operably linked to a gene fusion encoding a fusion protein where the gene fusion contains a first gene encoding a first polypeptide and a second gene encoding a variant of the major coat protein of the bacteriophage used in the phage display system. That is, a library is constructed in which the second gene encodes for a plurality of variant phage major coat proteins and the phage display system or method is used to select for the variant sequence or sequences which give the desired degree of fusion protein surface display of a polypeptide. The degree of randomization of the major coat protein to produce the variants is optional. That is, libraries may be constructed in which each amino acid residue in the coat protein may be randomized to any amino acid or each residue may be limited to a subset of amino acids to produce a more limited library having predetermined constraints. It is also possible to construct a library in which a subset of residues are allowed to vary within a subset of amino acids, i.e. selected residues are incompletely randomized. For example, it is possible to limit the range of variants for a particular amino acid residue to polar amino acids, hydrophobic amino acids, hydrophilic amino acids, aromatic amino acids, positively or negatively charged amino acids, sterically small or large amino acids, or to a particular desired combination of amino acids to obtain a smaller library having particular constraints. Any combination of amino acids may be used to prepare the desired libraries.

It is also possible to produce libraries in which amino acids residues within desired segments of the major coat protein are varied to obtain a library of major coat protein variants having amino acid additions, substitutions or deletions within defined regions of the coat protein. As an example, the major coat protein may be divided into an arbitrary number of zones, generally 2-10 zones, and a library constructed of variants within one or more of the zones. The mature major coat proteins of M13, f1 and fd phage, for example, contain 50 amino acids and might be divided into 10 zones of 5 amino acid residues each or into zones with unequal numbers of residues in each zone, e.g. zones containing 15, 10, 9, and 8 residues. Zones corresponding to the cytoplasmic, transmembrane and periplasmic regions of the coat protein may be used. A separate library may be constructed for each of the zones in which amino acid alterations are desired. If fusion proteins are desired in which the major coat protein variant has an amino acid alteration in zone 1, for example, a single library may be constructed in which one or more of the amino acid residues within zone 1 is varied. Alternatively, one may wish to produce fusion proteins in which 2 zones contain amino acid alterations. Two libraries, each library containing alterations within one of the 2 zones, can be prepared.

The variant coat protein fusions will contain one or more alterations including substitutions, additions or deletions relative to the wild type coat protein sequence. Surprisingly, a large number of alterations are possible and are tolerated by the phage while retaining the ability to display polypeptides on the phage surface. Further, the chemical nature of the residue may be changed, i.e. a hydrophobic residue may be altered to a hydrophilic residue or vice versa. Variants containing 2-49, preferably 5-40, more preferably 7-20, altered residues are possible. As demonstrated by the construction of protein P12 below, any of the amino acids of a major coat protein may be varied, including varying all residues of the coat protein. Fusion proteins containing any mature coat protein sequence or portion thereof which varies from the wild type sequence of the coat protein or portion thereof is within the scope of the invention. Major coat protein variants containing 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 variant residues are possible. Variants containing substitutions or only a few deletions are preferred since these variants will have about the same length as the wild type coat protein sequence. Variants which do not enable surface display of the heterologous polypeptide are selected against during the phage display, panning and selection process.

The construction of such libraries for the M13 major coat protein is described in Example 3; the selection of protein VIII variants which increase the display of hGH or SAV is shown in Example 4. For library construction, the 50-residue protein VIII was divided into five zones encompassing approximately ten contiguous residues each. A library was constructed for each zone of the protein VIII moiety within the hGH-protein VIII fusion encoded by pS349. Most positions were not fully mutated, but variation was allowed at all non-lysine residues. Each library, encoding $10^9$ possible protein VIII variants, contained at least $3\times10^9$ independent transformants.

Figure 2:
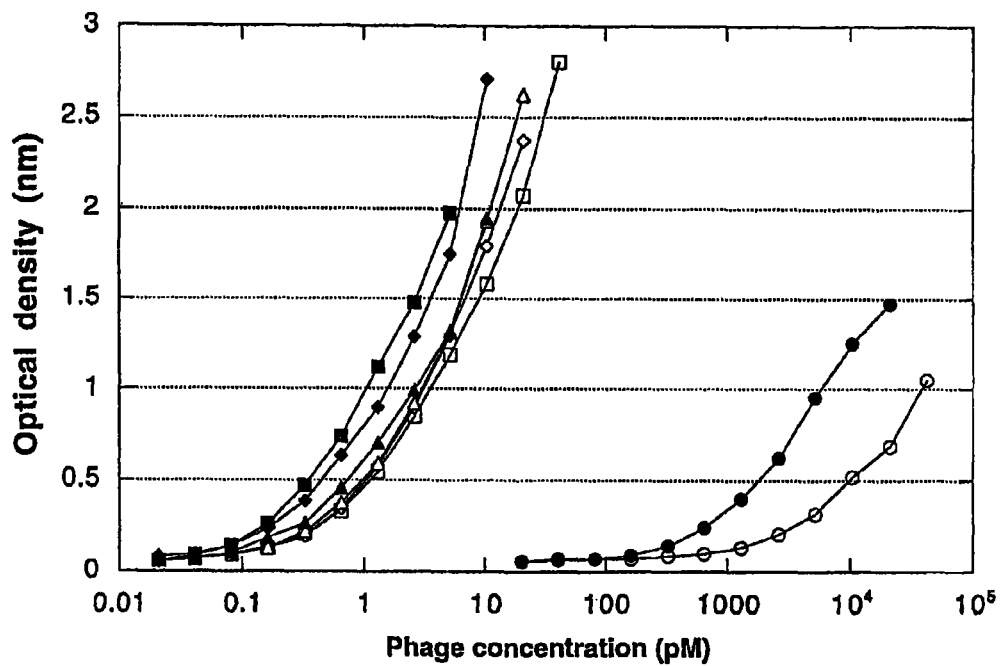
FIG. 2: Phage ELISAs for hGH display with protein VIII and selected protein VIII variants. The hGHbp was used as target ($K_d$=1.6 nM, Pearce, K. H. Jr., et al. (1997) *J. Biol. Chem.* 272:20595-20602). Display was measured for hGH-protein VIII (circles), hGH-protein VIII (1a) (squares), hGH-protein VIII (2a) (diamonds), and hGH-protein VIII (3a) (triangles). Phage were produced from cultures which were either uninduced (unfilled) or induced with 10 uM IPTG (filled). The sequences for the protein VIII variants are shown in FIG. 1.

The libraries were separately cycled through five rounds of binding selection on hGHbp-coated plates. Sequencing of individual clones revealed selectants from libraries encompassing zones 1, 2, and 3 (FIG. 2). The zone 4 and zone 5 sorts yielded contaminants from other libraries. The results suggest that zones 1, 2, and 3 are more tolerant to mutations and thus more suitable for use in the invention, but the results do not exclude the use of mutations in zones 4 and 5 for the purposes of the invention, and mutations in these zones are within the scope of the invention. Repeating the experiment with additional precautions to avoid contamination between libraries will yield variants with mutations in zones 4 and 5 which increase or decrease heterologous protein display.

Selectants were extremely divergent from the wild type sequence, containing seven mutations on average. For zones 1 and 3, a strong consensus was not obtained. Three of four zone 2 selectants were identical, but subsequent clones selected for streptavidin display (see below) yielded little consensus. Only one residue (Ala10) was completely conserved as wild type, six residues (Ala7, Leu14, Ala18, Ile22, Met28, and Val30) showed consensus to wild type. Eight positions showed consensus to a mutant sequence (E2K, D4E, P6F, K8R, F11Y, G23R, A27T, and V29Y).

All selectants increased hGH display; FIG. 2 shows phage ELISA data for the best selectant from each zone. hGH display with the protein VIII variants produced detectable ELISA signals with phage concentrations in the sub-picomolar range. In contrast, hGH display with wild type protein VIII produced detectable ELISA signals with phage concentrations in the nanomolar range. Thus, the protein VIII variants increase the signal strength (and decrease the detection limit) by at least three orders of magnitude.

Figure 4A:
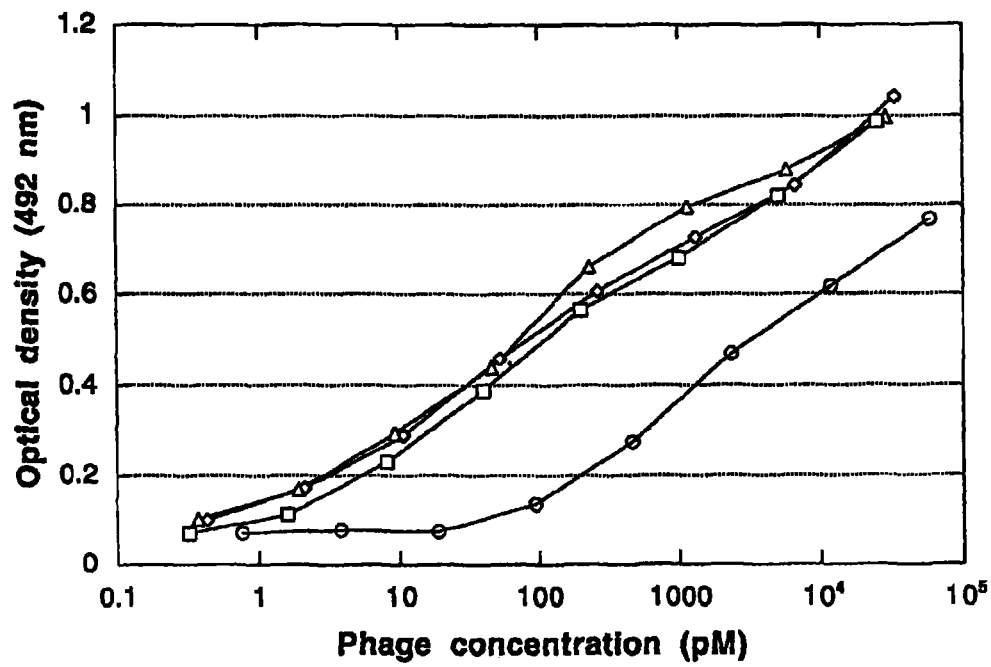
FIGS. 4A and 4B: Phage ELISAs for SAV display.
Figure 4B:
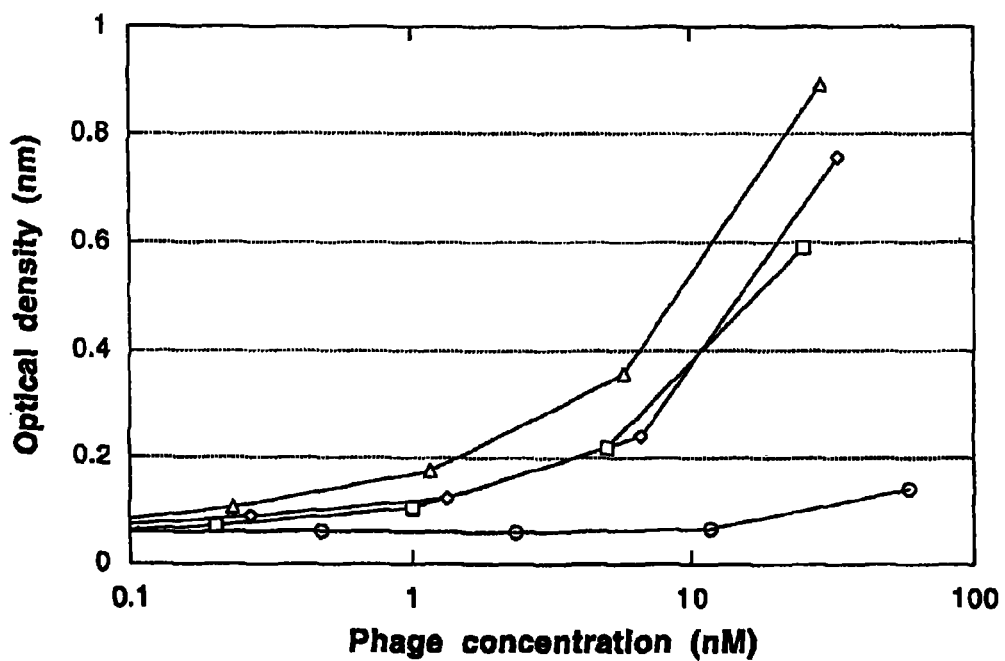

Selection for SAV display was conducted with pooled libraries for zone 1, zone 2, and zone 3 of the protein VIII moiety within the SAV-protein VIII fusion gene. All selectants were from the zone 2 library, but consensus was minimal (FIG. 1B). All selectants increased SAV display. Phage ELISA data for the two best selectants is shown in FIG. 4; the variants provide a 50-fold increase in signal' strength when assayed for binding to either anti-SAV antibody or to biotinylated BSA.

Figure 3:
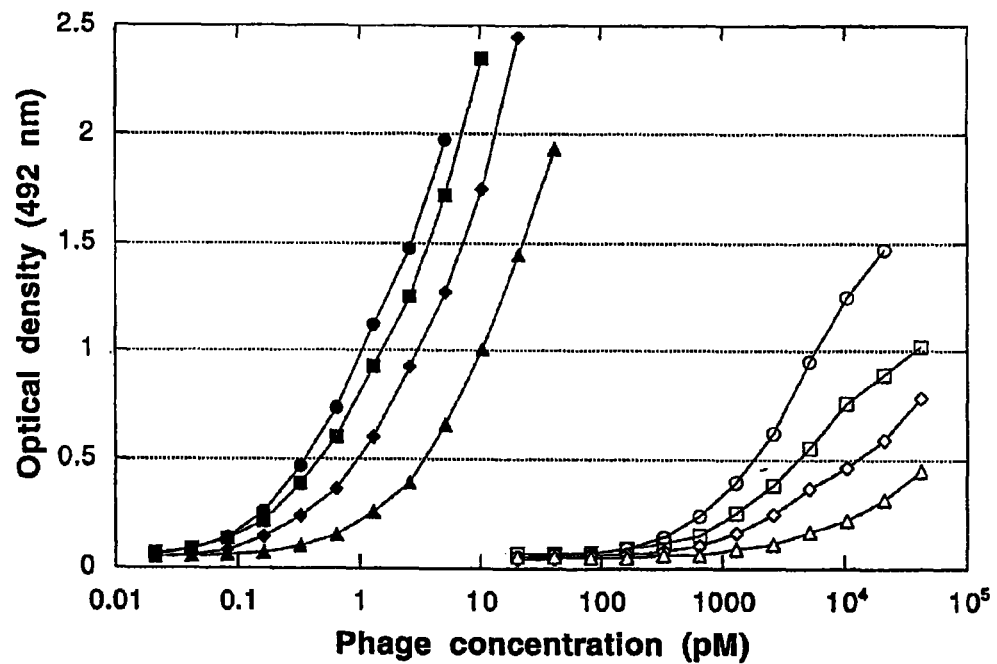
FIG. 3: Phage ELISAs for display of hGH mutants. The hGHbp was used as target. Display was measured for wild-type hGH (circles, $K_d$=1.6 nM), hGH(R64A) (squares, $K_d$=13.8 nM), hGH(Y164A/R178A) (diamonds, $K_d$=169 nM), and hGH(K172A/R178A), (triangles, $K_d$=820 nM). hGH was fused to either wild-type protein VIII (unfilled) or protein VIII(1a) (filled). Phage were produced from cultures induced with 10 μM IPTG.

In Example 8, hGH mutants with reduced binding affinity for hGHbp were displayed as fusions to either wild type protein VIII or variant protein VIII(1a). Phage ELISA data are shown in FIG. 3. As expected, reductions in binding affinity produce corresponding reductions in signal strength. When displayed on wild type protein VIII, the lowest affinity interaction ($K_d$=820 nM, 500-fold weaker than wild type) is barely detectable. The same interaction provides an extremely strong signal when displayed on the protein VIII variant. In fact, display of the lowest affinity interaction on the protein VIII variant provides an ELISA signal at least two orders of magnitude greater than that of wild type hGH linked to wild type protein VIII.

Variants with alterations in more than one zone are possible as noted above. Such variants may be obtained by first obtaining a variant with mutations in a single zone (e.g., zone 1) and then using this variant as a template for a second round of selection in which another zone is mutated (e.g., zone 2). Thus, variants obtained by this process will have mutations in two zones (e.g., zones 1 and 2). Alternatively, site-directed mutagenesis can be used to combine mutations from different variants into a single variant. For example, the mutations from a variant with mutations in zone 1 can be introduced into a variant with mutations in zone 2 to produce a new variant with mutations in both zones 1 and 2. This process shown in Example 9.

Obviously, both methods can be extended further to any number of zones which may eventually encompass the entire major coat protein sequence. Thus, it is possible to derive variants of the major coat protein with only minimal homology to the wild type. The potential for extreme variation in sequence in turn provides for extreme variation in function; variants ranging from extremely hyper-functional to extremely hypo-functional can be readily obtained. Thus, the invention can be used to tailor the display level of any heterologous protein fused to a coat protein. It is important to note that while the invention allows for the production of proteins with only limited homology to wild type coat protein, the new proteins are still variants of wild type protein (see definitions above) and are thus within the scope of this invention.

If a variant major coat protein which improves display of a heterologous polypeptide on the surface of phage particles contains multiple mutations relative to wild type, it is also possible to obtain variants which display the heterologous polypeptide at levels intermediate between the levels obtained with the new variant and wild type major coat protein. This can be accomplished by separately back mutating each mutated amino acid of the variant back to the wild type sequence or to another altered residue. These back mutations will generally reduce display levels of the heterologous polypeptide to levels varying between display levels obtained with the variant and wild type major coat protein. By combining the back mutations, it is possible to tailor display to a desired level which is between that obtained with the variant and wild type major coat protein. This process is shown in Example 10.

By a similar process, it is possible to obtain variants which display at a level below the level of the wild type coat protein. For example, mutations may be made in one or more zones and the libraries produced panned for phage which bind only weakly (weaker than phage displaying wild type fusions). The weaker binding phage will be displaced by phage displaying wild type coat protein fusions and can be isolated and sequenced using known methods.

Mutant coat proteins can be obtained which are hypofunctional for incorporation into the viral coat and thus reduce fusion protein display relative to wild type coat protein. In this case, mutations are made in residues which tend to be conserved as wild type in the above described selections for hyperfunctional variants (e.g. Ala10, Ala7, Leu14, Ala18, Ile22, Met28, and Va130 in protein VIII). Conservation of these residues as wild type during the selection for hyperfunctional variants indicates that mutations at these residues are not well tolerated and will tend to produce hypofunctional variants. Variants obtained through mutations at these sites can then be screened for their ability to display a given fusion protein relative to the wild type coat protein display levels. The heterologous peptide portion of the fusion protein may be any polypeptide or protein which can be captured or bound by a binding partner. Suitable fusions may display an epitope tag or other polypeptide which can be bound by an antibody or binding partner. Hypofunctional variants displaying the fusion at the desired reduced levels relative to wild type can then be used for the construction of libraries of the fusion protein for the purposes of phage display. Although the preferred residues for the production of hypofunctional variants are those which were conserved as wild type, any residue of the coat protein can be mutated and the resulting variant tested for its ability to allow display of a fusion protein. In this way, it is possible to select a display level below that afforded by wild type simply by using the appropriate hypofunctional mutant. As with the hyperfunctional variants described above, several hypofunctional mutations can be combined to produce further reductions in display to levels desired. While, the selection of hypofunctional variants requires a screen rather than a selection, the method is relatively simple since most mutations in proteins cause reductions in activity rather increases and suitable screening procedures are known. Thus, most mutations in the coat protein should be deleterious mutations which result in hypofunctional variants.

The libraries of expression vectors are optionally mixed and used to transform suitable host cells which are subsequently cultured under conditions suitable to form phage or phagemid particles. The phage or phagemid particles are contacted with a target molecule capable of binding to the polypeptide portion of the fusion protein displayed on the surface of the phage, so that at least a portion of the phage particles bind to the target molecule. Particles which contain fusion proteins displayed in greater numbers on the virus particles will be preferentially bound by the target molecule. Separation of particles which bind to the target from those that do not bind enables one to obtain an enriched library of particles containing fusion proteins which display greater numbers of the heterologous protein on the surface of the particles. This panning process can be repeated multiple times, generally from 2-10, preferably 2-6, times to obtain further enriched libraries containing clones which contain fusion genes encoding fusion proteins of the heterologous polypeptide linked to the selected variants of the major coat protein, the variants which allow improved incorporation of the fusion protein into the virus coat in the phage display system. This method allows one to select major coat protein variants which are best able to display the particular heterologous polypeptide and optionally other polypeptides as a fusion protein on the surface of the phage particle.

The clones selected by the process described above will have an improved capacity to display the heterologous protein on the surface of the phage in the phage display system. The method is, therefore, generally useful in displaying heterologous polypeptides which are difficult to display using fusion proteins based on wild type coat protein amino acid sequence. The improved fusion protein may be used in monovalent and/or polyvalent phage display systems. In polyvalent systems, the improved fusion protein can be used to increase the number of fusion proteins which are expressed on phage particles or to modulate the number of displayed proteins to a desired range. Phage particles displaying a greater number of fusion proteins will have a greater affinity for target molecules and will be preferentially bound and separated from particles which display fewer heterologous polypeptides as fusion proteins. This is useful in processes for the discovery of weakly binding ligands where the binding affinity of the ligand will be increased by known protein engineering techniques, such as the maturing of antibodies or antibody fragments by humanization, etc. In polyvalent display, the fusion proteins of the invention allow display of only a few to several hundreds of polypeptides on the phage surface. Generally, about 3 to about 50 polypeptides will be displayed in a moderate display system. However, with the fusion protein and phage display system of the invention it is also possible to display about 50, preferably 100-900, and up to about 1000 polypeptides or more by selecting a coat protein variant through phage display which is capable of high display numbers.

Vaccination techniques based upon phage expressing antigenic proteins fused to the coat protein have been described (Fanutti, C., et al. (1998) *Biochem. Soc. Trans.*, 26: S8; Jiang, J., et al. (1997) *Infect. Immun.*, 65:4770; Delmastro, P., et al. (1997) *Vaccine*, 15:1276; Galfre, G., et al. (1996) *Methods Enzymol.*, 267:109). This invention can also be used to enhance the effectiveness of phage vaccinations. The variants of the coat protein which increase expression of protein fusions on the surface of phage increase the antigenicity of phage vaccinations. Furthermore, the method can be used to generate variants of the coat protein which stimulate the immune system as haptens. Alternatively, the invention can be used to ameliorate immune response to the phage carrying the antigenic protein.

Alternatively, in monovalent display systems the method and fusion proteins of the invention can be used to precisely tailor display of a protein to a level which is high enough to allow for detection and enrichment of desired affinities, but is low enough to avoid avidity effects associated with polyvalency. Proteins which display polyvalently as fusions to wild type major coat protein can be displayed monovalently as fusions to an appropriate hypo-functional major coat protein variant. Proteins which do not display at all on wild type major coat protein (i.e., cannot be detected as phage-associated entities) can be displayed monovalently as fusions to an appropriate hyper-functional major coat protein variant.

Having obtained a variant major coat protein which improves/tailors display of the heterologous polypeptide on the surface of phage particles, it is then possible to use conventional phage display technologies to construct libraries of variants of the originally displayed heterologous polypeptide and select for a desired property, e.g., binding, enzymatic activity, etc. The fusion protein of the invention, containing a selected variant of the major coat protein of the phage which provides the desired display characteristics, can be used to replace a fusion protein in conventional phage display systems where the conventional fusion protein contains the wild type amino acid sequence of the major coat protein or coat protein fragment. Replacement of the conventional fusion protein with the variant fusion protein of the invention improves the display of heterologous polypeptide in the phage display system. That is, the coat protein portion has been optimized for the polypeptide which is displayed as a fusion protein.

Further, it is possible to replace the original heterologous polypeptide in the new fusion protein obtained as described above with a second different heterologous polypeptide and maintain the benefits of improved incorporation of the fusion protein into virus particles. See Example 7. In this aspect of the invention, the fusion gene which encodes the original polypeptide/major coat protein variant fusion obtained by phage display panning and selection as discussed above is modified to replace the gene encoding the first polypeptide with a gene encoding a second polypeptide of interest. Conventional phage display libraries can then be constructed in which one or more residues of the second polypeptide are varied and selected by phage display panning and selection to obtain variants of the second polypeptide with the desired (e.g., improved) binding properties. This result is also surprising since the variant coat protein portion of the fusion protein was originally selected for the ability to display a different (e.g., the original) polypeptide. Nevertheless, it has been discovered that a fusion protein containing a variant coat protein portion which has been selected for improved display of a heterologous polypeptide will also generally provide improved display of other unrelated heterologous polypeptides as well, even other polypeptides containing multiple subunits. The fusion protein containing the variant coat protein portion can, therefore, be used in general phage display systems.

The phage, display system of the invention can also be used to isolate polypeptides which are produced as therapeutic polypeptides using conventional recombinant DNA technology. In this embodiment, the method described above is used to identify a fusion protein containing a desired coat protein variant portion for use in phage display. The heterologous polypeptide portion of the fusion protein may be the desired product polypeptide itself or may be a different polypeptide where this phage display step is used to select for the coat protein variant portion providing improved surface display as described above. Using a gene for the selected coat protein variant portion in the fusion gene together with a gene for a heterologous polypeptide, one can then use phage display to optimize and select from a library of different potential product heterologous polypeptide sequences to obtain a product polypeptide sequence. This product polypeptide sequence is then cloned into an expression plasmid containing a transcription regulatory element operably linked to a gene fusion encoding the product polypeptide. Expression of the gene fusion in mammalian or bacterial cells yields the product polypeptide using well known recombinant technology. See Sambrook et al.

It is also within the scope of the invention to prepare fusion proteins of a heterologous polypeptide and a portion of a phage coat protein, which is not necessarily the major coat protein of the phage, used to display the polypeptide. In this embodiment, for example, a minor coat protein such as coat protein III of a filamentous phage is mutated to form families and libraries of fusion proteins and phage variants as described above and phage display selection and panning are used to obtain specific phage displaying a fusion protein of a heterologous polypeptide and at least a portion of a coat protein variant. Preferably, the coat protein portion is a mutant having at least one altered residue in the transmembrane domain or in the cytoplasmic domain of the coat protein. With respect to coat protein III, these altered residues will preferably be in the region of residues 377 to 406 as counted from the amino terminal end of the mature coat protein III (Marvin, D. A., Filamentous phage structure, infection, and assembly, *Current Opinion in Structural Biology*, 1998, 8:150-158). Coat protein III variants may contain a plurality of variant residues as generally described above for major coat proteins.

Suitable gene III vectors for display of polypeptides include fUSE5 (Scott, J. K. and Smith G. P. (1990). Searching for peptide ligands with an epitope library. Science 249, 386-390); fAFF1 (Cwirla., S. E., Peters, E. A., Barrett, R. W., and Dower, W. J. (1990). Peptides of phage: A vast display library of peptides for identifying ligands. *Proc. Natl. Acad. Sci. U.S.A.* 87, 6378-6382); fd-CAT1 (McCafferty, J., Griffiths, A., D., Winter, G., and Chiswell, D., J. (1990). Phage antibodies: Filamentous phage displaying antibody variable domains. *Nature* (London) 348, 552-554); m663 (Fowlkes, D., Adams, M., Fowler, V., and Kay, B. (1992). Mutlipurpose vectors for peptide expression on the M13 viral surface. *Biotechniques* 13, 422-427); fdtetDOG, pHEN1 (Hoogenboom, H., Griffiths, A., Johnson, K., Chisswell, D., Hudson, P., and Winter, G. (1991). Multi-subunit proteins on the surfaces of filamentous phage: Methodologies for displaying antibody (Fab) heavy and light chains. *Nucleic Acids Res.* 19:4133-

4137); pComb3 (Gram, H., Marconi, L. A., Barbas, C. F., Collet, T. A., Lerner, R. A., and Kang, A. S. (1992) In vitro selection and affinity maturation of antibodies from a naive combinatorial immunoglobulin library. *Proc. Natl. Acad. Sci. U.S.A.* 89, 3576-3580); pCANTAB 5E (Pharmacia); and LamdaSurfZap (Hogrefe, H. H., Amberg, J. R., Hay, B. N., Sorge, J. A., and Shopes, B. (1993) Cloning in a bacteriophage lambda vector for the display of binding of binding proteins on filamentous phage. *Gene* 137, 85-91).

Phage display methods for proteins, peptides and mutated variants thereof, including constructing a family of variant replicable vectors containing a transcription regulatory element operably linked to a gene fusion encoding a fusion polypeptide, transforming suitable host cells, culturing the transformed cells to form phage particles which display the fusion polypeptide on the surface of the phage particle, contacting the recombinant phage particles with a target molecule so that at least a portion of the particle bind to the target, separating the particles which bind from those that do not bind, are known and may be used with the method of the invention. See U.S. 5,750,373; WO 97/09446; U.S. Pat. Nos. 5,514,548; 5,498,538; 5,516,637; 5,432,018; WO 96/22393; U.S. Pat. Nos. 5,658,727; 5,627,024; WO 97/29185; O'Boyle et al., 1997, *Virology*, 236:338-347; Soumillion et al., 1994, *Appl. Biochem. Biotech.*, 47:175-190; O'Neil and Hoess, 1995, *Curr. Opin. Struct. Biol.*, 5:443-449; Makowski, 1993, *Gene*, 128:5-11; Dunn, 1996, *Curr. Opin. Struct. Biol.*, 7:547-553; Choo and Klug, 1995, *Curr. Opin. Struct. Biol.*, 6:431-436; Bradbury and Cattaneo, 1995, *TINS*, 18:242-249; Cortese et al., 1995, *Curr. Opin. Struct. Biol.*, 6:73-80; Allen et al., 1995, *TIBS*, 20:509-516; Lindquist and Naderi, 1995, *FEMS Micro. Rev.*, 17:33-39; Clarkson and Wells, 1994, *Tibtech*, 12:173-184; Barbas, 1993, *Curr. Opin. Biol.*, 4:526-530; McGregor, 1996, *Mol. Biotech.*, 6:155-162; Cortese et al., 1996, *Curr. Opin. Biol.*, 7:616-621; McLafferty et al., 1993, *Gene*, 128:29-36.

The heterologous polypeptide portion of the fusion protein may contain as few as 4-10 or up to 20-30 amino acid residues and even up to about 50-80 residues. These smaller peptides are useful in determining the antigenic properties of the peptides, in mapping the antigenic sites of proteins, etc. The heterologous polypeptide may also contain one or more subunits containing at least about 100 amino acid residues which may be folded to form a plurality of rigid secondary structures displaying a plurality of amino acids capable of interacting with the target. If the heterologous polypeptide portion of the fusion protein is mutated to form a library and subjected to phage display selection, it is preferred that polypeptide be mutated at codons corresponding to the amino acids capable of interacting with the target so that the integrity of the rigid secondary structures will be preserved. The residues can be determined by alanine scanning mutagenesis, for example. U.S. Pat. Nos. 5,580,723 and 5,766,854.

The heterologous polypeptide portion may also be a protein, preferably a mammalian protein, such as a cytokine, and the protein may be selected from human growth hormone (hGH), N-methionyl human growth hormone, bovine growth hormone, parathyroid hormone, thyroxine, insulin A-chain, insulin B-chain, proinsulin, relaxin A-chain, relaxin B-chain, prorelaxin, glycoprotein hormones such as follicle stimulating hormone(FSH), thyroid stimulating hormone(TSH), leutinizing hormone(LH), glycoprotein hormone receptors, calcitonin, glucagon, factor VIII, an antibody, lung surfactant, urokinase, streptokinase, human tissue-type plasminogen activator (t-PA), bombesin, coagulation cascade factors including factor VII, factor IX, and factor X, thrombin, hemopoietic growth factor, tumor necrosis factor-alpha and -beta, enkephalinase, human serum albumin, mullerian-inhibiting substance, mouse gonadotropin-associated peptide, a microbial protein, such as betalactamase, tissue factor protein, inhibin, activin, vascular endothelial growth factor (VEGF), receptors for hormones or growth factors; integrin, thrombopoietin (TPO), protein A or D, rheumatoid factors, nerve growth factors such as NGF-alpha, platelet-growth factor, transforming growth factors (TGF) such as TGF-alpha and TGF-beta, insulin-like growth factor-I and -II, insulin-like growth factor binding proteins, CD-4, DNase, latency associated peptide, erythropoietin (EPO), osteoinductive factors, interferons such as interferon-alpha, -alphacon-1, -beta, and -gamma, colony stimulating factors (CSFs) such as M-CSF, GM-CSF, and G-CSF, interleukins (ILs) such as IL-1, IL-2, IL-3, IL-4, IL-6, IL-8, IL-10, IL-12, superoxide dismutase; decay accelerating factor, viral antigen, HIV envelope proteins such as GP120, GP140, atrial natriuretic peptides A, B or C, Apo2L, novel erythropoiesis stimulating protein (NESP), ancestim, keratinocyte growth factor (KGF), brain-derived neurotrophic factor (BDNF), glial cell line-derived neurotrophic factor (GDNF), leptin, IL-1 receptor antagonist (IL-1ra), soluble tumor necrosis factor-a receptor type I (sTNF-RI), immunoglobulins, as well as variants and fragments of any of the above-listed proteins The heterologous polypeptide portion may also include a molecular tag, also known as an epitope tag, for identifying and/or capturing and purifying the fusion protein. For example, the tag may be Herpes simplex virus glycoprotein D (Paborsky et al. 1990, *Protein Engineering*, 3:547-553) which can be used to affinity purify the fusion protein through binding to an anti-gD antibody, protein A or a fragment thereof (Li et al. (1998) *Mol. Biotech.*, 9:187), a polyhistidine tag, e.g., (his)$_6$ (Sporeno et al., 1994, *J. Biol. Chem.*, 269: 10991-10995; Stuber et al., 1990, *Immunol. Methods*, 4:121-152, Waeber et al., 1993, *FEBS Letters*, 324:109-112), etc., which can be used to identify and/or purify the fusion protein through binding to a metal ion (Ni) column (QIAEXPRESS Ni-NTA protein Purification System, Quiagen, Inc.). Other affinity tags known in the art may be used.

In a particularly preferred embodiment, the heterologous polypeptide portion of the fusion protein is the light chain or the heavy chain of an antibody or fragments thereof, such Fab, F(ab')$_2$, Fv, diabodies, linear antibodies, etc. The polypeptide may also be a single chain antibody (scFv). The preparation of libraries of antibodies or fragments thereof is well known in the art and any of the known methods may be used to construct a family of transformation vectors which may be transformed into host cells using the method and fusion protein of the invention. Libraries of antibody light and heavy chains in phage (Huse et al., 1989, *Science*, 246:1275) and as fusion proteins in phage or phagemid are well known and can be prepared according to known procedures. See Vaughan et al., Barbas et al., Marks et al., Hoogenboom et al., Griffiths et al., de Kruif et al., noted above, and WO 98/05344; WO 98/15833; WO 97/47314; WO 97/44491; WO 97/35196; WO 95/34648; U.S. Pat. Nos. 5,712,089; 5,702,892; 5,427, 908; 5,403,484 ; 5,432,018; 5,270,170; WO 92/06176; U.S. Pat. No. 5,702,892. Reviews have also published. Hoogenboom, 1997, *Tibtech*, 15:62-70; Neri et al., 1995, *Cell Biophysics*, 27:47; Winter et al., 1994, *Annu. Rev. Immunol.*, 12:433-455; Soderlind et al., 1992, *Immunol. Rev.*, 130:109-124; Jefferies, 1998, *Parasitology*, 14:202-206.

Specific antibodies contemplated as the heterologous polypeptide portion include antibodies which bind to human leukocyte surface markers, cytokines and cytokine receptors, enzymes, etc. Specific leukocyte surface markers include CD1a-c, CD2, CD2R, CD3-CD10, CD11a-c, CDw12, CD13, CD14, CD15, CD15s, CD16, CD16b, CDw17, CD18-C41, CD42a-d, CD43, CD44, CD44R, CD45, CD45A, CD45B, CD450, CD46-CD48, CD49a-f, CD50-CD51, CD52, CD53-CD59, CDw60, CD61, CD62E, CD62L, CD62P, CD63, CD64, CDw65, CD66a-e, CD68-CD74, CDw75, CDw76, CD77, CDw78, CD79a-b, CD80-CD83, CDw84, CD85-CD89, CDw90, CD91, CDw92, CD93-CD98, CD99, CD99R, CD100, CDw101, CD102-CD106, CD107a-b, CDw108, CDw109, CD115, CDw116, CD117, CD119, CD120a-b, CD121a-b, CD122, CDw124, CD126-CD129, and CD130.

Other antibody binding targets include cytokines and cytokine superfamily receptors, hematopoietic growth factor superfamily receptors and preferably the extracellular domains thereof, which are a group of closely related glycoprotein cell surface receptors that share considerable homology including frequently a WSXWS domain and are generally classified as members of the cytokine receptor superfamily (see e.g. Nicola et al., *Cell*, 67:1-4 (1991) and Skoda, R. C. et al. *EMBO J.* 12:2645-2653 (1993)). Generally, these targets are receptors for interleukins (IL) or colony-stimulating factors (CSF). Members of the superfamily include, but are not limited to, receptors for: IL-2 (b and g chains) (Hatakeyama et al., *Science*, 244:551-556 (1989); Takeshita et al., *Science*, 257:379-382 (1991)), IL-3 (Itoh et al., *Science*, 247:324-328 (1990); Gorman et al., *Proc. Natl. Acad. Sci. USA*, 87:5459-5463 (1990); Kitamura et al., *Cell*, 66:1165-1174 (1991a); Kitamura et al., *Proc. Natl. Acad. Sci. USA*, 88:5082-5086 (1991b)), IL-4 (Mosley et al., *Cell*, 59:335-348 (1989), IL-5 (Takaki et al., *EMBO J.*, 9:4367-4374 (1990); Tavernier et al., *Cell*, 66:1175-1184 (1991)), IL-6 (Yamasaki et al., *Science*, 241:825-828 (1988); Hibi et al., *Cell*, 63:1149-1157 (1990)), IL-7 (Goodwin et al., *Cell*, 60:941-951 (1990)), IL-9 (Renault et al., *Proc. Natl. Acad. Sci. USA*, 89:5690-5694 (1992)), granulocyte-macrophage colony-stimulating factor (GM-CSF) (Gearing et al., *EMBO J.*, 8:3667-3676 (1991); Hayashida et al., *Proc. Natl. Acad. Sci. USA*, 244:9655-9659 (1990)), granulocyte colony-stimulating factor (G-CSF) (Fukunaga et al., *Cell*, 61:341-350 (1990a); Fukunaga et al., *Proc. Natl. Acad. Sci. USA*, 87:8702-8706 (1990b); Larsen et al., *J. Exp. Med.*, 172:1559-1570 (1990)), EPO (D'Andrea et al., *Cell*, 57:277-285 (1989); Jones et al., *Blood*, 76:31-35 (1990)), Leukemia inhibitory factor (LIF) (Gearing et al., *EMBO J.*, 10:2839-2848 (1991)), oncostatin M (OSM) (Rose et al., *Proc. Natl. Acad. Sci. USA*, 88:8641-8645 (1991)) and also receptors for prolactin (Boutin et al., *Proc. Natl. Acad. Sci. USA*, 88:7744-7748 (1988); Edery et al., *Proc. Natl. Acad. Sci. USA*, 86:2112-2116 (1989)), growth hormone (GH) (Leung et al., *Nature*, 330:537-543 (1987)), ciliary neurotrophic factor (CNTF) (Davis et al., *Science*, 253:59-63 (1991) and c-Mpl (M. Souyri et al., *Cell* 63:1137 (1990); I. Vigon et al., *Proc. Natl. Acad. Sci.* 89:5640 (1992)). Still other targets for antibodies made by the invention are erb2, erb3, erb4, IL-10, IL-12, IL-13, IL-15, tumor necrosis factor alpha, thrombin, etc. The variant coat protein fusions and the variant heterologous polypeptides and libraries containing the same can be prepared using conventional mutagenesis techniques. These methods include but are not limited to oligonucleotide-mediated mutagenesis and cassette mutagenesis.

The heterologous polypeptide may be linked to the coat protein or portion thereof through a peptide linker. A linker peptide segment will generally vary in length from about 3 to about 50 amino acid residues, preferably from 5 to 30 residues, more preferably from 10 to 25 residues. Further, the net charge on the linker segment is preferably positive. The identity of and order of the amino acid residues is optional, although one or more specific sequences of the linker peptide segment will generally provide better display of the heterologous polypeptide. The method of this invention can also be used to modulate display levels of a fusion protein by mutating the linker between the fused protein and the coat protein and selecting linkers which afford the desired level of display. In this embodiment, a library of linker segment variants is made by mutating a linker sequence template and the linker sequences which give the best display on phage are selected using phage display selection, for example, an affinity selection for binding to the displayed heterologous polypeptide. Linkers which allow for greater numbers of displayed polypeptides will be selected based on increased affinity for the affinity matrix.

Figure 7B:
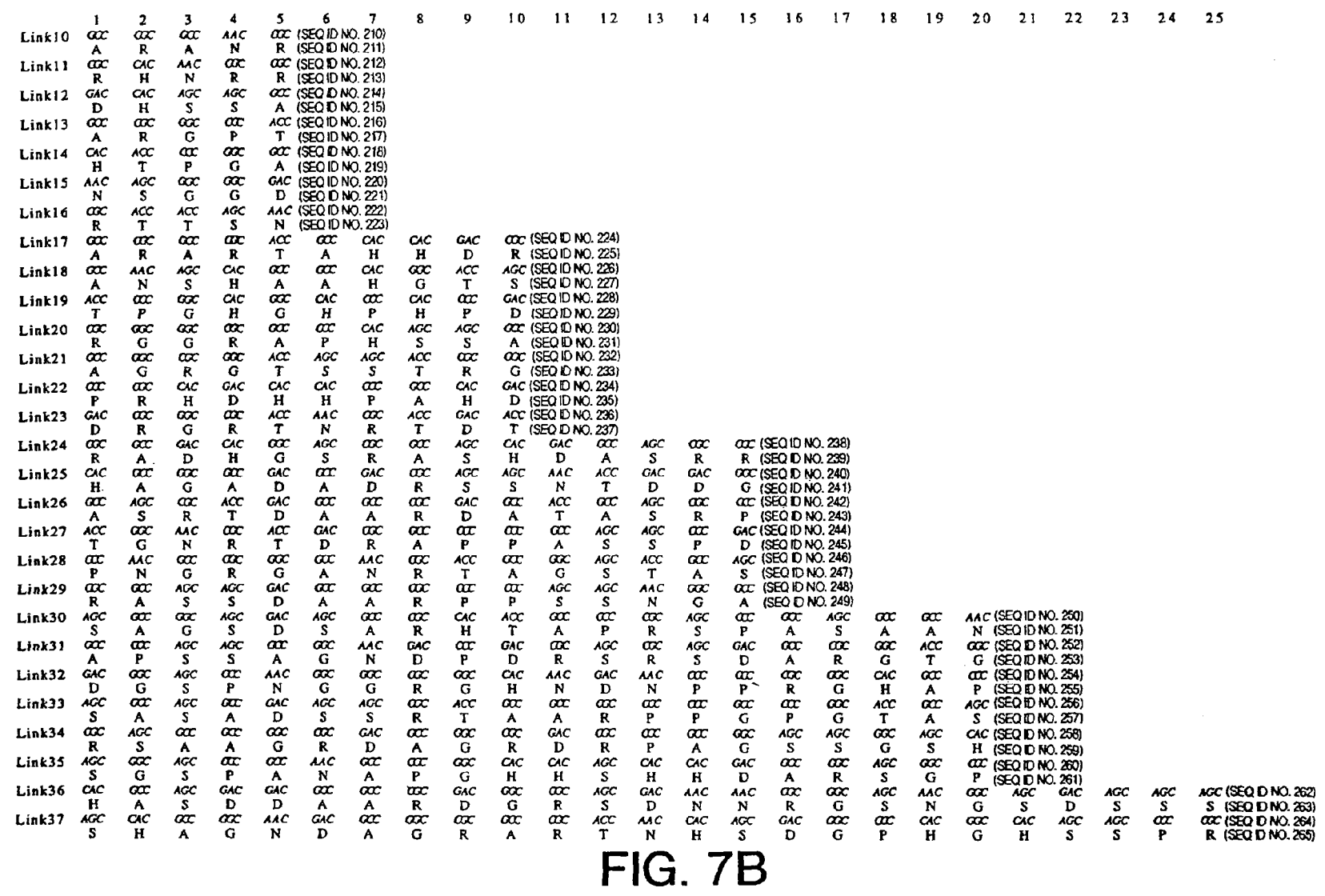
Figure 8A:
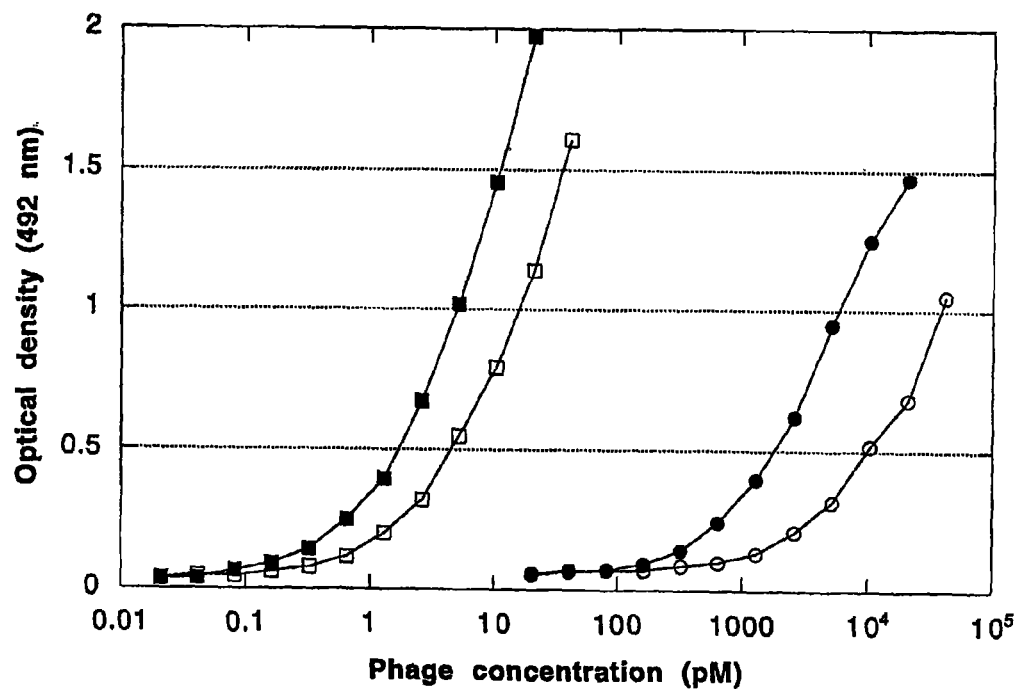
FIGS. 8A and 8B: Phage ELISAs for protein display with selected linkers. 8A) hGH displayed on protein VIII using either a Gly/Ser linker (phagemid pS349, circles) or the linker selectant Link1 (FIG. 7A, squares). Phage were produced from cultures which were either uninduced (unfilled) or induced with 10 uM IPTG (filled). The hGHbp was used as target. 8B) SAV displayed on wild type protein VIII using a Gly/Ser linker (unfilled circles) or on variant protein VIII(2e) using either a Gly/Ser linker (unfilled squares), link18 (filled circles), link29 (filled squares), link34 (filled diamonds), or link37 (filled triangles). The Gly/Ser sequence was identical to the Gly/Ser linker encoded by pS349. The sequences of the other linkers are shown in FIG. 7B. Biotinylated BSA was used as target.
Figure 8B:
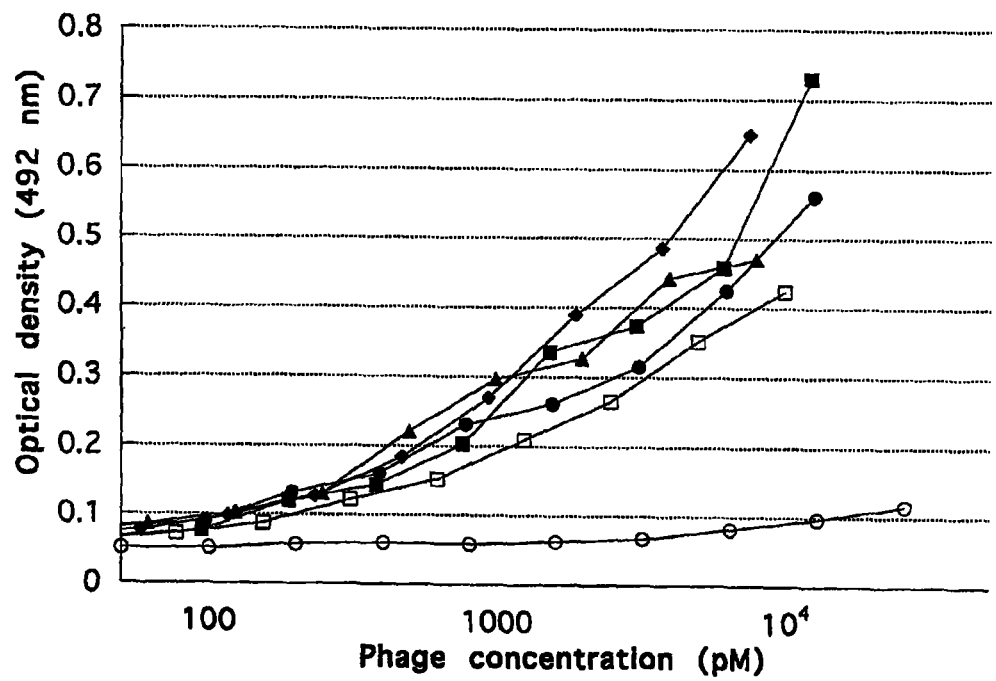

To date, researchers have used specific linkers designed to provide desired attributes. Linkers have been designed to provide flexibility (Wung et al. (1997) *J. Immunol. Methods* 204:33-41), such as the Gly-Ala$_3$ (Holmes et al. (1996) *Protein Pept. Lett.* 3:415-422) or Gly$_4$Ser$_3$ linkers (Michael et al. (1996) *Immunotechnology* 2:47-57) and to incorporate sites for specific proteolysis (Lucie, et al. (1998) *Australia. J. Biotechnol.* 61:95-108; Matthews, D. J. and Wells, J. A. (1993) *Science*, 26:1113-1117). Considerations for linker optimization include, among other factors, resistance to proteolysis, distance from the phage particle to the fused protein, and conformational effects of the linker upon fusion protein activity. The large number of variables involved makes the selection method of the invention an attractive approach. For example, selection of a linker for increased display of hGH on protein VIII (FIG. 7A) results in increased display relative to a designed Gly/Ser linker (FIG. 8A). A similar selection was also used to select linkers (FIG. 7B) for SAV display (FIG. 8B). In the SAV display, the selection was performed with SAV fused to a protein VIII variant (protein VIII(1e)) which had been previously selected for increased display of SAV (Example 4). This example demonstrates that optimized linkers can be combined with optimized coat protein variants, for example protein VIII variants, to obtain a desired display level, in a manner similar to the combination of different protein VIII variants described above.

The methods described above with reference to obtaining a gene encoding a heterologous polypeptide, variant polypeptide or a fusion protein containing at least a portion of a phage coat protein and a heterologous peptide or variant and isolating the same, oligonucleotide-mediated and cassette mutagenesis, cleaving DNA using restriction enzymes, ligation, separation and selection of DNA using electrophoresis, purification and transformation (e.g., electroporation) procedures, library construction, suitable host or recipient cells and cell concentrations, etc. and the prior art methods noted above may be used in, this embodiment of the invention and the description thereof is incorporated here specifically with respect to this embodiment.

C. Carboxyl-Terminal Display and More New Phage Coat Proteins and Fusions Thereof.

Another aspect of the invention is the carboxyl-terminal (C-terminal) display of a heterologous polypeptide on the surface of a filamentous phage using protein fusions with protein III or protein VIII. C-terminal display has been reported on protein VI of M13 (Jespers, L. et al., 1995, *Biotechnology* 13:378-382). This paper states that protein VI is distinct from proteins III and VIII in its ability to allow for the attachment of polypeptides at the C-terminus. Surprisingly, as a part of this invention, it has been discovered that C-terminal display is also possible with fusions to protein III and VIII. The invention, therefore, allows the C-terminal display of a heterologous polypeptide or library of polypeptides in a manner similar to display at the N-terminus (N-terminal display) of a phage coat protein. In this aspect of the invention, the C-terminal display may be accomplished using a wild type protein III/VIII or a mutant protein III/VIII as described above where the phage display process was applied to the coat protein sequence itself.

Any of the methods of phage or phagemid display, creating coat protein variants and protein fusions thereof with a heterologous polypeptide, libraries of such variants and fusion proteins, expression vectors encoding the variants and protein fusions, libraries of the vectors, a library of host cells containing the vectors, methods for preparing and panning the same to obtain binding polypeptides, etc. described above with reference to N-terminal display may also be used in this aspect of the invention for C-terminal display and the descriptions above are hereby incorporated here and should be considered as part of the description of C-terminal display of the invention.

The invention allows one to evolve new virus particles containing non-wild type coat proteins and coat protein fusions.

The variant protein IL/VIE fusion proteins will contain one or more alterations including substitutions, additions or deletions relative to the wild type coat protein sequence. Again, it is surprisingly, that a large number of alterations are possible and are tolerated by the phage while retaining the ability to display polypeptides on the phage surface, in this case as C-terminal fusions. The chemical nature of the residue may be changed, i.e. a hydrophobic residue may be altered to a hydrophilic residue or vice versa. Variants containing 2-50, preferably 5-40, more preferably 7-20, altered residues are possible. Fusion proteins containing any mature coat protein sequence or portion thereof which varies from the wild type sequence of the coat protein or portion thereof is within the scope of the invention. Major coat protein variants containing 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 variant residues are possible. This aspect of the invention allows one to design a coat protein which is any coat protein other that the wild type coat protein and select for C-terminal fusion proteins which display on the surface of phage. Variants containing substitutions are preferred since these variants will have about the same length as the wild type coat protein sequence. However, deletions of residues to prepare shorter coat proteins and protein fusions thereof are within the scope of the invention. Preferably, the first few residues will be deleted, more preferably N-terminal or C-terminal residues 1 to about 5 can be deleted. Variants which do not enable surface display of the heterologous polypeptide are selected against during the phage display, panning and selection process.

As with N-terminal display described above, it is also possible to produce libraries in which amino acids residues within desired segments of the coat protein are varied to obtain a library of coat protein variants having amino acid additions, substitutions or deletions within defined regions of the coat protein. As an example, the coat protein may be divided into an arbitrary number of zones, generally 2-10 zones, and a library constructed of variants within one or more of the zones. The mature coat proteins of M13, f1 and fd phage, for example, contain 50 amino acids and might be divided into 10 zones of 5 amino acid residues each or into zones with unequal numbers of residues in each zone, e.g. zones containing 15, 10, 9, and 8 residues. Zones corresponding to the cytoplasmic, transmembrane and periplasmic regions of the coat protein may be used. A separate library may be constructed for each of the zones in which amino acid alterations are desired. If fusion proteins are desired in which the coat protein variant has an amino acid alteration in zone 1, for example, a single library may be constructed in which one or more of the amino acid residues within zone 1 is varied. Alternatively, one may wish to produce fusion proteins in which 2 zones contain amino acid alterations. Two libraries, each library containing alterations within one of the 2 zones, can be prepared.

Preferably, the heterologous polypeptide is attached to the coat protein or variant thereof through a linker peptide. The linker may contain any number of residues which allow C-terminal display, and will generally contain about 4 to about 30, preferably about 8 to about 20, amino acid residues. The linker may contain any of the naturally occurring residues, although linkers containing predominantly (greater than 50%) glycine and/or serine are preferred. The optimum linker composition and length for display of a particular polypeptide may be selected using phage display as described above and demonstrated in the examples. For example, phage libraries each containing a different linker length may be constructed and phage selection and panning used to isolate the amino acid composition of the linker of any length which optimizes expression and display of the heterologous polypeptide.

As with N-terminal display described above, if a variant coat protein which improves display of a heterologous polypeptide on the surface of phage particles contains multiple mutations relative to wild type, it is also possible to obtain variants which display the heterologous polypeptide at levels intermediate between the levels obtained with the new variant and wild type coat protein. This can be accomplished by separately back mutating each mutated amino acid of the variant back to the wild type sequence or to another altered residue. These back mutations will generally reduce display levels of the heterologous polypeptide to levels varying between display levels obtained with the variant and wild type coat protein. By combining the back mutations, it is possible to tailor display to a desired level which is between that obtained with the variant and wild type coat protein.

By a similar process, it is possible to obtain variants which display at a level below the level of the wild type coat protein. For example, mutations may be made in one or more zones and the libraries produced panned for phage which bind only weakly (weaker than phage displaying wild type fusions). The weaker binding phage will be displaced by phage displaying wild type coat protein fusions and can be isolated and sequenced using known methods.

Mutant coat proteins can also be obtained which are hypofunctional for incorporation into the viral coat and thus reduce fusion protein display relative to wild type coat protein. In this case, mutations are made in residues which tend to be conserved as wild type in the above described selections for hyperfunctional variants. Conservation of these residues as wild type during the selection for hyperfunctional variants indicates that mutations at these residues are not well tolerated and will tend to produce hypofunctional variants. Variants obtained through mutations at these sites can then be screened for their ability to display a given fusion protein relative to the wild type coat protein display levels. Hypofunctional variants displaying the fusion at the desired reduced levels relative to wild type can then be used for the construction of libraries of the fusion protein for the purposes of phage display. Although the preferred residues for the production of hypofunctional variants are those which were conserved as wild type, any residue of the coat protein can be mutated and the resulting variant tested for its ability to allow display of a fusion protein. In this way, it is possible to select a display level below that afforded by wild type simply by using the appropriate hypofunctional mutant. As with the hyperfunctional variants described above, several hypofunctional mutations can be combined to produce further reductions in display to levels desired. While, the selection of hypofunctional variants requires a screen rather than a selection, the method is relatively simple since most mutations in proteins cause reductions in activity rather increases and suitable screening procedures are known. Thus, most mutations in the coat protein should be deleterious mutations which result in hypofunctional variants.

C-terminal display is useful to display cDNA libraries on the surface of phage particles. mRNA can be purified from a tissue source of choice and double stranded cDNAs synthesized using standard techniques (Sambrook et al., 1989, Molecular Cloning: A Laboratory Manual, 2nd Ed. Cold Spring Harbor, N.Y.). A phagemid or phage vector (or a plurality thereof) containing an open reading frame is then constructed using well established techniques disclosed in Sambrook et al. and the phage and phagemid display references described above and the cDNAs are ligated into the vectors at the 3' end of the coat protein gene. Host cells are then transformed, preferably by electroporation, with the library of vectors and phage particles displaying heterologous polypeptides corresponding to the cDNA library members are obtained (with superinfection of helper phage for phagemid vectors). The C-terminal phage display library obtained may be panned and analyzed using conventional phage display techniques.

The C-terminal display of the invention is also useful to display intracellular, preferably mammalian intracellular, proteins or fragments thereof and polypeptides which are difficult to display using N-terminal display. C-terminal display is, therefore, a complementary display technique to N-terminal display. Intracellular proteins may be difficult to display in a correctly folded form using N-terminal display due to the difference in redox environment in which intracellular proteins normally exist relative to the environment in which secreted proteins fold and form disulfide bonds. The cytoplasm is a reducing environment whereas the periplasm is an oxidizing environment. C-terminal heterologous fusion proteins migrate to the periplasm as in normal phage particle assembly. However, since the heterologous polypeptide remains on the intracellular side of the periplasmic membrane, an intracellular polypeptide may correctly fold prior to incorporation into a phage particle. During assembly of the phage or phagemid particle, the C-terminal fusion protein is incorporated into the particle and displays the heterologous polypeptide on the surface thereof.

C-terminal display bypasses secretion problems encountered with N-terminal display systems. With N-terminal display, it is generally thought that the heterologous polypeptide on the N-terminus must pass through a pore-like structure in the periplasmic membrane in order to enter the periplasmic space with the C-terminus remaining as an anchor in the membrane. The fusion protein is then assembled into a phage particle from the membrane. Using C-terminal display, it is not necessary to have the fusion protein secrete into the host cell periplasm in order to assemble phage particles. C-terminal display is, therefore, useful to display any heterologous polypeptide and is particularly useful to display polypeptides which are difficult to display using N-terminal phage display techniques.

C-terminal display can also be used to display a foreign polypeptide which is secreted into the periplasm during virus particle assembly. For example, by constructing a library of potential membrane proteins and selecting members of the library capable of functioning as coat proteins, it is possible to apply selective pressure to the library and evolve coat proteins which have a foreign polypeptide as a C-terminal fusion and which orient in the cell membrane with the foreign polypeptide in the periplasm and the N-terminus of the fusion protein in the cytoplasm. Such fusion proteins preferably have a positively charged N-terminal portion as a cytoplasmic region and a hydrophobic core portion as a transmembrane region. Such a structure resembles a bacterial secretion signal. Some library members will function as secretion signals and insert into the bacterial membrane with the N-terminus in the cytoplasm and the C-terminus in the periplasm (inverse coat proteins). Some of the fusions which can insert into the membrane will incorporate into assembling virus particles by virtue of favorable interactions with the phage or phagemid coat. Suitable libraries may be designed in multiple stages. For example, inverse coat proteins may be selected from a library (or libraries) of potential coat proteins by using an epitope tag fused to the C-terminus of the library of coat proteins. After phage particle assembly, antibody binding to the epitope tag is used to isolate members of the virus particle library which display the tag on the surface of the particle. The particles which bind can be isolated/selected and cloned using conventional phage display techniques. In a second step, one of the selectants can be further evolved by phage display to select for improved incorporation into a particle coat. Again, one or more libraries can be constructed to vary different regions of the coat protein to select for those proteins which best display the epitope tag or other protein on the surface of the particle. Coat protein fusions and virus particles prepared according to the invention provide a diversity of tools which are useful to evaluate virus structure and assembly processes, to map the antibody binding epitopes on proteins, to affinity mature binding proteins such as antibodies and fragments thereof to provide binding proteins with higher binding affinities, to produce polypeptides which bind to active and allosteric sites on enzymes, etc. including all of the uses for which phage display is currently employed.

All patent and literature references cited above are incorporated herein by reference in their entirety.

EXAMPLES

Example 1

Construction of *E. coli* SS320

The new cell line SS320 was prepared by bacterial mating in which the F' episome was transferred from XL1-BLUE cells to MC1061 cells according to known protocols (J. H. Miller, 1972, *Experiments in Molecular Biology*, p190). More specifically, the SS320 cells can be obtained using the following steps:

Grow 1.0 mL cultures of MC1061 and XL1-BLUE in LB broth to OD600=0.5 (single colonies from freshly streaked plates. MC1061 was streaked on LB plates. XL1-BLUE was streaked on LB/tetracycline (10 μg/mL)).

Mix 0.5 mL of each culture and grow 1 hour at 37° C. with slow shaking (50 rpm on a rotary shaker). After mating for 1 hour, agitate at 250 rpm to disrupt the mating.

Plate dilutions on LB/tetracycline (10 μg/mL)/streptomycin(10 μg/mL).

MC1061 carries a streptomycin resistance chromosomal marker while the F' plasmid of XL1-BLUE confers tetracycline resistance. Thus, only the mating progeny (MC1061 harboring the XL1-BLUE F' episome will be resistant to both antibiotics. The unmixed cultures of MC1061 and XL1-BLUE can be plated on the selective media as controls, since neither parent is doubly resistant.

The resulting strain (SS320) can be used for electroporation and phage production.

The genotypes of the starting MC 1061 cells (available from Bio-Rad Laboratories, Inc.) and XL1-BLUE episome (available from Stratagene, Inc. in XL1-BLUE cells) and the resulting SS320 cells are as follows:

XL1-BLUE F' episome
F'::Tn10 proA$^+$B$^+$lacI$^q$D(lacZ)M15
MC1061
F-araD139D(ara-leu)7696galE15galK16D(lac)X74rpsL (Str$^r$)hsdR2($r_k^-$m$_k^+$)mcrAmcrB1
SS320
F'::Tn10 proA$^+$B$^+$lacI$^q$D(lacZ)M151
F-araD139D(ara-leu)7696galE15galK16D(lac)X74rpsL (Str$^r$)hsdR2($r_k^-$m$_k^+$)mcrAmcrB1

Various *E. coli* strains were evaluated for cell survival and viability after standard washing steps were performed to prepare the cells for electroporation. *E. coli* were grown in 250 mL cultures and prepared for electroporation as previously described. The total number of colony forming units were titered before and after the wash procedure and the results are shown below.

| Strain | Before wash (cfu) | After wash (cfu) | Survival (After/Before) |
|---|---|---|---|
| SS320 | $4.8 \times 10^{12}$ | $4.6 \times 10^{12}$ | 0.96 |
| TB1 | $1.7 \times 10^{11}$ | $1.9 \times 10^{11}$ | 1.1 |
| JM101 | $4.5 \times 10^{11}$ | $3.6 \times 10^{10}$ | 0.08 |
| JM107 | $2.3 \times 10^{11}$ | $1.0 \times 10^{10}$ | 0.045 |
| JM109 | $1.5 \times 10^{11}$ | $1.2 \times 10^{10}$ | 0.08 |

The transformation yield achieved with different *E. coli* strains at a fixed concentration of DNA is dependent on the concentration of viable *E. coli* cells in the electroporation reaction. It has now been discovered that the maximum concentration of viable cells which can be achieved with a given strain is dependent upon the resistance of that strain to the washing steps involved in the preparation of electrocompetent cells. The suitability of a particular bacterial (e.g., *E. coli*) strain for electroporation can be easily determined using the following procedure.

Grow a 250 mL culture of bacteria to OD600=0.6 in a 1-L baffled flask. Remove a small aliquot and plate dilutions on appropriate media to determine the total number of viable cells; this number is the input of cells (input, I). Follow the standard procedures for production of electrocompetent cells as described in Example 2 (scaled down appropriately for the volume of culture used). Plate dilutions of the final preparation of electrocompetent cells on appropriate media to determine the total number of viable cells; this is the number of cells surviving the electrocompetent cell preparation procedure (survivors, S). Divide S by I to determine the ratio of survivors to input (S/I). For a strain ideally suited for electroporation (i.e. a strain which gives the highest transformation yield in comparison with other strains at a fixed DNA concentration), the ratio S/I should be equal to one. This indicates that all the input cells survived the electrocompetent cell preparation procedure. A reduction in the ratio S/I corresponds to a reduction in the concentration of viable cells in the electrocompetent cell preparation; this in turn results in a reduction in the transformation yield. Thus, for the highest transformation yields at a given DNA concentration, a strain with the highest S/I value should be used.

Example 2

Preparation of *E. coli* for Electroporation

Electroporation competent cells were prepared as described below:

1. Inoculate 1 mL 2×YT media (5 mg/mL tetracycline) with SS-320 from a fresh LB/tet plate. Grow about 6 hours and inoculate 50 mL 2xYT/tetracyline in a 500-mL flask; grow overnight.

2. Inoculate 6×900 mL Superbroth (5 mg/mL tetracycline) in 2-L baffled flasks with 5 mL from above culture and grow cells to OD600=0.6-0.8 at 37° C., 200 rpm.

3. Chill three flask on ice (shake periodically). Further steps were performed in a cold room, on ice, with prechilled solutions and equipment.

4. Centrifuge 5.5K/5 min in a SORVALL GS3 ROTOR and decant all supernatant. Add culture from remaining three flasks to same tubes; respin and decant.

5. Resuspend in equal volume of 1 mM HEPES, pH7.4 by swirling or stirring. Centrifuge 5.5K/10 min and decant supernatant.

6. Resuspend in equal volume of 1 mM HEPES as in (5) above. Centrifuge 5.5K/10 min and decant supernatant. Resuspend each pellet in 100 mL of 10% (v/v) glycerol (filter sterilized; ultrapure glycerol (Gibco BRL #15514-011)).

7. Centrifuge 5.5K/15 mM and decant all supernatant. Resuspend in minimum volume of 10% glycerol. Using about 3 mL of 10% glycerol for 5 L of starting culture produces about 12 mL of concentrated cells with about $3-4 \times 10^{11}$ cfu/mL.

Example 3

Mutagenesis Fill-in

The mutagenesis reaction was conducted using the procedure described in U.S. Pat. No. 5,750,373 with the changes shown below:

1) Kinase oligo
   4 µL oligo (330 ng/mL stock; i.e., $A_{260}$=10)
   4 µL 10×TM buffer (0.5M tris pH7.5, 0.1M MgCl2)
   4 µL 10 mM ATP
   2 µL 100 mM DTT
   24 µl H$_2$O
   2 µL kinase (NEB, 10 U/µL)
   40 µL
   incubate at 37° C. for 0.5 hour.

2) Anneal oligo/template
   40 µg kunkel template
   1.2 µg kinased oligo (i.e. 40 µL from above kinase reaction; oligo/template=3)
   25 µL 10×TM buffer
   add H$_2$O to 250 µL final volume
   incubate at 90° C. for 2 minutes, 50° C. for 3 minutes.

3) Fill-in
   add:
   1 µL 100 mM ATP

10 μL 25 mM dNTPs (25 mM each dATP, dCTP, dGTP, dTTP)
15 μL 100 mM DTT
6 μL T4 ligase (NEB, 400 U/μL)
3 μL T7 polymerase (NEB, 10 U/μL)
incubate at 20° C. for 3 hours.

Example 4

E. coli Electroporation

Electroporation was conducted as described below:

1. Extract fill-in reaction with an equal volume of phenol/$CHCl_3$. Extract with an equal volume of $CHCl_3$. Purify and desalt DNA (60 micrograms) using QIAquick gel extraction kit (QIAGEN). Use two columns for each reaction. Follow wash and elution procedures as outlined by QIAGEN; elute each column with 30 μL of $H_2O$ to provide a final theoretical yield of 80 μg fill-in product (40 μg single strand DNA converted to double strand) in 60 μL of $H_2O$.

2. Electroporate DNA (60 μL) into 350 μL of competent E. coli SS320. Use 0.2 cm gaps cells with following settings: 2.5 kV, 200 ohms, 25 μF. Use two cells for each reaction (i.e. 200 μL for each cell). After the shock, transfer cells to 25 mL SOC media and culture for phenotype expression. After phenotype expression, remove a small aliquot for titre on selective and non-selective media. Transfer cells to 500 mL 2×YT (in a 2-L baffled flask) containing appropriate antibiotic for phagemid selection and VCS helper phage (m.o.i.=10). Grow overnight and harvest phage in the morning.

Example 5

Large Library Construction with Ultrahigh DNA and E. Coli Concentrations

The fill-in protocol of Example 3 was followed with two different single stranded templates (a and b) and a mismatch oligonucleotide. Three different input template quantities were used: 1) 20 μg, 2) 30 μg, or 3) 40 μg.

After the fill-in and purification the following double stranded DNA quantities were obtained in 60 μL of water:

| Reaction | OD260 | [DNA], μg/mL | DNA total, μg |
| --- | --- | --- | --- |
| a1 | 9.04 | 452 | 27 |
| a2 | 12.12 | 606 | 36 |
| a3 | 13.92 | 696 | 42 |
| b1 | 7.48 | 374 | 22 |
| b2 | 10.4 | 520 | 31 |
| b3 | 13.12 | 656 | 39 |

Each reaction was used to electroporate 340 μL of SS320 ($3 \times 10^{11}$ cfu/mL). This gives a total volume of 400 μL with $1 \times 10^{11}$ cells. Each reaction was electroporated in two 200 microliter aliquots.

| Reaction | [DNA], μg/mL | Time constants, ms* |
| --- | --- | --- |
| a1 | 68 | 4.1, 4.1 |
| a2 | 90 | 4.2, 4.3 |
| a3 | 105 | 4.2, 4.3 |
| b1 | 55 | 4.2, 4.2 |

-continued

| Reaction | [DNA], μg/mL | Time constants, ms* |
| --- | --- | --- |
| b2 | 78 | 4.3, 4.3 |
| b3 | 98 | 4.2, 4.2 |

*microseconds

These results indicate that the time constant for electroporations with high DNA concentrations are well above 3.0 ms and that electroporation is easily performed with high DNA concentrations.

The number of transformants and the survival of the cells during transformation was evaluated and is shown in the table below.

Titer of Library Size and Survivors:

| Reaction | survival | transform | S/I* | T/S** | T/I*** |
| --- | --- | --- | --- | --- | --- |
| a1 | $5 \times 10^{10}$ | $2.3 \times 10^{10}$ | 0.50 | 0.46 | 0.23 |
| a2 | $5 \times 10^{10}$ | $3.0 \times 10^{10}$ | 0.50 | 0.60 | 0.30 |
| a3 | $4.5 \times 10^{10}$ | $3.0 \times 10^{10}$ | 0.45 | 0.67 | 0.30 |
| b1 | $4 \times 10^{10}$ | $2.3 \times 10^{10}$ | 0.40 | 0.58 | 0.23 |
| b2 | $4 \times 10^{10}$ | $2.3 \times 10^{10}$ | 0.40 | 0.58 | 0.23 |
| b3 | $4 \times 10^{10}$ | $2.3 \times 10^{10}$ | 0.40 | 0.58 | 0.23 |

*survivors/input is the fraction that survive electroporation
**transformants/survivors is fraction of survivors with phagemid
***transformants/input is fraction that both survive and transform.

Example 6

High Concentration DNA Electroporation

The standard fill-in protocol was followed with a single stranded template and a mismatch oligonucleotide. Seven identical reactions were purified and pooled to produce 400 μL of DNA at 750 μg/mL ($OD_{260}$=15.0)

Various amounts of DNA were electroporated into E. coli SS320 in a final volume of 200 μL with a fixed E. coli concentration of $1.5 \times 10^{11}$ cells/mL. The following conditions were used: 0.2 cm cuvettes @ 2.5 kV/cm, 200 ohms, 25 μF. After electroporation, the reaction was grown in 10 mL SOC media for 30 minutes and then titered on both LB (survival) and LB/carbenicillin (50 μg/mL) (transformation).

| | [DNA] (μg/mL) | T.C. (ms) | LB (cfu) | carb (cfu) | S/I* | T/S** | T/I*** |
| --- | --- | --- | --- | --- | --- | --- | --- |
| 1 | 375 | 3.6 | $1.4 \times 10^{10}$ | $6.0 \times 10^9$ | .47 | .43 | .20 |
| 2 | 281 | 3.8 | $1.4 \times 10^{10}$ | $7.0 \times 10^9$ | .47 | .50 | .23 |
| 3 | 188 | 4.1 | $1.5 \times 10^{10}$ | $6.2 \times 10^9$ | .50 | .41 | .21 |
| 4 | 150 | 4.1 | $1.4 \times 10^{10}$ | $6.0 \times 10^9$ | .47 | .43 | .20 |
| 5 | 113 | 4.2 | $1.4 \times 10^{10}$ | $5.7 \times 10^9$ | .47 | .41 | .19 |
| 6 | 75 | 4.3 | $1.5 \times 10^{10}$ | $5.9 \times 10^9$ | .50 | .42 | .20 |
| 7 | 38 | 4.4 | $1.6 \times 10^{10}$ | $6.8 \times 10^9$ | .53 | .43 | .23 |
| 8 | 19 | 4.4 | $1.6 \times 10^{10}$ | $7.0 \times 10^9$ | .53 | .44 | .23 |
| 9 | 7.5 | 4.5 | $1.4 \times 10^{10}$ | $5.0 \times 10^9$ | .47 | .36 | .17 |
| 10 | 3.8 | 4.5 | $1.5 \times 10^{10}$ | $2.4 \times 10^9$ | .50 | .16 | .08 |
| 11 | 0 | 4.5 | $1.5 \times 10^{10}$ | 0 | .50 | 0 | 0 |

*survivors/input is the fraction that survive electroporation
**transformants/survivors is fraction of survivors with phagemid
***transformants/input is fraction that both survive and transform.

Example 7

Construction of an Extremely Large Library Using Multiple Electroporations with Ultrahigh DNA and E. Coli Concentrations The fill-in protocol of Example 3 was followed with a single stranded template and a mismatch oligonucleotide. The quantity of input template was 40 micrograms, and 35 identical reactions were performed.

After the fill-in, purification was conducted as described in Example 4 except that the extractions with phenol/$CHCl_3$ and $CHCl_3$ were omitted, and each column was eluted with 50 microL of $H_2O$. Two columns were used for each reaction, and thus, the final theoretical yield for each reaction was 80 micrograms of fill-in product in 100 microL of $H_2O$.

Each reaction was used to electroporate 700 microL of SS320 ($3 \times 10^{11}$ cfu/mL). This gives a total volume of 800 microL with $2 \times 10^{11}$ cells. Each reaction was electroporated in two 400 microL aliquotes as described in Example 4, except that the cells were transferred to 50 mL of SOC media after the shock. After phenotype expression, the cells were titred on selective media. When combined together, the 35 independent reactions provided a library size of $1.79 \times 10^{12}$ different members. The results for the 35 independent reactions are presented below:

| Reaction | transformants |
|---|---|
| 1 | $5.0 \times 10^{10}$ |
| 2 | $4.6 \times 10^{10}$ |
| 3 | $4.6 \times 10^{10}$ |
| 4 | $5.4 \times 10^{10}$ |
| 5 | $5.2 \times 10^{10}$ |
| 6 | $5.8 \times 10^{10}$ |
| 7 | $4.6 \times 10^{10}$ |
| 8 | $5.0 \times 10^{10}$ |
| 9 | $5.0 \times 10^{10}$ |
| 10 | $4.6 \times 10^{10}$ |
| 11 | $5.2 \times 10^{10}$ |
| 12 | $5.6 \times 10^{10}$ |
| 13 | $5.6 \times 10^{10}$ |
| 14 | $5.0 \times 10^{10}$ |
| 15 | $4.6 \times 10^{10}$ |
| 16 | $4.6 \times 10^{10}$ |
| 17 | $5.8 \times 10^{10}$ |
| 18 | $5.6 \times 10^{10}$ |
| 19 | $5.0 \times 10^{10}$ |
| 20 | $5.0 \times 10^{10}$ |
| 21 | $4.8 \times 10^{10}$ |
| 22 | $4.8 \times 10^{10}$ |
| 23 | $5.0 \times 10^{10}$ |
| 24 | $5.2 \times 10^{10}$ |
| 25 | $5.6 \times 10^{10}$ |
| 26 | $4.6 \times 10^{10}$ |
| 27 | $5.4 \times 10^{10}$ |
| 28 | $5.4 \times 10^{10}$ |
| 29 | $5.8 \times 10^{10}$ |
| 30 | $4.6 \times 10^{10}$ |
| 31 | $5.0 \times 10^{10}$ |
| 32 | $5.4 \times 10^{10}$ |
| 33 | $5.8 \times 10^{10}$ |
| 34 | $5.0 \times 10^{10}$ |
| 35 | $4.8 \times 10^{10}$ |

Materials for Further Examples

Reagents for dideoxynucleotide sequencing were from United States Biochemicals. Enzymes and plasmid pMal-p2 were from New England Biolabs. Maxisorp immunoplates were from NUNC (Roskilde, Denmark). E. coli XL1-Blue was from Stratagene; the construction of E. coli SS-320 is described above. Bovine serum albumin (BSA), Tween 20, and o-phenylenediamine dihydrochloride were from Sigma. I-ERP/anti-M13 conjugate was from Pharmacia Biotech. Streptomyces avidinii was from ATCC (accession no. 27419). Goat anti-streptavidin polyclonal antibody was from Zymed Laboratories (South San Francisco, USA).

Oligonucleotides for Examples 8-21

DNA degeneracies are represented in the IUB code (K=G/T, N=A/C/G/T, R=A/G, S=G/C, W=A/T, Y=C/T).

IPTG-1:
(SEQ ID NO. 9)
AAAAGAATTCCCGACACCATCGAATGGTGC

IPTG-2:
(SEQ ID NO. 10)
ACCAGATGCATAAGCCGAGGCGGAAAACATCATCG

IPTG-3:
(SEQ ID NO. 11)
TTTTCTAGACAGGCCTCCCACCAGATGCATAAGCCGAGGCGGAAAACATC
ATCGTC

SAV-1:
(SEQ ID NO. 12)
GGCTATCGGAATGCATCGGGCATCACCGGCACCTG

SAV-2:
(SEQ ID NO. 13)
GAGTCATAGTCGTCAGGCGCCTCCTCCGGATCCTCCACCCACCTTGGTGA
AGGTGTCGTGG hGH-1:
(SEQ ID NO. 14)
GGGTATCTAGAGGTTGAG hGH-2:
(SEQ ID NO. 15)
TGGAGCTCCCGGATCCTCCACCGCTCTGGAAGCCACAGCTGCCCTC g8stop1:
(SEQ ID NO. 16)
GGATCCGGGAGCTCCAGCTGATGAGGTGACGATCCCGCAAAA g8stop2:
(SEQ ID NO. 17)
GATCCCGCAAAAGCGGCCTGATGATCCCTGCAAGCCTCAGCG g8stop3:
(SEQ ID NO. 18)
CAAGCCTCAGCGACCGAATGATGAGGTTATGCGTGGGCGATG g8stop4:
(SEQ ID NO. 19)
GCGTGGGCGATGGTTGTTTGATGAGTCGGCGCAACTATCGGT g8stop5:
(SEQ ID NO. 20)
GCAACTATCGGTATCAAGTGATGAAAGAAATTCACCTCGAAA g8V1:
(SEQ ID NO. 21)
GGATCCGGGAGCTCCAGCRNTNASRNTNASNASNYCRNTRNARNTRNTTT
TAACTCCCTGCAAGCC g8V2:
(SEQ ID NO. 22)
GATCCCGCAAAAGCGGCCNWTNASRNTNYTNASRNTRNTRNTRNTNASTA
TATCGGTTATGCGTGG g8V3:
(SEQ ID NO. 23)
CAAGCCTCAGCGACCGAANWCNWCNKTNWCNYYTNKGNYTNKGNWTNWTG
TCATTGTCGGCGCAACTATC -continued g8V4:
(SEQ ID NO. 24)
GCGTGGGCGATGGTTGTTNWTNWCNWTNKTNYTNYTNNTNNTNNTAAGCT

GTTTAAGAAATTCACC g8V5:
(SEQ ID NO. 25)
GCAACTATCGGTATCAAGNNGNNSAAGAAAANNSNNGNNGAAAANNGNNGTG

ATAAACCGATACAATTAAAGGC g8(1a):
(SEQ ID NO. 26)
GATCCCGCAAAAGCGGCCTATGAGGCTCTTGAGGATATTGCTACTAACTA

TATCGGTTATGCGTGG

R64A:
(SEQ ID NO. 27)
CCGACACCCTCCAATGCTGAGGAAACACAACAGAAA

D171A:
(SEQ ID NO. 28)
TTCAGGAAGGACATGGCTAAGGTCGAGACATTCCTG

Y164A/R178A:
(SEQ ID NO. 29)
AACTACGGGCTGCTCGCTTGCTTCAGGAAGGACATGGACAAGGTCGAGAC

ATTCCTGGCTATCGTGCAGTGCCGC

K172A/R178A:
(SEQ ID NO. 30)
TTCAGGAAGGACATGGACGCTGTCGAGACATTCCTGGCTATCGTCCAGTG

CCGCTCT

Lstop:
(SEQ ID NO. 31)
GGTGGAGGATCCGGGAGCTGATGAGCCGAGGGTGACGATCCC

Lstop2:
(SEQ ID NO. 32)
CACCAAGGTGGTCTAGAGCTAATAATAAGCCGAGGGTGACGATCCC

LV:
GAGGGCAGCTGTGGCTTCGGTGGCGGTVVCVVCVVCVVCVVCV (SEQ ID NO. 34)
VCVVCVVCVVCVVCVVCVVCVVCGGCGGTGCCGAGGGTGACGATCCC

LV5:
(SEQ ID NO. 35)
CACCAAGGTGGTCTAGAGCVVCVVCVVCVVCVVCGCCGAGGGTGACGATC

CC

LV10:
(SEQ ID NO. 36)
CACCAAGGTGGTCTAGAGCVVCVVCVVCVVCVVCVVCVVCVVCVVCVVCG

CCGAGGGTGACGATCCC

LV15:
(SEQ ID NO. 37)
CACCAAGGTGGTCTAGAGCVVCVVCVVCVVCVVCVVCVVCVVCVVCVVCV

VCVVCVVCVVCVVCGCCGAGGGTGACGATCCC

LV20:
(SEQ ID NO. 38)
CACCAAGGTGGTCTAGAGCVVCVVCVVCVVCVVCVVCVVCVVCVVCVVCV

VCVVCVVCVVCVVCVVCVVCVVCVVCVVCGCCGAGGGTGACGATCCC

LV25:
(SEQ ID NO. 39)
CACCAAGGTGGTCTAGAGCVVCVVCVVCVVCVVCVVCVVCVVCVVCVVCV

VCVVCVVCVVCVVCVVCVVCVVCVVCVVCVVCVVCVVCVVCGCCGAG

GGTGACGATCCC g8V2c:
(SEQ ID NO. 40)
AAGTTCGCTAGAGATGCTTATGAGGCTCTTGAGGATATTGCTACTAACTA

TATCGGTTATGCGTGG g8V3c:
(SEQ ID NO. 41)
GAGGATATTGCTACTAACCTTTTCTTTCTCCTTGGGACTGTGCATCTTGT

CATTGTCGGCGCAACT g8V2-E12N:
(SEQ ID NO. 42)
GCAAAAGCGGCCTATAACGCTCTTGAGGATATT g8V2-D16A:
(SEQ ID NO. 43)
TATGAGGCTCTTGAGGCCATTGCTACTAACTAT g8V2-I17S:
(SEQ ID NO. 44)
GAGGCTCTTGAGGATTCAGCTACTAACTATATC g8V2b:
(SEQ ID NO. 45)
GATCCCGCAAAAGCGGCCTATGAGGCTCTTGAGGATATTGCTACTAACTA

TATCGGTTATGCGTGG

L-wt:
(SEQ ID NO. 46)
GAGGGCAGCTGTGGCTTCCAGAGCGGTGGAGGATCCGGGAGCTCCAGCGC

CGAGGGTGACGATCCC

S13A/S171:
(SEQ ID NO. 47)
CCCGCAAAAGCGGCCTTTAACGCTCTGCAAGCCATTGCGACCGAATATAT

CGGTTATGCG g8V3b:
(SEQ ID NO. 48)
CAAGCCTCAGCGACCGAACTTTTCTTTCTCCTTGGGACTGTGCATCTTGT

CATTGTCGGCGCAACT

D1A:
(SEQ ID NO. 49)
TCCGGGAGCTCCAGCGCCAAGAGTGAGAAGTTC

K2E:
(SEQ ID NO. 50)
GGGAGCTCCAGCGATGAGAGTGAGAAGTTCGCT

S3G:
(SEQ ID NO. 51)
AGCTCCAGCGATAAGGGTGAGAAGTTCGCTAGA

E4D:
(SEQ ID NO. 52)
TCCAGCGATAAGAGTGACAAGTTCGCTAGAGAT

K5D:
(SEQ ID NO. 53)
AGCGATAAGAGTGAGGATTTCGCTAGAGATGCT

F6P:
(SEQ ID NO. 54)
GATAAGAGTGAGAAGCCCGCTAGAGATGCTTTT

R8K:
(SEQ ID NO. 55)
AGTGAGAAGTTCGCTAAAGATGCTTTTAACTCC

D9A:
(SEQ ID NO. 56)
GAGAAGTTCGCTAGAGCGGCTTTTAACTCCCTG

Y11F:
(SEQ ID NO. 57)
CCCGCAAAAGCGGCCTTTGAGGCTCTTGAGGAT

E12N:
(SEQ ID NO. 58)
GCAAAAGCGGCCTATAAACGCTCTTGAGGATATT

A13S:
(SEQ ID NO. 59)
AAAGCGGCCTATGAGTCCCTTGAGGATATTGCT

E15Q:
(SEQ ID NO. 60)
GCCTATGAGGCTCTTCAAGATATTGCTACTAAC

D16A:
(SEQ ID NO. 61)
TATGAGGCTCTTGAGGCCATTGCTACTAACTAT

I17S:
(SEQ ID NO. 62)
GAGGCTCTTGAGGATTCAGCTACTAACTATATC

N20E:
(SEQ ID NO. 63)
GAGGATATTGCTACTGAATATATCGGTTATGCG

L21Y:
(SEQ ID NO. 64)
GCCTCAGCGACCGAATATTTCTTTCTCCTTGGG

F22I:
(SEQ ID NO. 65)
TCAGCGACCGAACTTATCTTTCTCCTTGGGACT

F23G:
(SEQ ID NO. 66)
GCGACCGAACTTTTCGGTCTCCTTGGGACTGTG

L24Y:
(SEQ ID NO. 67)
ACCGAACTTTTCTTTTATCTTGGGACTGTGCAT

L25A:
(SEQ ID NO. 68)
GAACTTTTCTTTCTCGCGGGGACTGTGCATCTT

G26W:
(SEQ ID NO. 69)
CTTTTCTTTCTCCTTTGGACTGTGCATCTTGTC

T27A:
(SEQ ID NO. 70)
TTCTTTCTCCTTGGGGCGGTGCATCTTGTCATT

V28M:
(SEQ ID NO. 71)
TTTCTCCTTGGGACTATGCATCTTGTCATTGTC

H29V:
(SEQ ID NO. 72)
CTCCTTGGGACTGTGGTTCTTGTCATTGTCGGC

L30V:
(SEQ ID NO. 73)
CTTGGGACTGTGCATGTTGTCATTGTCGGCGCA

E12N/A13S:
(SEQ ID NO. 74)
GCAAAAGCGGCCTATAACTCCCTTGAGGATATTGCT

E12N/I17S:
(SEQ ID NO. 75)
GCAAAAGCGGCCTATAACGCTCTTGAGGATTCAGCTACTAACTATATC

A13S/I17S:
(SEQ ID NO. 76)
CCCGCAAAAGCGGCCTATGAGTCCCTTGAGGATTCAGCTACTAACTATAT
CGGTTATGCG

E12N/A13S/I17S:
(SEQ ID NO. 77)
GCAAAAGCGGCCTATAACTCCCTTGAGGATTCAGCTACTAACTATATC

Example 8-pS349

A Phagemid for Phage Display of hGH on Protein VIII

A DNA fragment containing the gene for hGH was amplified using the PCR (with a derivative of plasmid pB0475 (Cunningham, B. C., Jhurani, P., Ng, P., and Wells, J. A. (1989) Science 243:1330-1336) as template and oligonucleotides hGH-1 and hGH-2 as primers). The DNA fragment was digested with NsiI and cloned into a protein VIII display phagemid (Lowman, H. B., Chen Y. M., Skelton, N. J., Mortensen, D. L., Tomlinson, E. E., Sadick, M. D., Robinson, I. C. A. F., and Clark, R. G. (1998) Biochemistry 37:8870-8878) which had been first digested with Kan and treated with T4 DNA polymerase to produce blunt ends and subsequently digested with NsiI. The resulting phagemid was designated pS135a.

The PCR was used with primers IPTG-1 and IPTG-2 to amplify a 1.6 kbp fragment of pMal-p2 (New England Biolabs Product Catalog (1996-97) p212) containing the lacIq gene and a gene fragment encoding the signal peptide from maltose binding protein under the control of the $P_{tac}$ promoter. The DNA fragment was digested with EcoRI and NsiI and ligated with the large fragment resulting from a similar digestion of pS135a. The resulting phagemid (designated pS349) contains a gene encoding a fusion product (the maltose binding protein signal peptide, followed by hGH, followed by a Gly/Ser-rich linker peptide (QSGGGSGSSS) (SEQ ID NO. 78), and protein VIII of E. coli bacteriophage M13 under the control of the IPTG-inducible $P_{tac}$ promoter (New England Biolabs). In addition, pS349 also contains the lacI9 gene for effective transcription repression in the absence of IPTG.

Example 9-pW277e

A Phagemid for Phage Display of SAV on Protein VIII

A derivative of pS349 was constructed and designated pS657a. pS657a differs from pS349 in two respects. Firstly, the gene encoding hGH has been replaced by sequence encoding a pentapeptide (GGRPV) (SEQ ID NO. 79). Secondly, the introduction of an XbaI site in the linker preceding protein VIII has changed the codon encoding glutamine to an amber (TAG) stop codon. Digestion with NsiI and XbaI excises the pentapeptide-encoding sequence and allows for the directional cloning of appropriately digested DNA fragments into a position analogous to that of the hGH gene in pS349.

A PCR was performed with Streptomyces avidinii genomic DNA as template and oligonucleotides SAV-1 and SAV-2 as primers. The amplified DNA fragment contained codons 16 to 133 of the streptavidin (SAV) gene open reading frame flanked by an NsiI site at the 5' end and an XbaI site at the 3' end. The fragment was digested with NsiI and XbaI and cloned into similarly digested phagemid pS657a. The resulting phagemid (pW277e) encodes a fusion product similar to that encoded by pS349 except that hGH has been replaced by SAV. Also, an amber codon has been positioned between the segments encoding SAV and protein VIII.

Example 10

Construction of Mutant Protein VIII Libraries

For library construction, protein VIII was divided into five zones encompassing approximately 10 contiguous residues each (zone 1, residues 1 to 10; zone 2, residues 11 to 20; zone 3, residues 21 to 30; zone 4, residues 31 to 39; zone 5, residues 40 to 50). Libraries were constructed using a modified version (SS320 described above) of a previously described method (Lowman, H. B. (1998) Phage Display of Peptide Libraries on Protein Scaffolds. From: *Methods in Molecular Biology, vol. 87: Combinatorial Peptide Library Protocols*. Edited by: S. Cabilly. Publisher: Humana Press Inc., Totowa, N.J.). Briefly for each zone, an oligonucleotide (g8stopn, where "n" is the zone number) was used with either pS349 (for hGH display) or pW277e (for SAV display) as template to introduce two consecutive TGA stop codons within the zone, using the method of Kunkel (Kunkel, T. A. (1985) *Proc. Natl. Acad. Sci. USA* 82:488-492). The resulting phagemid was used as template in a second round of the Kunkel method with a degenerate oligonucleotide (g8Vn, where "n" is the zone number) designed to introduce mutations at the desired sites.

Libraries were constructed for each zone of the protein VIII moiety within the hGH-protein VIII fusion product of pS349. The diversities of these libraries were as follows: zone-1, $2.5 \times 10^{10}$; zone-2, $2.5 \times 10^{10}$; zone-3, $2.5 \times 10^{10}$; zone-4, $1.3 \times 10^{10}$; and zone-5, $5.0 \times 10^9$. Libraries were constructed for zone-1, zone-2, and zone-3 of the protein VIII moiety within the SAV-protein VIII fusion product of pW277e. The diversities of these libraries were as follows: zone-1, $3.0 \times 10^9$; zone-2, $6.8 \times 10^9$; and zone-3, $8.6 \times 10^9$.

Libraries were also constructed to vary the linker between the fused protein and protein VIII. For hGH display, the oligonucleotide Lstop was used to introduce two consecutive TGA stop codons within the linker between hGH and protein VIII. The resulting phagemid was used as template in a second round of the Kunkel method with a degenerate oligonucleotide (ZF) designed to introduce a linker of the form (Gly) 3 (Xaa) i4 (Gly) 2 (where Xaa is a variable position) (SEQ ID NO: 292) in place of the Gly/Ser-rich linker encoded by pS349. For SAV display, the linker was varied between SAV and variant protein VIII (1e) (see FIG. 2, for the sequence of protein VIII (1e)). The oligonucleotide Lstop2 was used to introduce three consecutive TAA stop codons within the linker between SAV and protein VIII (1e). The resulting phagemid was used as template for the production of libraries with linkers of variable length and sequence. The oligonucleotides LV5, LV10, LVI S>LY20, and LV25 were used to construct libraries with linkers containing 5, 10, 15, 20, or 25 variable residues, respectively.

The diversities of the linker libraries were as follows: hGH-LV-protein VIII, $1.8 \times 10^{10}$; SAV-LV5-protein VIII, $1.4 \times 10^{10}$; SAV-LV10-protein VIII, $9.8 \times 10^9$; SAV-LV15-protein VIII, $1.2 \times 10^{10}$; SAV-LV20-protein VIII, $1.1 \times 10^{10}$; SAV-LV25-protein VIII, $6.0 \times 10^9$.

Example 11

Selection of Protein VIII Variants which Increase Fusion Protein Display

Phage from the hGH-protein VIII libraries described above were cycled through rounds of binding selection with hGHbp (Fuh, G. et al. (1990) *J. Biol. Chem.* 265:3111; Cunningham, B. C., Ultsch, M., De Vos, A. M., Mulkerrin, M. G., Clauser, K. R., and Wells, J. A. (1991) *Science* 254:821-825) coated on 96-well Maxisorp immunoplates as a target. All libraries were sorted separately. Phage were propagated in *E. coli* SS320 cells with M13-VCS helper phage (Stratagene). After five rounds of binding selection, individual phage were isolated and analyzed for hGH display using a phage ELISA with hGHbp as target (see below). Phage exhibiting strong signals in the phage ELISA were sequenced (Sanger, F. et al. (1979) *Proc. Natl. Acad. Sci. USA*, 74:5463-5467).

The SAV-protein VIII libraries were pooled and binding selection was performed as described above for the hGH-protein VIII libraries, except that the binding target was an anti-SAV polyclonal antibody. Phage were propagated in the SupE *E. coli* strain XL1-Blue in which the amber stop codon is suppressed as glutamine (Bullock, W. 0., Fernandez, J. M., and Short, J. M. (1987) *Biotechniques* 5:376-379).

Example 12

Site-Directed Mutagenesis

Mutageneses were performed using the method of Kunkel (Kunkel, et al. (1987) *Meth. Enzymol.* 154:367-382). Template DNA was prepared by growing an appropriate plasmid (e.g., containing the hGH gene fused to the carboxy-terminal half of M13 gene III) in host cells with M13-K07 phage added as helper phage. Single-stranded, uracil-containing DNA was prepared for mutagenesis to introduce the desired mutation into the hGH-protein VIII gene fusion. Oligonucleotide-directed mutagenesis was carried out using T7 DNA polymerase and the appropriate oligodeoxy-nucleotides. Clones from the mutagenesis were confirmed by dideoxy DNA sequencing.

The mutagenic oligonucleotide g8(1a) was used to introduce the protein VIII mutations of selectant hGH-protein VIII (1a) into phagemid pW277e. Mutant hGH genes were constructed using the appropriately named oligonucleotide (e.g., oligonucleotide R64A encodes the mutation of Arg64 to Ala).

The mutagenic oligonucleotide g8V2c was used to introduce the mutations of protein VIII(2a) into the gene encoding protein VIII(1a). The mutagenic oligonucleotide g8V3c was used to introduce the mutations of protein VIII(3a) into the gene encoding protein VIII(2a). The mutation E12N, D16A, or 117S was introduced into the gene encoding protein VIII (2a) using the mutagenic oligonucleotide g8V2-E12N, g8V2-D16A, or g8V2-117S.

Example 13

Phage ELISAs for Determining Relative Levels of Fusion Protein Display on Protein VIII and Protein VIII Variants Thereof Cultures of *E. coli* XL1-Blue (Bullock, W. 0., Fernandez, J. M., and Short, J. M. (1987) *Biotechniques* 5:376-379) harboring phagemids were grown for 8 hours at 37° C. in 1 mL of 2YT, 50 µg/mL carbenicillin, 10 µg/mL tetracycline. The cultures were transferred to 30 mL of the same media (supplemented with M13-VCS helper phage ($10^{10}$ phage/mL) and IPTG at the appropriate concentration) for overnight growth at 37° C. Phage were harvested from the culture supernatant by precipitation twice with PEG/NaCl (Lowman, H. B., (1998) Phage Display of Peptide Libraries on Protein Scaffolds. From: *Methods in Molecular Biology, vol. 87: Combinatorial Peptide Library Protocols*. Edited by: S. Cabilly. Publisher: Humana Press Inc., Totowa, N.J.) and resuspended in 1 mL of PBS, 0.2% BSA, 0.1% Tween (BSA blocking buffer). Phage concentrations were determined spectrophotometrically ($\epsilon_2 68=1.2\times10^8$ $M^{-1}$ $cm^{-1}$).

Maxisorp immunoplates (96-well) were coated with target protein for 2 hours at room temperature (100 μL at 5 μg/mL in 50 mM carbonate buffer, pH 9.6). The plates were then blocked for 1 h with 0.2% BSA in phosphate-buffered saline (PBS) and washed (8×) with PBS, 0.05% Tween 20. Phage particles were diluted serially using PBS, 0.2% BSA, 0.1% Tween (BSA blocking buffer) and then transferred (100 μL) to coated wells. After 1 h, plates were washed (8×) with PBS, 0.05% Tween 20, incubated with 100 FL of 1:3000 HRP/anti-M13 conjugate in BSA blocking buffer for 30 min, and then washed with PBS, 0.05% Tween 20 (8×) and PBS (2×). Plates were developed using an o-phenylenediamine dihydrochloride/$H_2O_2$ solution (100 μL), stopped with 2.5 M $H_2SO_4$ (50 μL), and read spectrophotometrically at 492 nm. Li, B. et al., (1995) *Science* 270:165-1660.

Example 14

Display of SAV on a Protein VIII Variant Selected for Increased Display of hGH

The method of Kunkel (Example 12) was used with the mutagenic oligonucleotide g8V2b* to introduce the protein VIII mutations of selectant hGH-protein VIII(2a) into phagemid pW277e. The resulting phagemid encoded a fusion protein identical to that encoded by pW277e except that the protein VIII within the fusion moiety contained the mutations of variant protein VIII(2a). SAV display was measured by phage ELISAs (Example 13) with either anti-SAV polyclonal antibody (FIG. 4a) or biotinylated BSA (FIG. 4b) as target.

Example 15

Display and detection of hGH variants with attenuated binding affinities.

hGH mutants with reduced site 1 binding affinity for hGHbp (Pierce et al., above) were displayed as fusions to either wild type protein VIII or variant protein VIII(1a). Mutant hGH genes were constructed using the method of Kunkel (Example 12) with the following mutagenic oligonucleotides: hGH(R64A), oligonucleotide R64A; hGH (D171A), oligonucleotide D 171A; hGH(Y164A/R178A), oligonucleotide Y164A/R178.A; hGH(K172A/R178A), oligonucleotide K172A/R178A. For display of hGH fused with wild type protein VIII, the mutagenesis template was pS349. For display of hGH fused with variant protein VIII(1a), the template was a derivative of pS349 encoding a fusion protein consisting of hGH fused to protein VIII(1a). hGH display was measured by phage ELISA (Example 13) with the hGHbp as target (FIG. 3).

Example 16

Figure 5:
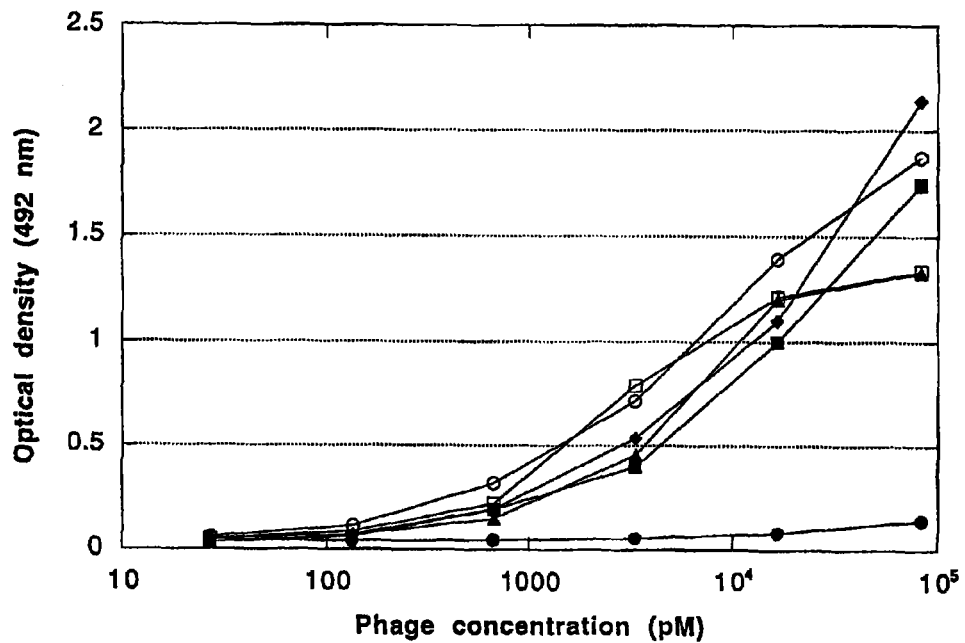
FIG. 5: Phage ELISAs for hGH display with protein VIII variants combining mutations in different zones. An anti-hGH monoclonal antibody was used as target. Display was measured for hGH displayed as a fusion with protein VIII (filled circles), protein VIII(1a) (filled squares), protein VIII (2a) (filled diamonds), protein VIII(3a) (filled triangles), protein VIII containing the mutations of protein VIII(1a) and protein VIII(2a) (unfilled circles), or protein VIII containing the mutations of protein VIII(2a) and protein VIII(3a) (unfilled squares).

Display of hGH with Protein VIII Variants Combining Mutations in Different Zones The method of Kunkel (Example 12) was used to combine mutations from protein VIII variants independently selected for increased hGH display. The oligonucleotide g8V2c was used to introduce the mutations of protein VIII(2a) into the gene encoding protein VIII(1a). The oligonucleotide g8V3c was used to introduce the mutations of protein VIII(3a) into the gene encoding protein VIII(2a). hGH display was measured by phage ELISA (Example 13) with an anti-hGH monoclonal antibody as target (FIG. 5).

Example 17

Figure 6:
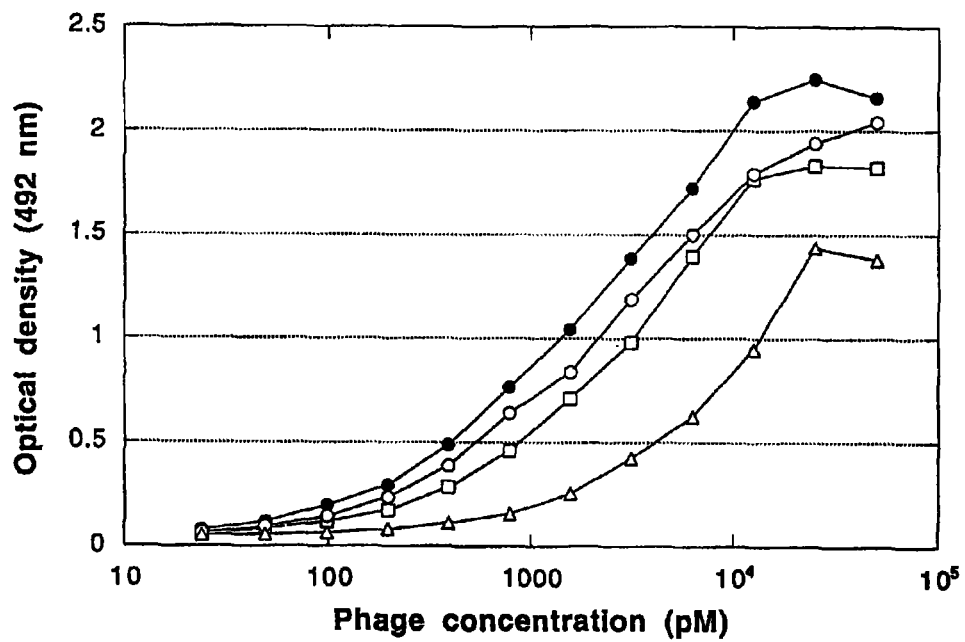
FIG. 6: Phage ELISAs for hGH display with protein VIII variants derived from protein VIII(2a). An anti-hGH monoclonal antibody was used as target. Display was measured for hGH displayed as a fusion with either protein VIII(2a) (filled circles) or with protein VIII(2a) containing the following mutation: E12N (unfilled squares), D16A (unfilled circles), or I17S (unfilled triangles).

Display of hGH with Protein VIII Variants Derived from Protein VIII(2a) Through Back Mutations to the Wild Type Sequence The method of Kunkel (Example 12) was used to introduce the mutation E12N, D 16A, or I17S into the gene encoding protein VIII(2a) using the mutagenic oligonucleotide g8V2-E12IV, g8V2-D16A, or g8V2-I17S, respectively. hGH display was measured by phage ELISA (Example 13) with an anti-hGH monoclonal antibody as target (FIG. 6).

Example 18

Display of hGH with Phagemid pS1607

Figure 9:
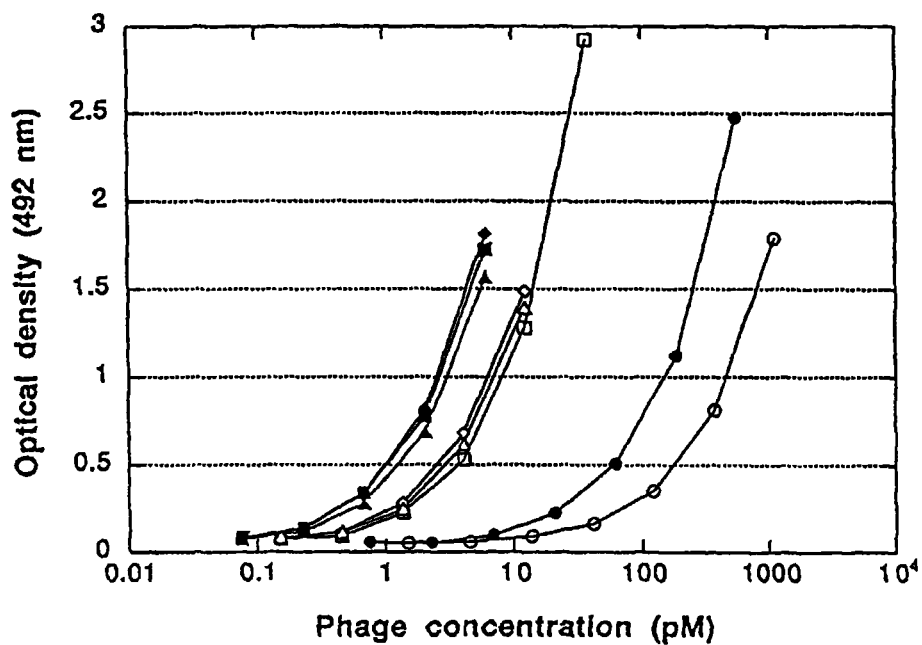
FIG. 9: Phage ELISAs for hGH display with protein VIII and selected protein VIII variants. The hGHbp was used as target (Kd=1.6 nM, Pearce, K. H. Jr. et al., (1997) *J. Biol. Chem.* 272:20595-20602). Display was measured for hGH-protein VIII expressed from phagemid pS1607 (see Example 11) (circles), hGH-protein VIII(1a) (squares), hGH-protein VIII(2a) (diamonds), and hGH-protein VIII(3a) (triangles). Phage were produced from cultures which were either uninduced (unfilled) or induced with 10 uM IPTG (filled). The sequences for the protein VIII variants are show in FIG. 1.
Figure 10:
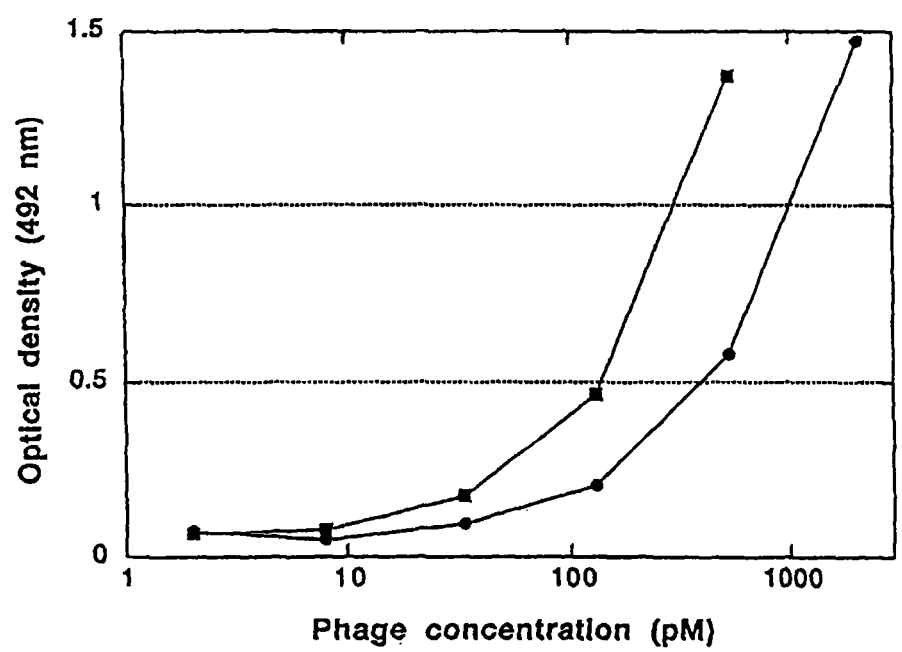
FIG. 10: Phage ELISAs for Fab display with protein VIII and a protein VIII mutant. A monoclonal antibody specific for a peptide flag fused to the N-terminus of the Fab heavy chain was used as target. Display was measured for Fab-protein VIII (circles) or Fab-protein VIII(S13A/S17I).

Further sequence analysis revealed that the fusion-protein VIII gene contained within the pS349 clone used in FIGS. 2, 3, 5, and 8 had a deletion of five base pairs consisting of the final base pair encoding the linker between hGH and protein VIII and the first four base pairs encoding protein VIII. This deletion introduced a frameshift which reduced hGH display. The method of Kunkel (Example 12) was used with the mutagenic oligonucleotide L-wt to correct the frameshift in pS349. The resulting phagemid was designated pS1607. Phagemid pS1607 differs from pS349 only in the addition of five base pairs to correct this frameshift. In pS349, the sequence following the hGH gene is as follows: CAGAGCG-GTGGAGGATCCGGGAGCTCCAGAGGGT (the underlined bases are part of the beginning of the protein VIII gene) (SEQ ID NO. 80). In pS1607, the corresponding sequence is as follows: CAGAGCGGTGGAGGATCCGGGAGCTC-CAgcgccGAGGGT (lower case indicates the bases inserted through mutagenisis with oligonucleotide L-wt) (SEQ ID NO. 81). hGH display was measured by phage ELISA (Example 13) with the hGHbp as target (FIG. 9).

Example 19

Fab Display with a Protein VIII Variant

Phagemid pS1705a directs secretion of a free Fab light-chain and a Fab heavy-chain fused to protein VIII. The Fab heavy-chain also contains a peptide flag (MADPNR-FRGKDL) (SEQ ID NO. 82) fused to its N-terminus which can be detected with a specific monoclonal antibody. The method of Kunkel (Example 12) was used with the mutagenic oligonucleotide S13A/S171 and the template pS1705a, the resulting phagemid was designated pS1709b. Phagemid pS1709b is identical to pS1705a except that the protein VIII gene linked to the Fab heavy-chain contains the mutations S13A/S17I which were observed in protein VIII variants selected for increased display of hGH (FIG. 1B). Fab display was measured by phage ELISA (Example 13) with a peptide flag-specific monoclonal antibody as target. Fab display with pS1709b was greater than Fab display with pS1705a (FIG.

10). Thus protein VIII mutations which were selected for increased display of hGH also increased Fab display.

Example 20

Figure 11:
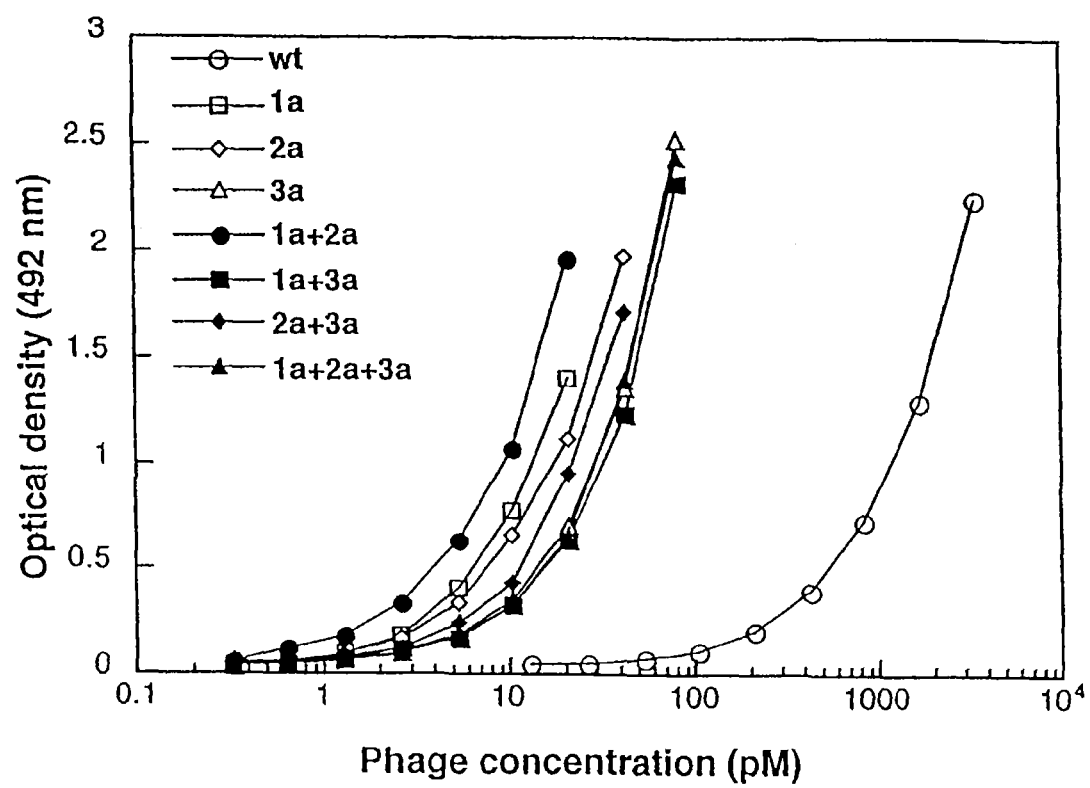
FIG. 11: Phage ELISAs for hGH display with protein VIII variants combining mutations in different zones. An anti-hGH monoclonal antibody was used as target. hGH was fused to wild-type protein VIII (wt), a protein VIII selectant from zone 1, 2, or 3 (1a, 2a, or 3a, respectively) or protein VIII variants combining mutations from these selectants (e.g. 1a+2a combines 1a residues 1 through 10 with 2a residues 11 through 20 and wild type residues 21 through 50). Sequences for the protein VIII selectants are shown in FIG. 1.
Figure 12A:
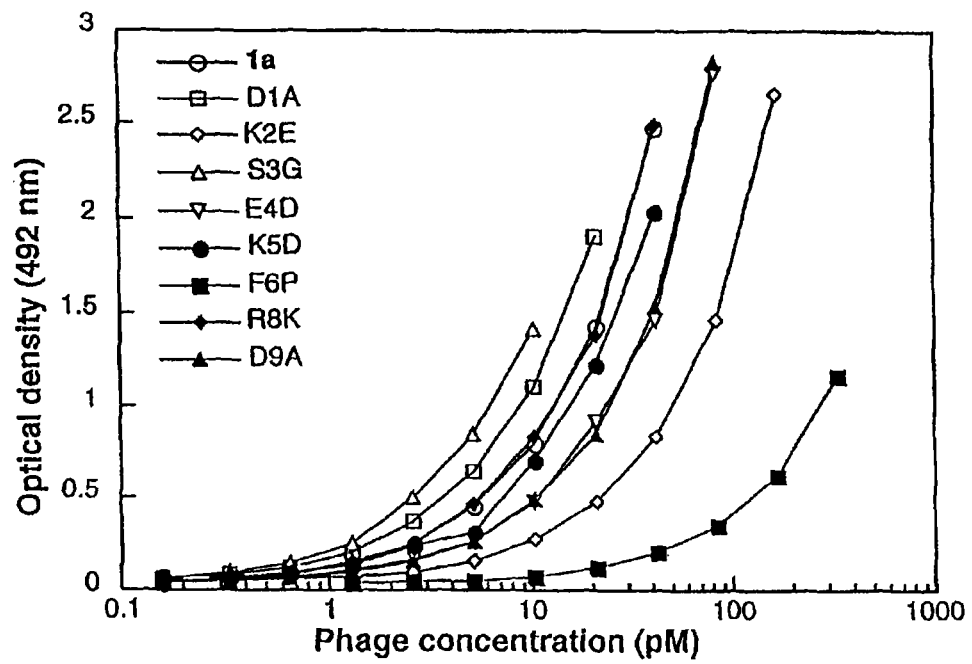
FIG. 12: Site directed mutagenesis of protein VIII variants highlights key positions for enhanced display and enables modulated hGH display. hGH was fused to variants derived from A) zone 1 selectant 1a, B) zone 2 selectant 2a, or C) zone 3 selectant 3a. For each protein VIII selectant, the effect of every possible single back mutation to, the wild-type sequence is shown (e.g. D1A indicates the protein VIII variant obtained by introducing the mutation D1A into selectant 1a. In addition, D) double and triple back mutations were introduced into zone 2 selectant 2a to further modulate hGH display. Sequences for the protein VIII selectants are shown in FIG. 1.
Figure 12B:
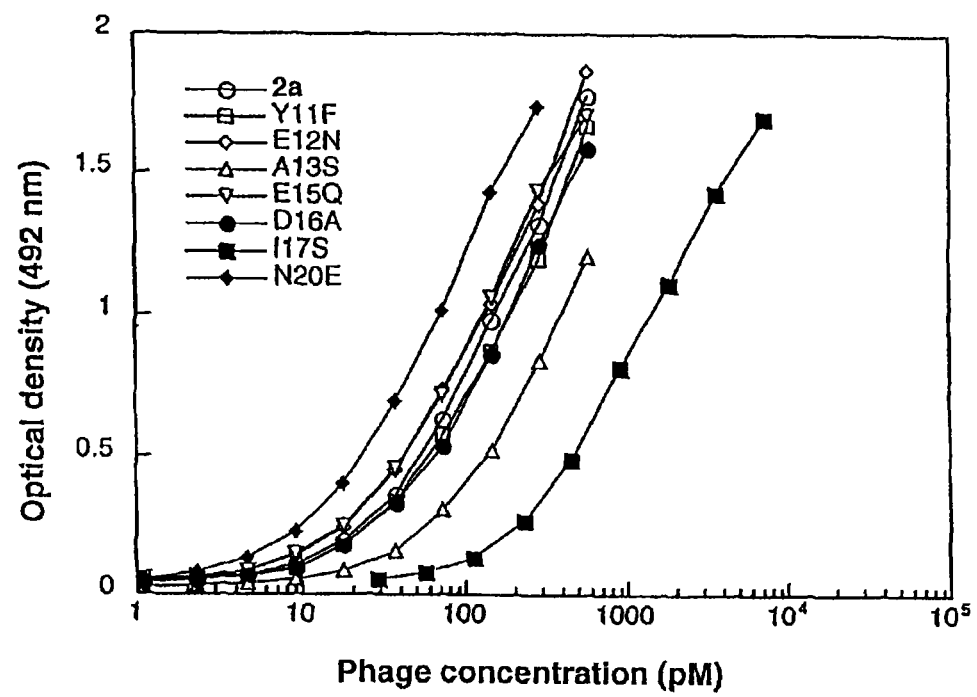
Figure 12C:
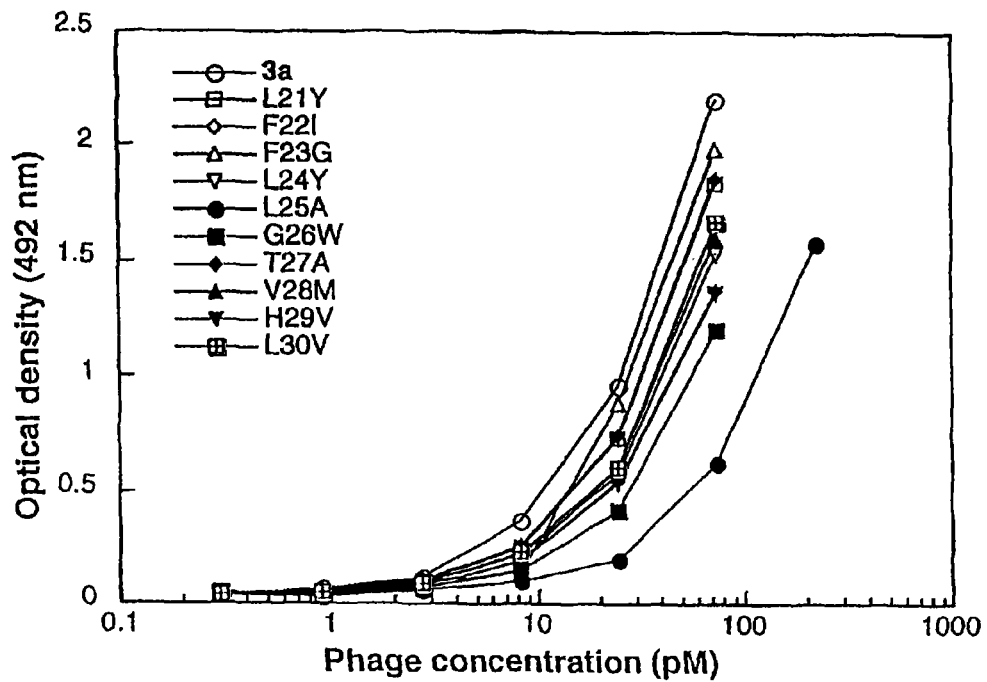
Figure 12D:
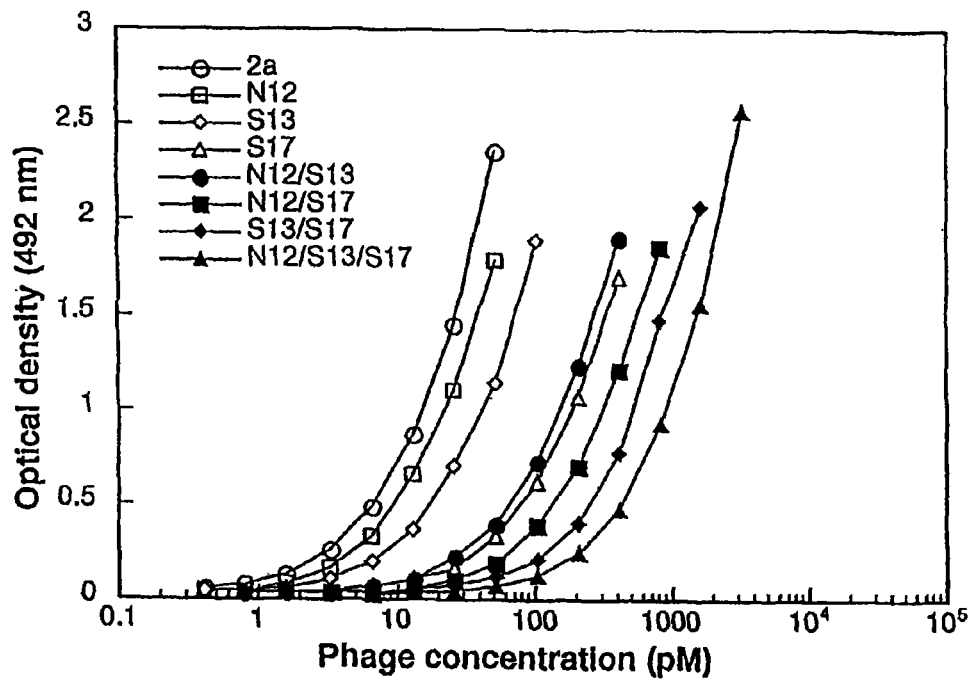

Display of hGH with Protein VIII Variants Combining Mutations in Different Zones The method of Kunkel (Example 12) was used to combine mutations from protein VIII variants independently selected for increased hGH display. The oligonucleotide g8V2c was used to introduce the mutations of protein VIII(2a) into the gene encoding protein VIII(1a). The oligonucleotide g8V3c was used to introduce the mutations of protein VIII(3a) into the gene encoding protein VIII(2a). The oligonucleotide g8V3b was used to introduce the mutations of protein VIII (3a) into the gene encoding protein VIII(1a). The oligonucleotide g8V3c was used to introduce the mutations of protein VIII(3a) into the gene encoding protein VIII containing the mutations of protein VIII(1a) and protein VIII(2a). hGH display was measured by phage ELISA (Example 13) with an anti-hGH monoclonal antibody as target. All protein VIII variants increased hGH display in comparison with wild-type protein VIII (FIG. 11).

Example 21

Modulated Display of hGH with Protein VIII Variants Derived from Protein VIII Selectants Through Back Mutations to the Wild-Type Sequence Back mutation scanning is the independent conversion of each mutation within a coat protein, such as protein VIII, variant back to the wild-type sequence. A protein VIII selectant with mutations in either zone 1, 2, or 3 was subjected to back mutation scanning analysis. The following selectants were analyzed: protein VIII(1a), protein VIII(2a), and protein VIII(3a) (FIG. 1). The method of Kunkel (Example 12) was used to mutate each mutation in a given variant back to the wild-type sequence. Appropriately designed and named oligonucleotides were used (e.g. the oligonucleotide D1A mutates Asp 1 in protein VIII(1a) to Ala). In addition, double and triple back mutations were introduced into protein VIII (2a), again using appropriately designed and named oligonucleotides (e.g., the oligonucleotide A13S/I17S simultaneously mutates A13 and I17 to Ser).

hGH display was measured by phage ELISA (Example 13) with an anti-hGH monoclonal antibody as target. Some of the back mutations reduced hGH display, allowing for the modulation of hGH display (FIG. 12).

Oligonucleotides for Examples 22-25

Add-NX:
(SEQ ID NO: 83)
GATGGTGAAGCTGCGGCTGATGCATCTGGTAGCGTCTAGAGCCACCAT

CACCATCACCAT add-P12-7:
(SEQ ID NO: 84)
GCTGTCGGTATTATTTACATGCTCCTCGTGGAGGCGTCGCCCTGGGCT

GCTAAGGCGCCA

-continued

G-0:
(SEQ ID NO: 85)
ACCTCGAAAGCAAGCCATCACCATCACCATGCG

G-1:
(SEQ ID NO: 86)
ACCTCGAAAGCAAGCGGCCATCACCATCACCATGCG

G-2:
(SEQ ID NO: 87)
ACCTCGAAAGCAAGCGGTGGCCATCACCATCACCATGCG

G-3:
(SEQ ID NO: 88)
ACCTCGAAAGCAAGCGGTGGTGGCCATCACCATCACCATGCG

G-4:
(SEQ ID NO: 89)
ACCTCGAAAGCAAGCGGCGGTGGTGGCCATCACCATCACCATGCG

G-6:
(SEQ ID NO: 90)
ACCTCGAAAGCAAGCGGTGGTGGCGGTGGTGGCCATCACCATCACCAT

GCG

G-7:
(SEQ ID NO: 91)
ACCTCGAAAGCAAGCGGCGGTGGTGGCGGTGGTGGCCATCACCATCAC

CATGCG

G8:
(SEQ ID NO: 92)
ACCTCGAAAGCAAGCGGTGGCGGTGGTGGCGGTGGTGGCCATCACCAT

CACCATGCG

G-9:
(SEQ ID NO: 93)
ACCTCGAAAGCAAGCGGCGGTGGCGGTGGTGGCGGTGGTGGCCATCAC

CATCACCATGCG

G-10:
(SEQ ID NO: 94)
ACCTCGAAAGCAAGCGGTGGCGGTGGCGGTGGTGGCGGTGGTGGCCAT

CACCATCACCATGCG

G-12:
(SEQ ID NO: 95)
ACCTCGAAAGCAAGCGGTGGCGGTGGCGGTGGCGGTGGTGGCGGTGGT

GGCCATCACCATCACCATGCG

G-14:
(SEQ ID NO: 96)
ACCTCGAAAGCAAGCGGTGGTGGCGGTGGCGGTGGTGGC

GGTGGTGGCCATCACCATCACCATGCG

G-16:
(SEQ ID NO: 97)
ACCTCGAAAGCAAGCGGCGGCGGTGGTGGCGGTGGCGGTGGCGGT

GGTGGCGGTGGTGGCCATCACCATCACCATGCG

G-18:
(SEQ ID NO: 98)
ACCTCGAAAGCAAGCGGCGGTGGCGGCGGTGGTGGCGGTGGCGGT

GGCGGTGGTGGCGGTGGTGGCCATCACCATCACCATGCG

-continued

G-20:
(SEQ ID NO: 99)
ACCTCGAAAGCAAGCGGTGGTGGCGGTGGCGGCGGTGGTGGTGGCGGT

GGCGGTGGCGGTGGTGGCGGTGGTGGCCATCACCATCACCATGCG

Lib-zone1:
(SEQ ID NO: 100)
CAAGGACCATAGATTATGNNSNNSNNSNNSNNSNNSAAGTTTCTGAAA

GTTTTTGTTTTT

Lib-zone2:
(SEQ ID NO: 101)
ATTATGAGCAAGAGCACTNNSNNSNNSNNSNNSNNSGTTTTTGTTTTT

TCTGTTGAT

Lib-zone3:
(SEQ ID NO: 102)
TTCAAAAAGTTTCTGAAANNSNNSNNSNNSNNSNNSNNSNNSNNSNNS

AATTGGATTTGGGCTGTCGGT

Lib-zone4:
(SEQ ID NO: 103)
GTTTTTTTCTGTTGATGTTGATNNSNNSNNSNNSNNSNNSNNSNNSNN

SNNSGCGGCTGATGCATTCCCA

Lib-zone5:
(SEQ ID NO: 104)
TGGGCTGTCGGTATTATTNNSNNSNNSNNSNNSNNSNNSNNSNNSNNS

GCTGCTAAGGCGCCAGACGATGGT

Lib-zone6:
(SEQ ID NO: 105)
AGCGCTCAGCTGAGCAACTTCNNSNNSNNSNNSNNSNNSNNSNNSNNS

NNSGCGGCTGATGCATTCCCA

Lib-linker:
(SEQ ID NO: 106)
GATGGTGAAGCTGCGGCTVVCVVCVVCVVCVVCVVCVVCVVCVVCVVC

VVCVVCVVCVVCFATGCATTCCCAACTATACCA

Pep-ins:
(SEQ ID NO: 107)
ACTTTCAAAAAGTTTCTGAAANWTNKTNKTNWTNYTNYTNKYNWTNWT

NWTNWTNWTNKGNYTNKGNYTNWCNKTNWTNWTGAGACTGCTAGCGCT

CAG

Example 22

Figure 13:
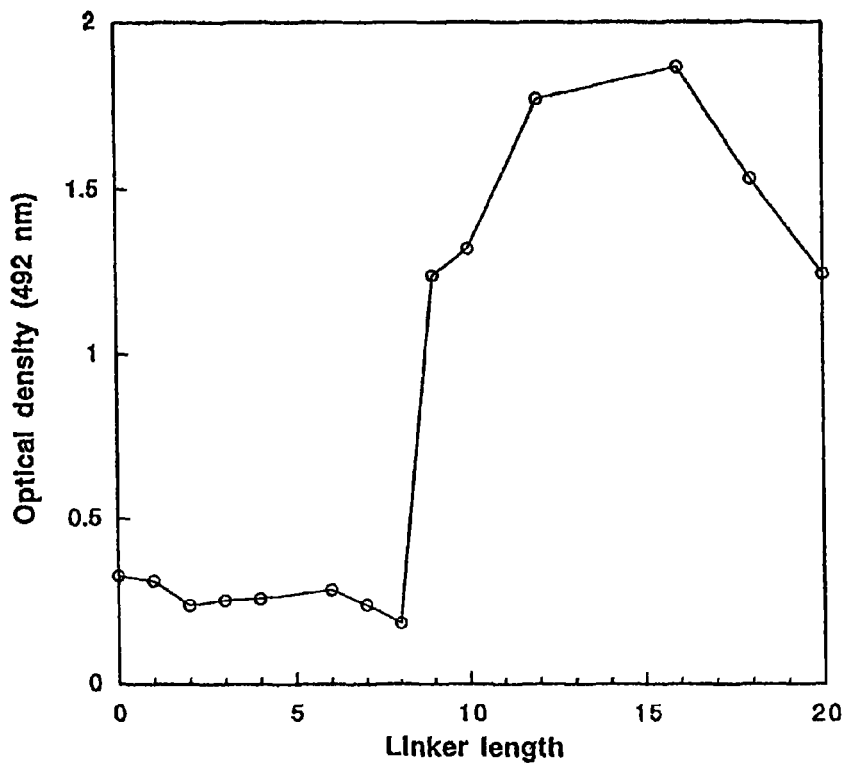
FIG. 13: Phage ELISAs for the display of a peptide fused to the C-terminus of protein VIII using poly-glycine linkers. A hexapeptide (HHHHHA (SEQ ID NO. 279 ), referred to as a pentaHis flag) was fused to the C-terminus of protein VIII with intervening linkers containing varying numbers of Gly residues as indicated (linker length, X-axis). There is a large increase in display when the linker length is increased from eight to nine residues. The phage were used at a concentration of $2 \times 10^{12}$ phage/mL. An anti-(His)5 antibody (Qiagen) was used as the capture target. See Example 22.

Determination of Optimal Linker Length for the Display of a Peptide Fused to the C-Terminus of Protein VIII Standard molecular biology techniques were used to construct a phagemid designated pS1290a. pS1290a is identical to phagemid pS349 (see Example 8) except that the open reading frame (ORF) under the control of the IPTG-inducible Ptac promoter (New England Biolabs) has been deleted and replaced by a new ORF. The new ORF encodes a fusion product consisting of the maltose binding protein signal peptide, followed by a Ser residue, followed by residues 2-50 of mature protein VIII of E. coli bacteriophage M13. The ORF is followed by two TAA stop codons, followed by. sequence (CACCATCACCATCACCATGCG) (SEQ ID NO: 108) encoding a heptapeptide (HHHHHHA (SEQ ID NO: 280), hexaHis) flag or epitope tag, followed by two stop codons (TGATAA).

pS 1290a was mutated using the method of Kunkel (Example 12). The two TAA stop codons and the first His codon following the protein VIII C-terminus were replaced by various numbers of Gly codons. Appropriately designed and named mutagenic oligonucleotides were used (e.g., oligonucleotide G-6 inserts six Gly codons). This resulted in the construction of a series of phagemids encoding ORFs designed to secrete protein VIII molecules with C-terminal fusions consisting of linkers containing varying numbers of Gly residues followed by a pentaHis flag (HHHHHA (SEQ ID NO: 279)). The number of Gly residues was varied from zero (i.e., the polyHis flag was fused directly to the protein VIII C-terminus) to 20. PentaHis flag display was measured by phage ELISA (Example 13) with an anti-(His)5 antibody (Qiagen) as the capture target (FIG. 13).

Example 23

Optimization of the Linker Sequence for Display of a Peptide Fused to the C-Terminus of Protein VIII Libraries were constructed to vary the linker between protein VIII and the hexaHis flag encoded by pS1290a. Libraries were constructed using a modified version of a previously described method (see Example 10). Mutagenic oligonucleotides were used to replace the two TAA stop codons between protein VIII and the hexaHis flag with libraries of linkers. The lengths of the linkers were varied and depended on the mutagenic oligonucleotides used: oligonucleotides UH-L4, UH-L5, UH-L6, UH-L8, or UH-L10 introduced linkers containing 4, 5, 6, 8, or 10 residues respectively. The total diversity of the linker libraries was $5.7 \times 10^{10}$.

Phage from the linker libraries described above were pooled together and cycled through rounds of binding selection with an anti-(His)4 antibody (Qiagen) as the capture target. After two rounds of selection, individual clones were assayed for hexaHis flag display using a phage ELISA with the anti-(His)4 antibody as target. Clones exhibiting the strongest signals were subjected to DNA sequence analysis and the linker sequences were deduced from the DNA sequence and are shown below.

```
GCC  TGG GAG GAG AAC ATC GAC AGC GCC CCC  (SEQ ID NO. 109)
A    W   E   E   N   I   D   S   A   P    (SEQ ID NO. 110)

CAG  TAC GGG ACG CCG GAC ACC GAC ACC GAC  (SEQ ID NO. 111)
Q    Y   G   T   P   D   T   D   T   D    (SEQ ID NO. 112)

ACG  GGG TGG TTG GAG GGG CCC GAC ACC CCC  (SEQ ID NO. 113)
T    G   W   L   E   G   P   D   T   P    (SEQ ID NO. 114)

CTC  ATG GGC CCC GGC GCG GAC GGC          (SEQ ID NO. 115)
L    M   G   P   G   A   D   G            (SEQ ID NO. 116)

CAC  GAC TCG GTC CCG AGC AAC GGC          (SEQ ID NO. 117)
H    D   S   V   P   S   N   G            (SEQ ID NO. 118)
```

Linkers selected for display of a peptide fused to the C-terminus of protein VIII. The sequences shown were inserted between the final residue of protein VIII and a heptapeptide (HHHHHHA (SEQ ID NO: 280), referred to as a hexaHis flag). For each selectant, the DNA sequence is shown with the deduced amino acid sequence below. The numerical designation for each sequence is shown to the left.

Figure 14:
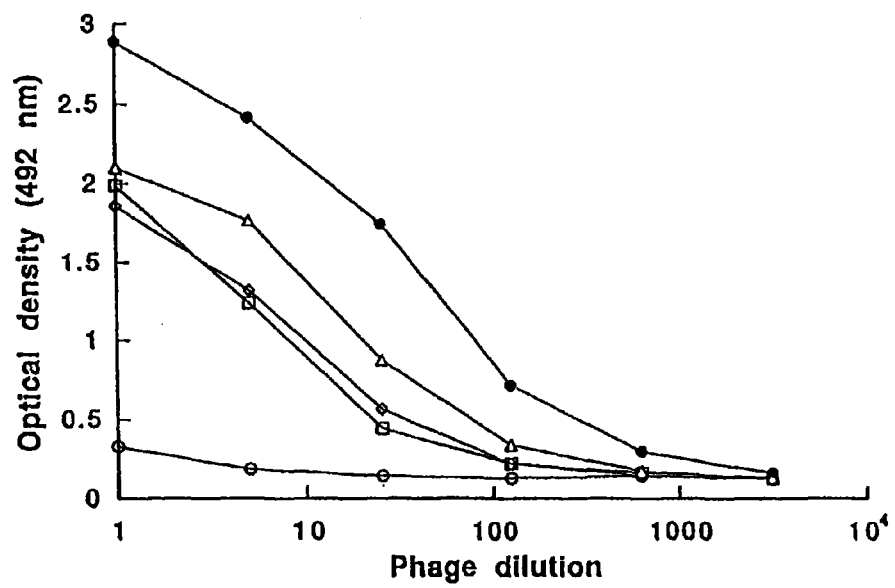
FIG. 14: Phage ELISAs for the display of a peptide fused to the C-terminus of protein VIII using an optimized linker sequence. A polyHis flag was fused to the C-terminus of protein VIII with intervening linkers as follows: (Gly)8 (SEQ ID NO: 288) (open circles), (Gly)9 (SEQ ID NO: 289) (squares), (Gly)10 (SEQ ID NO: 290) (diamonds), (Gly) 12 (SEQ ID NO: 291) (triangles), or optimized linker-1 (filled circles). The highest levels of display were observed with the optimized linker. Phage were serially diluted 5-fold from a starting concentration of 10'3 phage/mL. An anti-(His) 5 (SEQ ID NO: 279) antibody (Qiagen) was used as the capture target.

The level of polyHis flag display achieved with an optimized linker was compared with levels of display achieved with poly-glycine linkers of various length (Example 22)

using a phage ELISA with an anti-(His)5 antibody (Qiagen) as the capture target (FIG. 14).

Example 24

Design and Selection of a New Phage Coat Protein (Protein-12, P12) for the Display of Polypeptides as C-Terminal Fusions This example demonstrates the de novo design of a phage coat protein and the display of a protein of interest on the surface of phage particles containing the fusion protein, illustrating the broad scope of the method of the invention to prepare any variant phage coat protein. The retrotranslation of a peptide is the backward reading of the primary sequence and the resulting peptide is the retro-peptide of the original peptide. For example, the retrotranslation of the peptide Gly-Ala-Leu is the retro-peptide Leu-Ala-Gly.

Standard molecular biology techniques were used to construct a phagemid designated pS1207a. pS1207a is identical to phagemid pS349 (Example 8) except that the ORF under the control of the IPTG-inducible Ptac promoter (New England Biolabs) has been deleted and replaced by a new ORE The DNA sequence of the new ORF is as follows:

(SEQ ID NO: 119)
ATGAGCAAGAGCACTTTCAAAAAGTTTCTGAAAGAGACTGCTAGCGCT

CAGCTGAGCAACTTCGCTGCTAAGGCGCCAGACGATGGTGAAGCTGCG

GCTCACCATCACCATCACCATGCG

The new ORF encodes the following polypeptide:

(SEQ ID NO: 120)
MSKSTFKKFLICETASAQLSNFAAKAPDDGEAAAHHHHHHA.

This ORF was designed as follows. The first two residues were (Met-Ser) chosen to allow good translation initiation. This dipeptide was followed by a retrotranslation of residues 40-48 of mature protein VIII from M13 bacteriophage (KLFKKFTSK (SEQ ID NO: 282) retrotranslated to KSTFKKFLK SEQ ID NO: 283) which was in turn followed by a retrotranslation of protein VIII residues 1-20 (AEGDDPA-KAAFNSLQASATE (SEQ ID NO: 285) retrotranslated to ETASAQLSNSAAKAPDDGEA (SEQ ID NO: 284)). To the C-terminus of this nonapeptide was fused a nonapeptide (AAHHHHHHA (SEQ ID NO: 281)) hexaHis flag. Thus, this ORF consists of the dipeptide Met-Ser, followed by a retrotranslation of residues 1-48 of mature protein VIII with the central hydrophobic section (residues 21-30) deleted, followed by a hexaHis flag.

A library of 19-mer peptides was inserted between residues 11 and 12 of the above described ORF, using a modified version of a previously described method (see Example 10) with pS1207a as the template and Pep-ins as the mutagenic oligonucleotide. The resulting library encoded ORFS with the following sequences:

(SEQ ID NO: 121)
MSKSTFKKFLK-(x)19-ETASAQLSNFAAKAPDDGEAAAHHHHHHA where "(x)19" indicates a random 19-mer peptide library. The degenerate codons used at each position within the library are shown in FIG. 15. The library diversity was $8.3 \times 10^{10}$.

Phage from the library were cycled through rounds of binding selection with an anti-(His)4 antibody (Qiagen) as the capture target. After three or four rounds of selection, individual clones were assayed for hexaHis flag display using a phage ELISA with either the anti-(His)4 antibody or bovine serum albumin (BSA) as target. Of 72 clones assayed, six exhibited at least a two-fold greater signal when captured with the anti-(His)4 antibody rather than with BSA (FIG. 16). These clones were subjected to DNA sequence analysis and the protein sequence was deduced from the DNA sequence.

These protein sequences represent a new class of phage coat proteins which we designate "Protein-12" (P12). The individual unique clones are designated by an additional numeral (eg. Protein-12-1 or P12-1). As shown in FIG. 16, peptides fused to the C-terminus of P12 are displayed on the surface of M13 phage. The phagemid containing the gene encoding P12-1 was named pS1230a.

Example 25

Selection of a Second Generation P12 for the Display of a Large Protein as a Cterminal Fusion The method of Kunkel (Example 12) was used with the mutagenic oligonucleotide add-NX to insert an NsiI restriction site followed by an XbaI restriction site into phagemid pS1230a, between the regions encoding P12-1 and the poly-His flag. The resulting sequence was as follows: . . . gctgeg-gctGATGCATCTGGTAGCG TCTAGAGCcaccatcaccatcaccat . . . (SEQ ID NO: 122) The inserted sequence is shown in upper case text with the NisI and XbaI restriction sites. The inserted sequence is preceded by sequence encoding the final residues of P12-1 and followed by sequence encoding the polyHis flag (both shown in lower case text). The new phagemid was designated pS1232a.

Phagemid pS 1232a was digested with NsiI and XbaI and a similarly digested DNA fragment encoding an hGH variant (hGH supermutant, hGHsm) with improved afffinity for the hGH binding protein (hGHbp) was inserted. The phagemid was designated pS 1239b; it contains an ORF encoding P12-1 followed by a tetrapeptide linker (Ala-Ala-Asp-Ala), followed by hGHsm as shown below. The protein product of the pS1239b ORF is depicted; it consists of P12-1, followed by a tetrapeptide linker (AADA (SEQ ID NO: 286)), followed by hGHsm. P12-1 was divided into six zones as indicated, and a library was constructed for each zone. In addition, a linker library was constructed in which random 14-residue peptides were inserted in the middle of the tetrapeptide linker as shown.

```
                                                     (SEQ ID NO. 123)
M   S   K   S   T   F   K   K   F   L   K
    |---------------------------------|
        zone 1              |---------------------------------------|
                                            zone 2

V   F   V   F   S   V   D   V   D   N   N   W   I   W   A   V   G   I   I
|-----------------------------|
         zone 3              |-------------------------------|
                                            zone 4

E   T   A   S   A   Q   L   S   N   F   A   A   K   A   P   D   D   G   E   A
|-------------------------------------|-------------------------------|
            zone 5                                zone 6

A   A   D   A   |---hGHsm
                |
        linker library
(insert 14 VVC condons between Ala-Asp)
```

Phage particles produced from pS1239b did not display hGHsm at levels detectable in a phage ELISA with hGHbp as the capture target.

To obtain a P12 variant capable of displaying hGHsm as a C-terminal fusion, libraries were constructed to vary the sequence of P12-1 encoded by pS1239b. For library construction, a previously described method was used (Example 10). P12-1 was divided into six zones with each zone containing a stretch of contiguous residues (zone 1, residues 2 to 7; zone 2, residues 6 to 11; zone 3, residues 12 to 21; zone 4, residues 21 to 30; zone 5, residues 31 to 40; zone 6, residues 41 to 50). Oligonucleotides were designed to simultaneously replace all codons within the zone with an equal number of degenerate codons (NNS, where N=A, C, G, or T) encoding all twenty natural amino acids. Each oligonucleotide was named according to the zone it mutated (e.g. Oligonucleotide Lib-zone1 mutated zone 1). In addition, an oligonucleotide (Lib-linker) was designed to insert 14 degenerate codons (VVC, where V=A, C, or G; encoding Ala, Arg, Asn, Asp, Gly, H is, Pro, Ser, or Thr) into the middle of the tetrapeptide linker connecting P12-1 to hGHsm. The diversities of these libraries were as follows: zone 1, $2.5\times10^{10}$; zone 2, $2.5\times10^{10}$; zone 3, $2.6\times10^{10}$; zone 4, $2.4\times10^{10}$; zone 5, $2.4\times10^{10}$; zone 6, $2.3\times10^{10}$; linker library, $2.8\times10^{10}$.

Phage from all the libraries were pooled and cycled through rounds of binding selection with hGHbp (Example 11) coated on 96-well Maxisorp immunoplates as a target. Phage were propagated in *E. coli* SS320 cells with M13-VCS helper phage (Stratagene). After four rounds of binding selection, individual clones were analyzed for hGHsm display. For each of the rounds 2, 3, and 4, 24 clones were analyzed. Phage were isolated from each clone and hGHsm display was detected using a phage ELISA (Example 13). A single clone from round 2 exhibited 10-fold greater binding to plates coated with hGHbp in comparison with plates coated with BSA; all other clones exhibited similar binding to either hGHbp or BSA coated plates. The phagemid corresponding to the positive clone was designated pS1258.

The complete DNA sequence of the P12-1 variant encoding ORF of pS1258 was determined and the protein sequence was deduced and shown below. The amino acid numbering is shown to the right.

```
ATG AGC AAG AGC ACT TTC AAA AAG TTT CTG   (SEQ ID NO. 124)
 M   S   K   S   T   F   K   K   F   L    (SEQ ID NO. 33)

AAA GTT TTT GTT TTT TCT GTT GAT GTT GAT
 K   V   F   V   F   S   V   D   V   D

AAT AAT TGG ATT TGG GCT GTC GGT ATT ATT
 N   N   W   I   W   A   V   G   I   I

TAC ATG CTC CTC GTG GAG GCG TCG CCC TGG
 Y   M   L   L   V   E   A   S   P   W

GCT GCT AAG GCG CCA GAC GAT GGT GAA GCT
 A   A   K   A   P   D   D   G   E   A
```

The new variant coat protein was named P12-7; its sequence differs from that of P12-1 in zone 5. The fusion of hGHsm to the C-terminus of P12-7 permits the display of hGHsm on the surface of M13 phage, as evidenced by a phage ELISA.

We also wished to demonstrate that P12-7 permits the display of other proteins, for example wild-type hGH. A phagemid analogous to pS1239b (described above) was constructed and designated pS1239a, with the only difference being that pS1239b encodes a fusion protein consisting of P12-1 followed by wild-type hGH (Example 8). Phage particles produced from pS1239a did not display hGH at levels detectable in a phage ELISA. The method of Kunkel (Example 12) was used with a mutagenic oligonucleotide (add-P12-7) to convert the pS1239a DNA sequence encoding P12-I to DNA sequence encoding P 12-7. The new phagemid was designated pW930a; it contains an ORF encoding a fusion protein consisting of P12-7 followed by wild-type hGH. Phage particles isolated from *E. coli* cultures harboring pW930a displayed hGH on their surface, as evidenced by a phage ELISA.

Example 26

Optimization of Linker Sequences for Display of a Peptide Fused to the C-Terminus of the Protein III C-Terminal Domain Oligonucleotides for Example 26:

```
UH-L4:
                                         (SEQ ID NO: 125)
TTCACCTCGAAAGCAAGCNNSNNSNNSNNSCACCATCACCATCAC
CAT
```

-continued

UH-L5:
(SEQ ID NO: 126)
TTCACCTCGAAAGCAAGCNNSNNSNNSNNSNNSCACCATCACCAT

CACCAT

UH-L6:
(SEQ ID NO: 127)
TTCACCTCGAAAGCAAGCNNSNNSNNSNNSNNSNNSCACCATCAC

CATCACCAT

UH-L8:
(SEQ ID NO: 128)
TTCACCTCGAAAGCAAGCNNSNNSNNSNNSNNSNNSVVCVVCCAC

CATCACCATCACCAT

UH-L10:
(SEQ ID NO: 129)
TTCACCTCGAAAGCAAGCNNSNNSNNSNNSNNSNNSVVCVVCVVC

VVCCACCATCACCATCACCAT

UHg3-L6:
(SEQ ID NO: 130)
CTGCGTAATAAGGAGTCTNNSNNSNNSNNSNNSNNSCACCATCAC

CATCACCATTAATCATGCCAGTTGTTTTGG

UHg3-L8:
(SEQ ID NO: 131)
CTGCGTAATAAGGAGTCTNNSNNSNNSNNSNNSNNSNNSNNSCAC

CATCACCATCACCATTAATCATGCCAGTTCTTTTGG

UHg3-L10:
(SEQ ID NO: 132)
CTGCGTAATAAGGAGTCTNNSNNSNNSNNSNNSNNSNNSNNSNNS

NNSCACCATCACCATCACCATTAATCATGCCAGTTCTTTTGG

Standard molecular biology techniques were used to construct a phagemid designated pS1428d. Phagemid pS1428d is similar to pS1290a, except that the ORF under the control of the IPTG-inducible Ptac promoter (New England Biolabs) consists of the maltose binding protein signal peptide followed by the C-terminal domain of M13 protein III (Lowman et al., (1999) Biochemistry, 30:10832). The method of Kunkel (Example 12) was used to fuse libraries to the C-terminus of the protein III C-terminal domain encoded by pS1428d. The libraries consisted of random linkers of various lengths followed by a hexaHis flag (HHHHHH (SEQ ID NO: 287)). The end result was libraries containing ORFs which encoded the C-terminal domain of protein III, followed by random polypeptide linker sequences, followed by the hexaHis flag. The lengths of the linkers were varied and depended on the mutagenic oligonucleotides used: oligonucleotides UHg3-L6, UHg3-L8, or UHg3-L10 introduced linkers containing 6, 8, or 10 residues respectively. The diversities of the libraries were as follows: UHg3-L6, 3.5×10$^{10}$; UHg3-L8, 1.2×10$^{10}$; UHg3-L10, 2.8×10$^{10}$.

Phage from the libraries were pooled together and cycled through binding selection with an anti-(His)4 antibody (Qiagen) as the capture target. After two rounds of selection, individual clones were assayed for hexaHis flag display using a phage ELISA with the anti-(His)4 antibody as target. Three clones exhibiting strong signals were subjected to DNA sequence analysis and the selected linker sequences are shown below.

g3-1
(SEQ ID NO. 133)
GGG CAG GCC AGG ATC GTC TAC CGG CAG AAG (SEQ ID NO. 134)
G    Q    A    R    I    V    Y    R    Q    K g3-2
(SEQ ID NO. 135)
AGG ATC AGG GTC CTG CAG AAG GGC AAG GAG (SEQ ID NO. 136)
R    I    R    V    L    Q    K    G    K    E g3-3
(SEQ ID NO 137)
CGC GCC AAG ATC GAG CAG ATC TGC AAG GAG (SEQ ID NO. 138)
R    A    K    I    E    Q    I    C    K    E

The sequences shown were inserted between the final residue of the protein III C-terminal domain and a hexaHis flag. For each selectant, the DNA sequence is shown with the deduced amino acid sequence below. A designation for each sequence is shown to the left.

The levels of polyHis flag display were compared with levels of display achieved with C-terminal or N-terminal fusions to protein VIII. Interestingly, display with C-terminal fusion to the protein III C-terminal domain was equivalent to display with N-terminal fusion to protein VIII and about 10-fold higher than display with C-terminal fusion to protein VIII (FIG. 18).

The foregoing written specification is considered to be sufficient to enable one skilled in the art to practice the invention. The present invention is not to be limited in scope by the cultures deposited, since the deposited embodiments are intended as separate illustrations of certain aspects of the invention and any cultures that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

While the invention has necessarily been described in conjunction with preferred embodiments, one of ordinary skill, after reading the foregoing specification, will be able to effect various changes, substitutions of equivalents, and alterations to the subject matter set forth herein, without departing from the spirit and scope thereof. Hence, the invention can be practiced in ways other than those specifically described herein. It is therefore intended that the protection granted by Letters Patent hereon be limited only by the appended claims and equivalents thereof.

What is claimed:

1. A library of virus particles comprising a plurality of virus particles, the virus particles displaying a plurality of different fusion proteins on the surface thereof, wherein each fusion protein comprises at least a portion of a protein III or protein VIII filamentous phage coat protein and a heterologous polypeptide, wherein said heterologous polypeptide is fused to the carboxyl-terminus of said filamentous phage coat protein.

2. The library of claim 1, wherein the fusion proteins comprise a full length phage coat protein.

3. The library of claim 1, wherein the phage coat protein is a wild type protein.

4. The library of claim 1, wherein the heterologous polypeptides contain about 4 to about 80 amino acid residues.

5. The library of claim 1, wherein the heterologous polypeptides contain at least about 100 amino acid residues.

6. The library of claim 1, wherein the heterologous polypeptides are attached to the coat protein through a linker peptide.

7. The library of claim 6, wherein the linker peptide has about 4 to about 30 residues.

8. The library of claim 7, wherein the linker peptide has about 8 to about 20 residues.

9. The library of claim 6, wherein more than about 50 % of the residues in the linker peptide are glycine or serine.

10. The library of claim 1, wherein the filamentous phage is selected from the group consisting of M13, f1, and fd filamentous phage.

\* \* \* \* \*

UNITED STATES PATENT AND TRADEMARK OFFICE
CERTIFICATE OF CORRECTION

| | | |
|---|---|---|
| PATENT NO. | : 8,685,893 B2 | Page 1 of 1 |
| APPLICATION NO. | : 12/181222 | |
| DATED | : April 1, 2014 | |
| INVENTOR(S) | : Sidhu et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1225 days.

Signed and Sealed this
Twenty-second Day of September, 2015

Michelle K. Lee
*Director of the United States Patent and Trademark Office*

SEQUENCE LISTING

<160> NUMBER OF SEQ ID NOS: 300

<210> SEQ ID NO 1
<211> LENGTH: 50
<212> TYPE: PRT
<213> ORGANISM: Artificial sequence
<220> FEATURE:
<223> OTHER INFORMATION: Synthetic coat protein
<220> FEATURE:
<221> NAME/KEY: VARIANT
<222> LOCATION: 12
<223> OTHER INFORMATION: where Xaa is Phe, Leu, Ile, Val, Asn, His, or
      Asp
<220> FEATURE:
<221> NAME/KEY: VARIANT
<222> LOCATION: 13
<223> OTHER INFORMATION: where Xaa is Phe, Leu, Ile, Val, Cys, Arg, Ser,
      or Gly
<220> FEATURE:
<221> NAME/KEY: VARIANT
<222> LOCATION: 14
<223> OTHER INFORMATION: where Xaa is Phe, Leu, Ile, Val, Asn, His, or
      Asp
<220> FEATURE:
<221> NAME/KEY: VARIANT
<222> LOCATION: 15-16
<223> OTHER INFORMATION: where Xaa is Phe, Leu, Ile, Val, Ser, Pro, Thr,
      or Ala
<220> FEATURE:
<221> NAME/KEY: VARIANT
<222> LOCATION: 17
<223> OTHER INFORMATION: where Xaa is Phe, Leu, Ile, Val, Cys, Arg, Ser,
      or Gly
<220> FEATURE:
<221> NAME/KEY: VARIANT
<222> LOCATION: 18-22
<223> OTHER INFORMATION: where Xaa is Phe, Leu, Ile, Val, Asn, His, or
      Arg
<220> FEATURE:
<221> NAME/KEY: VARIANT
<222> LOCATION: 23
<223> OTHER INFORMATION: where Xaa is Leu, Met, Val, Trp, Arg, or Gly
<220> FEATURE:
<221> NAME/KEY: VARIANT
<222> LOCATION: 24
<223> OTHER INFORMATION: where Xaa is Phe, Leu, Ile, Val, Ser, Pro, Thr,
      or Ala
<220> FEATURE:
<221> NAME/KEY: VARIANT
<222> LOCATION: 25
<223> OTHER INFORMATION: where Xaa is Leu, Met, Val, Trp, Arg, or Gly
<220> FEATURE:
<221> NAME/KEY: VARIANT
<222> LOCATION: 26
<223> OTHER INFORMATION: where Xaa is Phe, Leu, Ile, Val, Ser, Pro, Thr,
      or Ala
<220> FEATURE:
<221> NAME/KEY: VARIANT
<222> LOCATION: 27
<223> OTHER INFORMATION: where Xaa is Phe, Leu, Ile, Val, Tyr, His, Asn,
      or Asp
<220> FEATURE:
<221> NAME/KEY: VARIANT
<222> LOCATION: 28
<223> OTHER INFORMATION: where Xaa is Phe, Leu, Ile, Val, Cys, Arg, Ser,
      or Gly
<220> FEATURE:
<221> NAME/KEY: VARIANT
<222> LOCATION: 29
<223> OTHER INFORMATION: where Xaa is Phe, Leu, Ile, Val, Asn, His, or
      Asp
<220> FEATURE:
<221> NAME/KEY: VARIANT
<222> LOCATION: 30
<223> OTHER INFORMATION: where Xaa is Phe, Leu, Ile, Val, Asn, His, or
      Asp

```
-continued

<400> SEQUENCE: 1

Met Ser Lys Ser Thr Phe Lys Lys Phe Leu Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Glu Thr Ala Ser Ala Gln Leu Ser Asn Phe Ala Ala Lys Ala Pro
                35                  40                  45

Asp Asp Gly Glu Ala
                50

<210> SEQ ID NO 2
<211> LENGTH: 50
<212> TYPE: PRT
<213> ORGANISM: M13 phage
<220> FEATURE:
<223> OTHER INFORMATION: coat protein VIII

<400> SEQUENCE: 2

Ala Glu Gly Asp Asp Pro Ala Lys Ala Ala Phe Asn Ser Leu Gln
1               5                   10                  15

Ala Ser Ala Thr Glu Tyr Ile Gly Tyr Ala Trp Ala Met Val Val
                20                  25                  30

Val Ile Val Gly Ala Thr Ile Gly Ile Lys Leu Phe Lys Lys Phe
                35                  40                  45

Thr Ser Lys Ala Ser
                50

<210> SEQ ID NO 3
<211> LENGTH: 50
<212> TYPE: PRT
<213> ORGANISM: f1 phage
<220> FEATURE:
<223> OTHER INFORMATION: coat protein VIII

<400> SEQUENCE: 3

Ala Glu Gly Asp Asp Pro Ala Lys Ala Ala Phe Asp Ser Leu Gln
1               5                   10                  15

Ala Ser Ala Thr Glu Tyr Ile Gly Tyr Ala Trp Ala Met Val Val
                20                  25                  30

Val Ile Val Gly Ala Thr Ile Gly Ile Lys Leu Phe Lys Lys Phe
                35                  40                  45

Thr Ser Lys Ala Ser
                50

<210> SEQ ID NO 4
<211> LENGTH: 50
<212> TYPE: PRT
<213> ORGANISM: fd phage
<220> FEATURE:
<223> OTHER INFORMATION: coat protein VIII

<400> SEQUENCE: 4

Ala Glu Gly Asp Asp Pro Ala Lys Ala Ala Phe Asp Ser Leu Gln
1               5                   10                  15

Ala Ser Ala Thr Glu Tyr Ile Gly Tyr Ala Trp Ala Met Val Val
                20                  25                  30

Val Ile Val Gly Ala Thr Ile Gly Ile Lys Leu Phe Lys Lys Phe
                35                  40                  45

Thr Ser Lys Ala Ser
                50
```

<210> SEQ ID NO 5
<211> LENGTH: 50
<212> TYPE: PRT
<213> ORGANISM: Zj-2 phage
<220> FEATURE:
<223> OTHER INFORMATION: coat protein VIII

<400> SEQUENCE: 5

Ala Glu Gly Asp Asp Pro Ala Lys Ala Ala Phe Asp Ser Leu Gln
1               5                   10                  15

Ala Ser Ala Thr Glu Tyr Ile Gly Tyr Ala Trp Ala Met Val Val
                20                  25                  30

Val Ile Val Gly Ala Thr Ile Gly Ile Lys Leu Phe Lys Lys Phe
            35                  40                  45

Ala Ser Lys Ala Ser
            50

<210> SEQ ID NO 6
<211> LENGTH: 50
<212> TYPE: PRT
<213> ORGANISM: If1 phage
<220> FEATURE:
<223> OTHER INFORMATION: coat protein VIII

<400> SEQUENCE: 6

Asp Asp Ala Thr Ser Gln Ala Lys Ala Ala Phe Asp Ser Leu Thr
1               5                   10                  15

Ala Gln Ala Thr Glu Met Ser Gly Tyr Ala Trp Ala Leu Val Val
                20                  25                  30

Leu Val Val Gly Ala Thr Val Gly Ile Lys Leu Phe Lys Lys Phe
            35                  40                  45

Val Ser Arg Ala Ser
            50

<210> SEQ ID NO 7
<211> LENGTH: 50
<212> TYPE: PRT
<213> ORGANISM: I2-2 phage
<220> FEATURE:
<223> OTHER INFORMATION: coat protein VIII

<400> SEQUENCE: 7

Ser Thr Ala Thr Ser Tyr Ala Thr Glu Ala Met Asn Ser Leu Lys
1               5                   10                  15

Thr Gln Ala Thr Asp Leu Ile Asp Gln Thr Trp Pro Val Val Thr
                20                  25                  30

Ser Val Ala Val Ala Gly Leu Ala Ile Arg Leu Phe Lys Lys Phe
            35                  40                  45

Ser Ser Lys Ala Val
            50

<210> SEQ ID NO 8
<211> LENGTH: 50
<212> TYPE: PRT
<213> ORGANISM: Ike phage
<220> FEATURE:
<223> OTHER INFORMATION: coat protein VIII

<400> SEQUENCE: 8

Asn Ala Ala Thr Asn Tyr Ala Thr Glu Ala Met Asp Ser Leu Lys
1               5                   10                  15

Thr Gln Ala Ile Asp Leu Ile Ser Gln Thr Trp Pro Val Val Thr

```
                    20                  25                  30
Thr Val Val Val Ala Gly Leu Val Ile Arg Leu Phe Lys Lys Phe
                35                  40                  45

Ser Ser Lys Ala Val
                50
```

<210> SEQ ID NO 9
<211> LENGTH: 30
<212> TYPE: DNA
<213> ORGANISM: Artificial sequence
<220> FEATURE:
<223> OTHER INFORMATION: oligonucleotide primer

<400> SEQUENCE: 9
aaaagaattc ccgacaccat cgaatggtgc                               30

<210> SEQ ID NO 10
<211> LENGTH: 35
<212> TYPE: DNA
<213> ORGANISM: Artificial sequence
<220> FEATURE:
<223> OTHER INFORMATION: oligonucleotide primer

<400> SEQUENCE: 10
accagatgca taagccgagg cggaaaacat catcg                         35

<210> SEQ ID NO 11
<211> LENGTH: 56
<212> TYPE: DNA
<213> ORGANISM: Artificial sequence
<220> FEATURE:
<223> OTHER INFORMATION: oligonucleotide primer

<400> SEQUENCE: 11
ttttctagac aggcctccca ccagatgcat aagccgaggc ggaaaacatc         50
atcgtc                                                         56

<210> SEQ ID NO 12
<211> LENGTH: 34
<212> TYPE: DNA
<213> ORGANISM: Artificial sequence
<220> FEATURE:
<223> OTHER INFORMATION: oligonucleotide primer

<400> SEQUENCE: 12
gctatcggaa tgcatcgggc atcaccggca cctg                          34

<210> SEQ ID NO 13
<211> LENGTH: 61
<212> TYPE: DNA
<213> ORGANISM: Artificial sequence
<220> FEATURE:
<223> OTHER INFORMATION: oligonucleotide primer

<400> SEQUENCE: 13
gagtcatagt cgtcaggcgc ctcctccgga tcctccaccc accttggtga         50
aggtgtcgtg g                                                   61

<210> SEQ ID NO 14
<211> LENGTH: 18
<212> TYPE: DNA
<213> ORGANISM: Artificial sequence
<220> FEATURE:
<223> OTHER INFORMATION: oligonucleotide primer -continued

<400> SEQUENCE: 14
gggtatctag aggttgag                                                      18

<210> SEQ ID NO 15
<211> LENGTH: 46
<212> TYPE: DNA
<213> ORGANISM: Artificial sequence
<220> FEATURE:
<223> OTHER INFORMATION: oligonucleotide primer

<400> SEQUENCE: 15
tggagctccc ggatcctcca ccgctctgga agccacagct gccctc                        46

<210> SEQ ID NO 16
<211> LENGTH: 42
<212> TYPE: DNA
<213> ORGANISM: Artificial sequence
<220> FEATURE:
<223> OTHER INFORMATION: mutagenic oligonucleotide

<400> SEQUENCE: 16
ggatccggga gctccagctg atgaggtgac gatcccgcaa aa                            42

<210> SEQ ID NO 17
<211> LENGTH: 42
<212> TYPE: DNA
<213> ORGANISM: Artificial sequence
<220> FEATURE:
<223> OTHER INFORMATION: mutagenic oligonucleotide

<400> SEQUENCE: 17
gatcccgcaa aagcggcctg atgatccctg caagcctcag cg                            42

<210> SEQ ID NO 18
<211> LENGTH: 42
<212> TYPE: DNA
<213> ORGANISM: Artificial sequence
<220> FEATURE:
<223> OTHER INFORMATION: mutagenic oligonucleotide

<400> SEQUENCE: 18
caagcctcag cgaccgaatg atgaggttat gcgtgggcga tg                            42

<210> SEQ ID NO 19
<211> LENGTH: 42
<212> TYPE: DNA
<213> ORGANISM: Artificial sequence
<220> FEATURE:
<223> OTHER INFORMATION: mutagenic oligonucleotide

<400> SEQUENCE: 19
cgctgggcga tggttgtttg atgagtcggc gcaactatcg gt                            42

<210> SEQ ID NO 20
<211> LENGTH: 42
<212> TYPE: DNA
<213> ORGANISM: Artificial sequence
<220> FEATURE:
<223> OTHER INFORMATION: mutagenic oligonucleotide

<400> SEQUENCE: 20
gcaactatcg gtatcaagtg atgaaagaaa ttcacctcga aa                            42

<210> SEQ ID NO 21
<211> LENGTH: 66
<212> TYPE: DNA

```
<213> ORGANISM: Artificial sequence
<220> FEATURE:
<223> OTHER INFORMATION: mutagenic oligonucleotide
<220> FEATURE:
<221> NAME/KEY: MISC_FEATURE
<222> LOCATION: 20
<223> OTHER INFORMATION: where n is A, G, C, or T
<220> FEATURE:
<221> NAME/KEY: MISC_FEATURE
<222> LOCATION: 22
<223> OTHER INFORMATION: where n is A, G, C, or T
<220> FEATURE:
<221> NAME/KEY: MISC_FEATURE
<222> LOCATION: 26
<223> OTHER INFORMATION: where n is A, G, C, or T
<220> FEATURE:
<221> NAME/KEY: MISC_FEATURE
<222> LOCATION: 28
<223> OTHER INFORMATION: where n is A, G, C, or T
<220> FEATURE:
<221> NAME/KEY: MISC_FEATURE
<222> LOCATION: 31
<223> OTHER INFORMATION: where n is A, G, C, or T
<220> FEATURE:
<221> NAME/KEY: MISC_FEATURE
<222> LOCATION: 34
<223> OTHER INFORMATION: where n is A, G, C, or T
<220> FEATURE:
<221> NAME/KEY: MISC_FEATURE
<222> LOCATION: 38
<223> OTHER INFORMATION: where n is A, G, C, or T
<220> FEATURE:
<221> NAME/KEY: MISC_FEATURE
<222> LOCATION: 41
<223> OTHER INFORMATION: where n is A, G, C, or T
<220> FEATURE:
<221> NAME/KEY: MISC_FEATURE
<222> LOCATION: 44
<223> OTHER INFORMATION: where n is A, G, C, or T
<220> FEATURE:
<221> NAME/KEY: MISC_FEATURE
<222> LOCATION: 47
<223> OTHER INFORMATION: where n is A, G, C, or T

<400> SEQUENCE: 21
ggatccggga gctccagcrn tnasrntnas nasnycrntr narntrnttt          50
taactccctg caagcc                                               66

<210> SEQ ID NO 22
<211> LENGTH: 66
<212> TYPE: DNA
<213> ORGANISM: Artificial sequence
<220> FEATURE:
<223> OTHER INFORMATION: mutagenic oligonucleotide
<220> FEATURE:
<221> NAME/KEY: MISC_FEATURE
<222> LOCATION: 19
<223> OTHER INFORMATION: where n is A, G, C, or T
<220> FEATURE:
<221> NAME/KEY: MISC_FEATURE
<222> LOCATION: 22
<223> OTHER INFORMATION: where n is A, G, C, or T
<220> FEATURE:
<221> NAME/KEY: MISC_FEATURE
<222> LOCATION: 26
<223> OTHER INFORMATION: where n is A, G, C, or T
<220> FEATURE:
<221> NAME/KEY: MISC_FEATURE
<222> LOCATION: 28
<223> OTHER INFORMATION: where n is A, G, C, or T
<220> FEATURE:
<221> NAME/KEY: MISC_FEATURE
<222> LOCATION: 31
<223> OTHER INFORMATION: where n is A, G, C, or T
<220> FEATURE:
<221> NAME/KEY: MISC_FEATURE
<222> LOCATION: 35
```

```
<223> OTHER INFORMATION: where n is A, G, C, or T
<220> FEATURE:
<221> NAME/KEY: MISC_FEATURE
<222> LOCATION: 38
<223> OTHER INFORMATION: where n is A, G, C, or T
<220> FEATURE:
<221> NAME/KEY: MISC_FEATURE
<222> LOCATION: 41
<223> OTHER INFORMATION: where n is A, G, C, or T
<220> FEATURE:
<221> NAME/KEY: MISC_FEATURE
<222> LOCATION: 44
<223> OTHER INFORMATION: where n is A, G, C, or T
<220> FEATURE:
<221> NAME/KEY: MISC_FEATURE
<222> LOCATION: 47
<223> OTHER INFORMATION: where n is A, G, C, or T

<400> SEQUENCE: 22
gatcccgcaa aagcggccnw tnasrntnyt nasrntrntr ntrntnasta         50
tatcggttat gcgtgg                                              66

<210> SEQ ID NO 23
<211> LENGTH: 70
<212> TYPE: DNA
<213> ORGANISM: Artificial sequence
<220> FEATURE:
<223> OTHER INFORMATION: mutagenic oligonucleotide
<220> FEATURE:
<221> NAME/KEY: MISC_FEATURE
<222> LOCATION: 19
<223> OTHER INFORMATION: where n is A, G, C, or T
<220> FEATURE:
<221> NAME/KEY: MISC_FEATURE
<222> LOCATION: 22
<223> OTHER INFORMATION: where n is A, G, C, or T
<220> FEATURE:
<221> NAME/KEY: MISC_FEATURE
<222> LOCATION: 25
<223> OTHER INFORMATION: where n is A, G, C, or T
<220> FEATURE:
<221> NAME/KEY: MISC_FEATURE
<222> LOCATION: 28
<223> OTHER INFORMATION: where n is A, G, C, or T
<220> FEATURE:
<221> NAME/KEY: MISC_FEATURE
<222> LOCATION: 31
<223> OTHER INFORMATION: where n is A, G, C, or T
<220> FEATURE:
<221> NAME/KEY: MISC_FEATURE
<222> LOCATION: 35
<223> OTHER INFORMATION: where n is A, G, C, or T
<220> FEATURE:
<221> NAME/KEY: MISC_FEATURE
<222> LOCATION: 38
<223> OTHER INFORMATION: where n is A, G, C, or T
<220> FEATURE:
<221> NAME/KEY: MISC_FEATURE
<222> LOCATION: 41
<223> OTHER INFORMATION: where n is A, G, C, or T
<220> FEATURE:
<221> NAME/KEY: MISC_FEATURE
<222> LOCATION: 44
<223> OTHER INFORMATION: where n is A, G, C, or T
<220> FEATURE:
<221> NAME/KEY: MISC_FEATURE
<222> LOCATION: 47
<223> OTHER INFORMATION: where n is A, G, C, or T

<400> SEQUENCE: 23
caagcctcag cgaccgaanw cnwcnktnwc nyytnkgnyt nkgnwtnwtg         50
tcattgtcgg cgcaactatc                                         70

<210> SEQ ID NO 24
```

```
<211> LENGTH: 66
<212> TYPE: DNA
<213> ORGANISM: Artificial sequence
<220> FEATURE:
<223> OTHER INFORMATION: mutagenic oligonucleotide
<220> FEATURE:
<221> NAME/KEY: MISC_FEATURE
<222> LOCATION: 19
<223> OTHER INFORMATION: where n is A, G, C, or T
<220> FEATURE:
<221> NAME/KEY: MISC_FEATURE
<222> LOCATION: 22
<223> OTHER INFORMATION: where n is A, G, C, or T
<220> FEATURE:
<221> NAME/KEY: MISC_FEATURE
<222> LOCATION: 25
<223> OTHER INFORMATION: where n is A, G, C, or T
<220> FEATURE:
<221> NAME/KEY: MISC_FEATURE
<222> LOCATION: 28
<223> OTHER INFORMATION: where n is A, G, C, or T
<220> FEATURE:
<221> NAME/KEY: MISC_FEATURE
<222> LOCATION: 31
<223> OTHER INFORMATION: where n is A, G, C, or T
<220> FEATURE:
<221> NAME/KEY: MISC_FEATURE
<222> LOCATION: 34
<223> OTHER INFORMATION: where n is A, G, C, or T
<220> FEATURE:
<221> NAME/KEY: MISC_FEATURE
<222> LOCATION: 37-38
<223> OTHER INFORMATION: where n is A, G, C, or T
<220> FEATURE:
<221> NAME/KEY: MISC_FEATURE
<222> LOCATION: 40-41
<223> OTHER INFORMATION: where n is A, G, C, or T
<220> FEATURE:
<221> NAME/KEY: MISC_FEATURE
<222> LOCATION: 43-44
<223> OTHER INFORMATION: where n is A, G, C, or T

<400> SEQUENCE: 24
gcgtgggcga tggttgttnw tnwcnwtnkt nytnytnntn ntnntaagct                50
gtttaagaaa ttcacc                                                    66

<210> SEQ ID NO 25
<211> LENGTH: 72
<212> TYPE: DNA
<213> ORGANISM: Artificial sequence
<220> FEATURE:
<223> OTHER INFORMATION: mutagenic oligonucleotide
<220> FEATURE:
<221> NAME/KEY: MISC_FEATURE
<222> LOCATION: 19-20
<223> OTHER INFORMATION: where n is A, G, C, or T
<220> FEATURE:
<221> NAME/KEY: MISC_FEATURE
<222> LOCATION: 22-23
<223> OTHER INFORMATION: where n is A, G, C, or T
<220> FEATURE:
<221> NAME/KEY: MISC_FEATURE
<222> LOCATION: 31-32
<223> OTHER INFORMATION: where n is A, G, C, or T
<220> FEATURE:
<221> NAME/KEY: MISC_FEATURE
<222> LOCATION: 34-35
<223> OTHER INFORMATION: where n is A, G, C, or T
<220> FEATURE:
<221> NAME/KEY: MISC_FEATURE
<222> LOCATION: 37-38
<223> OTHER INFORMATION: where n is A, G, C, or T
<220> FEATURE:
<221> NAME/KEY: MISC_FEATURE
<222> LOCATION: 43-44
<223> OTHER INFORMATION: where n is A, G, C, or T
<220> FEATURE:
```

```
<221> NAME/KEY: MISC_FEATURE
<222> LOCATION: 46-47
<223> OTHER INFORMATION: where n is A, G, C, or T

<400> SEQUENCE: 25
gcaactatcg gtatcaagnn gnnsaagaaa nnsnngnnga aanngnngtg         50
ataaaccgat acaattaaag gc                                      72

<210> SEQ ID NO 26
<211> LENGTH: 66
<212> TYPE: DNA
<213> ORGANISM: Artificial sequence
<220> FEATURE:
<223> OTHER INFORMATION: mutagenic oligonucleotide

<400> SEQUENCE: 26
gatcccgcaa aagcggccta tgaggctctt gaggatattg ctactaacta         50
tatcggttat gcgtgg                                              66

<210> SEQ ID NO 27
<211> LENGTH: 36
<212> TYPE: DNA
<213> ORGANISM: Artificial sequence
<220> FEATURE:
<223> OTHER INFORMATION: mutagenic oligonucleotide

<400> SEQUENCE: 27
ccgacaccct ccaatgctga ggaaacacaa cagaaa                        36

<210> SEQ ID NO 28
<211> LENGTH: 36
<212> TYPE: DNA
<213> ORGANISM: Artificial sequence
<220> FEATURE:
<223> OTHER INFORMATION: mutagenic oligonucleotide

<400> SEQUENCE: 28
ttcaggaagg acatggctaa ggtcgagaca ttcctg                        36

<210> SEQ ID NO 29
<211> LENGTH: 75
<212> TYPE: DNA
<213> ORGANISM: Artificial sequence
<220> FEATURE:
<223> OTHER INFORMATION: mutagenic oligonucleotide

<400> SEQUENCE: 29
aactacgggc tgctcgcttg cttcaggaag gacatggaca aggtcgagac         50
attcctggct atcgtgcagt gccgc                                    75

<210> SEQ ID NO 30
<211> LENGTH: 57
<212> TYPE: DNA
<213> ORGANISM: Artificial sequence
<220> FEATURE:
<223> OTHER INFORMATION: mutagenic oligonucleotide

<400> SEQUENCE: 30
ttcaggaagg acatggacgc tgtcgagaca ttcctggcta tcgtccagtg         50
ccgctct                                                        57

<210> SEQ ID NO 31
<211> LENGTH: 42
<212> TYPE: DNA
```

-continued

<213> ORGANISM: Artificial sequence
<220> FEATURE:
<223> OTHER INFORMATION: mutagenic oligonucleotide

<400> SEQUENCE: 31
ggtggaggat ccgggagctg atgagccgag ggtgacgatc cc        42

<210> SEQ ID NO 32
<211> LENGTH: 46
<212> TYPE: DNA
<213> ORGANISM: Artificial
<220> FEATURE:
<223> OTHER INFORMATION: mutagenic oligonucleotide

<400> SEQUENCE: 32
caccaaggtg gtctagagct aataataagc cgagggtgac gatccc    46

<210> SEQ ID NO 33
<211> LENGTH: 50
<212> TYPE: PRT
<213> ORGANISM: Artificial sequence
<220> FEATURE:
<223> OTHER INFORMATION: P12-1 variant

<400> SEQUENCE: 33

Met Ser Lys Ser Thr Phe Lys Lys Phe Leu Lys Val Phe Val Phe
 1               5                  10                  15

Ser Val Asp Val Asp Asn Asn Trp Ile Trp Ala Val Gly Ile Ile
                20                  25                  30

Tyr Met Leu Leu Val Glu Ala Ser Pro Trp Ala Ala Lys Ala Pro
                35                  40                  45

Asp Asp Gly Glu Ala
                50

<210> SEQ ID NO 34
<211> LENGTH: 93
<212> TYPE: DNA
<213> ORGANISM: Artificial sequence
<220> FEATURE:
<223> OTHER INFORMATION: oligonucleotide linker library

<400> SEQUENCE: 34
gagggcagct gtggcttcgg tggcggtvvc vvcvvcvvcv cvvcvvcvvc        50
cvvcvvcvvc vvcvvcvvcg gcggtgccga gggtgacgat ccc              93

<210> SEQ ID NO 35
<211> LENGTH: 51
<212> TYPE: DNA
<213> ORGANISM: Artificial sequence
<220> FEATURE:
<223> OTHER INFORMATION: oligonucleotide linker library

<400> SEQUENCE: 35
caccaaggtg gtctagagvv cvvcvvcvvc vvcgccgagg gtgacgatcc        50
c                                                             51

<210> SEQ ID NO 36
<211> LENGTH: 67
<212> TYPE: DNA
<213> ORGANISM: Artificial sequence
<220> FEATURE:
<223> OTHER INFORMATION: oligonucleotide linker library

<400> SEQUENCE: 36

```
caccaaggtg gtctagagcv vcvvcvvcvv cvvcvvcvvc vvcvvcvvcg        50
ccgagggtga cgatccc                                             67

<210> SEQ ID NO 37
<211> LENGTH: 82
<212> TYPE: DNA
<213> ORGANISM: Artificial sequence
<220> FEATURE:
<223> OTHER INFORMATION: oligonucleotide linker library

<400> SEQUENCE: 37
caccaaggtg gtctagagcv vcvvcvvcvv cvvcvvcvvc vvcvvcvvcv        50
vcvvcvvcvv cvvcgccgag ggtgacgatc cc                            82

<210> SEQ ID NO 38
<211> LENGTH: 97
<212> TYPE: DNA
<213> ORGANISM: Artificial sequence
<220> FEATURE:
<223> OTHER INFORMATION: oligonucleotide linker library

<400> SEQUENCE: 38
caccaaggtg gtctagagcv vcvvcvvcvv cvvcvvcvvc vvcvvcvvcv        50
vcvvcvvcvv cvvcvvcvvc vvcvvcvvcg ccgagggtga cgatccc            97

<210> SEQ ID NO 39
<211> LENGTH: 112
<212> TYPE: DNA
<213> ORGANISM: Artificial sequence
<220> FEATURE:
<223> OTHER INFORMATION: oligonucleotide linker library

<400> SEQUENCE: 39
caccaaggtg gtctagagcv vcvvcvvcvv cvvcvvcvvc vvcvvcvvcv        50
vcvvcvvcvv cvvcvvcvvc vvcvvcvvcv vcvvcvvcvv cvvcgccgag       100
ggtgacgatc cc                                                 112

<210> SEQ ID NO 40
<211> LENGTH: 66
<212> TYPE: DNA
<213> ORGANISM: Artificial sequence
<220> FEATURE:
<223> OTHER INFORMATION: mutagenic oligonucleotide

<400> SEQUENCE: 40
aagttcgcta gagatgctta tgaggctctt gaggatattg ctactaacta        50
tatcggttat gcgtgg                                              66

<210> SEQ ID NO 41
<211> LENGTH: 66
<212> TYPE: DNA
<213> ORGANISM: Artificial sequence
<220> FEATURE:
<223> OTHER INFORMATION: mutagenic oligonucleotide

<400> SEQUENCE: 41
gaggatattg ctactaacct tttctttctc cttgggactg tgcatcttgt        50
cattgtcggc gcaact                                              66

<210> SEQ ID NO 42
<211> LENGTH: 33
<212> TYPE: DNA
```

<213> ORGANISM: Artificial sequence
<220> FEATURE:
<223> OTHER INFORMATION: mutagenic oligonucleotide

<400> SEQUENCE: 42
gcaaaagcgg cctataacgc tcttgaggat att                         33

<210> SEQ ID NO 43
<211> LENGTH: 33
<212> TYPE: DNA
<213> ORGANISM: Artificial sequence
<220> FEATURE:
<223> OTHER INFORMATION: mutagenic oligonucleotide

<400> SEQUENCE: 43
tatgaggctc ttgaggccat tgctactaac tat                         33

<210> SEQ ID NO 44
<211> LENGTH: 33
<212> TYPE: DNA
<213> ORGANISM: Artificial sequence
<220> FEATURE:
<223> OTHER INFORMATION: mutagenic oligonucleotide

<400> SEQUENCE: 44
gaggctcttg aggattcagc tactaactat atc                         33

<210> SEQ ID NO 45
<211> LENGTH: 66
<212> TYPE: DNA
<213> ORGANISM: Artificial sequence
<220> FEATURE:
<223> OTHER INFORMATION: mutagenic oligonucleotide

<400> SEQUENCE: 45
gatcccgcaa aagcggccta tgaggctctt gaggatattg ctactaacta       50
tatcggttat gcgtgg                                            66

<210> SEQ ID NO 46
<211> LENGTH: 66
<212> TYPE: DNA
<213> ORGANISM: Artificial sequence
<220> FEATURE:
<223> OTHER INFORMATION: mutagenic oligonucleotide

<400> SEQUENCE: 46
gagggcagct gtggcttcca gagcggtgga ggatccggga gctccagcgc       50
cgagggtgac gatccc                                            66

<210> SEQ ID NO 47
<211> LENGTH: 60
<212> TYPE: DNA
<213> ORGANISM: Artificial sequence
<220> FEATURE:
<223> OTHER INFORMATION: mutagenic oligonucleotide

<400> SEQUENCE: 47
cccgcaaaag cggcctttaa cgctctgcaa gccattgcga ccgaatatat       50
cggttatgcg                                                   60

<210> SEQ ID NO 48
<211> LENGTH: 66
<212> TYPE: DNA
<213> ORGANISM: Artificial sequence
<220> FEATURE:

-continued

<223> OTHER INFORMATION: mutagenic oligonucleotide

<400> SEQUENCE: 48
caagcctcag cgaccgaact tttctttctc cttgggactg tgcatcttgt    50
cattgtcggc gcaact    66

<210> SEQ ID NO 49
<211> LENGTH: 33
<212> TYPE: DNA
<213> ORGANISM: Artificial sequence
<220> FEATURE:
<223> OTHER INFORMATION: mutagenic oligonucleotide

<400> SEQUENCE: 49
tccgggagct ccagcgccaa gagtgagaag ttc    33

<210> SEQ ID NO 50
<211> LENGTH: 33
<212> TYPE: DNA
<213> ORGANISM: Artificial sequence
<220> FEATURE:
<223> OTHER INFORMATION: mutagenic oligonucleotide

<400> SEQUENCE: 50
gggagctcca gcgatgagag tgagaagttc gct    33

<210> SEQ ID NO 51
<211> LENGTH: 33
<212> TYPE: DNA
<213> ORGANISM: Artificial sequence
<220> FEATURE:
<223> OTHER INFORMATION: mutagenic oligonucleotide

<400> SEQUENCE: 51
agctccagcg ataagggtga gaagttcgct aga    33

<210> SEQ ID NO 52
<211> LENGTH: 33
<212> TYPE: DNA
<213> ORGANISM: Artificial sequence
<220> FEATURE:
<223> OTHER INFORMATION: mutagenic oligonucleotide

<400> SEQUENCE: 52
tccagcgata agagtgacaa gttcgctaga gat    33

<210> SEQ ID NO 53
<211> LENGTH: 33
<212> TYPE: DNA
<213> ORGANISM: Artificial sequence
<220> FEATURE:
<223> OTHER INFORMATION: mutagenic oligonucleotide

<400> SEQUENCE: 53
agcgataaga gtgaggattt cgctagagat gct    33

<210> SEQ ID NO 54
<211> LENGTH: 33
<212> TYPE: DNA
<213> ORGANISM: Artificial sequence
<220> FEATURE:
<223> OTHER INFORMATION: mutagenic oligonucleotide

<400> SEQUENCE: 54
gataagagtg agaagcccgc tagagatgct ttt    33

<210> SEQ ID NO 55
<211> LENGTH: 33
<212> TYPE: DNA
<213> ORGANISM: Artificial sequence
<220> FEATURE:
<223> OTHER INFORMATION: mutagenic oligonucleotide

<400> SEQUENCE: 55
agtgagaagt tcgctaaaga tgcttttaac tcc            33

<210> SEQ ID NO 56
<211> LENGTH: 33
<212> TYPE: DNA
<213> ORGANISM: Artificial sequence
<220> FEATURE:
<223> OTHER INFORMATION: mutagenic oligonucleotide

<400> SEQUENCE: 56
gagaagttcg ctagagcggc ttttaactcc ctg            33

<210> SEQ ID NO 57
<211> LENGTH: 33
<212> TYPE: DNA
<213> ORGANISM: Artificial sequence
<220> FEATURE:
<223> OTHER INFORMATION: mutagenic oligonucleotide

<400> SEQUENCE: 57
cccgcaaaag cggcctttga ggctcttgag gat            33

<210> SEQ ID NO 58
<211> LENGTH: 34
<212> TYPE: DNA
<213> ORGANISM: Artificial sequence
<220> FEATURE:
<223> OTHER INFORMATION: mutagenic oligonucleotide

<400> SEQUENCE: 58
gcaaaagcgg cctataaacg ctcttgagga tatt            34

<210> SEQ ID NO 59
<211> LENGTH: 33
<212> TYPE: DNA
<213> ORGANISM: Artificial sequence
<220> FEATURE:
<223> OTHER INFORMATION: mutagenic oligonucleotide

<400> SEQUENCE: 59
aaagcggcct atgagtccct tgaggatatt gct            33

<210> SEQ ID NO 60
<211> LENGTH: 33
<212> TYPE: DNA
<213> ORGANISM: Artificial sequence
<220> FEATURE:
<223> OTHER INFORMATION: mutagenic oligonucleotide

<400> SEQUENCE: 60
gcctatgagg ctcttcaaga tattgctact aac            33

<210> SEQ ID NO 61
<211> LENGTH: 33
<212> TYPE: DNA
<213> ORGANISM: Artificial sequence
<220> FEATURE:
<223> OTHER INFORMATION: mutagenic oligonucleotide -continued

```
<400> SEQUENCE: 61
tatgaggctc ttgaggccat tgctactaac tat                                    33

<210> SEQ ID NO 62
<211> LENGTH: 33
<212> TYPE: DNA
<213> ORGANISM: Artificial sequence
<220> FEATURE:
<223> OTHER INFORMATION: mutagenic oligonucleotide

<400> SEQUENCE: 62
gaggctcttg aggattcagc tactaactat atc                                    33

<210> SEQ ID NO 63
<211> LENGTH: 33
<212> TYPE: DNA
<213> ORGANISM: Artificial sequence
<220> FEATURE:
<223> OTHER INFORMATION: mutagenic oligonucleotide

<400> SEQUENCE: 63
gaggatattg ctactgaata tatcggttat gcg                                    33

<210> SEQ ID NO 64
<211> LENGTH: 33
<212> TYPE: DNA
<213> ORGANISM: Artificial sequence
<220> FEATURE:
<223> OTHER INFORMATION: mutagenic oligonucleotide

<400> SEQUENCE: 64
gcctcagcga ccgaatattt ctttctcctt ggg                                    33

<210> SEQ ID NO 65
<211> LENGTH: 33
<212> TYPE: DNA
<213> ORGANISM: Artificial sequence
<220> FEATURE:
<223> OTHER INFORMATION: mutagenic oligonucleotide

<400> SEQUENCE: 65
tcagcgaccg aacttatctt tctccttggg act                                    33

<210> SEQ ID NO 66
<211> LENGTH: 33
<212> TYPE: DNA
<213> ORGANISM: Artificial sequence
<220> FEATURE:
<223> OTHER INFORMATION: mutagenic oligonucleotide

<400> SEQUENCE: 66
gcgaccgaac ttttcggtct ccttgggact gtg                                    33

<210> SEQ ID NO 67
<211> LENGTH: 33
<212> TYPE: DNA
<213> ORGANISM: Artificial sequence
<220> FEATURE:
<223> OTHER INFORMATION: mutagenic oligonucleotide

<400> SEQUENCE: 67
accgaacttt tcttttatct tgggactgtg cat                                    33

<210> SEQ ID NO 68
<211> LENGTH: 33
<212> TYPE: DNA
```

```
<213> ORGANISM: Artificial sequence
<220> FEATURE:
<223> OTHER INFORMATION: mutagenic oligonucleotide

<400> SEQUENCE: 68 gaactttct ttctcgcggg gactgtgcat ctt                              33

<210> SEQ ID NO 69
<211> LENGTH: 33
<212> TYPE: DNA
<213> ORGANISM: Artificial sequence
<220> FEATURE:
<223> OTHER INFORMATION: mutagenic oligonucleotide

<400> SEQUENCE: 69
cttttctttc tcctttggac tgtgcatctt gtc                              33

<210> SEQ ID NO 70
<211> LENGTH: 33
<212> TYPE: DNA
<213> ORGANISM: Artificial sequence
<220> FEATURE:
<223> OTHER INFORMATION: mutagenic oligonucleotide

<400> SEQUENCE: 70
ttctttctcc ttggggcggt gcatcttgtc att                              33

<210> SEQ ID NO 71
<211> LENGTH: 33
<212> TYPE: DNA
<213> ORGANISM: Artificial sequence
<220> FEATURE:
<223> OTHER INFORMATION: mutagenic oligonucleotide

<400> SEQUENCE: 71
tttctccttg ggactatgca tcttgtcatt gtc                              33

<210> SEQ ID NO 72
<211> LENGTH: 33
<212> TYPE: DNA
<213> ORGANISM: Artificial sequence
<220> FEATURE:
<223> OTHER INFORMATION: mutagenic oligonucleotide

<400> SEQUENCE: 72
ctccttggga ctgtggttct tgtcattgtc ggc                              33

<210> SEQ ID NO 73
<211> LENGTH: 33
<212> TYPE: DNA
<213> ORGANISM: Artificial sequence
<220> FEATURE:
<223> OTHER INFORMATION: mutagenic oligonucleotide

<400> SEQUENCE: 73
cttgggactg tgcatgttgt cattgtcggc gca                              33

<210> SEQ ID NO 74
<211> LENGTH: 36
<212> TYPE: DNA
<213> ORGANISM: Artificial sequence
<220> FEATURE:
<223> OTHER INFORMATION: mutagenic oligonucleotide

<400> SEQUENCE: 74
gcaaaagcgg cctataactc ccttgaggat attgct                           36
```

<210> SEQ ID NO 75
<211> LENGTH: 48
<212> TYPE: DNA
<213> ORGANISM: Artificial sequence
<220> FEATURE:
<223> OTHER INFORMATION: mutagenic oligonucleotide

<400> SEQUENCE: 75
gcaaaagcgg cctataacgc tcttgaggat tcagctacta actatatc        48

<210> SEQ ID NO 76
<211> LENGTH: 60
<212> TYPE: DNA
<213> ORGANISM: Artificial sequence
<220> FEATURE:
<223> OTHER INFORMATION: mutagenic oligonucleotide

<400> SEQUENCE: 76
cccgcaaaag cggcctatga gtcccttgag gattcagcta ctaactatat        50
cggttatgcg        60

<210> SEQ ID NO 77
<211> LENGTH: 48
<212> TYPE: DNA
<213> ORGANISM: Artificial sequence
<220> FEATURE:
<223> OTHER INFORMATION: mutagenic oligonucleotide

<400> SEQUENCE: 77
gcaaaagcgg cctataactc ccttgaggat tcagctacta actatatc        48

<210> SEQ ID NO 78
<211> LENGTH: 10
<212> TYPE: PRT
<213> ORGANISM: Artificial sequence
<220> FEATURE:
<223> OTHER INFORMATION: peptide linker

<400> SEQUENCE: 78

Gln Ser Gly Gly Gly Ser Gly Ser Ser Ser
 1               5                  10

<210> SEQ ID NO 79
<211> LENGTH: 5
<212> TYPE: PRT
<213> ORGANISM: Artificial sequence
<220> FEATURE:
<223> OTHER INFORMATION: penta peptide

<400> SEQUENCE: 79

Gly Gly Arg Pro Val
 1               5

<210> SEQ ID NO 80
<211> LENGTH: 34
<212> TYPE: DNA
<213> ORGANISM: Artificial sequence
<220> FEATURE:
<223> OTHER INFORMATION: linker oligonucleotide

<400> SEQUENCE: 80
cagagcggtg gaggatccgg gagctccaga gggt        34

<210> SEQ ID NO 81
<211> LENGTH: 39
<212> TYPE: DNA

```
<213> ORGANISM: Artificial sequence
<220> FEATURE:
<223> OTHER INFORMATION: linker oligonucleotide

<400> SEQUENCE: 81
cagagcggtg gaggatccgg gagctccagc gccgagggt                        39

<210> SEQ ID NO 82
<211> LENGTH: 12
<212> TYPE: PRT
<213> ORGANISM: Artificial sequence
<220> FEATURE:
<223> OTHER INFORMATION: peptide flag

<400> SEQUENCE: 82

Met Ala Asp Pro Asn Arg Phe Arg Gly Lys Asp Leu
 1               5                  10

<210> SEQ ID NO 83
<211> LENGTH: 60
<212> TYPE: DNA
<213> ORGANISM: Artificial sequence
<220> FEATURE:
<223> OTHER INFORMATION: mutagenic oligonucleotide

<400> SEQUENCE: 83
gatggtgaag ctgcggctga tgcatctggt agcgtctaga gccaccatca           50
ccatcaccat                                                       60

<210> SEQ ID NO 84
<211> LENGTH: 60
<212> TYPE: DNA
<213> ORGANISM: Artificial sequence
<220> FEATURE:
<223> OTHER INFORMATION: mutagenic oligonucleotide

<400> SEQUENCE: 84
gctgtcggta ttatttacat gctcctcgtg gaggcgtcgc cctgggctgc           50
taaggcgcca                                                       60

<210> SEQ ID NO 85
<211> LENGTH: 33
<212> TYPE: DNA
<213> ORGANISM: Artificial sequence
<220> FEATURE:
<223> OTHER INFORMATION: mutagenic oligonucleotide

<400> SEQUENCE: 85
acctcgaaag caagccatca ccatcaccat gcg                             33

<210> SEQ ID NO 86
<211> LENGTH: 36
<212> TYPE: DNA
<213> ORGANISM: Artificial sequence
<220> FEATURE:
<223> OTHER INFORMATION: mutagenic oligonucleotide

<400> SEQUENCE: 86
acctcgaaag caagcggcca tcaccatcac catgcg                          36

<210> SEQ ID NO 87
<211> LENGTH: 39
<212> TYPE: DNA
<213> ORGANISM: Artificial sequence
<220> FEATURE:
<223> OTHER INFORMATION: mutagenic oligonucleotide
```

-continued

<400> SEQUENCE: 87
acctcgaaag caagcggtgg ccatcaccat caccatgcg    39

<210> SEQ ID NO 88
<211> LENGTH: 42
<212> TYPE: DNA
<213> ORGANISM: Artificial sequence
<220> FEATURE:
<223> OTHER INFORMATION: mutagenic oligonucleotide

<400> SEQUENCE: 88
acctcgaaag caagcggtgg tggccatcac catcaccatg cg    42

<210> SEQ ID NO 89
<211> LENGTH: 45
<212> TYPE: DNA
<213> ORGANISM: Artificial sequence
<220> FEATURE:
<223> OTHER INFORMATION: mutagenic oligonucleotide

<400> SEQUENCE: 89
acctcgaaag caagcggcgg tggtggccat caccatcacc atgcg    45

<210> SEQ ID NO 90
<211> LENGTH: 51
<212> TYPE: DNA
<213> ORGANISM: Artificial sequence
<220> FEATURE:
<223> OTHER INFORMATION: mutagenic oligonucleotide

<400> SEQUENCE: 90
acctcgaaag caagcggtgg tggcggtggt ggccatcacc atcaccatgc    50
g    51

<210> SEQ ID NO 91
<211> LENGTH: 54
<212> TYPE: DNA
<213> ORGANISM: Artificial sequence
<220> FEATURE:
<223> OTHER INFORMATION: mutagenic oligonucleotide

<400> SEQUENCE: 91
acctcgaaag caagcggcgg tggtggcggt ggtggccatc accatcacca    50
tgcg    54

<210> SEQ ID NO 92
<211> LENGTH: 57
<212> TYPE: DNA
<213> ORGANISM: Artificial sequence
<220> FEATURE:
<223> OTHER INFORMATION: mutagenic oligonucleotide

<400> SEQUENCE: 92
acctcgaaag caagcggtgg cggtggtggc ggtggtggcc atcaccatca    50
ccatgcg    57

<210> SEQ ID NO 93
<211> LENGTH: 60
<212> TYPE: DNA
<213> ORGANISM: Artificial sequence
<220> FEATURE:
<223> OTHER INFORMATION: mutagenic oligonucleotide

<400> SEQUENCE: 93

```
acctcgaaag caagcggcgg tggcggtggt ggcggtggtg gccatcacca            50
tcaccatgcg                                                        60

<210> SEQ ID NO 94
<211> LENGTH: 63
<212> TYPE: DNA
<213> ORGANISM: Artificial sequence
<220> FEATURE:
<223> OTHER INFORMATION: mutagenic oligonucleotide

<400> SEQUENCE: 94
acctcgaaag caagcggtgg cggtggcggt ggtggcggtg gtggccatca            50
ccatcaccat gcg                                                    63

<210> SEQ ID NO 95
<211> LENGTH: 69
<212> TYPE: DNA
<213> ORGANISM: Artificial sequence
<220> FEATURE:
<223> OTHER INFORMATION: mutagenic oligonucleotide

<400> SEQUENCE: 95
acctcgaaag caagcggtgg cggtggcggt ggcggtggtg gcggtggtgg            50
ccatcaccat caccatgcg                                              69

<210> SEQ ID NO 96
<211> LENGTH: 75
<212> TYPE: DNA
<213> ORGANISM: Artificial sequence
<220> FEATURE:
<223> OTHER INFORMATION: mutagenic oligonucleotide

<400> SEQUENCE: 96
acctcgaaag caagcggtgg tggtggcggt ggcggtggcg gtggtggcgg            50
tggtggccat caccatcacc atgcg                                       75

<210> SEQ ID NO 97
<211> LENGTH: 81
<212> TYPE: DNA
<213> ORGANISM: Artificial sequence
<220> FEATURE:
<223> OTHER INFORMATION: mutagenic oligonucleotide

<400> SEQUENCE: 97
acctcgaaag caagcggcgg cggtggtggt ggcggtggcg gtggcggtgg            50
tggcggtggt ggccatcacc atcaccatgc g                                81

<210> SEQ ID NO 98
<211> LENGTH: 87
<212> TYPE: DNA
<213> ORGANISM: Artificial sequence
<220> FEATURE:
<223> OTHER INFORMATION: mutagenic oligonucleotide

<400> SEQUENCE: 98
acctcgaaag caagcggcgg tggcggcggt ggtggtggcg gtggcggtgg            50
cggtggtggc ggtggtggcc atcaccatca ccatgcg                          87

<210> SEQ ID NO 99
<211> LENGTH: 93
<212> TYPE: DNA
<213> ORGANISM: Artificial sequence
```

-continued

<220> FEATURE:
<223> OTHER INFORMATION: mutagenic oligonucleotide

<400> SEQUENCE: 99
acctcgaaag caagcggtgg tggcggtggc ggcggtggtg gtggcggtgg            50
cggtggcggt ggtggcggtg gtggccatca ccatcaccat gcg                   93

<210> SEQ ID NO 100
<211> LENGTH: 60
<212> TYPE: DNA
<213> ORGANISM: Artificial sequence
<220> FEATURE:
<223> OTHER INFORMATION: zone library
<220> FEATURE:
<221> NAME/KEY: MISC_FEATURE
<222> LOCATION: 19-20
<223> OTHER INFORMATION: where n is A, G, C, or T
<220> FEATURE:
<221> NAME/KEY: MISC_FEATURE
<222> LOCATION: 22-23
<223> OTHER INFORMATION: where n is A, G, C, or T
<220> FEATURE:
<221> NAME/KEY: MISC_FEATURE
<222> LOCATION: 25-26
<223> OTHER INFORMATION: where n is A, G, C, or T
<220> FEATURE:
<221> NAME/KEY: MISC_FEATURE
<222> LOCATION: 28-29
<223> OTHER INFORMATION: where n is A, G, C, or T
<220> FEATURE:
<221> NAME/KEY: MISC_FEATURE
<222> LOCATION: 31-32
<223> OTHER INFORMATION: where n is A, G, C, or T
<220> FEATURE:
<221> NAME/KEY: MISC_FEATURE
<222> LOCATION: 34-35
<223> OTHER INFORMATION: where n is A, G, C, or T

<400> SEQUENCE: 100
caaggaccat agattatgnn snnsnnsnns nnsnnsaagt ttctgaaagt            50
ttttgttttt                                                        60

<210> SEQ ID NO 101
<211> LENGTH: 57
<212> TYPE: DNA
<213> ORGANISM: Artificial sequence
<220> FEATURE:
<223> OTHER INFORMATION: zone library
<220> FEATURE:
<221> NAME/KEY: MISC_FEATURE
<222> LOCATION: 19-20
<223> OTHER INFORMATION: where n is A, G, C, or T
<220> FEATURE:
<221> NAME/KEY: MISC_FEATURE
<222> LOCATION: 22-23
<223> OTHER INFORMATION: where n is A, G, C, or T
<220> FEATURE:
<221> NAME/KEY: MISC_FEATURE
<222> LOCATION: 25-26
<223> OTHER INFORMATION: where n is A, G, C, or T
<220> FEATURE:
<221> NAME/KEY: MISC_FEATURE
<222> LOCATION: 28-29
<223> OTHER INFORMATION: where n is A, G, C, or T
<220> FEATURE:
<221> NAME/KEY: MISC_FEATURE
<222> LOCATION: 31-32
<223> OTHER INFORMATION: where n is A, G, C, or T
<220> FEATURE:
<221> NAME/KEY: MISC_FEATURE
<222> LOCATION: 34-35
<223> OTHER INFORMATION: where n is A, G, C, or T

<400> SEQUENCE: 101

```
attatgagca agagcactnn snnsnnsnns nnsnnsgttt tgttttttc       50 tgttgat                                                     57
```

```
<210> SEQ ID NO 102
<211> LENGTH: 69
<212> TYPE: DNA
<213> ORGANISM: Artificial sequence
<220> FEATURE:
<223> OTHER INFORMATION: zone library
<220> FEATURE:
<221> NAME/KEY: MISC_FEATURE
<222> LOCATION: 19-20
<223> OTHER INFORMATION: where n is A, G, C, or T
<220> FEATURE:
<221> NAME/KEY: MISC_FEATURE
<222> LOCATION: 22-23
<223> OTHER INFORMATION: where n is A, G, C, or T
<220> FEATURE:
<221> NAME/KEY: MISC_FEATURE
<222> LOCATION: 25-26
<223> OTHER INFORMATION: where n is A, G, C, or T
<220> FEATURE:
<221> NAME/KEY: MISC_FEATURE
<222> LOCATION: 28-29
<223> OTHER INFORMATION: where n is A, G, C, or T
<220> FEATURE:
<221> NAME/KEY: MISC_FEATURE
<222> LOCATION: 31-32
<223> OTHER INFORMATION: where n is A, G, C, or T
<220> FEATURE:
<221> NAME/KEY: MISC_FEATURE
<222> LOCATION: 34-35
<223> OTHER INFORMATION: where n is A, G, C, or T
<220> FEATURE:
<221> NAME/KEY: MISC_FEATURE
<222> LOCATION: 37-38
<223> OTHER INFORMATION: where n is A, G, C, or T
<220> FEATURE:
<221> NAME/KEY: MISC_FEATURE
<222> LOCATION: 40-41
<223> OTHER INFORMATION: where n is A, G, C, or T
<220> FEATURE:
<221> NAME/KEY: MISC_FEATURE
<222> LOCATION: 43-44
<223> OTHER INFORMATION: where n is A, G, C, or T
<220> FEATURE:
<221> NAME/KEY: MISC_FEATURE
<222> LOCATION: 46-47
<223> OTHER INFORMATION: where n is A, G, C, or T

<400> SEQUENCE: 102
ttcaaaaagt ttctgaaann snnsnnsnns nnsnnsnnsn nsnnsnnsaa      50
ttggatttgg gctgtcggt                                        69
```

```
<210> SEQ ID NO 103
<211> LENGTH: 69
<212> TYPE: DNA
<213> ORGANISM: Artificial sequence
<220> FEATURE:
<223> OTHER INFORMATION: zone library
<220> FEATURE:
<221> NAME/KEY: MISC_FEATURE
<222> LOCATION: 22-23
<223> OTHER INFORMATION: where n is A, G, C, or T
<220> FEATURE:
<221> NAME/KEY: MISC_FEATURE
<222> LOCATION: 25-26
<223> OTHER INFORMATION: where n is A, G, C, or T
<220> FEATURE:
<221> NAME/KEY: MISC_FEATURE
<222> LOCATION: 28-29
<223> OTHER INFORMATION: where n is A, G, C, or T
<220> FEATURE:
<221> NAME/KEY: MISC_FEATURE
```

```
<222> LOCATION: 31-32
<223> OTHER INFORMATION: where n is A, G, C, or T
<220> FEATURE:
<221> NAME/KEY: MISC_FEATURE
<222> LOCATION: 34-35
<223> OTHER INFORMATION: where n is A, G, C, or T
<220> FEATURE:
<221> NAME/KEY: MISC_FEATURE
<222> LOCATION: 37-38
<223> OTHER INFORMATION: where n is A, G, C, or T
<220> FEATURE:
<221> NAME/KEY: MISC_FEATURE
<222> LOCATION: 40-41
<223> OTHER INFORMATION: where n is A, G, C, or T
<220> FEATURE:
<221> NAME/KEY: MISC_FEATURE
<222> LOCATION: 43-44
<223> OTHER INFORMATION: where n is A, G, C, or T
<220> FEATURE:
<221> NAME/KEY: MISC_FEATURE
<222> LOCATION: 46-47
<223> OTHER INFORMATION: where n is A, G, C, or T
<220> FEATURE:
<221> NAME/KEY: MISC_FEATURE
<222> LOCATION: 49-50
<223> OTHER INFORMATION: where n is A, G, C, or T

<400> SEQUENCE: 103 gtttttctg ttgatgttga tnnsnnsnns nnsnnsnnsn nsnnsnnsnn          50
sgcggctgat gcattccca                                           69

<210> SEQ ID NO 104
<211> LENGTH: 72
<212> TYPE: DNA
<213> ORGANISM: Artificial sequence
<220> FEATURE:
<223> OTHER INFORMATION: zone library
<220> FEATURE:
<221> NAME/KEY: MISC_FEATURE
<222> LOCATION: 19-20
<223> OTHER INFORMATION: where n is A, G, C, or T
<220> FEATURE:
<221> NAME/KEY: MISC_FEATURE
<222> LOCATION: 22-23
<223> OTHER INFORMATION: where n is A, G, C, or T
<220> FEATURE:
<221> NAME/KEY: MISC_FEATURE
<222> LOCATION: 25-26
<223> OTHER INFORMATION: where n is A, G, C, or T
<220> FEATURE:
<221> NAME/KEY: MISC_FEATURE
<222> LOCATION: 28-29
<223> OTHER INFORMATION: where n is A, G, C, or T
<220> FEATURE:
<221> NAME/KEY: MISC_FEATURE
<222> LOCATION: 31-32
<223> OTHER INFORMATION: where n is A, G, C, or T
<220> FEATURE:
<221> NAME/KEY: MISC_FEATURE
<222> LOCATION: 34-35
<223> OTHER INFORMATION: where n is A, G, C, or T
<220> FEATURE:
<221> NAME/KEY: MISC_FEATURE
<222> LOCATION: 37-38
<223> OTHER INFORMATION: where n is A, G, C, or T
<220> FEATURE:
<221> NAME/KEY: MISC_FEATURE
<222> LOCATION: 40-41
<223> OTHER INFORMATION: where n is A, G, C, or T
<220> FEATURE:
<221> NAME/KEY: MISC_FEATURE
<222> LOCATION: 43-44
<223> OTHER INFORMATION: where n is A, G, C, or T
<220> FEATURE:
<221> NAME/KEY: MISC_FEATURE
<222> LOCATION: 46-47
<223> OTHER INFORMATION: where n is A, G, C, or T
```

<400> SEQUENCE: 104
tgggctgtcg gtattattnn snnsnnsnns nnsnnsnnsn nsnnsnnsgc    50
tgctaaggcg ccagacgatg gt                                  72

<210> SEQ ID NO 105
<211> LENGTH: 69
<212> TYPE: DNA
<213> ORGANISM: Artificial sequence
<220> FEATURE:
<223> OTHER INFORMATION: zone library
<220> FEATURE:
<221> NAME/KEY: MISC_FEATURE
<222> LOCATION: 22-23
<223> OTHER INFORMATION: where n is A, G, C, or T
<220> FEATURE:
<221> NAME/KEY: MISC_FEATURE
<222> LOCATION: 25-26
<223> OTHER INFORMATION: where n is A, G, C, or T
<220> FEATURE:
<221> NAME/KEY: MISC_FEATURE
<222> LOCATION: 28-29
<223> OTHER INFORMATION: where n is A, G, C, or T
<220> FEATURE:
<221> NAME/KEY: MISC_FEATURE
<222> LOCATION: 31-32
<223> OTHER INFORMATION: where n is A, G, C, or T
<220> FEATURE:
<221> NAME/KEY: MISC_FEATURE
<222> LOCATION: 34-35
<223> OTHER INFORMATION: where n is A, G, C, or T
<220> FEATURE:
<221> NAME/KEY: MISC_FEATURE
<222> LOCATION: 37-38
<223> OTHER INFORMATION: where n is A, G, C, or T
<220> FEATURE:
<221> NAME/KEY: MISC_FEATURE
<222> LOCATION: 40-41
<223> OTHER INFORMATION: where n is A, G, C, or T
<220> FEATURE:
<221> NAME/KEY: MISC_FEATURE
<222> LOCATION: 43-44
<223> OTHER INFORMATION: where n is A, G, C, or T
<220> FEATURE:
<221> NAME/KEY: MISC_FEATURE
<222> LOCATION: 46-47
<223> OTHER INFORMATION: where n is A, G, C, or T
<220> FEATURE:
<221> NAME/KEY: MISC_FEATURE
<222> LOCATION: 49-50
<223> OTHER INFORMATION: where n is A, G, C, or T

<400> SEQUENCE: 105
agcgctcagc tgagcaactt cnnsnnsnns nnsnnsnnsn nsnnsnnsnn    50
sgcggctgat gcattccca                                      69

<210> SEQ ID NO 106
<211> LENGTH: 81
<212> TYPE: DNA
<213> ORGANISM: Artificial sequence
<220> FEATURE:
<223> OTHER INFORMATION: linker library

<400> SEQUENCE: 106
gatggtgaag ctgcggctvv cvvcvvcvvc vvcvvcvvcv vcvvcvvcvv    50
cvvcvvcvvc gatgcattcc caactatacc a                        81

<210> SEQ ID NO 107
<211> LENGTH: 96
<212> TYPE: DNA
<213> ORGANISM: Artificial sequence

```
<220> FEATURE:
<223> OTHER INFORMATION: mutagenic oligonucleotide
<220> FEATURE:
<221> NAME/KEY: MISC_FEATURE
<222> LOCATION: 22
<223> OTHER INFORMATION: where n is A, G, C, or T
<220> FEATURE:
<221> NAME/KEY: MISC_FEATURE
<222> LOCATION: 25
<223> OTHER INFORMATION: where n is A, G, C, or T
<220> FEATURE:
<221> NAME/KEY: MISC_FEATURE
<222> LOCATION: 28
<223> OTHER INFORMATION: where n is A, G, C, or T
<220> FEATURE:
<221> NAME/KEY: MISC_FEATURE
<222> LOCATION: 31
<223> OTHER INFORMATION: where n is A, G, C, or T
<220> FEATURE:
<221> NAME/KEY: MISC_FEATURE
<222> LOCATION: 34
<223> OTHER INFORMATION: where n is A, G, C, or T
<220> FEATURE:
<221> NAME/KEY: MISC_FEATURE
<222> LOCATION: 37
<223> OTHER INFORMATION: where n is A, G, C, or T
<220> FEATURE:
<221> NAME/KEY: MISC_FEATURE
<222> LOCATION: 40
<223> OTHER INFORMATION: where n is A, G, C, or T
<220> FEATURE:
<221> NAME/KEY: MISC_FEATURE
<222> LOCATION: 43
<223> OTHER INFORMATION: where n is A, G, C, or T
<220> FEATURE:
<221> NAME/KEY: MISC_FEATURE
<222> LOCATION: 46
<223> OTHER INFORMATION: where n is A, G, C, or T
<220> FEATURE:
<221> NAME/KEY: MISC_FEATURE
<222> LOCATION: 49
<223> OTHER INFORMATION: where n is A, G, C, or T
<220> FEATURE:
<221> NAME/KEY: MISC_FEATURE
<222> LOCATION: 52
<223> OTHER INFORMATION: where n is A, G, C, or T
<220> FEATURE:
<221> NAME/KEY: MISC_FEATURE
<222> LOCATION: 55
<223> OTHER INFORMATION: where n is A, G, C, or T
<220> FEATURE:
<221> NAME/KEY: MISC_FEATURE
<222> LOCATION: 58
<223> OTHER INFORMATION: where n is A, G, C, or T
<220> FEATURE:
<221> NAME/KEY: MISC_FEATURE
<222> LOCATION: 61
<223> OTHER INFORMATION: where n is A, G, C, or T
<220> FEATURE:
<221> NAME/KEY: MISC_FEATURE
<222> LOCATION: 64
<223> OTHER INFORMATION: where n is A, G, C, or T
<220> FEATURE:
<221> NAME/KEY: MISC_FEATURE
<222> LOCATION: 67
<223> OTHER INFORMATION: where n is A, G, C, or T
<220> FEATURE:
<221> NAME/KEY: MISC_FEATURE
<222> LOCATION: 70
<223> OTHER INFORMATION: where n is A, G, C, or T
<220> FEATURE:
<221> NAME/KEY: MISC_FEATURE
<222> LOCATION: 73
<223> OTHER INFORMATION: where n is A, G, C, or T
<220> FEATURE:
<221> NAME/KEY: MISC_FEATURE
<222> LOCATION: 76
<223> OTHER INFORMATION: where n is A, G, C, or T

<400> SEQUENCE: 107
```

```
actttcaaaa agtttctgaa anwtnktnwt nytnytnktn wtnwtnwtnw        50
tnwtnkgnyt nkgnytnwcn ktnwtnwtga gactgctagc gctcag            96
```

<210> SEQ ID NO 108
<211> LENGTH: 21
<212> TYPE: DNA
<213> ORGANISM: Artificial sequence
<220> FEATURE:
<223> OTHER INFORMATION: synthetic oligonucleotide

<400> SEQUENCE: 108

```
caccatcacc atcaccatgc g                                      21
```

<210> SEQ ID NO 109
<211> LENGTH: 30
<212> TYPE: DNA
<213> ORGANISM: Artificial sequence
<220> FEATURE:
<223> OTHER INFORMATION: linker oligonucleotide

<400> SEQUENCE: 109

```
gcctgggagg agaacatcga cagcgccccc                             30
```

<210> SEQ ID NO 110
<211> LENGTH: 10
<212> TYPE: PRT
<213> ORGANISM: Artificial sequence
<220> FEATURE:
<223> OTHER INFORMATION: linker peptide

<400> SEQUENCE: 110

```
Ala Trp Glu Glu Asn Ile Asp Ser Ala Pro
 1               5                  10
```

<210> SEQ ID NO 111
<211> LENGTH: 30
<212> TYPE: DNA
<213> ORGANISM: Artificial sequence
<220> FEATURE:
<223> OTHER INFORMATION: linker oligonucleotide

<400> SEQUENCE: 111

```
cagtacggga cgccggacac cgacaccgac                             30
```

<210> SEQ ID NO 112
<211> LENGTH: 10
<212> TYPE: PRT
<213> ORGANISM: Artificial sequence
<220> FEATURE:
<223> OTHER INFORMATION: linker peptide

<400> SEQUENCE: 112

```
Gln Tyr Gly Thr Pro Asp Thr Asp Thr Asp
 1               5                  10
```

<210> SEQ ID NO 113
<211> LENGTH: 30
<212> TYPE: DNA
<213> ORGANISM: Artificial sequence
<220> FEATURE:
<223> OTHER INFORMATION: linker oligonucleotide

<400> SEQUENCE: 113

```
acggggtggt tggaggggcc cgacaccccc                             30
```

```
<210> SEQ ID NO 114
<211> LENGTH: 10
<212> TYPE: PRT
<213> ORGANISM: Artificial sequence
<220> FEATURE:
<223> OTHER INFORMATION: linker peptide

<400> SEQUENCE: 114

Thr Gly Trp Leu Glu Gly Pro Asp Thr Pro
 1               5                  10

<210> SEQ ID NO 115
<211> LENGTH: 24
<212> TYPE: DNA
<213> ORGANISM: Artificial sequence
<220> FEATURE:
<223> OTHER INFORMATION: linker oligonucleotide

<400> SEQUENCE: 115
ctcatgggcc ccggcgcgga cggc                                          24

<210> SEQ ID NO 116
<211> LENGTH: 8
<212> TYPE: PRT
<213> ORGANISM: Artificial sequence
<220> FEATURE:
<223> OTHER INFORMATION: linker peptide

<400> SEQUENCE: 116

Leu Met Gly Pro Gly Ala Asp Gly
 1               5

<210> SEQ ID NO 117
<211> LENGTH: 24
<212> TYPE: DNA
<213> ORGANISM: Artificial sequence
<220> FEATURE:
<223> OTHER INFORMATION: linker oligonucleotide

<400> SEQUENCE: 117
cacgactcgg tcccgagcaa cggc                                          24

<210> SEQ ID NO 118
<211> LENGTH: 8
<212> TYPE: PRT
<213> ORGANISM: Artificial sequence
<220> FEATURE:
<223> OTHER INFORMATION: linker peptide

<400> SEQUENCE: 118

His Asp Ser Val Pro Ser Asn Gly
 1               5

<210> SEQ ID NO 119
<211> LENGTH: 120
<212> TYPE: DNA
<213> ORGANISM: Artificial sequence
<220> FEATURE:
<223> OTHER INFORMATION: linker oligonucleotide

<400> SEQUENCE: 119
atgagcaaga gcactttcaa aaagtttctg aaagagactg ctagcgctca              50
gctgagcaac ttcgctgcta aggcgccaga cgatggtgaa gctgcggctc              100
accatcacca tcaccatgcg                                               120

<210> SEQ ID NO 120
```

```
<211> LENGTH: 40
<212> TYPE: PRT
<213> ORGANISM: Artificial sequence
<220> FEATURE:
<223> OTHER INFORMATION: linker peptide

<400> SEQUENCE: 120

Met Ser Lys Ser Thr Phe Lys Lys Phe Leu Lys Glu Thr Ala Ser
 1               5                  10                  15

Ala Gln Leu Ser Asn Phe Ala Ala Lys Ala Pro Asp Asp Gly Glu
            20                  25                  30

Ala Ala Ala His His His His His His Ala
        35                  40

<210> SEQ ID NO 121
<211> LENGTH: 41
<212> TYPE: PRT
<213> ORGANISM: Artificial sequence
<220> FEATURE:
<223> OTHER INFORMATION: M13 coat protein VIII library
<220> FEATURE:
<221> NAME/KEY: VARIANT
<222> LOCATION: 12
<223> OTHER INFORMATION: where Xaa is any amino acid

<400> SEQUENCE: 121

Met Ser Lys Ser Thr Phe Lys Lys Phe Leu Lys Xaa Glu Thr Ala
 1               5                  10                  15

Ser Ala Gln Leu Ser Asn Phe Ala Ala Lys Ala Pro Asp Asp Gly
            20                  25                  30

Glu Ala Ala Ala His His His His His His Ala
        35                  40

<210> SEQ ID NO 122
<211> LENGTH: 51
<212> TYPE: DNA
<213> ORGANISM: Artificial sequence
<220> FEATURE:
<223> OTHER INFORMATION: mutagenic oligonucleotide

<400> SEQUENCE: 122
gctgcggctg atgcatctgg tagcgtctag agccaccatc accatcacca          50
t                                                               51

<210> SEQ ID NO 123
<211> LENGTH: 54
<212> TYPE: PRT
<213> ORGANISM: Artificial sequence
<220> FEATURE:
<223> OTHER INFORMATION: P1-1 plus linker

<400> SEQUENCE: 123

Met Ser Lys Ser Thr Phe Lys Lys Phe Leu Lys Val Phe Val Phe
 1               5                  10                  15

Ser Val Asp Val Asp Asn Asn Trp Ile Trp Ala Val Gly Ile Ile
            20                  25                  30

Glu Thr Ala Ser Ala Gln Leu Ser Asn Phe Ala Ala Lys Ala Pro
        35                  40                  45

Asp Asp Gly Glu Ala Ala Ala Asp Ala
                50

<210> SEQ ID NO 124
<211> LENGTH: 150
<212> TYPE: DNA
```

```
<213> ORGANISM: Artificial sequence
<220> FEATURE:
<223> OTHER INFORMATION: M13 coat protein VIII variant

<400> SEQUENCE: 124
atgagcaaga gcactttcaa aaagtttctg aaagtttttg ttttttctgt         50
tgatgttgat aataattgga tttgggctgt cggtattatt tacatgctcc        100
tcgtggaggc gtcgccctgg gctgctaagg cgccagacga tggtgaagct        150

<210> SEQ ID NO 125
<211> LENGTH: 48
<212> TYPE: DNA
<213> ORGANISM: Artificial sequence
<220> FEATURE:
<223> OTHER INFORMATION: mutagenic oligonucleotide library
<220> FEATURE:
<221> NAME/KEY: MISC_FEATURE
<222> LOCATION: 19-20
<223> OTHER INFORMATION: where n is A, G, C, or T
<220> FEATURE:
<221> NAME/KEY: MISC_FEATURE
<222> LOCATION: 22-23
<223> OTHER INFORMATION: where n is A, G, C, or T
<220> FEATURE:
<221> NAME/KEY: MISC_FEATURE
<222> LOCATION: 25-26
<223> OTHER INFORMATION: where n is A, G, C, or T
<220> FEATURE:
<221> NAME/KEY: MISC_FEATURE
<222> LOCATION: 28-29
<223> OTHER INFORMATION: where n is A, G, C, or T

<400> SEQUENCE: 125
ttcacctcga aagcaagcnn snnsnnsnns caccatcacc atcaccat          48

<210> SEQ ID NO 126
<211> LENGTH: 51
<212> TYPE: DNA
<213> ORGANISM: Artificial sequence
<220> FEATURE:
<223> OTHER INFORMATION: mutagenic oligonucleotide library
<220> FEATURE:
<221> NAME/KEY: MISC_FEATURE
<222> LOCATION: 19-20
<223> OTHER INFORMATION: where n is A, G, C, or T
<220> FEATURE:
<221> NAME/KEY: MISC_FEATURE
<222> LOCATION: 22-23
<223> OTHER INFORMATION: where n is A, G, C, or T
<220> FEATURE:
<221> NAME/KEY: MISC_FEATURE
<222> LOCATION: 25-26
<223> OTHER INFORMATION: where n is A, G, C, or T
<220> FEATURE:
<221> NAME/KEY: MISC_FEATURE
<222> LOCATION: 28-29
<223> OTHER INFORMATION: where n is A, G, C, or T
<220> FEATURE:
<221> NAME/KEY: MISC_FEATURE
<222> LOCATION: 31-32
<223> OTHER INFORMATION: where n is A, G, C, or T

<400> SEQUENCE: 126
ttcacctcga aagcaagcnn snnsnnsnns nnscaccatc accatcacca        50
t                                                             51

<210> SEQ ID NO 127
<211> LENGTH: 54
<212> TYPE: DNA
<213> ORGANISM: Artificial sequence
<220> FEATURE:
```

```
<223> OTHER INFORMATION: mutagenic oligonucleotide library
<220> FEATURE:
<221> NAME/KEY: MISC_FEATURE
<222> LOCATION: 19-20
<223> OTHER INFORMATION: where n is A, G, C, or T
<220> FEATURE:
<221> NAME/KEY: MISC_FEATURE
<222> LOCATION: 22-23
<223> OTHER INFORMATION: where n is A, G, C, or T
<220> FEATURE:
<221> NAME/KEY: MISC_FEATURE
<222> LOCATION: 25-26
<223> OTHER INFORMATION: where n is A, G, C, or T
<220> FEATURE:
<221> NAME/KEY: MISC_FEATURE
<222> LOCATION: 28-29
<223> OTHER INFORMATION: where n is A, G, C, or T
<220> FEATURE:
<221> NAME/KEY: MISC_FEATURE
<222> LOCATION: 31-32
<223> OTHER INFORMATION: where n is A, G, C, or T
<220> FEATURE:
<221> NAME/KEY: MISC_FEATURE
<222> LOCATION: 34-35
<223> OTHER INFORMATION: where n is A, G, C, or T

<400> SEQUENCE: 127
ttcacctcga aagcaagcnn snnsnnsnns nnsnnscacc atcaccatca        50
ccat                                                          54

<210> SEQ ID NO 128
<211> LENGTH: 60
<212> TYPE: DNA
<213> ORGANISM: Artificial sequence
<220> FEATURE:
<223> OTHER INFORMATION: mutagenic oligonucleotide library
<220> FEATURE:
<221> NAME/KEY: MISC_FEATURE
<222> LOCATION: 19-20
<223> OTHER INFORMATION: where n is A, G, C, or T
<220> FEATURE:
<221> NAME/KEY: MISC_FEATURE
<222> LOCATION: 22-23
<223> OTHER INFORMATION: where n is A, G, C, or T
<220> FEATURE:
<221> NAME/KEY: MISC_FEATURE
<222> LOCATION: 25-26
<223> OTHER INFORMATION: where n is A, G, C, or T
<220> FEATURE:
<221> NAME/KEY: MISC_FEATURE
<222> LOCATION: 28-29
<223> OTHER INFORMATION: where n is A, G, C, or T
<220> FEATURE:
<221> NAME/KEY: MISC_FEATURE
<222> LOCATION: 31-32
<223> OTHER INFORMATION: where n is A, G, C, or T
<220> FEATURE:
<221> NAME/KEY: MISC_FEATURE
<222> LOCATION: 34-35
<223> OTHER INFORMATION: where n is A, G, C, or T

<400> SEQUENCE: 128
ttcacctcga aagcaagcnn snnsnnsnns nnsnnsvvcv vccaccatca        50
ccatcaccat                                                    60

<210> SEQ ID NO 129
<211> LENGTH: 66
<212> TYPE: DNA
<213> ORGANISM: Artificial sequence
<220> FEATURE:
<223> OTHER INFORMATION: mutagenic oligonucleotide library
<220> FEATURE:
<221> NAME/KEY: MISC_FEATURE
<222> LOCATION: 19-20
```

```
<223> OTHER INFORMATION: where n is A, G, C, or T
<220> FEATURE:
<221> NAME/KEY: MISC_FEATURE
<222> LOCATION: 22-23
<223> OTHER INFORMATION: where n is A, G, C, or T
<220> FEATURE:
<221> NAME/KEY: MISC_FEATURE
<222> LOCATION: 25-26
<223> OTHER INFORMATION: where n is A, G, C, or T
<220> FEATURE:
<221> NAME/KEY: MISC_FEATURE
<222> LOCATION: 28-29
<223> OTHER INFORMATION: where n is A, G, C, or T
<220> FEATURE:
<221> NAME/KEY: MISC_FEATURE
<222> LOCATION: 31-32
<223> OTHER INFORMATION: where n is A, G, C, or T
<220> FEATURE:
<221> NAME/KEY: MISC_FEATURE
<222> LOCATION: 34-35
<223> OTHER INFORMATION: where n is A, G, C, or T

<400> SEQUENCE: 129
ttcacctcga aagcaagcnn snnsnnsnns nnsnnsvvcv vcvvcvvcca        50
ccatcaccat caccat                                             66

<210> SEQ ID NO 130
<211> LENGTH: 75
<212> TYPE: DNA
<213> ORGANISM: Artificial sequence
<220> FEATURE:
<223> OTHER INFORMATION: mutagenic oligonucleotide library
<220> FEATURE:
<221> NAME/KEY: MISC_FEATURE
<222> LOCATION: 19-20
<223> OTHER INFORMATION: where n is A, G, C, or T
<220> FEATURE:
<221> NAME/KEY: MISC_FEATURE
<222> LOCATION: 22-23
<223> OTHER INFORMATION: where n is A, G, C, or T
<220> FEATURE:
<221> NAME/KEY: MISC_FEATURE
<222> LOCATION: 25-26
<223> OTHER INFORMATION: where n is A, G, C, or T
<220> FEATURE:
<221> NAME/KEY: MISC_FEATURE
<222> LOCATION: 28-29
<223> OTHER INFORMATION: where n is A, G, C, or T
<220> FEATURE:
<221> NAME/KEY: MISC_FEATURE
<222> LOCATION: 31-32
<223> OTHER INFORMATION: where n is A, G, C, or T
<220> FEATURE:
<221> NAME/KEY: MISC_FEATURE
<222> LOCATION: 34-35
<223> OTHER INFORMATION: where n is A, G, C, or T

<400> SEQUENCE: 130
ctgcgtaata aggagtctnn snnsnnsnns nnsnnscacc atcaccatca        50
ccattaatca tgccagttct tttgg                                   75

<210> SEQ ID NO 131
<211> LENGTH: 81
<212> TYPE: DNA
<213> ORGANISM: Artificial sequence
<220> FEATURE:
<223> OTHER INFORMATION: mutagenic oligonucleotide library
<220> FEATURE:
<221> NAME/KEY: MISC_FEATURE
<222> LOCATION: 19-20
<223> OTHER INFORMATION: where n is A, G, C, or T
<220> FEATURE:
<221> NAME/KEY: MISC_FEATURE
<222> LOCATION: 22-23
```

```
<223> OTHER INFORMATION: where n is A, G, C, or T
<220> FEATURE:
<221> NAME/KEY: MISC_FEATURE
<222> LOCATION: 25-26
<223> OTHER INFORMATION: where n is A, G, C, or T
<220> FEATURE:
<221> NAME/KEY: MISC_FEATURE
<222> LOCATION: 28-29
<223> OTHER INFORMATION: where n is A, G, C, or T
<220> FEATURE:
<221> NAME/KEY: MISC_FEATURE
<222> LOCATION: 31-32
<223> OTHER INFORMATION: where n is A, G, C, or T
<220> FEATURE:
<221> NAME/KEY: MISC_FEATURE
<222> LOCATION: 34-35
<223> OTHER INFORMATION: where n is A, G, C, or T
<220> FEATURE:
<221> NAME/KEY: MISC_FEATURE
<222> LOCATION: 37-38
<223> OTHER INFORMATION: where n is A, G, C, or T
<220> FEATURE:
<221> NAME/KEY: MISC_FEATURE
<222> LOCATION: 40-41
<223> OTHER INFORMATION: where n is A, G, C, or T

<400> SEQUENCE: 131
ctgcgtaata aggagtctnn snnsnnsnns nnsnnsnnsn nscaccatca         50
ccatcaccat taatcatgcc agttcttttg g                            81

<210> SEQ ID NO 132
<211> LENGTH: 87
<212> TYPE: DNA
<213> ORGANISM: Artificial sequence
<220> FEATURE:
<223> OTHER INFORMATION: mutagenic oligonucleotide library
<220> FEATURE:
<221> NAME/KEY: MISC_FEATURE
<222> LOCATION: 19-20
<223> OTHER INFORMATION: where n is A, G, C, or T
<220> FEATURE:
<221> NAME/KEY: MISC_FEATURE
<222> LOCATION: 22-23
<223> OTHER INFORMATION: where n is A, G, C, or T
<220> FEATURE:
<221> NAME/KEY: MISC_FEATURE
<222> LOCATION: 25-26
<223> OTHER INFORMATION: where n is A, G, C, or T
<220> FEATURE:
<221> NAME/KEY: MISC_FEATURE
<222> LOCATION: 28-29
<223> OTHER INFORMATION: where n is A, G, C, or T
<220> FEATURE:
<221> NAME/KEY: MISC_FEATURE
<222> LOCATION: 31-32
<223> OTHER INFORMATION: where n is A, G, C, or T
<220> FEATURE:
<221> NAME/KEY: MISC_FEATURE
<222> LOCATION: 34-35
<223> OTHER INFORMATION: where n is A, G, C, or T
<220> FEATURE:
<221> NAME/KEY: MISC_FEATURE
<222> LOCATION: 37-38
<223> OTHER INFORMATION: where n is A, G, C, or T
<220> FEATURE:
<221> NAME/KEY: MISC_FEATURE
<222> LOCATION: 40-41
<223> OTHER INFORMATION: where n is A, G, C, or T
<220> FEATURE:
<221> NAME/KEY: MISC_FEATURE
<222> LOCATION: 43-44
<223> OTHER INFORMATION: where n is A, G, C, or T
<220> FEATURE:
<221> NAME/KEY: MISC_FEATURE
<222> LOCATION: 46-47
<223> OTHER INFORMATION: where n is A, G, C, or T
```

-continued

<400> SEQUENCE: 132
ctgcgtaata aggagtctnn snnsnnsnns nnsnnsnnsn nsnnsnnsca    50
ccatcaccat caccattaat catgccagtt cttttgg    87

<210> SEQ ID NO 133
<211> LENGTH: 30
<212> TYPE: DNA
<213> ORGANISM: Artificial sequence
<220> FEATURE:
<223> OTHER INFORMATION: linker oligonucleotide

<400> SEQUENCE: 133
gggcaggcca ggatcgtcta ccggcagaag    30

<210> SEQ ID NO 134
<211> LENGTH: 10
<212> TYPE: PRT
<213> ORGANISM: Artificial sequence
<220> FEATURE:
<223> OTHER INFORMATION: peptide linker

<400> SEQUENCE: 134

Gly Gln Ala Arg Ile Val Tyr Arg Gln Lys
 1               5                  10

<210> SEQ ID NO 135
<211> LENGTH: 30
<212> TYPE: DNA
<213> ORGANISM: Artificial sequence
<220> FEATURE:
<223> OTHER INFORMATION: linker oligonucleotide

<400> SEQUENCE: 135
aggatcaggg tcctgcagaa gggcaaggag    30

<210> SEQ ID NO 136
<211> LENGTH: 10
<212> TYPE: PRT
<213> ORGANISM: Artificial sequence
<220> FEATURE:
<223> OTHER INFORMATION: peptide linker

<400> SEQUENCE: 136

Arg Ile Arg Val Leu Gln Lys Gly Lys Glu
 1               5                  10

<210> SEQ ID NO 137
<211> LENGTH: 30
<212> TYPE: DNA
<213> ORGANISM: Artificial sequence
<220> FEATURE:
<223> OTHER INFORMATION: linker oligonucleotide

<400> SEQUENCE: 137
cgcgccaaga tcgagcagat ctgcaaggag    30

<210> SEQ ID NO 138
<211> LENGTH: 10
<212> TYPE: PRT
<213> ORGANISM: Artificial sequence
<220> FEATURE:
<223> OTHER INFORMATION: peptide linker

<400> SEQUENCE: 138

Arg Ala Lys Ile Glu Gln Ile Cys Lys Glu
 1               5                  10

-continued

```
<210> SEQ ID NO 139
<211> LENGTH: 27
<212> TYPE: DNA
<213> ORGANISM: Artificial sequence
<220> FEATURE:
<223> OTHER INFORMATION: M13 coat protein VIII fragment oligonucleotide
      library
<220> FEATURE:
<221> NAME/KEY: MISC_FEATURE
<222> LOCATION: 2
<223> OTHER INFORMATION: where n is A, G, C, or T
<220> FEATURE:
<221> NAME/KEY: MISC_FEATURE
<222> LOCATION: 4
<223> OTHER INFORMATION: where n is A, G, C, or T
<220> FEATURE:
<221> NAME/KEY: MISC_FEATURE
<222> LOCATION: 8
<223> OTHER INFORMATION: where n is A, G, C, or T
<220> FEATURE:
<221> NAME/KEY: MISC_FEATURE
<222> LOCATION: 10
<223> OTHER INFORMATION: where n is A, G, C, or T
<220> FEATURE:
<221> NAME/KEY: MISC_FEATURE
<222> LOCATION: 13
<223> OTHER INFORMATION: where n is A, G, C, or T
<220> FEATURE:
<221> NAME/KEY: MISC_FEATURE
<222> LOCATION: 17
<223> OTHER INFORMATION: where n is A, G, C, or T
<220> FEATURE:
<221> NAME/KEY: MISC_FEATURE
<222> LOCATION: 20
<223> OTHER INFORMATION: where n is A, G, C, or T
<220> FEATURE:
<221> NAME/KEY: MISC_FEATURE
<222> LOCATION: 23
<223> OTHER INFORMATION: where n is A, G, C, or T
<220> FEATURE:
<221> NAME/KEY: MISC_FEATURE
<222> LOCATION: 26
<223> OTHER INFORMATION: where n is A, G, C, or T

<400> SEQUENCE: 139
rntnasrntn asnycrntrn arntrnt                                             27

<210> SEQ ID NO 140
<211> LENGTH: 30
<212> TYPE: DNA
<213> ORGANISM: Artificial sequence
<220> FEATURE:
<223> OTHER INFORMATION: M13 wt coat protein VIII fragment
      oligonucleotide

<400> SEQUENCE: 140
gccgagggtg acgatcccgc aaaagcggcc                                          30

<210> SEQ ID NO 141
<211> LENGTH: 10
<212> TYPE: PRT
<213> ORGANISM: Artificial
<220> FEATURE:
<223> OTHER INFORMATION: M13 wt coat protein VIII fragment

<400> SEQUENCE: 141

Ala Glu Gly Asp Asp Pro Ala Lys Ala Ala
 1               5                  10

<210> SEQ ID NO 142
<211> LENGTH: 30
<212> TYPE: DNA
```

```
<213> ORGANISM: Artificial sequence
<220> FEATURE:
<223> OTHER INFORMATION: M13 variant coat protein VIII fragment
      oligonucleotide

<400> SEQUENCE: 142
gataagagtg agaagttcgc tagagatgct                                     30

<210> SEQ ID NO 143
<211> LENGTH: 10
<212> TYPE: PRT
<213> ORGANISM: Artificial sequence
<220> FEATURE:
<223> OTHER INFORMATION: M13 variant coat protein VIII fragment

<400> SEQUENCE: 143

Asp Lys Ser Glu Lys Phe Ala Arg Asp Ala
 1               5                  10

<210> SEQ ID NO 144
<211> LENGTH: 30
<212> TYPE: DNA
<213> ORGANISM: Artificial sequence
<220> FEATURE:
<223> OTHER INFORMATION: M13 variant coat protein VIII fragment
      oligonucleotide

<400> SEQUENCE: 144
aataaggatg agcagttcgc tagagctgct                                     30

<210> SEQ ID NO 145
<211> LENGTH: 10
<212> TYPE: PRT
<213> ORGANISM: Artificial sequence
<220> FEATURE:
<223> OTHER INFORMATION: M13 variant coat protein VIII fragment

<400> SEQUENCE: 145

Ile Lys Asp Glu Gly Phe Ala Arg Ala Ala
 1               5                  10

<210> SEQ ID NO 146
<211> LENGTH: 30
<212> TYPE: DNA
<213> ORGANISM: Artificial sequence
<220> FEATURE:
<223> OTHER INFORMATION: M13 variant coat protein VIII fragment
      oligonucleotide

<400> SEQUENCE: 146
atttacatta aggagaccag taaaaatgct                                     30

<210> SEQ ID NO 147
<211> LENGTH: 10
<212> TYPE: PRT
<213> ORGANISM: Artificial sequence
<220> FEATURE:
<223> OTHER INFORMATION: M13 variant coat protein VIII fragment

<400> SEQUENCE: 147

Ile Tyr Ile Lys Glu Thr Ser Lys Asn Ala
 1               5                  10

<210> SEQ ID NO 148
<211> LENGTH: 30
<212> TYPE: DNA
<213> ORGANISM: Artificial sequence
<220> FEATURE:
```

```
<223> OTHER INFORMATION: M13 variant coat protein VIII fragment
      oligonucleotide

<400> SEQUENCE: 148
aattacgttg accaggtcag taaaaatgct                                          30

<210> SEQ ID NO 149
<211> LENGTH: 10
<212> TYPE: PRT
<213> ORGANISM: Artificial sequence
<220> FEATURE:
<223> OTHER INFORMATION: M13 variant coat protein VIII fragment

<400> SEQUENCE: 149

Asn Tyr Val Asp Gln Val Ser Lys Asn Ala
 1               5                  10

<210> SEQ ID NO 150
<211> LENGTH: 30
<212> TYPE: DNA
<213> ORGANISM: Artificial sequence
<220> FEATURE:
<223> OTHER INFORMATION: M13 variant coat protein VIII fragment
      oligonucleotide

<400> SEQUENCE: 150
gctaaggctg aggagttcgc tgaagctgct                                          30

<210> SEQ ID NO 151
<211> LENGTH: 10
<212> TYPE: PRT
<213> ORGANISM: Artificial sequence
<220> FEATURE:
<223> OTHER INFORMATION: M13 variant coat protein VIII fragment

<400> SEQUENCE: 151

Ala Lys Ala Glu Glu Phe Ala Glu Ala Ala
 1               5                  10

<210> SEQ ID NO 152
<211> LENGTH: 30
<212> TYPE: DNA
<213> ORGANISM: Artificial sequence
<220> FEATURE:
<223> OTHER INFORMATION: M13 variant coat protein VIII fragment
      oligonucleotide

<400> SEQUENCE: 152
gctgacattg acgacttcgc tagaagtgct                                          30

<210> SEQ ID NO 153
<211> LENGTH: 10
<212> TYPE: PRT
<213> ORGANISM: Artificial sequence
<220> FEATURE:
<223> OTHER INFORMATION: M13 variant coat protein VIII fragment

<400> SEQUENCE: 153

Ala Asp Ile Asp Asp Phe Ala Arg Ser Ala
 1               5                  10

<210> SEQ ID NO 154
<211> LENGTH: 30
<212> TYPE: DNA
<213> ORGANISM: Artificial sequence
<220> FEATURE:
<223> OTHER INFORMATION: M13 coat protein VIII fragment oligonucleotide
      library
```

```
<220> FEATURE:
<221> NAME/KEY: MISC_FEATURE
<222> LOCATION: 1
<223> OTHER INFORMATION: where n is A, G, C, or T
<220> FEATURE:
<221> NAME/KEY: MISC_FEATURE
<222> LOCATION: 4
<223> OTHER INFORMATION: where n is A, G, C, or T
<220> FEATURE:
<221> NAME/KEY: MISC_FEATURE
<222> LOCATION: 8
<223> OTHER INFORMATION: where n is A, G, C, or T
<220> FEATURE:
<221> NAME/KEY: MISC_FEATURE
<222> LOCATION: 10
<223> OTHER INFORMATION: where n is A, G, C, or T
<220> FEATURE:
<221> NAME/KEY: MISC_FEATURE
<222> LOCATION: 13
<223> OTHER INFORMATION: where n is A, G, C, or T
<220> FEATURE:
<221> NAME/KEY: MISC_FEATURE
<222> LOCATION: 17
<223> OTHER INFORMATION: where n is A, G, C, or T
<220> FEATURE:
<221> NAME/KEY: MISC_FEATURE
<222> LOCATION: 20
<223> OTHER INFORMATION: where n is A, G, C, or T
<220> FEATURE:
<221> NAME/KEY: MISC_FEATURE
<222> LOCATION: 23
<223> OTHER INFORMATION: where n is A, G, C, or T
<220> FEATURE:
<221> NAME/KEY: MISC_FEATURE
<222> LOCATION: 26
<223> OTHER INFORMATION: where n is A, G, C, or T
<220> FEATURE:
<221> NAME/KEY: MISC_FEATURE
<222> LOCATION: 28
<223> OTHER INFORMATION: where n is A, G, C, or T

<400> SEQUENCE: 154
nwtnasrntn ytnasrntrn trntrntnas                                    30

<210> SEQ ID NO 155
<211> LENGTH: 30
<212> TYPE: DNA
<213> ORGANISM: Artificial sequence
<220> FEATURE:
<223> OTHER INFORMATION: M13 wt coat protein VIII fragment
      oligonucleotide

<400> SEQUENCE: 155
tttaactccc tgcaagcctc agcgaccgaa                                    30

<210> SEQ ID NO 156
<211> LENGTH: 10
<212> TYPE: PRT
<213> ORGANISM: Artificial sequence
<220> FEATURE:
<223> OTHER INFORMATION: M13 wt coat protein VIII fragment

<400> SEQUENCE: 156

Phe Asn Ser Leu Gln Ala Ser Ala Thr Glu
  1               5                  10

<210> SEQ ID NO 157
<211> LENGTH: 30
<212> TYPE: DNA
<213> ORGANISM: Artificial sequence
<220> FEATURE:
<223> OTHER INFORMATION: M13 variant coat protein VIII fragment
      oligonucleotide
```

-continued

<400> SEQUENCE: 157
tatgaggctc ttgaggatat tgctactaac					30

<210> SEQ ID NO 158
<211> LENGTH: 10
<212> TYPE: PRT
<213> ORGANISM: Artificial sequence
<220> FEATURE:
<223> OTHER INFORMATION: M13 variant coat protein VIII fragment

<400> SEQUENCE: 158

Tyr Glu Ala Leu Glu Asp Ile Ala Thr Asn
 1               5                  10

<210> SEQ ID NO 159
<211> LENGTH: 30
<212> TYPE: DNA
<213> ORGANISM: Artificial sequence
<220> FEATURE:
<223> OTHER INFORMATION: M13 variant coat protein VIII fragment
      oligonucleotide

<400> SEQUENCE: 159
tatgaggctc ttgaggatat tgctactaac					30

<210> SEQ ID NO 160
<211> LENGTH: 10
<212> TYPE: PRT
<213> ORGANISM: Artificial sequence
<220> FEATURE:
<223> OTHER INFORMATION: M13 variant coat protein VIII fragment

<400> SEQUENCE: 160

Tyr Glu Ala Leu Glu Asp Ile Ala Thr Asn
 1               5                  10

<210> SEQ ID NO 161
<211> LENGTH: 30
<212> TYPE: DNA
<213> ORGANISM: Artificial sequence
<220> FEATURE:
<223> OTHER INFORMATION: M13 variant coat protein VIII fragment
      oligonucleotide

<400> SEQUENCE: 161
tatgaggctc ttgaggatat tgctactaac					30

<210> SEQ ID NO 162
<211> LENGTH: 10
<212> TYPE: PRT
<213> ORGANISM: Artificial sequence
<220> FEATURE:
<223> OTHER INFORMATION: M13 variant coat protein VIII fragment

<400> SEQUENCE: 162

Tyr Glu Ala Leu Glu Asp Ile Ala Thr Asn
 1               5                  10

<210> SEQ ID NO 163
<211> LENGTH: 30
<212> TYPE: DNA
<213> ORGANISM: Artificial sequence
<220> FEATURE:
<223> OTHER INFORMATION: M13 variant coat protein VIII fragment
      oligonucleotide

<400> SEQUENCE: 163

```
tatgacgttc ttcagattgc tgctattaac                                          30
```

<210> SEQ ID NO 164
<211> LENGTH: 10
<212> TYPE: PRT
<213> ORGANISM: Artificial sequence
<220> FEATURE:
<223> OTHER INFORMATION: M13 variant coat protein VIII fragment

<400> SEQUENCE: 164

Tyr Asp Val Leu Gln Ile Ala Ala Ile Asn
 1               5                  10

<210> SEQ ID NO 165
<211> LENGTH: 30
<212> TYPE: DNA
<213> ORGANISM: Artificial sequence
<220> FEATURE:
<223> OTHER INFORMATION: M13 variant coat protein VIII fragment
      oligonucleotide

<400> SEQUENCE: 165

```
cttaaggatc ttaaggctac tgttattcag                                          30
```

<210> SEQ ID NO 166
<211> LENGTH: 10
<212> TYPE: PRT
<213> ORGANISM: Artificial sequence
<220> FEATURE:
<223> OTHER INFORMATION: M13 variant coat protein VIII fragment

<400> SEQUENCE: 166

Leu Lys Asp Leu Lys Ala Thr Val Ile Gln
 1               5                  10

<210> SEQ ID NO 167
<211> LENGTH: 30
<212> TYPE: DNA
<213> ORGANISM: Artificial sequence
<220> FEATURE:
<223> OTHER INFORMATION: M13 variant coat protein VIII fragment
      oligonucleotide

<400> SEQUENCE: 167

```
tatgagacta ttaaggatga tattgttaag                                          30
```

<210> SEQ ID NO 168
<211> LENGTH: 10
<212> TYPE: PRT
<213> ORGANISM: Artificial sequence
<220> FEATURE:
<223> OTHER INFORMATION: M13 variant coat protein VIII fragment

<400> SEQUENCE: 168

Tyr Glu Thr Ile Lys Asp Asp Ile Val Lys
 1               5                  10

<210> SEQ ID NO 169
<211> LENGTH: 30
<212> TYPE: DNA
<213> ORGANISM: Artificial sequence
<220> FEATURE:
<223> OTHER INFORMATION: M13 variant coat protein VIII fragment
      oligonucleotide

<400> SEQUENCE: 169

```
cttcagaata ttcacagtag tattagtaag                                          30
```

```
<210> SEQ ID NO 170
<211> LENGTH: 10
<212> TYPE: PRT
<213> ORGANISM: Artificial sequence
<220> FEATURE:
<223> OTHER INFORMATION: M13 variant coat protein VIII fragment

<400> SEQUENCE: 170

Leu Gln Asn Ile His Ser Ser Ile Ser Lys
 1               5                  10

<210> SEQ ID NO 171
<211> LENGTH: 30
<212> TYPE: DNA
<213> ORGANISM: Artificial sequence
<220> FEATURE:
<223> OTHER INFORMATION: M13 variant coat protein VIII fragment
      oligonucleotide

<400> SEQUENCE: 171
tataagactg ttcagggtgc tattgctaag                                    30

<210> SEQ ID NO 172
<211> LENGTH: 10
<212> TYPE: PRT
<213> ORGANISM: Artificial sequence
<220> FEATURE:
<223> OTHER INFORMATION: M13 variant coat protein VIII fragment

<400> SEQUENCE: 172

Tyr Lys Thr Val Gln Gly Ala Ile Ala Lys
 1               5                  10

<210> SEQ ID NO 173
<211> LENGTH: 30
<212> TYPE: DNA
<213> ORGANISM: Artificial sequence
<220> FEATURE:
<223> OTHER INFORMATION: M13 variant coat protein VIII fragment
      oligonucleotide

<400> SEQUENCE: 173
tataagacta ttaagagtat tgctaataag                                    30

<210> SEQ ID NO 174
<211> LENGTH: 10
<212> TYPE: PRT
<213> ORGANISM: Artificial sequence
<220> FEATURE:
<223> OTHER INFORMATION: M13 variant coat protein VIII fragment

<400> SEQUENCE: 174

Tyr Lys Thr Ile Lys Ser Ile Ala Asn Lys
 1               5                  10

<210> SEQ ID NO 175
<211> LENGTH: 30
<212> TYPE: DNA
<213> ORGANISM: Artificial sequence
<220> FEATURE:
<223> OTHER INFORMATION: M13 variant coat protein VIII fragment
      oligonucleotide

<400> SEQUENCE: 175
tattagagtc ttcagattat tgctgctcag                                    30

<210> SEQ ID NO 176
```

```
<211> LENGTH: 10
<212> TYPE: PRT
<213> ORGANISM: Artificial sequence
<220> FEATURE:
<223> OTHER INFORMATION: M13 variant coat protein VIII fragment

<400> SEQUENCE: 176

Tyr Gln Ser Leu Gln Ile Ile Ala Ala Gln
 1               5                  10

<210> SEQ ID NO 177
<211> LENGTH: 30
<212> TYPE: DNA
<213> ORGANISM: Artificial sequence
<220> FEATURE:
<223> OTHER INFORMATION: M13 variant coat protein VIII fragment
      oligonucleotide

<400> SEQUENCE: 177
tttcagagtc ttaaggatac tgctgatgag                                       30

<210> SEQ ID NO 178
<211> LENGTH: 10
<212> TYPE: PRT
<213> ORGANISM: Artificial sequence
<220> FEATURE:
<223> OTHER INFORMATION: M13 variant coat protein VIII fragment

<400> SEQUENCE: 178

Phe Gln Ser Leu Lys Asp Thr Ala Asp Glu
 1               5                  10

<210> SEQ ID NO 179
<211> LENGTH: 30
<212> TYPE: DNA
<213> ORGANISM: Artificial sequence
<220> FEATURE:
<223> OTHER INFORMATION: M13 variant coat protein VIII fragment
      oligonucleotide

<400> SEQUENCE: 179
tttgagaatc tttaggctac tattactaag                                       30

<210> SEQ ID NO 180
<211> LENGTH: 10
<212> TYPE: PRT
<213> ORGANISM: Artificial sequence
<220> FEATURE:
<223> OTHER INFORMATION: M13 variant coat protein VIII fragment

<400> SEQUENCE: 180

Phe Glu Asn Leu Gln Ala Thr Ile Thr Lys
 1               5                  10

<210> SEQ ID NO 181
<211> LENGTH: 30
<212> TYPE: DNA
<213> ORGANISM: Artificial sequence
<220> FEATURE:
<223> OTHER INFORMATION: M13 coat protein VIII fragment oligonucleotide
      library
<220> FEATURE:
<221> NAME/KEY: MISC_FEATURE
<222> LOCATION: 1
<223> OTHER INFORMATION: where n is A, G, C, or T
<220> FEATURE:
<221> NAME/KEY: MISC_FEATURE
<222> LOCATION: 4
<223> OTHER INFORMATION: where n is A, G, C, or T
<220> FEATURE:
```

<220> FEATURE:
<221> NAME/KEY: MISC_FEATURE
<222> LOCATION: 7
<223> OTHER INFORMATION: where n is A, G, C, or T
<220> FEATURE:
<221> NAME/KEY: MISC_FEATURE
<222> LOCATION: 10
<223> OTHER INFORMATION: where n is A, G, C, or T
<220> FEATURE:
<221> NAME/KEY: MISC_FEATURE
<222> LOCATION: 13
<223> OTHER INFORMATION: where n is A, G, C, or T
<220> FEATURE:
<221> NAME/KEY: MISC_FEATURE
<222> LOCATION: 16
<223> OTHER INFORMATION: where n is A, G, C, or T
<220> FEATURE:
<221> NAME/KEY: MISC_FEATURE
<222> LOCATION: 19
<223> OTHER INFORMATION: where n is A, G, C, or T
<220> FEATURE:
<221> NAME/KEY: MISC_FEATURE
<222> LOCATION: 22
<223> OTHER INFORMATION: where n is A, G, C, or T
<220> FEATURE:
<221> NAME/KEY: MISC_FEATURE
<222> LOCATION: 25
<223> OTHER INFORMATION: where n is A, G, C, or T
<220> FEATURE:
<221> NAME/KEY: MISC_FEATURE
<222> LOCATION: 28
<223> OTHER INFORMATION: where n is A, G, C, or T

<400> SEQUENCE: 181
nwcnwcnktn wcnytnkgny tnkgnwtnwt                                30

<210> SEQ ID NO 182
<211> LENGTH: 30
<212> TYPE: DNA
<213> ORGANISM: Artificial sequence
<220> FEATURE:
<223> OTHER INFORMATION: M13 wt coat protein VIII fragment
      oligonucleotide

<400> SEQUENCE: 182
tatatcggtt atcgctgggc gatggttgtt                                30

<210> SEQ ID NO 183
<211> LENGTH: 10
<212> TYPE: PRT
<213> ORGANISM: Artificial sequence
<220> FEATURE:
<223> OTHER INFORMATION: M13 wt coat protein VIII fragment

<400> SEQUENCE: 183

Tyr Ile Gly Tyr Ala Trp Ala Met Val Val
  1               5                  10

<210> SEQ ID NO 184
<211> LENGTH: 30
<212> TYPE: DNA
<213> ORGANISM: Artificial sequence
<220> FEATURE:
<223> OTHER INFORMATION: M13 variant coat protein VIII fragment
      oligonucleotide

<400> SEQUENCE: 184
cttttctttc tccttgggac tgtgcatctt                                30

<210> SEQ ID NO 185
<211> LENGTH: 10
<212> TYPE: PRT
<213> ORGANISM: Artificial sequence

```
<220> FEATURE:
<223> OTHER INFORMATION: M13 variant coat protein VIII fragment

<400> SEQUENCE: 185

Leu Phe Phe Leu Leu Gly Thr Val His Leu
 1               5                  10

<210> SEQ ID NO 186
<211> LENGTH: 30
<212> TYPE: DNA
<213> ORGANISM: Artificial sequence
<220> FEATURE:
<223> OTHER INFORMATION: M13 variant coat protein VIII fragment
      oligonucleotide

<400> SEQUENCE: 186
tactacctta acattttggc tgtgtatgtt                                      30

<210> SEQ ID NO 187
<211> LENGTH: 10
<212> TYPE: PRT
<213> ORGANISM: Artificial sequence
<220> FEATURE:
<223> OTHER INFORMATION: M13 variant coat protein VIII fragment

<400> SEQUENCE: 187

Tyr Tyr Leu Asn Ile Leu Ala Val Tyr Val
 1               5                  10

<210> SEQ ID NO 188
<211> LENGTH: 30
<212> TYPE: DNA
<213> ORGANISM: Artificial sequence
<220> FEATURE:
<223> OTHER INFORMATION: M13 variant coat protein VIII fragment
      oligonucleotide

<400> SEQUENCE: 188
ttcatccgtg tcacttggac tatgtatgtt                                      30

<210> SEQ ID NO 189
<211> LENGTH: 10
<212> TYPE: PRT
<213> ORGANISM: Artificial sequence
<220> FEATURE:
<223> OTHER INFORMATION: M13 variant coat protein VIII fragment

<400> SEQUENCE: 189

Phe Ile Arg Val Thr Trp Thr Met Tyr Val
 1               5                  10

<210> SEQ ID NO 190
<211> LENGTH: 30
<212> TYPE: DNA
<213> ORGANISM: Artificial sequence
<220> FEATURE:
<223> OTHER INFORMATION: M13 variant coat protein VIII fragment
      oligonucleotide

<400> SEQUENCE: 190
gtcatccgtt acgttatgtc tatgtatgtt                                      30

<210> SEQ ID NO 191
<211> LENGTH: 10
<212> TYPE: PRT
<213> ORGANISM: Artificial sequence
<220> FEATURE:
<223> O

<400> SEQUENCE: 191

Val Ile Arg Tyr Val Met Ser Met Tyr Val
 1               5                  10

<210> SEQ ID NO 192
<211> LENGTH: 42
<212> TYPE: DNA
<213> ORGANISM: Artificial sequence
<220> FEATURE:
<223> OTHER INFORMATION: linker
      oligonucleotide

<400> SEQUENCE: 192
gacggcagca acagcaccca cccccaccgc cacaaccgcc gc                         42

<210> SEQ ID NO 193
<211> LENGTH: 14
<212> TYPE: PRT
<213> ORGANISM: Artificial sequence
<220> FEATURE:
<223> OTHER INFORMATION: linker peptide

<400> SEQUENCE: 193

Asp Gly Ser Asn Ser Thr His Pro His Arg His Asn Arg Arg
 1               5                  10

<210> SEQ ID NO 194
<211> LENGTH: 42
<212> TYPE: DNA
<213> ORGANISM: Artificial sequence
<220> FEATURE:
<223> OTHER INFORMATION: linker oligonucleotide

<400> SEQUENCE: 194
accgcccgcc acgccaacga caacgacggc gcccaccgcc cc                         42

<210> SEQ ID NO 195
<211> LENGTH: 14
<212> TYPE: PRT
<213> ORGANISM: Artificial sequence
<220> FEATURE:
<223> OTHER INFORMATION: linker peptide

<400> SEQUENCE: 195

Thr Ala Arg His Ala Asn Asp Asn Asp Gly Ala His Arg Pro
 1               5                  10

<210> SEQ ID NO 196
<211> LENGTH: 42
<212> TYPE: DNA
<213> ORGANISM: Artificial sequence
<220> FEATURE:
<223> OTHER INFORMATION: linker oligonucleotide

<400> SEQUENCE: 196 acccaccca accccgcaa cgccgccggc cccgccccg gc                            42

<210> SEQ ID NO 197
<211> LENGTH: 14
<212> TYPE: PRT
<213> ORGANISM: Artificial sequence
<220> FEATURE:
<223> OTHER INFORMATION: linker peptide

<400> SEQUENCE: 197

Thr His Pro Asn Pro Arg Asn Ala Ala Gly Pro Ala Pro Gly

```
                  1               5                  10
```

<210> SEQ ID NO 198
<211> LENGTH: 42
<212> TYPE: DNA
<213> ORGANISM: Artificial sequence
<220> FEATURE:
<223> OTHER INFORMATION: linker oligonucleotide

<400> SEQUENCE: 198
caccgcaacg gcaccgaccc cggcggcccc cgcgcccgcc ac                    42

<210> SEQ ID NO 199
<211> LENGTH: 14
<212> TYPE: PRT
<213> ORGANISM: Artificial sequence
<220> FEATURE:
<223> OTHER INFORMATION: linker peptide

<400> SEQUENCE: 199

His Arg Asn Gly Thr Asp Pro Gly Gly Pro Arg Ala Arg His
  1               5                  10

<210> SEQ ID NO 200
<211> LENGTH: 42
<212> TYPE: DNA
<213> ORGANISM: Artificial sequence
<220> FEATURE:
<223> OTHER INFORMATION: linker oligonucleotide

<400> SEQUENCE: 200 gcccccgcg acaccaccgc ccaccgccac acccaccgcc ac                     42

<210> SEQ ID NO 201
<211> LENGTH: 14
<212> TYPE: PRT
<213> ORGANISM: Artificial sequence
<220> FEATURE:
<223> OTHER INFORMATION: linker peptide

<400> SEQUENCE: 201

Ala Pro Arg Asp Thr Thr Ala His Arg His Thr His Arg His
  1               5                  10

<210> SEQ ID NO 202
<211> LENGTH: 42
<212> TYPE: DNA
<213> ORGANISM: Artificial sequence
<220> FEATURE:
<223> OTHER INFORMATION: linker oligonucleotide

<400> SEQUENCE: 202
ccccgcagcg cccgcagccg caacaccaac gaccgccacg ac                    42

<210> SEQ ID NO 203
<211> LENGTH: 14
<212> TYPE: PRT
<213> ORGANISM: Artificial sequence
<220> FEATURE:
<223> OTHER INFORMATION: linker peptide

<400> SEQUENCE: 203

Pro Arg Ser Ala Arg Ser Arg Asn Thr Asn Asp Arg His Asp
  1               5                  10

<210> SEQ ID NO 204
<211> LENGTH: 42

-continued

<212> TYPE: DNA
<213> ORGANISM: Artificial sequence
<220> FEATURE:
<223> OTHER INFORMATION: linker oligonucleotide

<400> SEQUENCE: 204
accgccccct accgcagcag caactacgcc cacgccccca cc        42

<210> SEQ ID NO 205
<211> LENGTH: 14
<212> TYPE: PRT
<213> ORGANISM: Artificial sequence
<220> FEATURE:
<223> OTHER INFORMATION: linker peptide

<400> SEQUENCE: 205

Thr Ala Pro Asp Arg Ser Ser Asn Asp Ala His Ala Pro Thr
 1               5                   10

<210> SEQ ID NO 206
<211> LENGTH: 42
<212> TYPE: DNA
<213> ORGANISM: Artificial sequence
<220> FEATURE:
<223> OTHER INFORMATION: linker oligonucleotide

<400> SEQUENCE: 206
ggcagcccca gcaaccccgg cgcccgcacc cgcgccggca cc        42

<210> SEQ ID NO 207
<211> LENGTH: 14
<212> TYPE: PRT
<213> ORGANISM: Artificial sequence
<220> FEATURE:
<223> OTHER INFORMATION: linker peptide

<400> SEQUENCE: 207

Gly Ser Pro Ser Asn Pro Gly Ala Arg Thr Arg Ala Gly Thr
 1               5                   10

<210> SEQ ID NO 208
<211> LENGTH: 42
<212> TYPE: DNA
<213> ORGANISM: Artificial sequence
<220> FEATURE:
<223> OTHER INFORMATION: linker oligonucleotide

<400> SEQUENCE: 208
ggccacgccg gccaccccca ccgccccgc caccccgccc gc         42

<210> SEQ ID NO 209
<211> LENGTH: 14
<212> TYPE: PRT
<213> ORGANISM: Artificial sequence
<220> FEATURE:
<223> OTHER INFORMATION: linker peptide

<400> SEQUENCE: 209

Gly His Ala Gly His Pro His Arg Pro Arg His Pro Ala Arg
 1               5                   10

<210> SEQ ID NO 210
<211> LENGTH: 15
<212> TYPE: DNA
<213> ORGANISM: Artificial sequence
<220> FEATURE:
<223> OTHER INFORMATION: linker oligonucleotide

```
<400> SEQUENCE: 210
gcccgcgcca accgc                                                    15

<210> SEQ ID NO 211
<211> LENGTH: 5
<212> TYPE: PRT
<213> ORGANISM: Artificial sequence
<220> FEATURE:
<223> OTHER INFORMATION: linker peptide

<400> SEQUENCE: 211

Ala Arg Ala Asn Arg
 1               5

<210> SEQ ID NO 212
<211> LENGTH: 15
<212> TYPE: DNA
<213> ORGANISM: Artificial sequence
<220> FEATURE:
<223> OTHER INFORMATION: linker oligonucleotide

<400> SEQUENCE: 212
cgccacaacc gccgc                                                    15

<210> SEQ ID NO 213
<211> LENGTH: 5
<212> TYPE: PRT
<213> ORGANISM: Artificial sequence
<220> FEATURE:
<223> OTHER INFORMATION: linker peptide

<400> SEQUENCE: 213

Arg His Asn Arg Arg
 1               5

<210> SEQ ID NO 214
<211> LENGTH: 15
<212> TYPE: DNA
<213> ORGANISM: Artificial sequence
<220> FEATURE:
<223> OTHER INFORMATION: linker oligonucleotide

<400> SEQUENCE: 214
gaccacagca gcgcc                                                    15

<210> SEQ ID NO 215
<211> LENGTH: 5
<212> TYPE: PRT
<213> ORGANISM: Artificial sequence
<220> FEATURE:
<223> OTHER INFORMATION: linker peptide

<400> SEQUENCE: 215

Asp His Ser Ser Ala
 1               5

<210> SEQ ID NO 216
<211> LENGTH: 15
<212> TYPE: DNA
<213> ORGANISM: Artificial sequence
<220> FEATURE:
<223> OTHER INFORMATION: linker oligonucleotide

<400> SEQUENCE: 216
gcccgcggcc ccacc                                                    15
```

```
<210> SEQ ID NO 217
<211> LENGTH: 5
<212> TYPE: PRT
<213> ORGANISM: Artificial sequence
<220> FEATURE:
<223> OTHER INFORMATION: linker peptide

<400> SEQUENCE: 217

Ala Arg Gly Pro Thr
 1               5

<210> SEQ ID NO 218
<211> LENGTH: 15
<212> TYPE: DNA
<213> ORGANISM: Artificial sequence
<220> FEATURE:
<223> OTHER INFORMATION: linker oligonucleotide

<400> SEQUENCE: 218 cacaccccccg gcgcc                                                       15

<210> SEQ ID NO 219
<211> LENGTH: 5
<212> TYPE: PRT
<213> ORGANISM: Artificial sequence
<220> FEATURE:
<223> OTHER INFORMATION: linker peptide

<400> SEQUENCE: 219

His Thr Pro Gly Ala
 1               5

<210> SEQ ID NO 220
<211> LENGTH: 15
<212> TYPE: DNA
<213> ORGANISM: Artificial sequence
<220> FEATURE:
<223> OTHER INFORMATION: linker oligonucleotide

<400> SEQUENCE: 220
aacagcggcg gcgac                                                        15

<210> SEQ ID NO 221
<211> LENGTH: 5
<212> TYPE: PRT
<213> ORGANISM: Artificial sequence
<220> FEATURE:
<223> OTHER INFORMATION: linker peptide

<400> SEQUENCE: 221

Asn Ser Gly Gly Asp
 1               5

<210> SEQ ID NO 222
<211> LENGTH: 15
<212> TYPE: DNA
<213> ORGANISM: Artificial sequence
<220> FEATURE:
<223> OTHER INFORMATION: linker oligonucleotide

<400> SEQUENCE: 222
cgcaccacca gcaac                                                        15

<210> SEQ ID NO 223
<211> LENGTH: 5
<212> TYPE: PRT
<213> ORGANISM: Artificial sequence
<220> FEATURE:
```

```
<223> OTHER INFORMATION: linker peptide

<400> SEQUENCE: 223

Arg Thr Thr Ser Asn
 1               5

<210> SEQ ID NO 224
<211> LENGTH: 30
<212> TYPE: DNA
<213> ORGANISM: Artificial sequence
<220> FEATURE:
<223> OTHER INFORMATION: linker oligonucleotide

<400> SEQUENCE: 224
gcccgcgccc gcaccgccca ccacgaccgc                                        30

<210> SEQ ID NO 225
<211> LENGTH: 10
<212> TYPE: PRT
<213> ORGANISM: Artificial sequence
<220> FEATURE:
<223> OTHER INFORMATION: linker peptide

<400> SEQUENCE: 225

Ala Arg Ala Arg Thr Ala His His Asp Arg
 1               5                  10

<210> SEQ ID NO 226
<211> LENGTH: 30
<212> TYPE: DNA
<213> ORGANISM: Artificial sequence
<220> FEATURE:
<223> OTHER INFORMATION: linker oligonucleotide

<400> SEQUENCE: 226
gccaacagcc acgccgccca cggcaccagc                                        30

<210> SEQ ID NO 227
<211> LENGTH: 10
<212> TYPE: PRT
<213> ORGANISM: Artificial sequence
<220> FEATURE:
<223> OTHER INFORMATION: linker peptide

<400> SEQUENCE: 227

Ala Asn Ser His Ala Ala His Gly Thr Ser
 1               5                  10

<210> SEQ ID NO 228
<211> LENGTH: 30
<212> TYPE: DNA
<213> ORGANISM: Artificial sequence
<220> FEATURE:
<223> OTHER INFORMATION: linker oligonucleotide

<400> SEQUENCE: 228
acccccggcc acggccaccc ccaccccgac                                        30

<210> SEQ ID NO 229
<211> LENGTH: 10
<212> TYPE: PRT
<213> ORGANISM: Artificial sequence
<220> FEATURE:
<223> OTHER INFORMATION: linker peptide

<400> SEQUENCE: 229

Thr Pro Gly His Gly His Pro His Pro Asp
```

<210> SEQ ID NO 230
<211> LENGTH: 30
<212> TYPE: DNA
<213> ORGANISM: Artificial sequence
<220> FEATURE:
<223> OTHER INFORMATION: linker oligonucleotide

<400> SEQUENCE: 230
cgcggcggcc gcgcccccca cagcagcgcc                30

<210> SEQ ID NO 231
<211> LENGTH: 10
<212> TYPE: PRT
<213> ORGANISM: Artificial sequence
<220> FEATURE:
<223> OTHER INFORMATION: linker peptide

<400> SEQUENCE: 231

Arg Gly Gly Arg Ala Pro His Ser Ser Ala
 1               5                  10

<210> SEQ ID NO 232
<211> LENGTH: 30
<212> TYPE: DNA
<213> ORGANISM: Artificial sequence
<220> FEATURE:
<223> OTHER INFORMATION: linker oligonucleotide

<400> SEQUENCE: 232
gccggccgcg gcaccagcag cacccgcggc                30

<210> SEQ ID NO 233
<211> LENGTH: 10
<212> TYPE: PRT
<213> ORGANISM: Artificial sequence
<220> FEATURE:
<223> OTHER INFORMATION: linker peptide

<400> SEQUENCE: 233

Ala Gly Arg Gly Thr Ser Ser Thr Arg Gly
 1               5                  10

<210> SEQ ID NO 234
<211> LENGTH: 30
<212> TYPE: DNA
<213> ORGANISM: Artificial sequence
<220> FEATURE:
<223> OTHER INFORMATION: linker oligonucleotide

<400> SEQUENCE: 234
ccccgccacg accaccaccc cgcccacgac                30

<210> SEQ ID NO 235
<211> LENGTH: 10
<212> TYPE: PRT
<213> ORGANISM: Artificial sequence
<220> FEATURE:
<223> OTHER INFORMATION: linker peptide

<400> SEQUENCE: 235

Pro Arg His Asp His His Pro Ala His Asp
 1               5                  10

<210> SEQ ID NO 236
<211> LENGTH: 30

<212> TYPE: DNA
<213> ORGANISM: Artificial sequence
<220> FEATURE:
<223> OTHER INFORMATION: linker oligonucleotide

<400> SEQUENCE: 236
gaccgcggcc gcaccaaccg caccgacacc                                    30

<210> SEQ ID NO 237
<211> LENGTH: 10
<212> TYPE: PRT
<213> ORGANISM: Artificial sequence
<220> FEATURE:
<223> OTHER INFORMATION: linker peptide

<400> SEQUENCE: 237

Asp Arg Gly Arg Thr Asn Arg Thr Asp Thr
 1               5                  10

<210> SEQ ID NO 238
<211> LENGTH: 45
<212> TYPE: DNA
<213> ORGANISM: Artificial sequence
<220> FEATURE:
<223> OTHER INFORMATION: linker oligonucleotide

<400> SEQUENCE: 238
cgcgccgacc acggcagccg cgccagccac gacgccagcc gccgc                   45

<210> SEQ ID NO 239
<211> LENGTH: 15
<212> TYPE: PRT
<213> ORGANISM: Artificial sequence
<220> FEATURE:
<223> OTHER INFORMATION: linker peptide

<400> SEQUENCE: 239

Arg Ala Asp His Gly Ser Arg Ala Ser His Asp Ala Ser Arg Arg
 1               5                  10                  15

<210> SEQ ID NO 240
<211> LENGTH: 45
<212> TYPE: DNA
<213> ORGANISM: Artificial sequence
<220> FEATURE:
<223> OTHER INFORMATION: linker oligonucleotide

<400> SEQUENCE: 240
cacgccggcg ccgacgccga ccgcagcagc aacaccgacg acggc                   45

<210> SEQ ID NO 241
<211> LENGTH: 15
<212> TYPE: PRT
<213> ORGANISM: Artificial sequence
<220> FEATURE:
<223> OTHER INFORMATION: linker peptide

<400> SEQUENCE: 241

His Ala Gly Ala Asp Ala Asp Arg Ser Ser Asn Thr Asp Asp Gly
 1               5                  10                  15

<210> SEQ ID NO 242
<211> LENGTH: 45
<212> TYPE: DNA
<213> ORGANISM: Artificial sequence
<220> FEATURE:
<223> OTHER INFORMATION: linker oligonucleotide

```
<400> SEQUENCE: 242
gccagccgca ccgacgccgc ccgcgacgcc accgccagcc gcccc              45

<210> SEQ ID NO 243
<211> LENGTH: 15
<212> TYPE: PRT
<213> ORGANISM: Artificial sequence
<220> FEATURE:
<223> OTHER INFORMATION: linker peptide

<400> SEQUENCE: 243

Ala Ser Arg Thr Asp Ala Ala Arg Asp Ala Thr Ala Ser Arg Pro
 1               5                  10                  15

<210> SEQ ID NO 244
<211> LENGTH: 45
<212> TYPE: DNA
<213> ORGANISM: Artificial sequence
<220> FEATURE:
<223> OTHER INFORMATION: linker oligonucleotide

<400> SEQUENCE: 244
accggcaacc gcaccgaccg cgcccccccc gccagcagcc ccgac              45

<210> SEQ ID NO 245
<211> LENGTH: 15
<212> TYPE: PRT
<213> ORGANISM: Artificial sequence
<220> FEATURE:
<223> OTHER INFORMATION: linker peptide

<400> SEQUENCE: 245

Thr Gly Asn Arg Thr Asp Arg Ala Pro Pro Ala Ser Ser Pro Asp
 1               5                  10                  15

<210> SEQ ID NO 246
<211> LENGTH: 45
<212> TYPE: DNA
<213> ORGANISM: Artificial sequence
<220> FEATURE:
<223> OTHER INFORMATION: linker oligonucleotide

<400> SEQUENCE: 246
cccaacgccc gcggcgccaa ccgcaccgcc ggcagcaccg ccagc              45

<210> SEQ ID NO 247
<211> LENGTH: 15
<212> TYPE: PRT
<213> ORGANISM: Artificial sequence
<220> FEATURE:
<223> OTHER INFORMATION: linker peptide

<400> SEQUENCE: 247

Pro Asn Gly Arg Gly Ala Asn Arg Thr Ala Gly Ser Thr Ala Ser
 1               5                  10                  15

<210> SEQ ID NO 248
<211> LENGTH: 45
<212> TYPE: DNA
<213> ORGANISM: Artificial sequence
<220> FEATURE:
<223> OTHER INFORMATION: linker oligonucleotide

<400> SEQUENCE: 248
cgcgccagca gcgacgccgc ccgcccccc agcagcaacg gcgcc               45
```

```
<210> SEQ ID NO 249
<211> LENGTH: 15
<212> TYPE: PRT
<213> ORGANISM: Artificial sequence
<220> FEATURE:
<223> OTHER INFORMATION: linker peptide

<400> SEQUENCE: 249

Arg Ala Ser Ser Asp Ala Ala Arg Pro Pro Ser Ser Asn Gly Ala
 1               5                  10                  15

<210> SEQ ID NO 250
<211> LENGTH: 60
<212> TYPE: DNA
<213> ORGANISM: Artificial sequence
<220> FEATURE:
<223> OTHER INFORMATION: linker oligonucleotide

<400> SEQUENCE: 250
agcgccggca gcgacagcgc ccgccacacc gccccccgca gccccgccag          50
cgccgccaac                                                      60

<210> SEQ ID NO 251
<211> LENGTH: 20
<212> TYPE: PRT
<213> ORGANISM: Artificial sequence
<220> FEATURE:
<223> OTHER INFORMATION: linker peptide

<400> SEQUENCE: 251

Ser Ala Gly Ser Asp Ser Ala Arg His Thr Ala Pro Arg Ser Pro
 1               5                  10                  15

Ala Ser Ala Ala Asn
                20

<210> SEQ ID NO 252
<211> LENGTH: 60
<212> TYPE: DNA
<213> ORGANISM: Artificial sequence
<220> FEATURE:
<223> OTHER INFORMATION: linker oligonucleotide

<400> SEQUENCE: 252
gcccccagca gcgccggcaa cgaccccgac cgcagccgca gcgacgcccg          50
cggcaccggc                                                      60

<210> SEQ ID NO 253
<211> LENGTH: 20
<212> TYPE: PRT
<213> ORGANISM: Artificial sequence
<220> FEATURE:
<223> OTHER INFORMATION: linker peptide

<400> SEQUENCE: 253

Ala Pro Ser Ser Ala Gly Asn Asp Pro Asp Arg Ser Arg Ser Asp
 1               5                  10                  15

Ala Arg Gly Thr Gly
                20

<210> SEQ ID NO 254
<211> LENGTH: 60
<212> TYPE: DNA
<213> ORGANISM: Artificial sequence
<220> FEATURE:
<223> OTHER INFORMATION: linker oligonucleotide
```

<400> SEQUENCE: 254
gacggcagcc ccaacggcgg ccgcggccac aacgacaacc cccccgcgg        50 ccacgccccc                                                    60

<210> SEQ ID NO 255
<211> LENGTH: 20
<212> TYPE: PRT
<213> ORGANISM: Artificial sequence
<220> FEATURE:
<223> OTHER INFORMATION: linker peptide

<400> SEQUENCE: 255

Asp Gly Ser Pro Asn Gly Gly Arg Gly His Asn Asp Asn Pro Pro
 1               5                  10                  15

Arg Gly His Ala Pro
            20

<210> SEQ ID NO 256
<211> LENGTH: 60
<212> TYPE: DNA
<213> ORGANISM: Artificial sequence
<220> FEATURE:
<223> OTHER INFORMATION: linker oligonucleotide

<400> SEQUENCE: 256
agcgccagcg ccgacagcag ccgcaccgcc gcccgccccc cgcccccgg         50 caccgccagc                                                    60

<210> SEQ ID NO 257
<211> LENGTH: 20
<212> TYPE: PRT
<213> ORGANISM: Artificial sequence
<220> FEATURE:
<223> OTHER INFORMATION: linker peptide

<400> SEQUENCE: 257

Ser Ala Ser Ala Asp Ser Ser Arg Thr Ala Ala Arg Pro Pro Gly
 1               5                  10                  15

Pro Gly Thr Ala Ser
            20

<210> SEQ ID NO 258
<211> LENGTH: 60
<212> TYPE: DNA
<213> ORGANISM: Artificial sequence
<220> FEATURE:
<223> OTHER INFORMATION: linker oligonucleotide

<400> SEQUENCE: 258
cgcagcgccg ccggccgcga cgccggccgc gaccgccccg ccggcagcag         50
cggcagccac                                                    60

<210> SEQ ID NO 259
<211> LENGTH: 20
<212> TYPE: PRT
<213> ORGANISM: Artificial sequence
<220> FEATURE:
<223> OTHER INFORMATION: linker peptide

<400> SEQUENCE: 259

Arg Ser Ala Ala Gly Arg Asp Ala Gly Arg Asp Arg Pro Ala Gly
 1               5                  10                  15

Ser Ser Gly Ser His

-continued

<210> SEQ ID NO 260
<211> LENGTH: 60
<212> TYPE: DNA
<213> ORGANISM: Artificial sequence
<220> FEATURE:
<223> OTHER INFORMATION: linker oligonucleotide

<400> SEQUENCE: 260
agcggcagcc ccgccaacgc ccccggccac cacagccacc acgacgcccg        50
cagcggcccc        60

<210> SEQ ID NO 261
<211> LENGTH: 20
<212> TYPE: PRT
<213> ORGANISM: Artificial sequence
<220> FEATURE:
<223> OTHER INFORMATION: linker peptide

<400> SEQUENCE: 261

Ser Gly Ser Pro Ala Asn Ala Pro Gly His His Ser His His Asp
 1               5                  10                  15

Ala Arg Ser Gly Pro
            20

<210> SEQ ID NO 262
<211> LENGTH: 75
<212> TYPE: DNA
<213> ORGANISM: Artificial sequence
<220> FEATURE:
<223> OTHER INFORMATION: linker oligonucleotide

<400> SEQUENCE: 262
cacgccagcg acgacgccgc ccgcgacggc cgcagcgaca caaccgcgg         50 cagcaacggc agcgacagca gcagc                                   75

<210> SEQ ID NO 263
<211> LENGTH: 25
<212> TYPE: PRT
<213> ORGANISM: Artificial sequence
<220> FEATURE:
<223> OTHER INFORMATION: linker peptide

<400> SEQUENCE: 263

His Ala Ser Asp Asp Ala Ala Arg Asp Gly Arg Ser Asp Asn Asn
 1               5                  10                  15

Arg Gly Ser Asn Gly Ser Asp Ser Ser Ser
            20                  25

<210> SEQ ID NO 264
<211> LENGTH: 75
<212> TYPE: DNA
<213> ORGANISM: Artificial sequence
<220> FEATURE:
<223> OTHER INFORMATION: linker oligonucleotide

<400> SEQUENCE: 264
agccacgccg gcaacgacgc cggccgcgcc cgcaccaacc acagcgacgg        50
cccccacggc cacagcagcc cccgc                                   75

<210> SEQ ID NO 265
<211> LENGTH: 25
<212> TYPE: PRT

```
<213> ORGANISM: Artificial sequence
<220> FEATURE:
<223> OTHER INFORMATION: linker peptide

<400> SEQUENCE: 265

Ser His Ala Gly Asn Asp Ala Gly Arg Ala Arg Thr Asn Gly Ser
 1               5                  10                  15

Asp Gly Pro His Gly His Ser Ser Pro Arg
                20                  25

<210> SEQ ID NO 266
<211> LENGTH: 57
<212> TYPE: DNA
<213> ORGANISM: Artificial sequence
<220> FEATURE:
<223> OTHER INFORMATION: M13 variant coat protein VIII oligonucleotide
      library
<220> FEATURE:
<221> NAME/KEY: MISC_FEATURE
<222> LOCATION: 1
<223> OTHER INFORMATION: where n is A, G, C, or T
<220> FEATURE:
<221> NAME/KEY: MISC_FEATURE
<222> LOCATION: 4
<223> OTHER INFORMATION: where n is A, G, C, or T
<220> FEATURE:
<221> NAME/KEY: MISC_FEATURE
<222> LOCATION: 7
<223> OTHER INFORMATION: where n is A, G, C, or T
<220> FEATURE:
<221> NAME/KEY: MISC_FEATURE
<222> LOCATION: 10
<223> OTHER INFORMATION: where n is A, G, C, or T
<220> FEATURE:
<221> NAME/KEY: MISC_FEATURE
<222> LOCATION: 13
<223> OTHER INFORMATION: where n is A, G, C, or T
<220> FEATURE:
<221> NAME/KEY: MISC_FEATURE
<222> LOCATION: 16
<223> OTHER INFORMATION: where n is A, G, C, or T
<220> FEATURE:
<221> NAME/KEY: MISC_FEATURE
<222> LOCATION: 19
<223> OTHER INFORMATION: where n is A, G, C, or T
<220> FEATURE:
<221> NAME/KEY: MISC_FEATURE
<222> LOCATION: 22
<223> OTHER INFORMATION: where n is A, G, C, or T
<220> FEATURE:
<221> NAME/KEY: MISC_FEATURE
<222> LOCATION: 25
<223> OTHER INFORMATION: where n is A, G, C, or T
<220> FEATURE:
<221> NAME/KEY: MISC_FEATURE
<222> LOCATION: 28
<223> OTHER INFORMATION: where n is A, G, C, or T
<220> FEATURE:
<221> NAME/KEY: MISC_FEATURE
<222> LOCATION: 31
<223> OTHER INFORMATION: where n is A, G, C, or T
<220> FEATURE:
<221> NAME/KEY: MISC_FEATURE
<222> LOCATION: 34
<223> OTHER INFORMATION: where n is A, G, C, or T
<220> FEATURE:
<221> NAME/KEY: MISC_FEATURE
<222> LOCATION: 37
<223> OTHER INFORMATION: where n is A, G, C, or T
<220> FEATURE:
<221> NAME/KEY: MISC_FEATURE
<222> LOCATION: 40
<223> OTHER INFORMATION: where n is A, G, C, or T
<220> FEATURE:
<221> NAME/KEY: MISC_FEATURE
<222> LOCATION: 43
<223> OTHER INFORMATION: where n is A, G, C, or T
```

```
<220> FEATURE:
<221> NAME/KEY: MISC_FEATURE
<222> LOCATION: 46
<223> OTHER INFORMATION: where n is A, G, C, or T
<220> FEATURE:
<221> NAME/KEY: MISC_FEATURE
<222> LOCATION: 49
<223> OTHER INFORMATION: where n is A, G, C, or T
<220> FEATURE:
<221> NAME/KEY: MISC_FEATURE
<222> LOCATION: 52
<223> OTHER INFORMATION: where n is A, G, C, or T
<220> FEATURE:
<221> NAME/KEY: MISC_FEATURE
<222> LOCATION: 55
<223> OTHER INFORMATION: where n is A, G, C, or T

<400> SEQUENCE: 266
nwtnktnwtn ytnytnktnw tnwtnwtnwt nwtnkgnytn kgnytnwcnk        50 tnwtnwt                                                      57

<210> SEQ ID NO 267
<211> LENGTH: 57
<212> TYPE: DNA
<213> ORGANISM: Artificial sequence
<220> FEATURE:
<223> OTHER INFORMATION: M13 variant coat protein VIII fragment
      oligonucleotide

<400> SEQUENCE: 267
gtttttgttt tttctgttga tgttgataat aattggattt gggctgtcgg        50
tattgtt                                                      57

<210> SEQ ID NO 268
<211> LENGTH: 19
<212> TYPE: PRT
<213> ORGANISM: Artificial sequence
<220> FEATURE:
<223> OTHER INFORMATION: M13 variant coat protein VIII fragment

<400> SEQUENCE: 268

Val Phe Val Phe Ser Val Asp Val Asp Asn Asn Trp Ile Trp Ala
 1               5                  10                  15

Val Gly Ile Val

<210> SEQ ID NO 269
<211> LENGTH: 57
<212> TYPE: DNA
<213> ORGANISM: Artificial sequence
<220> FEATURE:
<223> OTHER INFORMATION: M13 variant coat protein VIII fragment
      oligonucleotide

<400> SEQUENCE: 269
catagtcttg ctgttattga tgataatttt tattgggttg ggttttacgg        50
ttatgtt                                                      57

<210> SEQ ID NO 270
<211> LENGTH: 19
<212> TYPE: PRT
<213> ORGANISM: Artificial sequence
<220> FEATURE:
<223> OTHER INFORMATION: M13 variant coat protein VIII fragment

<400> SEQUENCE: 270

His Ser Leu Ala Val Ile Asp Asp Asn Phe Tyr Trp Val Gly Phe
 1               5                  10                  15
```

Tyr Gly Tyr Val

<210> SEQ ID NO 271
<211> LENGTH: 57
<212> TYPE: DNA
<213> ORGANISM: Artificial sequence
<220> FEATURE:
<223> OTHER INFORMATION: M13 variant coat protein VIII fragment
      oligonucleotide

<400> SEQUENCE: 271
cttttttatc ctgttagtgt tcatattgtt attcggtttt tgtctctctt          50
tcttgtt                                                         57

<210> SEQ ID NO 272
<211> LENGTH: 19
<212> TYPE: PRT
<213> ORGANISM: Artificial sequence
<220> FEATURE:
<223> OTHER INFORMATION: M13 variant coat protein VIII fragment

<400> SEQUENCE: 272

Leu Phe Tyr Pro Val Ser Val His Ile Val Ile Arg Phe Leu Ser
 1               5                  10                  15

Leu Phe Leu Val

<210> SEQ ID NO 273
<211> LENGTH: 57
<212> TYPE: DNA
<213> ORGANISM: Artificial sequence
<220> FEATURE:
<223> OTHER INFORMATION: M13 variant coat protein VIII fragment
      oligonucleotide

<400> SEQUENCE: 273
cttagtgttg ttgttcgtga tcttatttat aatgtggtta tgtttcacgt          50
tgttaat                                                         57

<210> SEQ ID NO 274
<211> LENGTH: 19
<212> TYPE: PRT
<213> ORGANISM: Artificial sequence
<220> FEATURE:
<223> OTHER INFORMATION: M13 variant coat protein VIII fragment

<400> SEQUENCE: 274

Leu Ser Val Val Val Arg Asp Leu Ile Tyr Asn Val Val Met Phe
 1               5                  10                  15

His Val Val Asn

<210> SEQ ID NO 275
<211> LENGTH: 57
<212> TYPE: DNA
<213> ORGANISM: Artificial sequence
<220> FEATURE:
<223> OTHER INFORMATION: M13 variant coat protein VIII fragment
      oligonucleotide

<400> SEQUENCE: 275
cttggttttt ctactcgtgt tcttgttgat gattggctta tggttaacag          50
ttttgat                                                         57

<210> SEQ ID NO 276

```
<211> LENGTH: 19
<212> TYPE: PRT
<213> ORGANISM: Artificial sequence
<220> FEATURE:
<223> OTHER INFORMATION: M13 variant coat protein VIII fragment

<400> SEQUENCE: 276

Leu Gly Phe Ser Thr Arg Val Leu Val Asp Asp Trp Leu Met Val
 1               5                  10                  15

Asn Ser Phe Asp

<210> SEQ ID NO 277
<211> LENGTH: 57
<212> TYPE: DNA
<213> ORGANISM: Artificial sequence
<220> FEATURE:
<223> OTHER INFORMATION: M13 variant coat protein VIII fragment
      oligonucleotide

<400> SEQUENCE: 277
tattttcttg cttttagtat tattgatctt tttaggcttt ggctttactt         50
tgttaat                                                        57

<210> SEQ ID NO 278
<211> LENGTH: 19
<212> TYPE: PRT
<213> ORGANISM: Artificial sequence
<220> FEATURE:
<223> OTHER INFORMATION: M13 variant coat protein VIII fragment

<400> SEQUENCE: 278

Tyr Phe Leu Ala Phe Ser Ile Ile Asp Leu Phe Arg Leu Trp Leu
 1               5                  10                  15

Tyr Phe Val Asn

<210> SEQ ID NO 279
<211> LENGTH: 6
<212> TYPE: PRT
<213> ORGANISM: Artificial sequence
<220> FEATURE:
<223> OTHER INFORMATION: pentaHis flag

<400> SEQUENCE: 279

His His His His His Ala
 1               5

<210> SEQ ID NO 280
<211> LENGTH: 7
<212> TYPE: PRT
<213> ORGANISM: Artificial sequence
<220> FEATURE:
<223> OTHER INFORMATION: hexaHis flag

<400> SEQUENCE: 280

His His His His His His Ala
 1               5

<210> SEQ ID NO 281
<211> LENGTH: 9
<212> TYPE: PRT
<213> ORGANISM: Artificial sequence
<220> FEATURE:
<223> OTHER INFORMATION: nona peptide flag

<400> SEQUENCE: 281

Ala Ala His His His His His His Ala
```

-continued

```
                1               5

<210> SEQ ID NO 282
<211> LENGTH: 9
<212> TYPE: PRT
<213> ORGANISM: Artificial sequence
<220> FEATURE:
<223> OTHER INFORMATION: M13 phage fragment

<400> SEQUENCE: 282

Lys Leu Phe Lys Lys Phe Thr Ser Lys
1               5

<210> SEQ ID NO 283
<211> LENGTH: 9
<212> TYPE: PRT
<213> ORGANISM: Artificial sequence
<220> FEATURE:
<223> OTHER INFORMATION: retrotranslation of SEQ ID NO.282

<400> SEQUENCE: 283

Lys Ser Thr Phe Lys Lys Phe Leu Lys
1               5

<210> SEQ ID NO 284
<211> LENGTH: 20
<212> TYPE: PRT
<213> ORGANISM: Artificial sequence
<220> FEATURE:
<223> OTHER INFORMATION: retrotranslation of SEQ ID NO.285

<400> SEQUENCE: 284

Glu Thr Ala Ser Ala Gln Leu Ser Asn Ser Ala Ala Lys Ala Pro
1               5                   10                  15

Asp Asp Gly Glu Ala
                20

<210> SEQ ID NO 285
<211> LENGTH: 20
<212> TYPE: PRT
<213> ORGANISM: Artificial sequence
<220> FEATURE:
<223> OTHER INFORMATION: M13 phage fragment

<400> SEQUENCE: 285

Ala Glu Gly Asp Asp Pro Ala Lys Ala Ala Phe Asn Ser Leu Gln
1               5                   10                  15

Ala Ser Ala Thr Glu
                20

<210> SEQ ID NO 286
<211> LENGTH: 4
<212> TYPE: PRT
<213> ORGANISM: Artificial sequence
<220> FEATURE:
<223> OTHER INFORMATION: tetra peptide linker

<400> SEQUENCE: 286

Ala Ala Asp Ala
1

<210> SEQ ID NO 287
<211> LENGTH: 6
<212> TYPE: PRT
<213> ORGANISM: Artificial sequence
<220> FEATURE:
<223> OTHER INFORMATION: hexaHis
```

```
<400> SEQUENCE: 287

His His His His His His
  1               5

<210> SEQ ID NO 288
<211> LENGTH: 8
<212> TYPE: PRT
<213> ORGANISM: Artificial sequence
<220> FEATURE:
<223> OTHER INFORMATION: Synthetic linker

<400> SEQUENCE: 288

Gly Gly Gly Gly Gly Gly Gly Gly
  1               5

<210> SEQ ID NO 289
<211> LENGTH: 9
<212> TYPE: PRT
<213> ORGANISM: Artificial sequence
<220> FEATURE:
<223> OTHER INFORMATION: Synthetic linker

<400> SEQUENCE: 289

Gly Gly Gly Gly Gly Gly Gly Gly Gly
  1               5

<210> SEQ ID NO 290
<211> LENGTH: 10
<212> TYPE: PRT
<213> ORGANISM: Artificial sequence
<220> FEATURE:
<223> OTHER INFORMATION: Synthetic linker

<400> SEQUENCE: 290

Gly Gly Gly Gly Gly Gly Gly Gly Gly Gly
  1               5                  10

<210> SEQ ID NO 291
<211> LENGTH: 12
<212> TYPE: PRT
<213> ORGANISM: Artificial sequence
<220> FEATURE:
<223> OTHER INFORMATION: Synthetic linker

<400> SEQUENCE: 291

Gly Gly Gly Gly Gly Gly Gly Gly Gly Gly Gly Gly
  1               5                  10

<210> SEQ ID NO 292
<211> LENGTH: 19
<212> TYPE: PRT
<213> ORGANISM: Artificial sequence
<220> FEATURE:
<223> OTHER INFORMATION: Synthetic linker
<220> FEATURE:
<221> NAME/KEY: VARIANT
<222> LOCATION: 4-17
<223> OTHER INFORMATION: where Xaa is any amino acid

<400> SEQUENCE: 292

Gly Gly Gly Xaa Xaa Xaa Xaa Xaa Xaa Xaa Xaa Xaa Xaa Xaa Xaa Xaa
  1               5                  10                  15

Xaa Gly Gly

<210> SEQ ID NO 293
<211> LENGTH: 4
```

```
<212> TYPE: PRT
<213> ORGANISM: Artificial sequence
<220> FEATURE:
<223> OTHER INFORMATION: Synthetic poly quad His tag

<400> SEQUENCE: 293

His His His His
  1

<210> SEQ ID NO 294
<211> LENGTH: 50
<212> TYPE: PRT
<213> ORGANISM: M13 phage
<220> FEATURE:
<223> OTHER INFORMATION: coat protein VIII
<220> FEATURE:
<221> NAME/KEY: VARIANT
<222> LOCATION: 1
<223> OTHER INFORMATION: where Xaa is Glu, Leu, Val, Gln, Asp, Ile, Asn
      or Ala
<220> FEATURE:
<221> NAME/KEY: VARIANT
<222> LOCATION: 2
<223> OTHER INFORMATION: where Xaa is Arg, His, Phe, Trp, Glu, Lys, Tyr
      or Asp
<220> FEATURE:
<221> NAME/KEY: VARIANT
<222> LOCATION: 3
<223> OTHER INFORMATION: where Xaa is Thr, Glu, Leu, Ser, Asp, Ile, Val,
      Ala or Gly
<220> FEATURE:
<221> NAME/KEY: VARIANT
<222> LOCATION: 4
<223> OTHER INFORMATION: where Xaa is Asp, Arg, His, Glu or Lys
<220> FEATURE:
<221> NAME/KEY: VARIANT
<222> LOCATION: 5
<223> OTHER INFORMATION: where Xaa is Arg, His, Asn, Asp, Lys, Gln or
      Glu
<220> FEATURE:
<221> NAME/KEY: VARIANT
<222> LOCATION: 6
<223> OTHER INFORMATION: where Xaa is Tyr, Trp, Ser, Ile, Leu, Phe, Thr,
      Val or Pro
<220> FEATURE:
<221> NAME/KEY: VARIANT
<222> LOCATION: 7
<223> OTHER INFORMATION: where Xaa is Thr, Asn, Ser or Ala
<220> FEATURE:
<221> NAME/KEY: VARIANT
<222> LOCATION: 8
<223> OTHER INFORMATION: where Xaa is Asp, His, Arg, Glu or Lys
<220> FEATURE:
<221> NAME/KEY: VARIANT
<222> LOCATION: 9
<223> OTHER INFORMATION: where Xaa is Glu, Gln, Thr, Asp, Asn, Ser or
      Ala
<220> FEATURE:
<221> NAME/KEY: VARIANT
<222> LOCATION: 11
<223> OTHER INFORMATION: where Xaa is Trp, Ile, Val, Tyr, Leu or Phe
<220> FEATURE:
<221> NAME/KEY: VARIANT
<222> LOCATION: 12
<223> OTHER INFORMATION: where Xaa is Arg, His, Asn, Glu, Asp, Lys or
      Gln
<220> FEATURE:
<221> NAME/KEY: VARIANT
<222> LOCATION: 13
<223> OTHER INFORMATION: where Xaa is Ile, Leu, Glu, Gln, Ala, Val, Asp,
      Thr, Asn or Ser
<220> FEATURE:
<221> NAME/KEY: VARIANT
<222> LOCATION: 14
<223> OTHER INFORMATION: where Xaa is Leu, Ile or Val
<220> FEATURE:
<221> NAME/KEY: VARIANT
<222> LOCATION: 15
```

```
<223> OTHER INFORMATION: where Xaa is Asp, Arg, Asn, Glu, Lys, His or
      Gln
<220> FEATURE:
<221> NAME/KEY: VARIANT
<222> LOCATION: 16
<223> OTHER INFORMATION: where Xaa is Glu, Val, Leu, Phe, Asp, Ile, Ala,
      Ser or Gly
<220> FEATURE:
<221> NAME/KEY: VARIANT
<222> LOCATION: 17
<223> OTHER INFORMATION: where Xaa is Glu, Val, Leu, Ile, Ala, Thr, Asp
      or Ser
<220> FEATURE:
<221> NAME/KEY: VARIANT
<222> LOCATION: 18
<223> OTHER INFORMATION: where Xaa is Leu, Val, Ile or Ala
<220> FEATURE:
<221> NAME/KEY: VARIANT
<222> LOCATION: 19
<223> OTHER INFORMATION: where Xaa is Leu, Thr, Gln, Glu, Ile, Val, Ser,
      Ala, Asn or Asp
<220> FEATURE:
<221> NAME/KEY: VARIANT
<222> LOCATION: 20
<223> OTHER INFORMATION: where Xaa is Arg, Asp, His, Asn, Gln, Lys or
      Glu
<220> FEATURE:
<221> NAME/KEY: VARIANT
<222> LOCATION: 21
<223> OTHER INFORMATION: where Xaa is Trp, Tyr, Ile, Leu, Phe or Val
<220> FEATURE:
<221> NAME/KEY: VARIANT
<222> LOCATION: 22
<223> OTHER INFORMATION: where Xaa is Trp, Phe, Tyr or Ile
<220> FEATURE:
<221> NAME/KEY: VARIANT
<222> LOCATION: 23
<223> OTHER INFORMATION: where Xaa is Trp, Tyr, Ile, Val, His, Lys, Phe,
      Leu, Arg or Gly
<220> FEATURE:
<221> NAME/KEY: VARIANT
<222> LOCATION: 24
<223> OTHER INFORMATION: where Xaa is Ile, Gln, Leu, Asn, Val or Tyr
<220> FEATURE:
<221> NAME/KEY: VARIANT
<222> LOCATION: 25
<223> OTHER INFORMATION: where Xaa is Ser, Leu, Ile, Thr, Val or Ala
<220> FEATURE:
<221> NAME/KEY: VARIANT
<222> LOCATION: 26
<223> OTHER INFORMATION: where Xaa is Ala, Ile, Val, Gly, Leu, Met or
      Trp
<220> FEATURE:
<221> NAME/KEY: VARIANT
<222> LOCATION: 27
<223> OTHER INFORMATION: where Xaa is Asn, Thr, Ser or Ala
<220> FEATURE:
<221> NAME/KEY: VARIANT
<222> LOCATION: 28
<223> OTHER INFORMATION: where Xaa is Ile, Leu, Val or Met
<220> FEATURE:
<221> NAME/KEY: VARIANT
<222> LOCATION: 29
<223> OTHER INFORMATION: where Xaa is Lys, Arg, Phe, Trp, His, Tyr or
      Val
<220> FEATURE:
<221> NAME/KEY: VARIANT
<222> LOCATION: 30
<223> OTHER INFORMATION: where Xaa is Ile, Val or Leu

<400> SEQUENCE: 294

Xaa Xaa Xaa Xaa Xaa Xaa Xaa Xaa Xaa Ala Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Val Ile
                20                  25                  30

Val Gly Ala Thr Ile Gly Ile Lys Leu Phe Lys Lys Phe Thr Ser Lys
        35                  40                  45
```

```
<210> SEQ ID NO 295
<211> LENGTH: 50
<212> TYPE: PRT
<213> ORGANISM: M13 phage
<220> FEATURE:
<223> OTHER INFORMATION: coat protein VIII
<220> FEATURE:
<221> NAME/KEY: VARIANT
<222> LOCATION: 1
<223> OTHER INFORMATION: where Xaa is any amino acid except Ala
<220> FEATURE:
<221> NAME/KEY: VARIANT
<222> LOCATION: 2
<223> OTHER INFORMATION: where Xaa is any amino acid except Glu
<220> FEATURE:
<221> NAME/KEY: VARIANT
<222> LOCATION: 3
<223> OTHER INFORMATION: where Xaa is any amino acid except Gly
<220> FEATURE:
<221> NAME/KEY: VARIANT
<222> LOCATION: 4
<223> OTHER INFORMATION: where Xaa is any amino acid except Asp
<220> FEATURE:
<221> NAME/KEY: VARIANT
<222> LOCATION: 5
<223> OTHER INFORMATION: where Xaa is any amino acid except Asp
<220> FEATURE:
<221> NAME/KEY: VARIANT
<222> LOCATION: 6
<223> OTHER INFORMATION: where Xaa is any amino acid except Pro
<220> FEATURE:
<221> NAME/KEY: VARIANT
<222> LOCATION: 8
<223> OTHER INFORMATION: where Xaa is any amino acid except Lys
<220> FEATURE:
<221> NAME/KEY: VARIANT
<222> LOCATION: 9
<223> OTHER INFORMATION: where Xaa is any amino acid except Ala

<400> SEQUENCE: 295

Xaa Xaa Xaa Xaa Xaa Xaa Ala Xaa Xaa Ala Phe Asn Ser Leu Gln Ala
 1               5                  10                  15

Ser Ala Thr Glu Tyr Ile Gly Tyr Ala Trp Ala Met Val Val Val Ile
            20                  25                  30

Val Gly Ala Thr Ile Gly Ile Lys Leu Phe Lys Lys Phe Thr Ser Lys
        35                  40                  45

Ala Ser
    50

<210> SEQ ID NO 296
<211> LENGTH: 50
<212> TYPE: PRT
<213> ORGANISM: M13 phage
<220> FEATURE:
<223> OTHER INFORMATION: coat protein VIII
<220> FEATURE:
<221> NAME/KEY: VARIANT
<222> LOCATION: 11
<223> OTHER INFORMATION: where Xaa is any amino acid except Phe
<220> FEATURE:
<221> NAME/KEY: VARIANT
<222> LOCATION: 12
<223> OTHER INFORMATION: where Xaa is any amino acid except Asn
<220> FEATURE:
<221> NAME/KEY: VARIANT
<222> LOCATION: 13
<223> OTHER INFORMATION: where Xaa is any amino acid except Ser
<220> FEATURE:
<221> NAME/KEY: VARIANT
<222> LOCATION: 15
```

Ala Ser
    50

<223> OTHER INFORMATION: where Xaa is any amino acid except Gln
<220> FEATURE:
<221> NAME/KEY: VARIANT
<222> LOCATION: 16
<223> OTHER INFORMATION: where Xaa is any amino acid except Ala
<220> FEATURE:
<221> NAME/KEY: VARIANT
<222> LOCATION: 17
<223> OTHER INFORMATION: where Xaa is any amino acid except Ser
<220> FEATURE:
<221> NAME/KEY: VARIANT
<222> LOCATION: 20
<223> OTHER INFORMATION: where Xaa is any amino acid except Glu

<400> SEQUENCE: 296

Ala Glu Gly Asp Asp Pro Ala Lys Ala Ala Xaa Xaa Xaa Leu Xaa Xaa
1               5                   10                  15

Xaa Ala Thr Xaa Tyr Ile Gly Tyr Ala Trp Ala Met Val Val Val Ile
            20                  25                  30

Val Gly Ala Thr Ile Gly Ile Lys Leu Phe Lys Lys Phe Thr Ser Lys
        35                  40                  45

Ala Ser
    50

<210> SEQ ID NO 297
<211> LENGTH: 50
<212> TYPE: PRT
<213> ORGANISM: M13 phage
<220> FEATURE:
<223> OTHER INFORMATION: coat protein VIII
<220> FEATURE:
<221> NAME/KEY: VARIANT
<222> LOCATION: 21
<223> OTHER INFORMATION: where Xaa is any amino acid except Tyr
<220> FEATURE:
<221> NAME/KEY: VARIANT
<222> LOCATION: 22
<223> OTHER INFORMATION: where Xaa is any amino acid except Ile
<220> FEATURE:
<221> NAME/KEY: VARIANT
<222> LOCATION: 23
<223> OTHER INFORMATION: where Xaa is any amino acid except Gly
<220> FEATURE:
<221> NAME/KEY: VARIANT
<222> LOCATION: 24
<223> OTHER INFORMATION: where Xaa is any amino acid except Tyr
<220> FEATURE:
<221> NAME/KEY: VARIANT
<222> LOCATION: 25
<223> OTHER INFORMATION: where Xaa is any amino acid except Ala
<220> FEATURE:
<221> NAME/KEY: VARIANT
<222> LOCATION: 26
<223> OTHER INFORMATION: where Xaa is any amino acid except Trp
<220> FEATURE:
<221> NAME/KEY: VARIANT
<222> LOCATION: 27
<223> OTHER INFORMATION: where Xaa is any amino acid except Ala
<220> FEATURE:
<221> NAME/KEY: VARIANT
<222> LOCATION: 28
<223> OTHER INFORMATION: where Xaa is any amino acid except Met
<220> FEATURE:
<221> NAME/KEY: VARIANT
<222> LOCATION: 29
<223> OTHER INFORMATION: where Xaa is any amino acid except Val
<220> FEATURE:
<221> NAME/KEY: VARIANT
<222> LOCATION: 30
<223> OTHER INFORMATION: where Xaa is any amino acid except Val

<400> SEQUENCE: 297

Ala Glu Gly Asp Asp Pro Ala Lys Ala Ala Phe Asn Ser Leu Gln Ala
1               5                   10                  15

```
Ser Ala Thr Glu Xaa Xaa Xaa Xaa Xaa Xaa Xaa Xaa Xaa Val Ile
             20                  25                  30

Val Gly Ala Thr Ile Gly Ile Lys Leu Phe Lys Lys Phe Thr Ser Lys
         35                  40                  45

Ala Ser
    50

<210> SEQ ID NO 298
<211> LENGTH: 50
<212> TYPE: PRT
<213> ORGANISM: M13 phage
<220> FEATURE:
<223> OTHER INFORMATION: coat protein VIII
<220> FEATURE:
<221> NAME/KEY: VARIANT
<222> LOCATION: 1
<223> OTHER INFORMATION: where Xaa is any amino acid except Ala
<220> FEATURE:
<221> NAME/KEY: VARIANT
<222> LOCATION: 2
<223> OTHER INFORMATION: where Xaa is any amino acid except Glu
<220> FEATURE:
<221> NAME/KEY: VARIANT
<222> LOCATION: 3
<223> OTHER INFORMATION: where Xaa is any amino acid except Gly
<220> FEATURE:
<221> NAME/KEY: VARIANT
<222> LOCATION: 4
<223> OTHER INFORMATION: where Xaa is any amino acid except Asp
<220> FEATURE:
<221> NAME/KEY: VARIANT
<222> LOCATION: 5
<223> OTHER INFORMATION: where Xaa is any amino acid except Asp
<220> FEATURE:
<221> NAME/KEY: VARIANT
<222> LOCATION: 6
<223> OTHER INFORMATION: where Xaa is any amino acid except Pro
<220> FEATURE:
<221> NAME/KEY: VARIANT
<222> LOCATION: 8
<223> OTHER INFORMATION: where Xaa is any amino acid except Lys
<220> FEATURE:
<221> NAME/KEY: VARIANT
<222> LOCATION: 9
<223> OTHER INFORMATION: where Xaa is any amino acid except Ala
<220> FEATURE:
<221> NAME/KEY: VARIANT
<222> LOCATION: 11
<223> OTHER INFORMATION: where Xaa is any amino acid except Phe
<220> FEATURE:
<221> NAME/KEY: VARIANT
<222> LOCATION: 12
<223> OTHER INFORMATION: where Xaa is any amino acid except Asn
<220> FEATURE:
<221> NAME/KEY: VARIANT
<222> LOCATION: 13
<223> OTHER INFORMATION: where Xaa is any amino acid except Ser
<220> FEATURE:
<221> NAME/KEY: VARIANT
<222> LOCATION: 15
<223> OTHER INFORMATION: where Xaa is any amino acid except Gln
<220> FEATURE:
<221> NAME/KEY: VARIANT
<222> LOCATION: 16
<223> OTHER INFORMATION: where Xaa is any amino acid except Ala
<220> FEATURE:
<221> NAME/KEY: VARIANT
<222> LOCATION: 17
<223> OTHER INFORMATION: where Xaa is any amino acid except Ser
<220> FEATURE:
<221> NAME/KEY: VARIANT
<222> LOCATION: 20
<223> OTHER INFORMATION: where Xaa is any amino acid except Glu

<400> SEQUENCE: 298
```

```
Xaa Xaa Xaa Xaa Xaa Ala Xaa Ala Xaa Xaa Xaa Leu Xaa Xaa
 1               5                  10                  15

Xaa Ala Thr Xaa Tyr Ile Gly Tyr Ala Trp Ala Met Val Val Ile
             20                  25                  30

Val Gly Ala Thr Ile Gly Ile Lys Leu Phe Lys Lys Phe Thr Ser Lys
         35                  40                  45

Ala Ser
     50

<210> SEQ ID NO 299
<211> LENGTH: 50
<212> TYPE: PRT
<213> ORGANISM: M13 phage
<220> FEATURE:
<223> OTHER INFORMATION: coat protein VIII
<220> FEATURE:
<221> NAME/KEY: VARIANT
<222> LOCATION: 11
<223> OTHER INFORMATION: where Xaa is any amino acid except Phe
<220> FEATURE:
<221> NAME/KEY: VARIANT
<222> LOCATION: 12
<223> OTHER INFORMATION: where Xaa is any amino acid except Asn
<220> FEATURE:
<221> NAME/KEY: VARIANT
<222> LOCATION: 13
<223> OTHER INFORMATION: where Xaa is any amino acid except Ser
<220> FEATURE:
<221> NAME/KEY: VARIANT
<222> LOCATION: 15
<223> OTHER INFORMATION: where Xaa is any amino acid except Gln
<220> FEATURE:
<221> NAME/KEY: VARIANT
<222> LOCATION: 16
<223> OTHER INFORMATION: where Xaa is any amino acid except Ala
<220> FEATURE:
<221> NAME/KEY: VARIANT
<222> LOCATION: 17
<223> OTHER INFORMATION: where Xaa is any amino acid except Ser
<220> FEATURE:
<221> NAME/KEY: VARIANT
<222> LOCATION: 20
<223> OTHER INFORMATION: where Xaa is any amino acid except Glu
<220> FEATURE:
<221> NAME/KEY: VARIANT
<222> LOCATION: 21
<223> OTHER INFORMATION: where Xaa is any amino acid except Tyr
<220> FEATURE:
<221> NAME/KEY: VARIANT
<222> LOCATION: 22
<223> OTHER INFORMATION: where Xaa is any amino acid except Ile
<220> FEATURE:
<221> NAME/KEY: VARIANT
<222> LOCATION: 23
<223> OTHER INFORMATION: where Xaa is any amino acid except Gly
<220> FEATURE:
<221> NAME/KEY: VARIANT
<222> LOCATION: 24
<223> OTHER INFORMATION: where Xaa is any amino acid except Tyr
<220> FEATURE:
<221> NAME/KEY: VARIANT
<222> LOCATION: 25
<223> OTHER INFORMATION: where Xaa is any amino acid except Ala
<220> FEATURE:
<221> NAME/KEY: VARIANT
<222> LOCATION: 26
<223> OTHER INFORMATION: where Xaa is any amino acid except Trp
<220> FEATURE:
<221> NAME/KEY: VARIANT
<222> LOCATION: 27
<223> OTHER INFORMATION: where Xaa is any amino acid except Ala
<220> FEATURE:
<221> NAME/KEY: VARIANT
<222> LOCATION: 28
<223> OTHER INFORMATION: where Xaa is any amino acid except Met
<220> FEATURE:
```

```
<221> NAME/KEY: VARIANT
<222> LOCATION: 29
<223> OTHER INFORMATION: where Xaa is any amino acid except Val
<220> FEATURE:
<221> NAME/KEY: VARIANT
<222> LOCATION: 30
<223> OTHER INFORMATION: where Xaa is any amino acid except Val

<400> SEQUENCE: 299

Ala Glu Gly Asp Asp Pro Ala Lys Ala Ala Xaa Xaa Xaa Leu Xaa Xaa
 1               5                  10                  15

Xaa Ala Thr Xaa Xaa Xaa Xaa Xaa Xaa Xaa Xaa Xaa Xaa Xaa Val Ile
             20                  25                  30

Val Gly Ala Thr Ile Gly Ile Lys Leu Phe Lys Lys Phe Thr Ser Lys
         35                  40                  45

Ala Ser
 50

<210> SEQ ID NO 300
<211> LENGTH: 50
<212> TYPE: PRT
<213> ORGANISM: M13 phage
<220> FEATURE:
<223> OTHER INFORMATION: coat protein VIII
<220> FEATURE:
<221> NAME/KEY: VARIANT
<222> LOCATION: 1
<223> OTHER INFORMATION: where Xaa is any amino acid except Ala
<220> FEATURE:
<221> NAME/KEY: VARIANT
<222> LOCATION: 2
<223> OTHER INFORMATION: where Xaa is any amino acid except Glu
<220> FEATURE:
<221> NAME/KEY: VARIANT
<222> LOCATION: 3
<223> OTHER INFORMATION: where Xaa is any amino acid except Gly
<220> FEATURE:
<221> NAME/KEY: VARIANT
<222> LOCATION: 4
<223> OTHER INFORMATION: where Xaa is any amino acid except Asp
<220> FEATURE:
<221> NAME/KEY: VARIANT
<222> LOCATION: 5
<223> OTHER INFORMATION: where Xaa is any amino acid except Asp
<220> FEATURE:
<221> NAME/KEY: VARIANT
<222> LOCATION: 6
<223> OTHER INFORMATION: where Xaa is any amino acid except Pro
<220> FEATURE:
<221> NAME/KEY: VARIANT
<222> LOCATION: 8
<223> OTHER INFORMATION: where Xaa is any amino acid except Lys
<220> FEATURE:
<221> NAME/KEY: VARIANT
<222> LOCATION: 9
<223> OTHER INFORMATION: where Xaa is any amino acid except Ala
<220> FEATURE:
<221> NAME/KEY: VARIANT
<222> LOCATION: 11
<223> OTHER INFORMATION: where Xaa is any amino acid except Phe
<220> FEATURE:
<221> NAME/KEY: VARIANT
<222> LOCATION: 12
<223> OTHER INFORMATION: where Xaa is any amino acid except Asn
<220> FEATURE:
<221> NAME/KEY: VARIANT
<222> LOCATION: 13
<223> OTHER INFORMATION: where Xaa is any amino acid except Ser
<220> FEATURE:
<221> NAME/KEY: VARIANT
<222> LOCATION: 15
<223> OTHER INFORMATION: where Xaa is any amino acid except Gln
<220> FEATURE:
<221> NAME/KEY: VARIANT
<222> LOCATION: 16
```

```
<223> OTHER INFORMATION: where Xaa is any amino acid except Ala
<220> FEATURE:
<221> NAME/KEY: VARIANT
<222> LOCATION: 17
<223> OTHER INFORMATION: where Xaa is any amino acid except Ser
<220> FEATURE:
<221> NAME/KEY: VARIANT
<222> LOCATION: 20
<223> OTHER INFORMATION: where Xaa is any amino acid except Glu
<220> FEATURE:
<221> NAME/KEY: VARIANT
<222> LOCATION: 21
<223> OTHER INFORMATION: where Xaa is any amino acid except Tyr
<220> FEATURE:
<221> NAME/KEY: VARIANT
<222> LOCATION: 22
<223> OTHER INFORMATION: where Xaa is any amino acid except Ile
<220> FEATURE:
<221> NAME/KEY: VARIANT
<222> LOCATION: 23
<223> OTHER INFORMATION: where Xaa is any amino acid except Gly
<220> FEATURE:
<221> NAME/KEY: VARIANT
<222> LOCATION: 24
<223> OTHER INFORMATION: where Xaa is any amino acid except Tyr
<220> FEATURE:
<221> NAME/KEY: VARIANT
<222> LOCATION: 25
<223> OTHER INFORMATION: where Xaa is any amino acid except Ala
<220> FEATURE:
<221> NAME/KEY: VARIANT
<222> LOCATION: 26
<223> OTHER INFORMATION: where Xaa is any amino acid except Trp
<220> FEATURE:
<221> NAME/KEY: VARIANT
<222> LOCATION: 27
<223> OTHER INFORMATION: where Xaa is any amino acid except Ala
<220> FEATURE:
<221> NAME/KEY: VARIANT
<222> LOCATION: 28
<223> OTHER INFORMATION: where Xaa is any amino acid except Met
<220> FEATURE:
<221> NAME/KEY: VARIANT
<222> LOCATION: 29
<223> OTHER INFORMATION: where Xaa is any amino acid except Val
<220> FEATURE:
<221> NAME/KEY: VARIANT
<222> LOCATION: 30
<223> OTHER INFORMATION: where Xaa is any amino acid except Val

<400> SEQUENCE: 300

Xaa Xaa Xaa Xaa Xaa Xaa Ala Xaa Xaa Ala Xaa Xaa Xaa Leu Xaa Xaa
  1               5                  10                  15

Xaa Ala Thr Xaa Xaa Xaa Xaa Xaa Xaa Xaa Xaa Xaa Xaa Xaa Val Ile
             20                  25                  30

Val Gly Ala Thr Ile Gly Ile Lys Leu Phe Lys Lys Phe Thr Ser Lys
         35                  40                  45

Ala Ser
 50
```